US006545137B1

(12) United States Patent
Todd et al.

(10) Patent No.: US 6,545,137 B1
(45) Date of Patent: Apr. 8, 2003

(54) RECEPTOR

(76) Inventors: John A. Todd, 64 Rousham Road, Tackley, Oxon (GB), OX5 3AJ; John W. Hess, 566 Constitution Rd., Lansdale, PA (US) 19446; Charles T. Caskey, 6402 Bellmont, Houston, TX (US) 66005; Roger D Cox, 7 Park Road, Banbury, Oxon (GB), OX16 0DW; David Gerhold, 730 Tranquility La., Lansdale, PA (US) 19446; Holly Hammond, 621 Melvins Rd., Telford, PA (US) 18969; Patricia Hey, 1133 Bloomfield Cir., Lansdale, PA (US) 19446; Yoshihiko Kawaguchi, Yamadanishi 3-33-B-206, Suita Shi, Osaka (JP), 565; Tony R. Merriman, 16 A Cromwell Close, Marston, Oxford (GB), OX3 0RX; Michael L. Metzker, 7400 Encampment Rd., Lansdale, PA (US) 19446; Yusuke Nakagawa, 17 Latimer Grange, Latimer Road, Headington, Oxford (GB), OX3 7PQ; Michael S. Phillips, 608 Poplar Ct., Lansdale, PA (US) 19446; Rebecca C.J. Twells, 75 Park Street, Thame, Oxon (GB), OX9 3HU ( * ) Notice: Subject to any disclaimer, the term of this patent is extended or adjusted under 35 U.S.C. 154(b) by 0 days.

(21) Appl. No.: 09/060,299

(22) Filed: Apr. 15, 1998

Related U.S. Application Data

(60) Provisional application No. 60/048,740, filed on Jun. 5, 1997, and provisional application No. 60/043,553, filed on Apr. 15, 1997.

(51) Int. Cl.[7] .............................. C07H 21/04; C12Q 5/68
(52) U.S. Cl. ................... 536/23.1; 536/24.3; 536/23.4; 536/23.5; 435/6; 435/69.1
(58) Field of Search ............................ 435/69.1, 320.1, 435/325, 172.3, 352.3, 6; 536/24.3, 23.1, 23.4, 23.5; 530/350, 300

(56) References Cited

U.S. PATENT DOCUMENTS 5,474,796 A  * 12/1995  Brennan ..................... 427/2.13
5,639,616 A  *  6/1997  Liao et al. .................... 435/7.1

FOREIGN PATENT DOCUMENTS

WO    WO 95 30774 A    11/1995
WO    WO 01/77327      10/2001

OTHER PUBLICATIONS

Reiger. R. et al. Glossary of Genetics and Cytogenetics, Classical and Molecular, Fourth Edition, Springer-Verlag, Berlin Heidelberg, New York, pp. 16–19, 1976.*

Genbank Accession No. AL022324, "Human DNA sequence from clone CTA–246H3 on chromosome 22". Dec. 1999.*

Genabnk Alignments.*

Hillier, L. et al., "The WashU–Merck EST project, AC AA203279" EMBL Database, Jan. 30, 1997.

Univ Leicester: "PCR primer WG2G4B, AC Q95283", EMBL Database, Feb. 9, 1996, XP002076212 Heidelberg.

Ribozyme Pharm Inc.: "AC T52084" EMBL Database Mar. 24, 1997, XP002076213 Heidelberg.

Van Der Zee, A. et al. Genomic cloning of the mouse LDL receptor related protein/alpha 2–macroglubulin receptor.

Davies, J. et al, "A genome–wide Search For Human Type 1 Diabetes Susceptibility Genes" Nature vol. 371, Sep. 8, 1994, pp. 130–136, XP002076215.

Luo, D.: "Confirmation of three susceptibility genes to insulin–dependent diabetes mellitus: IDDM5, and IDDM8" Human Molecular Genetics, vol. 5, No. 5, 1996, pp. 693–698, XP02076216.

Todd, J. and Farrall, M.: "Panning for gold: genome–wide scanning for linkage in type 1 diabetes" Human Molecular Genetics, vol. 5, 1996, pp. 1443–1448, XP00202076217.

Gong et al, 2001 "LDL Receptor Related Protein (LRP5) Affects Bone Accrual and Eye Development" Cell, vol. 107, pp. 513–523.

Little et al, 2002 "A mutation in the LDL receptor–related protein 5 gene results in the autosomal dominant high–bone––mass trait", Am. J. Hum. Genet 7–(1): pp. 11–19.

* cited by examiner

Primary Examiner—W. Gary Jones
Assistant Examiner—Jeanine Goldberg
(74) Attorney, Agent, or Firm—Nixon & Vanderhye

(57) ABSTRACT

A novel receptor, "LDL-receptor related protein-3" ("LRP-3"), is provided, along with encoding nucleic acid. The gene is associated with type 1 diabetes (insulin dependent diabetes mellitus), and experimental evidence provides indication that it is the IDDM susceptibility gene IDDM4. In various aspects the invention provides nucleic acid, including coding sequences, oligonucleotide primers and probes, polypeptides, pharmaceutical compositions, methods of diagnosis or prognosis, and other methods relating to and based on the gene, including methods of treatment of diseases in which the gene may be implicated, including autoimmune diseases, such as glomerulonephritis, diseases and disorders involving disruption of endocytosis and/or antigen presentation, diseases and disorders involving cytokine clearance and/or inflammation, viral infection, elevation of free fatty acids or hypercholesterolemia, osteoporosis, Alzheimer's disease, and diabetes.

10 Claims, 67 Drawing Sheets

Figure 5(a)

```
ATGGAGCCCGAGTGAGCGCGGCGCGGGCCCGTCCGGCCGCCGGACAACATGGAGG
CAGCGCCGCCCGGGCCGCCGTGGCCGCTGCTGCTGCTGCTGCTGCTGCTGGCG
CTGTGCGGCTGCCCGGCCCCGCCGCGGCCTCGCCGCTCCTGCTATTTGCCAACCG
CCGGGACGTACGGCTGGTGGACGCCGGCGGAGTCAAGCTGGAGTCCACCATCGTG
GTCAGCGGCCTGGAGGATGCGGCCGCAGTGGACTTCCAGTTTTCCAAGGGAGCCGT
GTACTGGACAGACGTGAGCGAGGAGGCCATCAAGCAGACCTACCTGAACCAGACG
GGGGCCGCCGTGCAGAACGTGGTCATCTCCGGCCTGGTCTCTCCCGACGGCCTCGC
CTGCGACTGGGTGGGCAAGAAGCTGTACTGGACGGACTCAGAGACCAACCGCATC
GAGGTGGCCAACCTCAATGGCACATCCCGGAAGGTGCTCTTCTGGCAGGACCTTGA
CCAGCCGAGGGCCATCGCCTTGGACCCCGCTCACGGGTACATGTACTGGACAGACT
GGGGTGAGACGCCCGGATTGAGCGGGCAGGGATGGATGGCAGCACCCGGAAGAT
CATTGTGGACTCGGACATTTACTGGCCCAATGGACTGACCATCGACCTGGAGGAGC
AGAAGCTCTACTGGGCTGACGCCAAGCTCAGCTTCATCCACCGTGCCAACCTGGAC
GGCTCGTTCCGGCAGAAGGTGGTGGAGGGCAGCCTGACGCACCCCTTCGCCCTGAC
GCTCTCCGGGGACACTCTGTACTGGACAGACTGGCAGACCCGCTCCATCCATGCCT
GCAACAAGCGCACTGGGGGGAAGAGGAAGGAGATCCTGAGTGCCCTCTACTCACC
CATGGACATCCAGGTGCTGAGCCAGGAGCGGCAGCCTTTCTTCCACACTCGCTGTG
AGGAGGACAATGGCGGCTGCTCCCACCTGTGCCTGCTGTCCCCAAGCGAGCCTTTC
TACACATGCGCCTGCCCCACGGGTGTGCAGCTGCAGGACAACGGCAGGACGTGTA
AGGCAGGAGCCGAGGAGGTGCTGCTGCTGGCCCGGCGGACGGACCTACGGAGGAT
CTCGCTGGACACGCCGGACTTTACCGACATCGTGCTGCAGGTGGACGACATCCGGC
ACGCCATTGCCATCGACTACGACCCGCTAGAGGGCTATGTCTACTGGACAGATGAC
GAGGTGCGGGCCATCCGCAGGGCGTACCTGGACGGGTCTGGGGCGCAGACGCTGG
TCAACACCGAGATCAACGACCCCGATGGCATCGCGGTCGACTGGGTGGCCCGAAA
CCTCTACTGGACCGACACGGGCACGGACCGCATCGAGGTGACGCGCCTCAACGGC
ACCTCCCGCAAGATCCTGGTGTCGGAGGACCTGGACGAGCCCCGAGCCATCGCACT
GCACCCCGTGATGGGCCTCATGTACTGGACAGACTGGGGAGAGAACCCTAAAATCG
AGTGTGCCAACTTGGATGGGCAGGAGCGGCGTGTGCTGGTCAATGCCTCCCTCGGG
TGGCCCAACGGCCTGGCCCTGGACCTGCAGGAGGGGAAGCTCTACTGGGGAGACG
CCAAGACAGACAAGATCGAGGTGATCAATGTTGATGGGACGAAGAGGCGGACCCT
CCTGGAGGACAAGCTCCCGCACATTTTCGGGTTCACGCTGCTGGGGGACTTCATCT
ACTGGACTGACTGGCAGCGCCGCAGCATCGAGCGGGTGCACAAGGTCAAGGCCAG
CCGGGACGTCATCATTGACCAGCTGCCCGACCTGATGGGGCTCAAAGCTGTGAATG
TGGCCAAGGTCGTCGGAACCAACCCGTGTGCGGACAGGAACGGGGGGTGCAGCCA
CCTGTGCTTCTTCACACCCCACGCAACCCGGTGTGGCTGCCCCATCGGCCTGGAGC
TGCTGAGTGACATGAAGACCTGCATCGTGCCTGAGGCCTTCTTGGTCTTCACCAGC
AGAGCCGCCATCCACAGGATCTCCCTCGAGACCAATAACAACGACGTGCCATCCCG
CTCACGGGCGTCAAGGAGGCCTCAGCCCTGGACTTTGATGTGTCCAACAACCACAT
CTACTGGACAGACGTCAGCCTGAAGACCATCAGCCGCGCCTTCATGAACGGGAGCT
CGGTGGAGCACGTGGTGGAGTTTGGCCTTGACTACCCCGAGGGCATGGCCGTTGAC
TGGATGGGCAAGAACCTCTACTGGGCCGACACTGGGACCAACAGAATCGAAGTGG
CGCGGCTGGACGGGCAGTTCCGGCAAGTCCTCGTGTGGAGGGACTTGGACAACCCG
AGGTCGCTGGCCCTGGATCCCACCAAGGGCTACATCTACTGGACCGAGTGGGGCGG
```

Figure 5(a-1)

```
CAAGCCGAGGATCGTGCGGGCCTTCATGGACGGGACCAACTGCATGACGCTGGTGG
ACAAGGTGGGCCGGGCCAACGACCTCACCATTGACTACGCTGACCAGCGCCTCTAC
TGGACCGACCTGGACACCAACATGATCGAGTCGTCCAACATGCTGGGTCAGGAGCG
GGTCGTGATTGCCGACGATCTCCCGCACCCGTTCGGTCTGACGCAGTACAGCGATT
ATATCTACTGGACAGACTGGAATCTGCACAGCATTGAGCGGGCCGACAAGACTAGC
GGCCGGAACCGCACCCTCATCCAGGGCCACCTGGACTTCGTGATGGACATCCTGGT
GTTCCACTCCTCCCGCCAGGATGGCCTCAATGACTGTATGCACAACAACGGGCAGT
GTGGGCAGCTGTGCCTTGCCATCCCCGGCGGCCACCGCTGCGGCTGCGCCTCACAC
TACACCCTGGACCCCAGCAGCCGCAACTGCAGCCCGCCCACCACCTTCTTGCTGTT
CAGCCAGAAATCTGCCATCAGTCGGATGATCCCGGACGACCAGCACAGCCCGGATC
TCATCCTGCCCCTGCATGGACTGAGGAACGTCAAAGCCATCGACTATGACCCACTG
GACAAGTTCATCTACTGGGTGGATGGGCGCCAGAACATCAAGCGAGCCAAGGACG
ACGGGACCCAGCCCTTTGTTTTGACCTCTCTGAGCCAAGGCCAAAACCCAGACAGG
CAGCCCCACGACCTCAGCATCGACATCTACAGCCGGACACTGTTCTGGACGTGCGA
GGCCACCAATACCATCAACGTCCACAGGCTGAGCGGGGAAGCCATGGGGGTGGTG
CTGCGTGGGGACCGCGACAAGCCCAGGGCCATCGTCGTCAACGCGGAGCGAGGGT
ACCTGTACTTCACCAACATGCAGGACCGGGCAGCAAGATCGAACGCGCAGCCCTG
GACGGCACCGAGCGCGAGGTCCTCTTCACCACCGGCCTCATCCGCCCTGTGGCCCT
GGTGGTAGACAACACACTGGGCAAGCTGTTCTGGGTGGACGCGGACCTGAAGCGC
ATTGAGAGCTGTGACCTGTCAGGGGCCAACCGCCTGACCCTGGAGGACGCCAACAT
CGTGCAGCCTCTGGGCCTGACCATCCTTGGCAAGCATCTCTACTGGATCGACCGCC
AGCAGCAGATGATCGAGCGTGTGGAGAAGACCACCGGGGACAAGCGGACTCGCAT
CCAGGGCCGTGTCGCCCACCTCACTGGCATCCATGCAGTGGAGGAAGTCAGCCTGG
AGGAGTTCTCAGCCCACCCATGTGCCCGTGACAATGGTGGCTGCTCCCACATCTGT
ATTGCCAAGGGTGATGGGACACCACGGTGCTCATGCCCAGTCCACCTCGTGCTCCT
GCAGAACCTGCTGACCTGTGGAGAGCCGCCCACCTGCTCCCCGGACCAGTTTGCAT
GTGCCACAGGGGAGATCGACTGTATCCCCGGGGCCTGGCGCTGTGACGGCTTTCCC
GAGTGCGATGACCAGAGCGACGAGGAGGGCTGCCCCGTGTGCTCCGCCGCCCAGTT
CCCCTGCGCGCGGGGTCAGTGTGTGGACCTGCGCCTGCGCTGCGACGGCGAGGCAG
ACTGTCAGGACCGCTCAGACGAGGCGGACTGTGAGGCCATCTGCCTGCCCAACCAG
TTCCGGTGTGCGAGCGGCCAGTGTGTCCTATCAAACAGCAGTGCGACTCCTTCCCC
GACTGTATCGACGGCTCCGACGAGCTCATGTGTGAAATCACCAAGCCGCCCTCAGA
CGACAGCCCGGCCCACAGCAGTGCCATCGGGCCCGTCATTGGCATCATCCTCTCTC
TCTTCGTCATGGGTGGTGTCTATTTTGTGTGCCAGCGCGTGGTGTGCCAGCGCTATG
CGGGGGCCAACGGGCCCTTCCCGCACGAGTATGTCAGCGGGACCCCGCACGTGCCC
CTCAATTTCATAGCCCCGGGCGGTTCCAGCATGGCCCCTTCACAGGCATCGCATG
CGGAAAGTCCATGATGAGCTCCGTGAGCCTGATGGGGGGCCGGGCGGGGTGCCC
CTCTACGACCGGAACCACGTCACAGGGGCCTCGTCCAGCAGCTCGTCCAGCACGAA
GGCCACGCTGTACCCGCCGATCCTGAACCCGCCGCCCTCCCCGGCCACGGACCCCT
CCCTGTACAACATGGACATGTTCTACTCTTCAAACATTCCGGCCACTGTGAGACCG
TACAGGCCCTACATCATTCGAGGAATGGCGCCCCGACGACGCCCTGCAGCACCGA
CGTGTGTGACAGCGACTACAGCGCCAGCCGCTGGAAGGCCAGCAAGTACTACCTG
GATTTGAACTCGGACTCAGACCCCTATCCACCCCCACCCACGCCCCACAGCCAGTA
```

Figure 5(a-2)

CCTGTCGGCGGAGGACAGCTGCCCGCCCTCGCCCGCCACCGAGAGGAGCTACTTCC
ATCTCTTCCCGCCCCCTCCGTCCCCTGCACGGACTCATCCTGACCTCGGCCGGGCC
ACTCTGGCTTCTCTGTGCCCCTGTAAATAGTTTTAAATATGAACAAAGAAAAAAAT
ATATTTTATGATTTAAAAAATAAATATAATTGGGATTTTAAAAACATGAGAAATGT
GAACTGTGATGGGGTGGGCAGGGCTGGGAGAACTTTGTACAGTGGAACAAATATTT
ATAAACTTAATTTTGTAAAACAG (SEQ ID NO: 1)

Figure 5(b)

```
ATGGAGGCAGCGCCGCCCGGGCCGCCGTGGCCGCTGCTGCTGCTGCTGCTG
CTGCTGGCGCTGTGCGGCTGCCCGGCCCCGCCGCGGCCTCGCCGCTCCTGCTA
TTTGCCAACCGCCGGGACGTACGGCTGGTGGACGCCGGCGGAGTCAAGCTGGA
GTCCACCATCGTGGTCAGCGGCCTGGAGGATGCGGCCGCAGTGGACTTCCAGTT
TTCCAAGGGAGCCGTGTACTGGACAGACGTGAGCGAGGAGGCCATCAAGCAGA
CCTACCTGAACCAGACGGGGGCCGCCGTGCAGAACGTGGTCATCTCCGGCCTGG
TCTCTCCCGACGGCCTCGCCTGCGACTGGGTGGGCAAGAAGCTGTACTGGACGG
ACTCAGAGACCAACCGCATCGAGGTGGCCAACCTCAATGGCACATCCCGGAAG
GTGCTCTTCTGGCAGGACCTTGACCAGCCGAGGGCCATCGCCTTGGACCCCGCT
CACGGGTACATGTACTGGACAGACTGGGGTGAGACGCCCCGGATTGAGCGGGC
AGGGATGGATGGCAGCACCCGGAAGATCATTGTGGACTCGGACATTTACTGGCC
CAATGGACTGACCATCGACCTGGAGGAGCAGAAGCTCTACTGGGCTGACGCCA
AGCTCAGCTTCATCCACCGTGCCAACCTGGACGGCTCGTTCCGGCAGAAGGTGG
TGGAGGGCAGCCTGACGCACCCCTTCGCCCTGACGCTCTCCGGGGACACTCTGT
ACTGGACAGACTGGCAGACCCGCTCCATCCATGCCTGCAACAAGCGCACTGGGG
GGAAGAGGAAGGAGATCCTGAGTGCCCTCTACTCACCCATGGACATCCAGGTGC
TGAGCCAGGAGCGGCAGCCTTTCTTCCACACTCGCTGTGAGGAGGACAATGGCG
GCTGCTCCCACCTGTGCCTGCTGTCCCCAAGCGAGCCTTTCTACACATGCGCCT
GCCCCACGGGTGTGCAGCTGCAGGACAACGGCAGGACGTGTAAGGCAGGAGCC
GAGGAGGTGCTGCTGCTGGCCCGGCGGACGGACCTACGGAGGATCTCGCTGGA
CACGCCGGACTTTACCGACATCGTGCTGCAGGTGGACGACATCCGGCACGCCAT
TGCCATCGACTACGACCCGCTAGAGGGCTATGTCTACTGGACAGATGACGAGGT
GCGGGCCATCCGCAGGGCGTACCTGGACGGGTCTGGGGCGCAGACGCTGGTCA
ACACCGAGATCAACGACCCCGATGGCATCGCGGTCGACTGGGTGGCCCGAAAC
CTCTACTGGACCGACACGGGCACGGACCGCATCGAGGTGACGCGCCTCAACGG
CACCTCCCGCAAGATCCTGGTGTCGGAGGACCTGGACGAGCCCCGAGCCATCGC
ACTGCACCCCGTGATGGGCCTCATGTACTGGACAGACTGGGGAGAGAACCCTAA
AATCGAGTGTGCCAACTTGGATGGGCAGGAGCGGCGTGTGCTGGTCAATGCCTC
CCTCGGGTGGCCCAACGGCCTGGCCCTGGACCTGCAGGAGGGGAAGCTCTACTG
GGGAGACGCCAAGACAGACAAGATCGAGGTGATCAATGTTGATGGGACGAAGA
GGCGGACCCTCCTGGAGGACAAGCTCCCGCACATTTTCGGGTTCACGCTGCTGG
GGGACTTCATCTACTGGACTGACTGGCAGCGCCGCAGCATCGAGCGGGTGCACA
AGGTCAAGGCCAGCCGGGACGTCATCATTGACCAGCTGCCCGACCTGATGGGGC
TCAAAGCTGTGAATGTGGCCAAGGTCGTCGGAACCAACCCGTGTGCGGACAGG
AACGGGGGGTGCAGCCACCTGTGCTTCTTCACACCCCACGCAACCCGGTGTGGC
TGCCCCATCGGCCTGGAGCTGCTGAGTGACATGAAGACCTGCATCGTGCCTGAG
GCCTTCTTGGTCTTCACCAGCAGAGCCGCCATCCACAGGATCTCCCTCGAGACC
AATAACAACGACGTGGCCATCCCGCTCACGGGCGTCAAGGAGGCCTCAGCCCTG
GACTTTGAGTGTCCAACAACCACATCTACTGGACAGACGTCAGCCTGAAGACCA
TCAGCCGCGCCTTCATGAACGGGAGCTCGGTGGAGCACGTGGTGGAGTTTGGCC
TTGACTACCCCGAGGGCATGGCCGTTGACTGGATGGGCAAGAACCTCTACTGGG
CCGACACTGGGACCAACAGAATCGAAGTGGCGCGGCTGGACGGGCAGTTCCGG
CAAGTCCTCGTGTGGAGGGACTTGGACAACCCGAGGTCGCTGGCCCTGGATCCC
ACCAAGGGCTACATCTACTGGACCGAGTGGGGCGGCAAGCCGAGGATCGTGCG
GGCCTTCATGGACGGGACCAACTGCATGACGCTGGTGGACAAGGTGGGCCGGG
CCAACGACCTCACCATTGACTACGCTGACCAGCGCCTCTACTGGACCGACCTGG
```

Figure 5(b-1)

```
ACACCAACATGATCGAGTCGTCCAACATGCTGGGTCAGGAGCGGGTCGTGATTG
CCGACGATCTCCCGCACCCGTTCGGTCTGACGCAGTACAGCGATTATATCTACT
GGACAGACTGGAATCTGCACAGCATTGAGCGGGCCGACAAGACTAGCGGCCGG
AACCGCACCCTCATCCAGGGCCACCTGGACTTCGTGATGGACATCCTGGTGTTC
CACTCCTCCCGCCAGGATGGCCTCAATGACTGTATGCACAACAACGGGCAGTGT
GGGCAGCTGTGCCTTGCCATCCCCGGCGGCCACCGCTGCGGCTGCGCCTCACAC
TACACCCTGGACCCCAGCAGCCGCAACTGCAGCCCGCCCACCACCTTCTTGCTG
TTCAGCCAGAAATCTGCCATCAGTCGGATGATCCCGGACGACCAGCACAGCCCG
GATCTCATCCTGCCCCTGCATGGACTGAGGAACGTCAAAGCCATCGACTATGAC
CCACTGGACAAGTTCATCTACTGGGTGGATGGGCGCCAGAACATCAAGCGAGCC
AAGGACGACGGGACCCAGCCCTTTGTTTTGACCTCTCTGAGCCAAGGCCAAAAC
CCAGACAGGCAGCCCCACGACCTCAGCATCGACATCTACAGCCGGACACTGTTC
TGGACGTGCGAGGCCACCAATACCATCAACGTCCACAGGCTGAGCGGGGAAGC
CATGGGGGTGGTGCTGCGTGGGGACCGCGACAAGCCCAGGGCCATCGTCGTCA
ACGCGGAGCGAGGGTACCTGTACTTCACCAACATGCAGGACCGGGCAGCCAAG
ATCGAACGCGCAGCCCTGGACGGCACCGAGCGCGAGGTCCTCTTCACCACCGGC
CTCATCCGCCCTGTGGCCCTGGTGGTAGACAACACACTGGGCAAGCTGTTCTGG
GTGGACGCGGACCTGAAGCGCATTGAGAGCTGTGACCTGTCAGGGCCAACCG
CCTGACCCTGGAGGACGCCAACATCGTGCAGCCTCTGGGCCTGACCATCCTTGG
CAAGCATCTCTACTGGATCGACCGCCAGCAGCAGATGATCGAGCGTGTGGAGAA
GACCACCGGGGACAAGCGGACTCGCATCCAGGGCCGTGTCGCCCACCTCACTGG
CATCCATGCAGTGGAGGAAGTCAGCCTGGAGGAGTTCTCAGCCCACCCATGTGC
CCGTGACAATGGTGGCTGCTCCCACATCTGTATTGCCAAGGGTGATGGGACACC
ACGGTGCTCATGCCCAGTCCACCTCGTGCTCCTGCAGAACCTGCTGACCTGTGG
AGAGCCGCCCACCTGCTCCCCGGACCAGTTTGCATGTGCCACAGGGGAGATCGA
CTGTATCCCCGGGGCCTGGCGCTGTGACGGCTTTCCCGAGTGCGATGACCAGAG
CGACGAGGAGGGCTGCCCCGTGTGCTCCGCCGCCCAGTTCCCCTGCGCGCGGGG
TCAGTGTGTGGACCTGCGCCTGCGCTGCGACGGCGAGGCAGACTGTCAGGACCG
CTCAGACGAGGCGGACTGTGACGCCATCTGCCTGCCCAACCAGTTCCGGTGTGC
GAGCGGCCAGTGTGTCCTCATCAAACAGCAGTGCGACTCCTTCCCCGACTGTAT
CGACGGCTCCGAGAGCTCATGTGTGAAATCACCAAGCCGCCCTCAGACGACAGC
CCGGCCCACAGCAGTGCCATCGGGCCCGTCATTGGCATCATCCTCTCTCTCTTC
GTCATGGGTGGTGTCTATTTTGTGTGCCAGCGCGTGGTGTGCCAGCGCTATGCG
GGGGCCAACGGGCCCTTCCCGCACGAGTATGTCAGCGGGACCCCGCACGTGCCC
CTCAATTTCATAGCCCCGGGCGGTTCCAGCATGGCCCCTTCACAGGCATCGCA
TGCGGAAAGTCCATGATGAGCTCCGTGAGCCTGATGGGGGGCCGGGGCGGGGT
GCCCCTCTACGACCGGAACCACGTCACAGGGGCCTCGTCCAGCAGCTCGTCCAG
CACGAAGGCCACGCTGTACCGCCGATCCTGAACCGCCGCCCTCCCCGGCCAC
GGACCCCTCCCTGTACAACATGGACATGTTCTACTCTTCAAACATTCCGGCCAC
TGTGAGACCGTACAGGCCCTACATCATTCGAGGAATGGCGCCCCGACGACGCC
CTGCAGCACCGACGTGTGTGACAGCGACTACAGCGCCAGCCGCTGGAAGGCCA
GCAAGTACTACCTGGATTTGAACTCGGACTCAGACCCCTATCCACCCCCACCCA
CGCCCCACAGCCAGTACCTGTCGGCGGAGGACAGCTGCCCGCCCTCGCCCGCCA
CCGAGAGGAGCTACTTCCATCTCTTCCCGCCCCCTCCGTCCCCTGCACGGA
CTCATCC (SEQ ID NO: 2)
```

Figure 5(c)

MEAAPPGPPWPLLLLLLLLLALCGCPAPAAASPLLLFANRRDVRLVDAGGVKLESTIV
VSGLEDAAAVDFQFSKGAVYWTDVSEEAIKQTYLNQTGAAVQNVVISGLVSPDGLAC
DWVGKKLYWTDSETNRIEVANLNGTSRKVLFWQDLDQPRAIALDPAHGYMYWTDW
GETPRIERAGMDGSTRKIIVDSDIYWPNGLTIDLEEQKLYWADAKLSFIHRANLDGSFR
QKVVEGSLTHPFALTLSGDTLYWTDWQTRSIHACNKRTGGKRKEILSALYSPMDIQVLS
QERQPFFHTRCEEDNGGCSHLCLLSPSEPFYTCACPTGVQLQDNGRTCKAGAEEVLLL
ARRTDLRRISLDTPDFTDIVLQVDDIRHAIAIDYDPLEGYVYWTDDEVRAIRRAYLDGS
GAQTLVNTEINDPDGIAVDWVARNLYWTDTGTDRIEVTRLNGTSRKILVSEDLDEPRAI
ALHPVMGLMYWTDWGENPKIECANLDGQERRVLVNASLGWPNGLALDLQEGKLYW
GDAKTDKIEVINVDGTKRRTLLEDKLPHIFGFTLLGDFIYWTDWQRRSIERVHKVKASR
DVIIDQLPDLMGLKAVNVAKVVGTNPCADRNGGCSHLCFFTPHATRCGCPIGLELLSD
MKTCIVPEAFLVFTSRAAIHRISLETNNNDVAIPLTGVKEASALDFDVSNNHIYWTDVSL
KTISRAFMNGSSVEHVVEFGLDYPEGMAVDWMGKNLYWADTGTNRIEVARLDGQFR
QVLVWRDLDNPRSLALDPTKGYIYWTEWGGKPRIVRAFMDGTNCMTLVDKVGRAND
LTIDYADQRLYWTDLDTNMIESSNMLGQERVVIADDLPHPFGLTQYSDYIYWTDWNL
HSIERADKTSGRNRTLIQGHLDFVMDILVFHSSRQDGLNDCMHNNGQCGQLCLAIPGG
HRCGCASHYTLDPSSRNCSPPTTFLLFSQKSAISRMIPDDQHSPDLILPLHGLRNVKAIDY
DPLDKFIYWVDGRQNIKRAKDDGTQPFVLTSLSQGQNPDRQPHDLSIDIYSRTLFWTCE
ATNTINVHRLSGEAMGVVLRGDRDKPRAIVVNAERGYLYFTNMQDRAAKIERAALDG
TEREVLFTTGLIRPVALVVDNTLGKLFWVDADLKRIESCDLSGANRLTLEDANIVQPLG
LTILGKHLYWIDRQQQMIERVEKTTGDKRTRIQGRVAHLTGIHAVEEVSLEEFSAHPCA
RDNGGCSHICIAKGDGTPRCSCPVHLVLLQNLLTCGEPPTCSPDQFACATGEIDCIPGA
WRCDGFPECDDQSDEEGCPVCSAAQFPCARGQCVDLRLRCDGEADCQDRSDEADCD
AICLPNQFRCASGQCVLIKQQCDSFPDCIDGSDELMCEITKPPSDDSPAHSSAIGPVIGIIL
SLFVMGGVYFVCQRVVCQRYAGANGPFPHEYVSGTPHVPLNFIAPGGSQHGPFTGIAC
GKSMMSSVSLMGGRGGVPLYDRNHVTGASSSSSSSTKATLYPPILNPPPSPATDPSLYN
MDMFYSSNIPATVRPYRPYIIRGMAPPTTPCSTDVCDSDYSASRWKASKYYLDLNSDSD
PYPPPPTPHSQYLSAEDSCPPSPATERSYFHLFPPPPSPCTDSS (SEQ ID NO: 3)

Figure 5(d)

```
MEAAPPGPFW PLLLLLLLLL ALCGCPAPAA ASPLLLFANR RDVRLVDAGG     50
VKLESTIVVS GLEDAAAVDF QFSKGAVYWT DVSEEAIKQT YLNQTGAAVQ    100
NVVISGLVSP DGLACDWVGK KLYWIDSEIN RIEVANLNGT SRKVLFWQDL    150
DQPRAIALDP AHGYMYWIDW GETPRIERAG MDGSTRKIIV DSDIYWPNGL    200
TIDLEEQKLY WADAKLSFIH RANLDGSFRQ KVVEGSLTHP FALTLSGDTL    250
YWIDWQTRSI HACNKRTGGK RKEILSALYS PMDIQVLSQE RQPFFHIRCE    300
EDNGGCSHLC LLSPSEPEVT CACPIGVOLQ ENGRICKAGA EEVLLLARRT    350
DLRRISLDTP DFTDIVLQVD DIRHAIAIDY DPLEGYVYWT DDEVRAIRRA    400
YLDGSGAQTL VNTEINDPDG IAVDWVARNL YWIDIGTDRI EVTRLNGTSR    450
KILVSEDLDE PRAIALHPVM GLMYWIDWGE NPKIECANLD GQERRVLVNA    500
SLGWPNGLAL DLQEGKLYWG DAKTDKIEVI NVDGTKRRTL LEDKLPHIFG    550
FTLLGDFTYW TDWQRRSIER VHKVKASRDV IIDQLPDLMG LKAVNVAKVV    600
GTNPCADRNG GCSHLCFFTP HATRGCGPIG LELLSDMKTC IVPEAFLVFT    650
SRAAIHRISL EINNNDVAIP LTGVKEASAL DFDVSNNHIY WIDVSLKTIS    700
RAFMNGSSVE HVVEFGLDYP EGMAVDWMGK NLYWADIGIN RIEVARLDGQ    750
FRQVLWRDL DNPRSLALDP TKGYIYWIEW GGKPRIVRAF MDGINCMILV     800
DKVGRANDLT IDYADQRLYW TDLDTNMIES SNMLGQERVV IADDLPHPFG    850
LTQYSDYIYW TDWNLHSIER ADKTSGRNRT LIQGHLDFVM DILVFHSSRQ    900
DGLNDCMHNN GGCGQLCIAI RGHRQGGAS HYTLDPSSRN CSPPTTFLLF     950
SQKSAISRMI PDDQHSPDLI LPLHGLRNVK AIDYDPLDKF IYWVDGRQNI   1000
KRAKDDGTQP FVLTSLSQGQ NPDRQPHDLS IDIYSRTLEW TCEATNTINV   1050
HRLSGEAMGV VLRGDRDKPR AIVVNAERGY LYFTNMQDRA AKIERAALDG   1100
TEREVLFTTG LIRPVALVVD NTLGKLFWVD ADLKRIESCD LSGANRLTLE   1150
DANIVQPLGL TILGKHLYWI DRQQQMIERV EKTIGDKRTR IQGRVAHLTG   1200
IHAVEEVSLE EFSAHPCARD NGGCSHICIA KGDGTPRCSC PVHLVLLQNL   1250
LLGCPPICS PDQFACAICG EDCIPGAWRC DGEPECDDQS DEEGCPVCSA   1300
AQFPCARGQC VDLRLRCDGE AHCQDRSDEA DCDAICLPNQ FRCASSGCVL   1350
IKQQCSFED CGDCSDEEMC EIIKPPSDDS PAHSSAIGPV IGIILSLFVM   1400
GGVYFVCQRV VCQRYAGANG PFPHEYVSGT PHVPLNFIAP GGSQHGPFIG   1450
IAQGKSMMSS VSLMGGRGGV APLIDRNHVIG ASSSSSSSIK ATLYPPIINP   1500
PPSPATDPSL YNMDMFYSSN IPATVRPYRPSYIIRGMAPPT TPCSIDVCDS   1550
DYSASRWKAS KYYLDLNSDS DPYPPPPTPH SQYLSAEDSC PPSPATERSY   1600
FHLFPPPPSP CIDSS  (SEQ ID NO: 3)                        1615
```

Figure 5(e)

```
CPAPAAASPLLLFANRRDVRLVDAGGVKLESTIVVSGLEDAAAVDFQFSKGAVYWTD
VSEEAIKQTYLNQTGAAVQNVVISGLVSPDGLACDWVGKKLYWTDSETNRIEVANLN
GTSRKVLFWQDLDQPRAIALDPAHGYMYWTDWGETPRIERAGMDGSTRKIIVDSDIY
WPNGLTIDLEEQKLYWADAKLSFIHRANLDGSFRQKVVEGSLTHPFALTLSGDTLYWT
DWQTRSIHACNKRTGGKRKEILSALYSPMDIQVLSQERQPFFHTRCEEDNGGCSHLCLL
SPSEPFYTCACPTGVQLQDNGRTCKAGAEEVLLLARRTDLRRISLDTPDFTDIVLQVDDI
RHAIAIDYDPLEGYVYWTDDEVRAIRRAYLDGSGAQTLVNTEINDPDGIAVDWVARNL
YWTDTGTDRIEVTRLNGTSRKILVSEDLDEPRAIALHPVMGLMYWTDWGENPKIECAN
LDGQERRVLVNASLGWPNGLALDLQEGKLYWGDAKTDKIEVINVDGTKRRTLLEDKL
PHIFGFTLLGDFIYWTDWQRRSIERVHKVKASRDVIIDQLPDLMGLKAVNVAKVVGTN
PCADRNGGCSHLCFFTPHATRCGCPIGLELLSDMKTCIVPEAFLVFTSRAAIHRISLETN
NNDVAIPLTGVKEASALDFDVSNNHIYWTDVSLKTISRAFMNGSSVEHVVEFGLDYPE
GMAVDWMGKNLYWADTGTNRIEVARLDGQFRQVLVWRDLDNPRSLALDPTKGYIY
WTEWGGKPRIVRAFMDGTNCMTLVDKVGRANDLTIDYADQRLYWTDLDTNMIESSN
MLGQERVVIADDLPHPFGLTQYSDYIYWTDWNLHSIERADKTSGRNRTLIQGHLDFVM
DILVFHSSRQDGLNDCMHNNGQCGQLCLAIPGGHRCGCASHYTLDPSSRNCSPPTTFLL
FSQKSAISRMIPDDQHSPDLILPLHGLRNVKAIDYDPLDKFIYWVDGRQNIKRAKDDGT
QPFVLTSLSQGQNPDRQPHDLSIDIYSRTLFWTCEATNTINVHRLSGEAMGVVLRGDRD
KPRAIVVNAERGYLYFTNMQDRAAKIERAALDGTEREVLFTTGLIRPVALVVDNTLGK
LFWVDADLKRIESCDLSGANRLTLEDANIVQPLGLTILGKHLYWIDRQQQMIERVEKTT
GDKRTRIQGRVAHLTGIHAVEEVSLEEFSAHPCARDNGGCSHICIAKGDGTPRCSCPVH
LVLLQNLLTCGEPPTCSPDQFACATGEIDCIPGAWRCDGFPECDDQSDEEGCPVCSAAQ
FPCARGQCVDLRLRCDGEADCQDRSDEADCDAICLPNQFRCASGQCVLIKQQCDSFPD
CIDGSDELMCEITKPPSDDSPAHSSAIGPVIGIILSLFVMGGVYFVCQRVVCQRYAGANG
PFPHEYVSGTPHVPLNFIAPGGSQHGPFTGIACGKSMMSSVSLMGGRGGVPLYDRNHV
TGASSSSSSSTKATLYPPILNPPPSPATDPSLYNMDMFYSSNIPATVRPYRPYIIRGMAPPT
TPCSTDVCDSDYSASRWKASKYYLDLNSDSPYPPPPTPHSQYLSAEDSCPPSPATERSY
FHLFPPPPSPCTDSS (SEQ ID NO: 4)
```

Figure 5(f)

```
Human   1 .................ATGGAGCCCGAGTGAGCGCGGCGCGGGCCCGT  32
                           |||||||||||||||||||||    ||| |
Mouse  51 ACCGCCGCCGCGCGCGCCATGGAGCCCGAGTGAGCGCG....CGGCGCTC  96

33 CCGGCCGCCGGACAACATGGAGGCAGCGCCGCCCGGGCCGCCGTGGCCGC  82
          ||||||||||||| |||||||  | |||||| || || | ||    ||||
       97 CCGGCCGCCGGACGACATGGAAACGGCGCCGACCCGGGCCCC...TCCGC 143

83 TGCTGCTGCTGCTGCTGCTGCTGCTGGCGCTGTGCGGCTGCCCGGCCCCC 132
          || || || ||  ||||||||||||  ||||| | || ||   || ||||
      144 CGCCGCCGCCGCCGCTGCTGCTGCTGGTGCTGTACTGCAGCTTGGTCCCC 193

133 GCCGCGGCCCTCGCCGCTCCTGCTATTTGCCAACCGCCGGACGTACGGCT 182
          |||||||||||| |||||||||| | |||||||||||||||| || |||||
      194 GCCGCGGCCCTCACCGCTCCTGTTGTTTGCCAACCGCCGGGATGTGCGGCT 243

183 GGTGGACGCCGGCGGAGTCAAGCTGGAGTCCACCATCGTGGTCAGCGGCC 232
          ||||| |||||||||||  |||||||||||||||||||||| |||| ||||
      244 AGTGGATGCCGGCGGAGTGAAGCTGGAGTCCACCATTGTGGCCAGTGGCC 293

233 TGGAGGATGCCGCCGCAGTGGACTTCCAGTTTTCCAAGGGAGCCGTGTAC 282
          ||||||||| || || || |||||||||||| || |||||| |||||||
      294 TGGAGGATGCAGCTGCTGTAGACTTCCAGTTCTCCAAGGGTGCTGTGTAC 343

283 TGGACAGACGTGAGCGAGGAGGCCATCAAGCAGACCTACCTGAACCAGAC 332
          ||||||||| |||||||||||||||||||||| ||||||||||||||||||
      344 TGGACAGATGTGAGCGAGGAGGCCATCAAACAGACCTACCTGAACCAGAC 393

333 GGGGCCGCCGTGCAGAACGTGGTCATCTCCGGCCTGGTCTCTCCCGACG 382
          || |  || |  |||||| | ||||||| ||||| || || || || |
      394 TGGAGGTGCTGCACAGAACATTGTCATCTCGGGCCTCGTGTCACCTGATG 443

383 GCCTCGCCTGCGACTGGGTGGGCAAGAAGCTGTACTGGACGGACTCAGAG 432 (SEQ ID NO: 5)
          ||||  |||| |||||||| ||||||||||||||||||||||||||| |||
      444 GCCTGGCCTGTGACTGGGTTGGCAAGAAGCTGTACTGGACGGACTCCGAG 493 (SEQ ID NO: 6)
```

Figure 5(g)

```
Human   1 MEAAPPGPFWPLLLLLLLLLALCGCPAPAAASPLLLFANRRDVRLVDAGG 50
          || ||  | |    ||||. |    |||||||||||||||||||||||
Mouse   1 METAPIRAPPPPPPPLLLLVLYCSL.VPAAASPLLLFANRRDVRLVDAGG 49

51 VKLESTIVVSGLEDAAAVDFQFSKGAVYWIDVSEEAIKQTYLNQTGAAVQ 100
          ||||||||  |||||||||||||||||||||||||||||||||||  | |
       50 VKLESTIVASGLEDAAAVDFQFSKGAVYWIDVSEEAIKQTYLNQTGGAAQ 99

101 NVVISGLVSPDGLACDWVGKKLYWIDSETNRIEVANLNGTSRKVLFWQDL 150
          |:|||||||||||||||||||||||||||||||||||||||||||||||
      100 NIVISGLVSPDGLACDWVGKKLYWIDSETNRIEVANLNGTSRKVLFWQDL 149

151 DQPRAIALDPAHGYMYWIDWGETPRIERAGMDGSTRKIIVDSDIYWPNGL 200
          |||||||||||||||||||||||| |||||||||||||||||||||||||
      150 DQPRAIALDPAHGYMYWIDWGEAPRIERAGMDGSTRKIIVDSDIYWPNGL 199

201 TIDLEEQKLYWADAKLSFIHRANLDGSFRQKVVEGSLTHPFALTLSGDIL 250
          ||||||||||||||||||||||||||||||||||||||||||||||||||
      200 TIDLEEQKLYWADAKLSFIHRANLDGSFRQKVVEGSLTHPFALTLSGDIL 249

251 YWIDWQIRSIHACNKRTGGKRKEILSALYSPMDIQVLSQERQPFFHTIRCE 300
          ||||||||||||| || .||||||||||||||||||||||| ||| ||
      250 YWIDWQIRSIHACNKWIGEQRKEILSALYSPMDIQVLSQERQPPFHTIPCE 299

301 EDNGGCSHLCLLSPSEPFYTCACPTGVQLQDNGRTCKAGAEEVLLLARRT 350
          ||||||||||||| ||||.|||||||||||||:||| ||||||||||||
      300 EDNGGCSHLCLLSPREPFYSCACPTGVQLQDNGKTCKTGAEEVLLLARRT 349

351 DLRRISLDTPDFTDIVLQVDDIRHAIAIDYDPLEGYVYWIDDEVRAIRRA 400
          |||||||||||||||||||| ||||||||||||||||||||||||||||
      350 DLRRISLDTPDFTDIVLQVGDIRHAIAIDYDPLEGYVYWIDDEVRAIRRA 399

401 YLDGSGAQTLVNTEINDPDGIAVDWARNLYWIDTGIDRIEVIRLNGTSR 450
          ||||||||||||||||||||||||||||||||||||||||||||||||
      400 YLDGSGAQTLVNTEINDPDGIAVDWARNLYWIDTGIDRIEVIRLNGTSR 449

451 KILVSEDLDEPRAIALHPVMGLMYWIDWGENPKIECANLDGQERRVLVNA 500
          ||||||||||||| ||||||||||||||||||||||||||||.:| ||||
      450 KILVSEDLDEPRAIVLHPVMGLMYWIDWGENPKIECANLDGRDRHVLVNT 499

501 SLGWPNGLALDLQEGKLYWGDAKTDKIEVINVDGTKRRTLLEDKLPHIFG 550 (SEQ ID NO: 7)
          |||||||||||||||||||||||||||||||:||
      500 SLGWPNGLALDLQEGKLYWGDAKTDKIEVINIDG................ 533 (SEQ ID NO: 8)
```

Figure 6(a)

EGF precursor motifs in LRP-5 isoform 1

| | | | |
|---|---|---|---|
| Isoform 1 | 268 | CEEINGGCSHLCLLSPSEPFYTCACPTGVQLQDNGRTC 345 | (SEQ ID NO: 9) |
| | | C  NGGCS LCLLSP  -  CACPT  L  GRTC | |
| LRP-EGF repeat | | CKVNNGGCSNLCLLSPGGG-HKCACPTNFYLGSDGRTC | (SEQ ID NO: 10) |

| | | | |
|---|---|---|---|
| Isoform 1 | 570 | GINPCADRNGGCSHLCFFTPHATRCGCPIGLELLSDMKTCI 650 | (SEQ ID NO: 11) |
| | | GIN C  NGGCS LC  TP    C C     L D  TC | |
| LRP-EGF repeat | | GINKCRVNNGGCSSLCLATPGSRQCACAEDQVLDADGVTCL | (SEQ ID NO: 12) |

| | | | |
|---|---|---|---|
| Isoform 1 | 871 | GLNDCMHNNGQCGQLCLAIPGGHRCGCASHYTLDPSSRNC 950 | (SEQ ID NO: 13) |
| | | G N C  NNG C  LCLA PG     C CA    LD    C | |
| LRP-EGF repeat | | GINKCRVNNGGCSSLCLATPGSRQCACAEDQVLDADGVTC | (SEQ ID NO: 14) |

| | | | |
|---|---|---|---|
| Isoform 1 | 1184 | HPCARDNGGCSHICIAKGDGTPRCSCPVHLVLLQNLLTC 1262 | (SEQ ID NO: 15) |
| | | HPC     NGGCS  C       G    C CP    L      TC | |
| LRP-EGF repeat | | HPCKVNNGGCSNLCLLSPGGGHKCACPTNFYLGSDGRTC | (SEQ ID NO: 16) |

LDL-receptor motifs in LRP-5 isoform 1

| | | | |
|---|---|---|---|
| Isoform 1 | 1226 | PTCSPDQFACAIGEIDCIPGAWRCDGFPECDDQSDEEGC 1304 | (SEQ ID NO: 17) |
| | | P C  DQF  C   G --CIP WRCD    C D SDEE C | |
| LRP-LDL repeat | | PRCDMDQFQCKSGH--CIPLRWRCDADADCMDGSDEEAC | (SEQ ID NO: 18) |

| | | | |
|---|---|---|---|
| Isoform 1 | 1267 | CSAAQFPCARGQCVDLRLRCDGEADCQDRSDEADCD 1342 | (SEQ ID NO: 19) |
| | | C    QF C  G C      CDG  DCQD SDEA CD | |
| LRP-LDL repeat | | CRPGQFQCSTGICTNPAFICDGDNDCQDNSDEANCD | (SEQ ID NO: 20) |

| | | | |
|---|---|---|---|
| Isoform 1 | 1305 | CLPNQFRCASGQCVLIKQQCDSFPDCIDGSDELMC 1379 | (SEQ ID NO: 21) |
| | | C   QF C SG C       CD   DC DGSDE  C | |
| LRP-LDL repeat | | CDMDQFQCKSGHCIPLRWRCDADADCMDGSDEEAC 37 | (SEQ ID NO: 22) |

Figure 6(b)
Motif Organization of the LDL- receptor and LRP-5
LDL -receptor
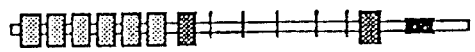
LRP-5
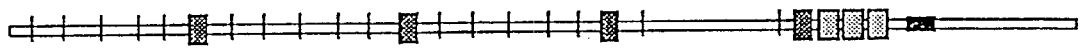
- EGF-precursor B.2 motif
- LDL-receptor motif
- YWTD motif
- Transmembrane region

Figure 11(a)

```
GAGAGGACACCGCATTCTTCTTCTCCAGAGGATGCAGCAGCAAGGCGCCATC
TTGAAACCAGAGACCAAACCAACCAGCAWTTTTGTCTTGAACTTCCCAGCC
TCCACAACTAATATAAACCCCATGAGGGCAGAGGCGTTCAGCCTGACTCCAG
CCTGGCAAAGCTGTCACAAATCTGGAGGAACACACGTTCACGGGCACTCA
GTTCTGTGAGCCTCGCCGCTCCTGCTATTTGCCAACCGCCGGGACGTACGGCTG
GTGGACGCCGGCGGAGTCAAGCTGGAGTCCACCATCGTGGTCAGCGGCCTGGA
GGATGCGGCCGCAGTGGACTTCCAGTTTTCCAAGGGAGCCGTGTACTGGACAG
ACGTGAGCGAGGAGGCCATCAAGCAGACCTACCTGAACCAGACGGGGGCCGC
CGTGCAGAACGTGGTCATCTCCGGCCTGGTCTCTCCCGACGGCCTCGCCTGCGAC
TGGGTGGGCAAGAAGCTGTACTGGACGGACTCAGAGACCAACCGCATCGAGG
TGGCCAACCTCAATGGCACATCCCGGAAGGTGCTCTTCTGGCAGGACCTTGAC
CAGCCGAGGGCCATCGCCTTGGACCCCGCTCACGGGTACATGTACTGGACAGA
CTGGGGTGAGACGCCCCGGATTGAGCGGGCAGGGATGGATGGCAGCACCCGGA
AGATCATTGTGGACTCGGACATTTACTGGCCCAATGGACTGACCATCGACCT
GGAGGAGCAGAAGCTCTACTGGGCTGACGCCAAGCTCAGCTTCATCCACCGTG
CCAACCTGGACGGCTCGTTCCGGCAGAAGGTGGTGGAGGGCAGCCTGACGCAC
CCCTTCGCCCTGACGCTCTCCGGGGACACTCTGTACTGGACAGACTGGCAGACC
CGCTCCATCCATGCCTGCAACAAGCGCACTGGGGGGAAGAGGAAGGAGATCC
TGAGTGCCCTCTACTCACCCATGGACATCCAGGTGCTGAGCCAGGAGCGGCAG
CCTTTCTTCCACACTCGCTGTGAGGAGGACAATGGCGGCTGCTCCCACCTGTGC
CTGCTGTCCCCAAGCGAGCCTTTCTACACATGCGCCTGCCCCACGGGTGTGCAG
CTGCAGGACAACGGCAGGACGTGTAAGGCAGGAGCCGAGGAGGTGCTGCTGC
TGGCCCGGCGGACGGACCTACGGAGGATCTCGCTGGACACGCCGGACTTTACCG
ACATCGTGCTGCAGGTGGACGACATCCGGCACGCCATTGCCATCGACTACGAC
CCGCTAGAGGGCTATGTCTACTGGACAGATGACGAGGTGCGGGCCATCCGCAG
GGCGTACCTGGACGGGTCTGGGGCGCAGACGCTGGTCAACACCGAGATCAACG
ACCCCGATGGCATCGCGGTCGACTGGGTGGCCCGAAACCTCTACTGGACCGAC
ACGGGCACGGACCGCATCGAGGTGACGCGCCTCAACGGCACCTCCCGCAAGAT
CCTGGTGTCGGAGGACCTGGACGAGCCCCGAGCCATCGCACTGCACCCCGTGAT
GGGCCTCATGTACTGGACAGACTGGGGAGAGAACCCTAAAATCGAGTGTGCC
AACTTGGATGGGCAGGAGCGGCGTGTGCTGGTCAATGCCTCCCTCGGGTGGCCC
AACGGCCTGGCCCTGGACCTGCAGGAGGGGAAGCTCTACTGGGGAGACGCCA
AGACAGACAAGATCGAGGTGATCAATGTTGATGGGACGAAGAGGCGGACC
CTCCTGGAGGACAAGCTCCCGCACATTTTCGGGTTCACGCTGCTGGGGACTTC
ATCTACTGGACTGACTGGCAGCGCCGCAGCATCGAGCGGGTGCACAAGGTCA
AGGCCAGCCGGGACGTCATCATTGACCAGCTGCCCGACCTGATGGGCTCAAA
GCTGTGAATGTGGCCAAGGTCGTCGGAACCAACCCGTGTGCGGACAGGAACG
GGGGGTGCAGCCACCTGTGCTTCTTCACACCCCACGCAACCCGGTGTGGCTGCCC
CATCGGCCTGGAGCTGCTGAGTGACATGAAGACCTGCATCGTGCCTGAGGCCT
```

Figure 11(a-1)

```
TCTTGGTCTTCACCAGCAGAGCCGCCATCCACAGGATCTCCCTCGAGACCAAT
AACAACGACGTGGCCATCCCGCTCACGGGCGTCAAGGAGGCCTCAGCCCTGGA
CTTTGATGTGTCCAACAACCACATCTACTGGACAGACGTCAGCCTGAAGACC
ATCAGCCGCGCCTTCATGAACGGGAGCTCGGTGGAGCACGTGGTGGAGTTTGG
CCTTGACTACCCCGAGGGCATGGCCGTTGACTGGATGGGCAAGAACCTCTACT
GGGCCGACACTGGGACCAACAGAATCGAAGTGGCGCGGCTGGACGGGCAGTT
CCGGCAAGTCCTCGTGTGGAGGGACTTGGACAACCCGAGGTCGCTGGCCCTGG
ATCCCACCAAGGGCTACATCTACTGGACCGAGTGGGGCGGCAAGCCGAGGAT
CGTGCGGGCCTTCATGGACGGGACCAACTGCATGACGCTGGTGGACAAGGTGG
GCCGGGCCAACGACCTCACCATTGACTACGCTGACCAGCGCCTCTACTGGACCG
ACCTGGACACCAACATGATCGAGTCGTCCAACATGCTGGGTCAGGAGCGGGT
CGTGATTGCCGACGATCTCCCGCACCCGTTCGGTCTGACGCAGTACAGCGATT
ATATCTACTGGACAGACTGGAATCTGCACAGCATTGAGCGGGCCGACAAGA
CTAGCGGCCGGAACCGCACCCTCATCCAGGGCCACCTGGACTTCGTGATGGAC
ATCCTGGTGTTCCACTCCTCCCGCCAGGATGGCCTCAATGACTGTATGCACAA
CAACGGGCAGTGTGGGCAGCTGTGCCTTGCCATCCCCGGCGGCCACCGCTGCGGC
TGCGCCTCACACTACACCCTGGACCCCAGCAGCCGCAACTGCAGCCCGCCCACC
ACCTTCTTGCTGTTCAGCCAGAAATCTGCCATCAGTCGGATGATCCCGGACGA
CCAGCACAGCCCGGATCTCATCCTGCCCCTGCATGGACTGAGGAACGTCAAAG
CCATCGACTATGACCCACTGGACAAGTTCATCTACTGGGTGGATGGGCGCCA
GAACATCAAGCGAGCCAAGGACGACGGGACCCAGCCCTTTGTTTTGACCTCT
CTGAGCCAAGGCCAAAACCCAGACAGGCAGCCCCACGACCTCAGCATCGACA
TCTACAGCCGGACACTGTTCTGGACGTGCGAGGCCACCAATACCATCAACGTC
CACAGGCTGAGCGGGGAAGCCATGGGGGTGGTGCTGCGTGGGGACCGCGACAA
GCCCAGGGCCATCGTCGTCAACGCGGAGCGAGGGTACCTGTACTTCACCAACA
TGCAGGACCGGGCAGCCAAGATCGAACGCGCAGCCCTGGACGGCACCGAGCGC
GAGGTCCTCTTCACCACCGGCCTCATCCGCCCTGTGGCCCTGGTGGTAGACAAC
ACACTGGGCAAGCTGTTCTGGGTGGACGCGGACCTGAAGCGCATTGAGAGCT
GTGACCTGTCAGGGGCCAACCGCCTGACCCTGGAGGACGCCAACATCGTGCAG
CCTCTGGGCCTGACCATCCTTGGCAAGCATCTCTACTGGATCGACCGCCAGCAG
CAGATGATCGAGCGTGTGGAGAAGACCACCGGGGACAAGCGGACTCGCATCC
AGGGCCGTGTCGCCCACCTCACTGGCATCCATGCAGTGGAGGAAGTCAGCCTG
GAGGAGTTCTCAGCCCACCCATGTGCCCGTGACAATGGTGGCTGCTCCCACAT
CTGTATTGCCAAGGGTGATGGGACACCACGGTGCTCATGCCCAGTCCACCTCG
TGCTCCTGCAGAACCTGCTGACCTGTGGAGAGCCGCCCACCTGCTCCCCGGACC
AGTTTGCATGTGCCACAGGGGAGATCGACTGTATCCCCGGGGCCTGGCGCTGT
GACGGCTTTCCCGAGTGCGATGACCAGAGCGACGAGGAGGGCTGCCCCGTGTG
CTCCGCCGCCCAGTTCCCCTGCGCGCGGGGTCAGTGTGTGGACCTGCGCCTGCGCT
GCGACGGCGAGGCAGACTGTCAGGACCGCTCAGACGAGGCGGACTGTGACGCC
ATCTGCCTGCCCAACCAGTTCCGGTGTGCGAGCGGCCAGTGTGTCCTCATCAA
ACAGCAGTGCGACTCCTTCCCCGACTGTATCGACGGCTCCGACGAGCTCATGT
```

Figure 11(a-2)

```
GTGAAATCACCAAGCCGCCCTCAGACGACAGCCCGGCCCACAGCAGTGCCATC
GGGCCCGTCATTGGCATCATCCTCTCTCTCTTCGTCATGGGTGGTGTCTATTTT
GTGTGCCAGCGCGTGGTGTGCCAGCGCTATGCGGGGGCCAACGGGCCCTTCCCGC
ACGAGTATGTCAGCGGGACCCCGCACGTGCCCCTCAATTTCATAGCCCGGGCG
GTTCCCAGCATGGCCCCTTCACAGGCATCGCATGCGGAAAGTCCATGATGAGC
TCCGTGAGCCTGATGGGGGGCCGGGGCGGGGTGCCCCTCTACGACGGAACCAC
GTCACAGGGGCCTCGTCCAGCAGCTCGTCCAGCACGAAGGCCACGCTGTACCCG
CCGATCCTGAACCCGCCGCCCTCCCCGGCCACGGACCCCTCCCTGTACAACATGG
ACATGTTCTACTCTTCAAACATTCCGGCCACTGTGAGACCGTACAGGCCCTAC
ATCATTCGAGGAATGGCGCCCCCGACGACGCCCTGCAGCACCGACGTGTGTGA
CAGCGACTACAGCGCCAGCCGCTGGAAGGCCAGCAAGTACTACCTGGATTTG
AACTCGGACTCAGACCCCTATCCACCCCCACCCACGCCCCACAGCCAGTACCTG
TCGGCGGAGGACAGCTGCCCGCCCTCGCCCGCCACCGAGAGGAGCTACTTCCAT
CTCTTCCCGCCCCCTCCGTCCCCCTGCACGGACTCATCCTGACCTCGGCCGGGCCA
CTCTGGCTTCTCTGTGCCCCTGTAAATAGTTTTAAATATGAACAAAGAAAA
AAATATATTTTATGATTTAAAAAATAAATATAATTGGGATTTTAAAA
ACATGAGAAATGTGAACTGTGATGGGGTGGGCAGGGCTGGGAGAACTTTGT
ACAGTGGAACAAATATTTATAAACTTAATTT (SEQ ID NO: 23)
```

Figure 11(b)

```
ATGTACTGGACAGACTGGGGTGAGACGCCCCGGATTGAGCGGGCAGGGATGG
ATGGCAGCACCCGGAAGATCATTGTGGACTCGGACATTTACTGGCCCAATGG
ACTGACCATCGACCTGGAGGAGCAGAAGCTCTACTGGGCTGACGCCAAGCTC
AGCTTCATCCACCGTGCCAACCTGGACGGCTCGTTCCGGCAGAAGGTGGTGGA
GGGCAGCCTGACGCACCCCTTCGCCCTGACGCTCTCCGGGGACACTCTGTACTGG
ACAGACTGGCAGACCCGCTCCATCCATGCCTGCAACAAGCGCACTGGGGGA
AGAGGAAGGAGATCCTGAGTGCCCTCTACTCACCCATGGACATCCAGGTGCT
GAGCCAGGAGCGGCAGCCTTTCTTCCACACTCGCTGTGAGGAGGACAATGGCG
GCTGCTCCCACCTGTGCCTGCTGTCCCCAAGCGAGCCTTTCTACACATGCGCCTG
CCCCACGGGTGTGCAGCTGCAGGACAACGGCAGGACGTGTAAGGCAGGAGCC
GAGGAGGTGCTGCTGCTGGCCCGGCGGACGGACCTACGGAGGATCTCGCTGGA
CACGCCGGACTTTACCGACATCGTGCTGCAGGTGGACGACATCCGGCACGCCA
TTGCCATCGACTACGACCCGCTAGAGGGCTATGTCTACTGGACAGATGACGA
GGTGCGGGCCATCCGCAGGGCGTACCTGGACGGGTCTGGGGCGCAGACGCTGGT
CAACACCGAGATCAACGACCCCGATGGCATCGCGGTCGACTGGGTGGCCCGAA
ACCTCTACTGGACCGACACGGGCACGGACCGCATCGAGGTGACGCGCCTCAAC
GGCACCTCCCGCAAGATCCTGGTGTCGGAGGACCTGGACGAGCCCCGAGCCATC
GCACTGCACCCCGTGATGGGCCTCATGTACTGGACAGACTGGGGAGAGAACCC
TAAAATCGAGTGTGCCAACTTGGATGGGCAGGAGCGGCGTGTGCTGGTCAAT
GCCTCCCTCGGGTGGCCCAACGGCCTGGCCCTGGACCTGCAGGAGGGGAAGCTC
TACTGGGGAGACGCCAAGACAGACAAGATCGAGGTGATCAATGTTGATGGG
ACGAAGAGGCGGACCCTCCTGGAGGACAAGCTCCCGCACATTTTCGGGTTCAC
GCTGCTGGGGGACTTCATCTACTGGACTGACTGGCAGCGCCGCAGCATCGAGC
GGGTGCACAAGGTCAAGGCCAGCCGGGACGTCATCATTGACCAGCTGCCCGAC
CTGATGGGGCTCAAAGCTGTGAATGTGGCCAAGGTCGTCGGAACCAACCCGT
GTGCGGACAGGAACGGGGGGTGCAGCCACCTGTGCTTCTTCACACCCCACGCA
ACCCGGTGTGGCTGCCCCATCGGCCTGGAGCTGCTGAGTGACATGAAGACCTG
CATCGTGCCTGAGGCCTTCTTGGTCTTCACCAGCAGAGCCGCCATCCACAGGA
TCTCCCTCGAGACCAATAACAACGACGTGGCCATCCCGCTCACGGGCGTCAAG
GAGGCCTCAGCCCTGGACTTTGATGTGTCCAACAACCACATCTACTGGACAG
ACGTCAGCCTGAAGACCATCAGCCGCGCCTTCATGAACGGGAGCTCGGTGGAG
CACGTGGTGGAGTTTGGCCTTGACTACCCCGAGGGCATGGCCGTTGACTGGAT
GGGCAAGAACCTCTACTGGGCCGACACTGGGACCAACAGAATCGAAGTGGCG
CGGCTGGACGGGCAGTTCCGGCAAGTCCTCGTGTGGAGGGACTTGGACAACCC
GAGGTCGCTGGCCCTGGATCCCACCAAGGGCTACATCTACTGGACCGAGTGGG
GCGGCAAGCCGAGGATCGTGCGGGCCTTCATGGACGGGACCAACTGCATGACG
CTGGTGGACAAGGTGGGCCGGGCCAACGACCTCACCATTGACTACGCTGACCA
GCGCCTCTACTGGACCGACCTGGACACCAACATGATCGAGTCGTCCAACATGC
TGGGTCAGGAGCGGGTCGTGATTGCCGACGATCTCCCGCACCCGTTCGGTCTGA
```

Figure 11(b-1)

```
CGCAGTACAGCGATTATATCTACTGGACAGACTGGAATCTGCACAGCATTG
AGCGGGCCGACAAGACTAGCGGCCGGAACCGCACCCTCATCCAGGGCCACCTG
GACTTCGTGATGGACATCCTGGTGTTCCACTCCTCCCGCCAGGATGGCCTCAAT
GACTGTATGCACAACAACGGGCAGTGTGGGCAGCTGTGCCTTGCCATCCCCGG
CGGCCACCGCTGCGGCTGCGCCTCACACTACACCCTGGACCCCAGCAGCCGCAA
CTGCAGCCCGCCCACCACCTTCTTGCTGTTCAGCCAGAAATCTGCCATCAGTCG
GATGATCCCGGACGACCAGCACAGCCCGGATCTCATCCTGCCCCTGCATGGAC
TGAGGAACGTCAAAGCCATCGACTATGACCCACTGGACAAGTTCATCTACT
GGGTGGATGGGCGCCAGAACATCAAGCGAGCCAAGGACGACGGGACCCAGCC
CTTTGTTTTGACCTCTCTGAGCCAAGGCCAAAACCCAGACAGGCAGCCCCACG
ACCTCAGCATCGACATCTACAGCCGGACACTGTTCTGGACGTGCGAGGCCACC
AATACCATCAACGTCCACAGGCTGAGCGGGGAAGCCATGGGGGTGGTGCTGC
GTGGGGACCGCGACAAGCCCAGGGCCATCGTCGTCAACGCGGAGCGAGGGTAC
CTGTACTTCACCAACATGCAGGACCGGGCAGCCAAGATCGAACGCGCAGCCC
TGGACGGCACCGAGCGCGAGGTCCTCTTCACCACCGGCCTCATCCGCCCTGTGGC
CCTGGTGGTAGACAACACACTGGGCAAGCTGTTCTGGGTGGACGCGGACCTG
AAGCGCATTGAGAGCTGTGACCTGTCAGGGGCCAACCGCCTGACCCTGGAGG
ACGCCAACATCGTGCAGCCTCTGGGCCTGACCATCCTTGGCAAGCATCTCTAC
TGGATCGACCGCCAGCAGCAGATGATCGAGCGTGTGGAGAAGACCACCGGGG
ACAAGCGGACTCGCATCCAGGGCCGTGTCGCCCACCTCACTGGCATCCATGCA
GTGGAGGAAGTCAGCCTGGAGGAGTTCTCAGCCCACCCATGTGCCCGTGACA
ATGGTGGCTGCTCCCACATCTGTATTGCCAAGGGTGATGGGACACCACGGTGC
TCATGCCCAGTCCACCTCGTGCTCCTGCAGAACCTGCTGACCTGTGGAGAGCCG
CCCACCTGCTCCCCGGACCAGTTTGCATGTGCCACAGGGGAGATCGACTGTAT
CCCCGGGGCCTGGCGCTGTGACGGCTTTCCCGAGTGCGATGACCAGAGCGACGA
GGAGGGCTGCCCCGTGTGCTCCGCCGCCCAGTTCCCCTGCGCGCGGGGTCAGTGT
GTGGACCTGCGCCTGCGCTGCGACGGCGAGGCAGACTGTCAGGACCGCTCAGAC
GAGGCGGACTGTGACGCCATCTGCCTGCCCAACCAGTTCCGGTGTGCGAGCGGC
CAGTGTGTCCTCATCAAACAGCAGTGCGACTCCTTCCCCGACTGTATCGACGG
CTCCGACGAGCTCATGTGTGAAATCACCAAGCCGCCCTCAGACGACAGCCCGG
CCCACAGCAGTGCCATCGGGCCCGTCATTGGCATCATCCTCTCTCTCTTCGTCA
TGGGTGGTGTCTATTTTGTGTGCCAGCGCGTGGTGTGCCAGCGCTATGCGGGGG
CCAACGGGCCCTTCCCGCACGAGTATGTCAGCGGGACCCCGCACGTGCCCCTCA
ATTTCATAGCCCCGGGCGGTTCCCAGCATGGCCCCTTCACAGGCATCGCATGCG
GAAAGTCCATGATGAGCTCCGTGAGCCTGATGGGGGCCGGGCGGGGTGCCC
CTCTACGACCGGAACCACGTCACAGGGCCTCGTCCAGCAGCTCGTCCAGCACG
AAGGCCACGCTGTACCCGCCGATCCTGAACCCGCCGCCCTCCCCGGCCACGGACC
CCTCCCTGTACAACATGGACATGTTCTACTCTTCAAACATTCCGGCCACTGTG
AGACCGTACAGGCCCTACATCATTCGAGGAATGGCGCCCCGACGACGCCCTG
CAGCACCGACGTGTGTGACAGCGACTACAGCGCCAGCCGCTGGAAGGCCAGCA
```

Figure 11(b-2)

AGTACTACCTGGATTTGAACTCGGACTCAGACCCCTATCCACCCCCACCCACG
CCCCACAGCCAGTACCTGTCGGCGGAGGACAGCTGCCCGCCCTCGCCCGCCACCG
AGAGGAGCTACTTCCATCTCTTCCCGCCCCCTCCGTCCCCCTGCACGGACTCATC
C (SEQ ID NO: 24)

Figure 11(c)

```
MYWTDWGETPRIERAGMDGSTRKIIVDSDIYWPNGLTIDLEEQKLYWADAK
LSFIHRANLDGSFRQKVVEGSLTHPFALTLSGDTLYWTDWQTRSIHACNKRT
GGKRKEILSALYSPMDIQVLSQERQPFFHTRCEEDNGGCSHLCLLSPSEPFYTCA
CPTGVQLQDNGRTCKAGAEEVLLLARRTDLRRISLDTPDFTDIVLQVDDIRHA
IAIDYDPLEGYVYWTDDEVRAIRRAYLDGSGAQTLVNTEINDPDGIAVDWV
ARNLYWTDTGTDRIEVTRLNGTSRKILVSEDLDEPRAIALHPVMGLMYWTD
WGENPKIECANLDGQERRVLVNASLGWPNGLALDLQEGKLYWGDAKTDKIE
VINVDGTKRRTLLEDKLPHIFGFTLLGDFTYWTDWQRRSIERVHKVKASRDVI
IDQLPDLMGLKAVNVAKVVGTNPCADRNGGCSHLCFFTPHATRCGCPIGLEL
LSDMKTCIVPEAFLVFTSRAAIHRISLETNNNDVAIPLTGVKEASALDFDVS
NNHIYWTDVSLKTISRAFMNGSSVEHVVEFGLDYPEGMAVDWMGKNLYW
ADTGTNRIEVARLDGQFRQVLVWRDLDNPRSLALDPTKGYIYWTEWGGKPR
IVRAFMDGTNCMTLVDKVGRANDLTIDYADQRLYWTDLDTNMIESSNMLG
QERVVIADDLPHPFGLTQYSDYIYWTDWNLHSIERADKTSGRNRTLIQGHLDF
VMDILVFHSSRQDGLNDCMHNNGQCGQLCLAIPGGHRCGCASHYTLDPSSRNC
SPPTTFLLFSQKSAISRMIPDDQHSPDLILPLHGLRNVKAIDYDPLDKFTYWV
DGRQNIKRAKDDGTQPFVLTSLSQGQNPDRQPHDLSIDIYSRTLFWTCEATNTI
NVHRLSGEAMGVVLRGDRDKPRAIVVNAERGYLYFTNMQDRAAKIERAAL
DGTEREVLFTTGLIRPVALVVDNTLGKLFWVDADLKRIESCDLSGANRLTLE
DANTVQPLGLTILGKHLYWIDRQQQMIERVEKTTGDKRTRIQGRVAHLTGIH
AVEEVSLEEFSAHPCARDNGGCSHICIAKGDGTPRCSCPVHLVLLQNLLTCGE
PPTCSPDQFACATGEIDCIPGAWRCDGFPECDDQSDEEGCPVCSAAQFPCARGQ
CVDLRLRCDGEADCQDRSDEADCDAICLPNQFRCASGQCVLIKQQCDSFPDCIDG
SDELMCEITKPPSDDSPAHSSAIGPVIGIILSLFVMGGVYFVCQRVVCQRYAG
ANGPFPHEYVSGTPHVPLNFIAPGGSQHGPFTGIACGKSMMSSVSLMGGRGG
VPLYDRNHVTGASSSSSSSTKATLYPPILNPPPSPATDPSLYNMDMFYSSNIP
ATVRPYRPYIRGMAPPTTPCSTDVCDSDYSASRWKASKYYLDLNSDSDPYP
PPPTPHSQYLSAEDSCPPSPATERSYFHLFPPPPSPCTDSS (SEQ ID NO: 25)
```

Figure 12(a)

```
TAAATGGCTTGGCAAAGGGAGTTCATTCCTTTTAGCGCTTCCATCTTCTGCA
GTGAGAGGACACCGCATTCTTCTTCTCCAGAGGATGCAGCAGCAAGGCGCCA
TCTTGAAACCAGAGACCAAACCAACCAGCAACTTCGTCTTGAACTTCCCAGC
CTCCACAACTCCTCGCCGCTCCTGCTATTTGCCAACCGCCGGGACGTACGGCTG
GTGGACGCCGGCGGAGTCAAGCTGGAGTCCACCATCGTGGTCAGCGGCCTGGA
GGATGCGGCCGCAGTGGACTTCCAGTTTTCCAAGGGAGCCGTGTACTGGACAG
ACGTGAGCGAGGAGGCCATCAAGCAGACCTACCTGAACCAGACGGGGCCGC
CGTGCAGAACGTGGTCATCTCCGGCCTGGTCTCTCCCGACGGCCTCGCCTGCGAC
TGGGTGGGCAAGAAGCTGTACTGGACGGACTCAGAGACCAACCGCATCGAGG
TGGCCAACCTCAATGGCACATCCCGGAAGGTGCTCTTCTGGCAGGACCTTGAC
CAGCCGAGGGCCATCGCCTTGGACCCCGCTCACGGGTACATGTACTGGACAGA
CTGGGGTGAGACGCCCGGATTGAGCGGGCAGGGATGGATGGCAGCACCCGGA
AGATCATTGTGGACTCGGACATTTACTGGCCCAATGGACTGACCATCGACCT
GGAGGAGCAGAAGCTCTACTGGGCTGACGCCAAGCTCAGCTTCATCCACCGTG
CCAACCTGGACGGCTCGTTCCGGCAGAAGGTGGTGGAGGGCAGCCTGACGCAC
CCCTTCGCCCTGACGCTCTCCGGGGACACTCTGTACTGGACAGACTGGCAGACC
CGCTCCATCCATGCCTGCAACAAGCGCACTGGGGGGAAGAGGAAGGAGATCC
TGAGTGCCCTCTACTCACCCATGGACATCCAGGTGCTGAGCCAGGAGCGGCAG
CCTTTCTTCCACACTCGCTGTGAGGAGGACAATGGCGGCTGCTCCCACCTGTGC
CTGCTGTCCCCAAGCGAGCCTTTCTACACATGCGCCTGCCCCACGGGTGTGCAG
CTGCAGGACAACGGCAGGACGTGTAAGGCAGGAGCCGAGGAGGTGCTGCTGC
TGGCCCGGCGGACGGACCTACGGAGGATCTCGCTGGACACGCCGGACTTTACCG
ACATCGTGCTGCAGGTGGACGACATCCGGCACGCCATTGCCATCGACTACGAC
CCGCTAGAGGGCTATGTCTACTGGACAGATGACGAGGTGCGGGCCATCCGCAG
GGCGTACCTGGACGGGTCTGGGGCGCAGACGCTGGTCAACACCGAGATCAACG
ACCCCGATGGCATCGCGGTCGACTGGGTGGCCCGAAACCTCTACTGGACCGAC
ACGGGCACGGACCGCATCGAGGTGACGCGCCTCAACGGCACCTCCCGCAAGAT
CCTGGTGTCGGAGGACCTGGACGAGCCCCGAGCCATCGCACTGCACCCCGTGAT
GGGCCTCATGTACTGGACAGACTGGGGAGAGAACCCTAAAATCGAGTGTGCC
AACTTGGATGGGCAGGAGCGGCGTGTGCTGGTCAATGCCTCCCTCGGGTGGCCC
AACGGCCTGGCCCTGGACCTGCAGGAGGGGAAGCTCTACTGGGGAGACGCCA
AGACAGACAAGATCGAGGTGATCAATGTTGATGGGACGAAGAGGCGGACC
CTCCTGGAGGACAAGCTCCCGCACATTTTCGGGTTCACGCTGCTGGGGGACTTC
ATCTACTGGACTGACTGGCAGCGCCGCAGCATCGAGCGGGTGCACAAGGTCA
AGGCCAGCCGGGACGTCATCATTGACCAGCTGCCCGACCTGATGGGCTCAAA
GCTGTGAATGTGGCCAAGGTCGTCGGAACCAACCCGTGTGCGGACAGGAACG
GGGGGTGCAGCCACCTGTGCTTCTTCACACCCCACGCAACCCGGTGTGGCTGCCC
CATCGGCCTGGAGCTGCTGAGTGACATGAAGACCTGCATCGTGCCTGAGGCCT
TCTTGGTCTTCACCAGCAGAGCCGCCATCCACAGGATCTCCCTCGAGACCAAT
```

Figure 12(a-1)

```
AACAACGACGTGGCCATCCCGCTCACGGGCGTCAAGGAGGCCTCAGCCCTGGA
CTTTGATGTGTCCAACAACCACATCTACTGGACAGACGTCAGCCTGAAGACC
ATCAGCCGCGCCTTCATGAACGGGAGCTCGGTGGAGCACGTGGTGGAGTTTGG
CCTTGACTACCCCGAGGGCATGGCCGTTGACTGGATGGGCAAGAACCTCTACT
GGGCCGACACTGGGACCAACAGAATCGAAGTGGCGCGGCTGGACGGGCAGTT
CCGGCAAGTCCTCGTGTGGAGGGACTTGGACAACCCGAGGTCGCTGGCCCTGG
ATCCCACCAAGGGCTACATCTACTGGACCGAGTGGGGCGGCAAGCCGAGGAT
CGTGCGGGCCTTCATGGACGGGACCAACTGCATGACGCTGGTGGACAAGGTGG
GCCGGGCCAACGACCTCACCATTGACTACGCTGACCAGCGCCTCTACTGGACCG
ACCTGGACACCAACATGATCGAGTCGTCCAACATGCTGGGTCAGGAGCGGGT
CGTGATTGCCGACGATCTCCCGCACCCGTTCGGTCTGACGCAGTACAGCGATT
ATATCTACTGGACAGACTGGAATCTGCACAGCATTGAGCGGGCCGACAAGA
CTAGCGGCCGGAACCGCACCCTCATCCAGGGCCACCTGGACTTCGTGATGGAC
ATCCTGGTGTTCCACTCCTCCCGCCAGGATGGCCTCAATGACTGTATGCACAA
CAACGGGCAGTGTGGGCAGCTGTGCCTTGCCATCCCCGGCGGCCACCGCTGCGGC
TGCGCCTCACACTACACCCTGGACCCCAGCAGCCGCAACTGCAGCCCGCCCACC
ACCTTCTTGCTGTTCAGCCAGAAATCTGCCATCAGTCGGATGATCCCGGACGA
CCAGCACAGCCCGGATCTCATCCTGCCCCTGCATGGACTGAGGAACGTCAAAG
CCATCGACTATGACCCACTGGACAAGTTCATCTACTGGGTGGATGGGCGCCA
GAACATCAAGCGAGCCAAGGACGACGGGACCCAGCCCTTTGTTTTGACCTCT
CTGAGCCAAGGCCAAAACCCAGACAGGCAGCCCCACGACCTCAGCATCGACA
TCTACAGCCGGACACTGTTCTGGACGTGCGAGGCCACCAATACCATCAACGTC
CACAGGCTGAGCGGGGAAGCCATGGGGGTGGTGCTGCGTGGGGACCGCGACAA
GCCCAGGGCCATCGTCGTCAACGCGGAGCGAGGGTACCTGTACTTCACCAACA
TGCAGGACCGGGCAGCCAAGATCGAACGCGCAGCCCTGGACGGCACCGAGCGC
GAGGTCCTCTTCACCACCGGCCTCATCCGCCCTGTGGCCCTGGTGGTAGACAAC
ACACTGGGCAAGCTGTTCTGGGTGGACGCGGACCTGAAGCGCATTGAGAGCT
GTGACCTGTCAGGGGCCAACCGCCTGACCCTGGAGGACGCCAACATCGTGCAG
CCTCTGGGCCTGACCATCCTTGGCAAGCATCTCTACTGGATCGACCGCCAGCAG
CAGATGATCGAGCGTGTGGAGAAGACCACCGGGGACAAGCGGACTCGCATCC
AGGGCCGTGTCGCCCACCTCACTGGCATCCATGCAGTGGAGGAAGTCAGCCTG
GAGGAGTTCTCAGCCCACCCATGTGCCCGTGACAATGGTGGCTGCTCCCACAT
CTGTATTGCCAAGGGTGATGGGACACCACGGTGCTCATGCCCAGTCCACCTCG
TGCTCCTGCAGAACCTGCTGACCTGTGGAGAGCCGCCCACCTGCTCCCCGGACC
AGTTTGCATGTGCCACAGGGGAGATCGACTGTATCCCCGGGGCCTGGCGCTGT
GACGGCTTTCCCGAGTGCGATGACCAGAGCGACGAGGAGGGCTGCCCCGTGTG
CTCCGCCGCCCAGTTCCCCTGCGCGCGGGGTCAGTGTGTGGACCTGCGCCTGCGCT
GCGACGGCGAGGCAGACTGTCAGGACCGCTCAGACGAGGCGGACTGTGACGCC
ATCTGCCTGCCCAACCAGTTCCGGTGTGCGAGCGGCCAGTGTGTCCTCATCAA
ACAGCAGTGCGACTCCTTCCCCGACTGTATCGACGGCTCCGACGAGCTCATGT
GTGAAATCACCAAGCCGCCCTCAGACGACAGCCCGGCCCACAGCAGTGCCATC
```

Figure 12(a-2)

```
GGGCCCGTCATTGGCATCATCCTCTCTCTCTTCGTCATGGGTGGTGTCTATTTT
GTGTGCCAGCGCGTGGTGTGCCAGCGCTATGCGGGGGCCAACGGGCCCTTCCCGC
ACGAGTATGTCAGCGGGACCCCGCACGTGCCCCTCAATTTCATAGCCCCGGGCG
GTTCCCAGCATGGCCCCTTCACAGGCATCGCATGCGGAAAGTCCATGATGAGC
TCCGTGAGCCTGATGGGGGGCCGGGGCGGGGTGCCCCTCTACGACCGGAACCAC
GTCACAGGGGCCTCGTCCAGCAGCTCGTCCAGCACGAAGGCCACGCTGTACCCG
CCGATCCTGAACCCGCCGCCCTCCCCGGCCACGGACCCCTCCCTGTACAACATGG
ACATGTTCTACTCTTCAAACATTCCGGCCACTGCGAGACCGTACAGGCCCTAC
ATCATTCGAGGAATGGCGCCCCCGACGACGCCCTGCAGCACCGACGTGTGTGA
CAGCGACTACAGCGCCAGCCGCTGGAAGGCCAGCAAGTACTACCTGGATTTG
AACTCGGACTCAGACCCCTATCCACCCCCACCCACGCCCCACAGCCAGTACCTG
TCGGCGGAGGACAGCTGCCCGCCCTCGCCCGCCACCGAGAGGAGCTACTTCCAT
CTCTTCCCGCCCCTCCGTCCCCCTGCACGGACTCATCCTGACCTGGCCGGGCCA
CTCTGGCTTCTCTGTGCCCCTGTAAATAGTTTTAAATATGAACAAAGAAAA
AAATATATTTTATGATTTAAAAAATAAATATAATTGGGATTTTAAAA
ACATGAGAAATGTGAACTGTGATGGGGTGGGCAGGGCTGGGAGAACTTTGT
ACAGTGGAACAAATATTTATAAACTTAATTTTGTAAAACAG
```

(SEQ ID NO: 26)

Figure 12(b)

TAAAATGGCTTGGCAAAGGGAGTTCATTCCTTTTAGCGCTTCCATCTTCTGC
AGTGAGAGGACACCGCATTCTTCTTCTCCAGAGGATGCAGCAGCAAGGCGCC
ATCTTGAAACCAGAGACCAAACCAACCAGCAACTTCGTCTTGAACTTCCCA
GCCTCCACAACT (SEQ ID NO: 27)

Figure 12(c)

ATGGCTTGGCAAAGGGAGTTCATTCCTTTTAGCGCTTCCATCTTCTGCAGTGA
GAGGACACCGCATTCTTCTTCTCCAGAGGATGCAGCAGCAAGGCGCCATCTTG
AAACCAGAGACCAAACCAACCAGCAACTTCGTCTTGAACTTCCCAGCCTCCA
CAACTCCTCGCCGCTCCTGCTATTTGCCAACCGCCGGGACGTACGGCTGGTGGA
CGCCGGCGGAGTCAAGCTGGAGTCCACCATCGTGGTCAGCGGCCTGGAGGATG
CGGCCGCAGTGGACTTCCAGTTTTCCAAGGGAGCCGTGTACTGGACAGACGTG
AGCGAGGAGGCCATCAAGCAGACCTACCTGAACCAGACGGGGGCCGCCGTGC
AGAACGTGGTCATCTCCGGCCTGGTCTCTCCCGACGGCCTCGCCTGCGACTGGGT
GGGCAAGAAGCTGTACTGGACGGACTCAGAGACCAACCGCATCGAGGTGGCC
AACCTCAATGGCACATCCCGGAAGGTGCTCTTCTGGCAGGACCTTGACCAGCC
GAGGGCCATCGCCTTGGACCCCGCTCACGGGTACATGTACTGGACAGACTGGG
GTGAGACGCCCCGGATTGAGCGGGCAGGGATGGATGGCAGCACCCGGAAGAT
CATTGTGGACTCGGACATTTACTGGCCCAATGGACTGACCATCGACCTGGAG
GAGCAGAAGCTCTACTGGGCTGACGCCAAGCTCAGCTTCATCCACCGTGCCAA
CCTGGACGGCTCGTTCCGGCAGAAGGTGGTGGAGGGCAGCCTGACGCACCCTT
CGCCCTGACGCTCTCCGGGGACACTCTGTACTGGACAGACTGGCAGACCCGCTC
CATCCATGCCTGCAACAAGCGCACTGGGGGGAAGAGGAAGGAGATCCTGAG
TGCCCTCTACTCACCCATGGACATCCAGGTGCTGAGCCAGGAGCGGCAGCCTT
TCTTCCACACTCGCTGTGAGGAGGACAATGGCGGCTGCTCCCACCTGTGCCTGC
TGTCCCCAAGCGAGCCTTTCTACACATGCGCCTGCCCCACGGGTGTGCAGCTGC
AGGACAACGGCAGGACGTGTAAGGCAGGAGCCGAGGAGGTGCTGCTGCTGGC
CCGGCGGACGGACCTACGGAGGATCTCGCTGGACACGCCGGACTTTACCGACA
TCGTGCTGCAGGTGGACGACATCCGGCACGCCATTGCCATCGACTACGACCCGC
TAGAGGGCTATGTCTACTGGACAGATGACGAGGTGCGGGCCATCCGCAGGGC
GTACCTGGACGGGTCTGGGGCGCAGACGCTGGTCAACACCGAGATCAACGACC
CCGATGGCATCGCGGTCGACTGGGTGGCCCGAAACCTCTACTGGACCGACACG
GGCACGGACCGCATCGAGGTGACGCGCCTCAACGGCACCTCCCGCAAGATCCT
GGTGTCGGAGGACCTGGACGAGCCCCGAGCCATCGCACTGCACCCCGTGATGGG
CCTCATGTACTGGACAGACTGGGGAGAGAACCCTAAAATCGAGTGTGCCAA
CTTGGATGGGCAGGAGCGGCGTGTGCTGGTCAATGCCTCCCTCGGGTGGCCCAA
CGGCCTGGCCCTGGACCTGCAGGAGGGGAAGCTCTACTGGGGAGACGCCAAGA
CAGACAAGATCGAGGTGATCAATGTTGATGGGACGAAGAGGCGGACCCTCC
TGGAGGACAAGCTCCCGCACATTTTCGGGTTCACGCTGCTGGGGGACTTCATC
TACTGGACTGACTGGCAGCGCCGCAGCATCGAGCGGGTGCACAAGGTCAAGG
CCAGCCGGGACGTCATCATTGACCAGCTGCCCGACCTGATGGGGCTCAAAGCT
GTGAATGTGGCCAAGGTCGTCGGAACCAACCCGTGTGCGGACAGGAACGGGG
GGTGCAGCCACCTGTGCTTCTTCACACCCACGCAACCCGGTGTGGCTGCCCCA
TCGGCCTGGAGCTGCTGAGTGACATGAAGACCTGCATCGTGCCTGAGGCCTTC
TTGGTCTTCACCAGCAGAGCCGCCATCCACAGGATCTCCCTCGAGACCAATA

Figure 12(c-1)

```
ACAACGACGTGGCCATCCCGCTCACGGGCGTCAAGGAGGCCTCAGCCCTGGAC
TTTGATGTGTCCAACAACCACATCTACTGGACAGACGTCAGCCTGAAGACC
ATCAGCCGCGCCTTCATGAACGGGAGCTCGGTGGAGCACGTGGTGGAGTTTGG
CCTTGACTACCCCGAGGGCATGGCCGTTGACTGGATGGGCAAGAACCTCTACT
GGGCCGACACTGGGACCAACAGAATCGAAGTGGCGCGGCTGGACGGGCAGTT
CCGGCAAGTCCTCGTGTGGAGGGACTTGGACAACCCGAGGTCGCTGGCCCTGG
ATCCCACCAAGGGCTACATCTACTGGACCGAGTGGGGCGGCAAGCCGAGGAT
CGTGCGGGCCTTCATGGACGGGACCAACTGCATGACGCTGGTGGACAAGGTGG
GCCGGGCCAACGACCTCACCATTGACTACGCTGACCAGCGCCTCTACTGGACCG
ACCTGGACACCAACATGATCGAGTCGTCCAACATGCTGGGTCAGGAGCGGGT
CGTGATTGCCGACGATCTCCCGCACCCGTTCGGTCTGACGCAGTACAGCGATT
ATATCTACTGGACAGACTGGAATCTGCACAGCATTGAGCGGGCCGACAAGA
CTAGCGGCCGGAACCGCACCCTCATCCAGGGCCACCTGGACTTCGTGATGGAC
ATCCTGGTGTTCCACTCCTCCCGCCAGGATGGCCTCAATGACTGTATGCACAA
CAACGGGCAGTGTGGGCAGCTGTGCCTTGCCATCCCCGGCGGCCACCGCTGCGGC
TGCGCCTCACACTACACCCTGGACCCCAGCAGCCGCAACTGCAGCCCGCCCACC
ACCTTCTTGCTGTTCAGCCAGAAATCTGCCATCAGTCGGATGATCCCGGACGA
CCAGCACAGCCCGGATCTCATCCTGCCCCTGCATGGACTGAGGAACGTCAAAG
CCATCGACTATGACCCACTGGACAAGTTCATCTACTGGGTGGATGGGCGCCA
GAACATCAAGCGAGCCAAGGACGACGGGACCCAGCCCTTTGTTTTGACCTCT
CTGAGCCAAGGCCAAAACCCAGACAGGCAGCCCCACGACCTCAGCATCGACA
TCTACAGCCGGACACTGTTCTGGACGTGCGAGGCCACCAATACCATCAACGTC
CACAGGCTGAGCGGGGAAGCCATGGGGGTGGTGCTGCGTGGGACCGCGACAA
GCCCAGGGCCATCGTCGTCAACGCGGAGCGAGGGTACCTGTACTTCACCAACA
TGCAGGACCGGGCAGCCAAGATCGAACGCGCAGCCCTGGACGGCACCGAGCGC
GAGGTCCTCTTCACCACCGGCCTCATCCGCCCTGTGGCCCTGGTGGTAGACAAC
ACACTGGGCAAGCTGTTCTGGGTGGACGCGGACCTGAAGCGCATTGAGAGCT
GTGACCTGTCAGGGGCCAACCGCCTGACCCTGGAGGACGCCAACATCGTGCAG
CCTCTGGGCCTGACCATCCTTGGCAAGCATCTCTACTGGATCGACCGCCAGCAG
CAGATGATCGAGCGTGTGGAGAAGACCACCGGGGACAAGCGGACTCGCATCC
AGGGCCGTGTCGCCCACCTCACTGGCATCCATGCAGTGGAGGAAGTCAGCCTG
GAGGAGTTCTCAGCCCACCCATGTGCCCGTGACAATGGTGGCTGCTCCCACAT
CTGTATTGCCAAGGGTGATGGGACACCACGGTGCTCATGCCCAGTCCACCTCG
TGCTCCTGCAGAACCTGCTGACCTGTGGAGAGCCGCCCACCTGCTCCCCGGACC
AGTTTGCATGTGCCACAGGGGAGATCGACTGTATCCCCGGGGCCTGGCGCTGT
GACGGCTTTCCCGAGTGCGATGACCAGAGCGACGAGGAGGGCTGCCCCGTGTG
CTCCGCCGCCCAGTTCCCCTGCGCGCGGGGTCAGTGTGTGGACCTGCGCCTGCGCT
GCGACGGCGAGGCAGACTGTCAGGACCGCTCAGACGAGGCGGACTGTGACGCC
ATCTGCCTGCCCAACCAGTTCCGGTGTGCGAGCGGCCAGTGTGTCCTCATCAA
ACAGCAGTGCGACTCCTTCCCCGACTGTATCGACGGCTCCGACGAGCTCATGT
GTGAAATCACCAAGCCGCCCTCAGACGACAGCCCGGCCCACAGCAGTGCCATC
```

Figure 12(c-2)

```
GGGCCCGTCATTGGCATCATCCTCTCTCTCTTCGTCATGGGTGGTGTCTATTTT
GTGTGCCAGCGCGTGGTGTGCCAGCGCTATGCGGGGGCCAACGGGCCCTTCCCGC
ACGAGTATGTCAGCGGGACCCCGCACGTGCCCCTCAATTTCATAGCCCCGGGCG
GTTCCCAGCATGGCCCCTTCACAGGCATCGCATGCGGAAAGTCCATGATGAGC
TCCGTGAGCCTGATGGGGGGCCGGGCGGGGTGCCCCTCTACGACCGGAACCAC
GTCACAGGGGCCTCGTCCAGCAGCTCGTCCAGCACGAAGGCCACGCTGTACCCG
CCGATCCTGAACCCGCCGCCCTCCCCGGCCACGGACCCCTCCCTGTACAACATGG
ACATGTTCTACTCTTCAAACATTCCGGCCACTGCGAGACCGTACAGGCCCTAC
ATCATTCGAGGAATGGCGCCCCGACGACGCCCTGCAGCACCGACGTGTGTGA
CAGCGACTACAGCGCCAGCCGCTGGAAGGCCAGCAAGTACTACCTGGATTTG
AACTCGGACTCAGACCCCTATCCACCCCCACCCACGCCCCACAGCCAGTACCTG
TCGGCGGAGGACAGCTGCCCGCCCTCGCCCGCCACCGAGAGGAGCTACTTCCAT
CTCTTCCCGCCCCCTCCGTCCCCCTGCACGGACTCATCC (SEQ ID NO: 28)
```

Figure 12(d)

```
MAWQREFIPFSASIFCSERTPHSSSPEDAAARRHLETRDQTNQQLRLELPSLH
NSSPLLLFANRRDVRLVDAGGVKLESTIVVSGLEDAAAVDFQFSKGAVYWT
DVSEEAIKQTYLNQTGAAVQNVVISGLVSPDGLACDWVGKKLYWTDSETNR
IEVANLNGTSRKVLFWQDLDQPRAIALDPAHGYMYWTDWGETPRIERAGM
DGSTRKIIVDSDIYWPNGLTIDLEEQKLYWADAKLSFIHRANLDGSFRQKVVE
GSLTHPFALTLSGDTLYWTDWQTRSIHACNKRTGGKRKEILSALYSPMDIQV
LSQERQPFFHTRCEEDNGGCSHLCLLSPSEPFYTCACPTGVQLQDNGRTCKAGA
EEVLLLARRTDLRRISLDTPDFTDIVLQVDDIRHAIAIDYDPLEGYVYWTDDE
VRAIRRAYLDGSGAQTLVNTEINDPDGIAVDWVARNLYWTDTGTDRIEVTR
LNGTSRKILVSEDLDEPRAIALHPVMGLMYWTDWGENPKIECANLDGQERR
VLVNASLGWPNGLALDLQEGKLYWGDAKTDKIEVINVDGTKRRTLLEDKLP
HIFGFTLLGDFIYWTDWQRRSIERVHKVKASRDVIIDQLPDLMGLKAVNVA
KVVGTNPCADRNGGCSHLCFFTPHATRCGCPIGLELLSDMKTCIVPEAFLVFT
SRAAIHRISLETNNNDVAIPLTGVKEASALDFDVSNNHIYWTDVSLKTISRA
FMNGSSVEHVVEFGLDYPEGMAVDWMGKNLYWADTGTNRIEVARLDGQFR
QVLVWRDLDNPRSLALDPTKGYTYWTEWGGKPRIVRAFMDGTNCMTLVDK
VGRANDLTIDYADQRLYWTDLDTNMIESSNMLGQERVVIADDLPHPFGLTQ
YSDYIYWTDWNLHSIERADKTSGRNRTLIQGHLDFVMDILVFHSSRQDGLND
CMHNNGQCGQLCLAIPGGHRCGCASHYTLDPSSRNCSPPTTFLLFSQKSAISR
MIPDDQHSPDLILPLHGLRNVKAIDYDPLDKFIYWVDGRQNIKRAKDDGTQPF
VLTSLSQGQNPDRQPHDLSIDIYSRTLFWTCEATNTINVHRLSGEAMGVVLR
GDRDKPRAIVVNAERGYLYFTNMQDRAAKIERAALDGTEREVLFTTGLIRPV
ALVVDNTLGKLFWVDADLKRIESCDLSGANRLTLEDANIVQPLGLTILGKHL
YWIDRQQQMIERVEKTTGDKRTRIQGRVAHLTGIHAVEEVSLEEFSAHPCAR
DNGGCSHICIAKGDGTPRCSCPVHLVLLQNLLTCGEPPTCSPDQFACATGEIDCI
PGAWRCDGFPECDDQSDEEGCPVCSAAQFPCARGQCVDLRLRCDGEADCQDRS
DEADCDAICLPNQFRCASGQCVLIKQQCDSFPDCIDGSDELMCEITKPPSDDSPA
HSSAIGPVIGIILSLFVMGGVYFVCQRVVCQRYAGANGPFPHEYVSGTPHVP
LNFIAPGGSQHGPFTGIACGKSMMSSVSLMGGRGGVPLYDRNHVTGASSSSS
SSTKATLYPPILNPPPSPATDPSLYNMDMFYSSNIPATARPYRPYIIRGMAP
PTTPCSTDVCDSDYSASRWKASKYYLDLNSDSDPYPPPPTPHSQYLSAEDSCP
PSPATERSYFHLFPPPPSPCTDSS (SEQ ID NO: 29)
```

Figure 12(e)

TATAAAATGGCTTGGCAAAGGGAGTTCATTCCTTTTAGCGCTTCCATCTTCT
GCAGTGAGAGGACACCGCATTCTTCTTCTCCAGAGGATG (SEQ ID NO: 30)

Figure 13(a)

```
TAAGAGTATAAAGGGCTCCTGAGACCAAAAAGGTTGAGAACCAGTGCTTT
AAAGCTTGATGTTTCTCAGGGTTTCATCCTTTGTGGATTAATGCCCATTATA
AAATGGCTTGGCAAAGGGAGTTCATTCCTTTTAGCGCTTCCATCTTCTGCAG
TGAGAGGACACCGCATTCTTCTTCTCCAGAGGATGCAGCAGCAAGGCGCCAT
CTTGAAACCAGAGACCAAACCAACCAGCAACTTCGTCTTGAACTTCCCAGCC
TCCACAACTCAGCAGTCTGTGCAGGACCCTGTGAGCAGAGCCGCAGCCTCGCC
GCTCCTGCTATTTGCCAACCGCCGGGACGTACGGCTGGTGGACGCCGGCGGAGT
CAAGCTGGAGTCCACCATCGTGGTCAGCGGCCTGGAGGATGCGGCCGCAGTGG
ACTTCCAGTTTTCCAAGGGAGCCGTGTACTGGACAGACGTGAGCGAGGAGGC
CATCAAGCAGACCTACCTGAACCAGACGGGGGCCGCCGTGCAGAACGTGGTC
ATCTCCGGCCTGGTCTCTCCCGACGGCCTCGCCTGCGACTGGGTGGGCAAGAAG
CTGTACTGGACGGACTCAGAGACCAACCGCATCGAGGTGGCCAACCTCAATG
GCACATCCCGGAAGGTGCTCTTCTGGCAGGACCTTGACCAGCCGAGGGCCATC
GCCTTGGACCCCGCTCACGGGTACATGTACTGGACAGACTGGGGTGAGACGCC
CCGGATTGAGCGGGCAGGGATGGATGGCAGCACCCGGAAGATCATTGTGGAC
TCGGACATTTACTGGCCCAATGGACTGACCATCGACCTGGAGGAGCAGAAGC
TCTACTGGGCTGACGCCAAGCTCAGCTTCATCCACCGTGCCAACCTGGACGGCT
CGTTCCGGCAGAAGGTGGTGGAGGGCAGCCTGACGCACCCCTTCGCCCTGACGC
TCTCCGGGGACACTCTGTACTGGACAGACTGGCAGACCCGCTCCATCCATGCCT
GCAACAAGCGCACTGGGGGGAAGAGGAAGGAGATCCTGAGTGCCCTCTACTC
ACCCATGGACATCCAGGTGCTGAGCCAGGAGCGGCAGCCTTTCTTCCACACTC
GCTGTGAGGAGGACAATGGCGGCTGCTCCCACCTGTGCCTGCTGTCCCAAGCG
AGCCTTTCTACACATGCGCCTGCCCCACGGGTGTGCAGCTGCAGGACAACGGC
AGGACGTGTAAGGCAGGAGCCGAGGAGGTGCTGCTGCTGGCCCGGCGGACGGA
CCTACGGAGGATCTCGCTGGACACGCCGGACTTTACCGACATCGTGCTGCAGG
TGGACGACATCCGGCACGCCATTGCCATCGACTACGACCCGCTAGAGGGCTAT
GTCTACTGGACAGATGACGAGGTGCGGGCCATCCGCAGGGCGTACCTGGACGG
GTCTGGGGCGCAGACGCTGGTCAACACCGAGATCAACGACCCCGATGGCATCG
CGGTCGACTGGGTGGCCCGAAACCTCTACTGGACCGACACGGGCACGGACCGC
ATCGAGGTGACGCGCCTCAACGGCACCTCCCGCAAGATCCTGGTGTCGGAGGA
CCTGGACGAGCCCCGAGCCATCGCACTGCACCCCGTGATGGGCCTCATGTACTG
GACAGACTGGGGAGAGAACCCTAAAATCGAGTGTGCCAACTTGGATGGGCA
GGAGCGGCGTGTGCTGGTCAATGCCTCCCTCGGGTGGCCCAACGGCCTGGCCCTG
GACCTGCAGGAGGGGAAGCTCTACTGGGGAGACGCCAAGACAGACAAGATC
GAGGTGATCAATGTTGATGGGACGAAGAGGCGGACCCTCCTGGAGGACAAG
CTCCCGCACATTTTCGGGTTCACGCTGCTGGGGACTTCATCTACTGGACTGAC
TGGCAGCGCCGCAGCATCGAGCGGGTGCACAAGGTCAAGGCCAGCCGGGACGT
CATCATTGACCAGCTGCCCGACCTGATGGGGCTCAAAGCTGTGAATGTGGCC
AAGGTCGTCGGAACCAACCCGTGTGCGGACAGGAACGGGGGGTGCAGCCACC
```

Figure 13(a-1)

```
TGTGCTTCTTCACACCCCACGCAACCCGGTGTGGCTGCCCCATCGGCCTGGAGCT
GCTGAGTGACATGAAGACCTGCATCGTGCCTGAGGCCTTCTTGGTCTTCACCA
GCAGAGCCGCCATCCACAGGATCTCCCTCGAGACCAATAACAACGACGTGGC
CATCCCGCTCACGGGCGTCAAGGAGGCCTCAGCCCTGGACTTTGATGTGTCCA
ACAACCACATCTACTGGACAGACGTCAGCCTGAAGACCATCAGCCGCGCCTT
CATGAACGGGAGCTCGGTGGAGCACGTGGTGGAGTTTGGCCTTGACTACCCCG
AGGGCATGGCCGTTGACTGGATGGGCAAGAACCTCTACTGGGCCGACACTGG
GACCAACAGAATCGAAGTGGCGCGGCTGGACGGGCAGTTCCGGCAAGTCCTC
GTGTGGAGGGACTTGGACAACCCGAGGTCGCTGGCCCTGGATCCCACCAAGGG
CTACATCTACTGGACCGAGTGGGGCGGCAAGCCGAGGATCGTGCGGGCCTTCA
TGGACGGGACCAACTGCATGACGCTGGTGGACAAGGTGGGCCGGGCCAACGA
CCTCACCATTGACTACGCTGACCAGCGCCTCTACTGGACCGACCTGGACACCA
ACATGATCGAGTCGTCCAACATGCTGGGTCAGGAGCGGGTCGTGATTGCCGA
CGATCTCCCGCACCCGTTCGGTCTGACGCAGTACAGCGATTATATCTACTGGA
CAGACTGGAATCTGCACAGCATTGAGCGGGCCGACAAGACTAGCGGCCGGAA
CCGCACCCTCATCCAGGGCCACCTGGACTTCGTGATGGACATCCTGGTGTTCCA
CTCCTCCCGCCAGGATGGCCTCAATGACTGTATGCACAACAACGGGCAGTGTG
GGCAGCTGTGCCTTGCCATCCCCGGCGGCCACCGCTGCGGCTGCGCCTCACACTA
CACCCTGGACCCCAGCAGCCGCAACTGCAGCCCGCCCACCACCTTCTTGCTGTTC
AGCCAGAAATCTGCCATCAGTCGGATGATCCCGGACGACCAGCACAGCCCGG
ATCTCATCCTGCCCCTGCATGGACTGAGGAACGTCAAAGCCATCGACTATGA
CCCACTGGACAAGTTCATCTACTGGGTGGATGGGCGCCAGAACATCAAGCGA
GCCAAGGACGACGGGACCCAGCCCTTTGTTTTGACCTCTCTGAGCCAAGGCCA
AAACCCAGACAGGCAGCCCCACGACCTCAGCATCGACATCTACAGCCGGACA
CTGTTCTGGACGTGCGAGGCCACCAATACCATCAACGTCCACAGGCTGAGCGG
GGAAGCCATGGGGGTGGTGCTGCGTGGGGACCGCGACAAGCCCAGGGCCATCG
TCGTCAACGCGGAGCGAGGGTACCTGTACTTCACCAACATGCAGGACCGGGC
AGCCAAGATCGAACGCGCAGCCCTGGACGGCACCGAGCGCGAGGTCCTCTTCA
CCACCGGCCTCATCCGCCCTGTGGCCCTGGTGGTAGACAACACACTGGGCAAGC
TGTTCTGGGTGGACGCGGACCTGAAGCGCATTGAGAGCTGTGACCTGTCAGGG
GCCAACCGCCTGACCCTGGAGGACGCCAACATCGTGCAGCCTCTGGGCCTGACC
ATCCTTGGCAAGCATCTCTACTGGATCGACCGCCAGCAGCAGATGATCGAGC
GTGTGGAGAAGACCACCGGGGACAAGCGGACTCGCATCCAGGGCCGTGTCGCC
CACCTCACTGGCATCCATGCAGTGGAGGAAGTCAGCCTGGAGGAGTTCTCAG
CCCACCCATGTGCCCGTGACAATGGTGGCTGCTCCCACATCTGTATTGCCAAG
GGTGATGGGACACCACGGTGCTCATGCCCAGTCCACCTCGTGCTCCTGCAGAA
CCTGCTGACCTGTGGAGAGCCGCCCACCTGCTCCCCGGACCAGTTTGCATGTGCC
ACAGGGGAGATCGACTGTATCCCCGGGGCCTGGCGCTGTGACGGCTTTCCCGAG
TGCGATGACCAGAGCGACGAGGAGGGCTGCCCCGTGTGCTCCGCCGCCCAGTTC
CCCTGCGCGCGGGGTCAGTGTGTGGACCTGCGCCTGCGCTGCGACGGCGAGGCAG
ACTGTCAGGACCGCTCAGACGAGGCGGACTGTGACGCCATCTGCCTGCCCAAC
```

Figure 13(a-2)

```
CAGTTCCGGTGTGCGAGCGGCCAGTGTGTCCTCATCAAACAGCAGTGCGACTC
CTTCCCCGACTGTATCGACGGCTCCGACGAGCTCATGTGTGAAATCACCAAGC
CGCCCTCAGACGACAGCCCGGCCCACAGCAGTGCCATCGGGCCCGTCATTGGCA
TCATCCTCTCTCTCTTCGTCATGGGTGGTGTCTATTTTGTGTGCCAGCGCGTGG
TGTGCCAGCGCTATGCGGGGGCCAACGGGCCCTTCCCGCACGAGTATGTCAGCG
GGACCCCGCACGTGCCCCTCAATTTCATAGCCCCGGGCGGTTCCCAGCATGGCCC
CTTCACAGGCATCGCATGCGGAAAGTCCATGATGAGCTCCGTGAGCCTGATG
GGGGGCCGGGGCGGGGTGCCCCTCTACGACCGGAACCACGTCACAGGGGCCTCG
TCCAGCAGCTCGTCCAGCACGAAGGCCACGCTGTACCCGCGGATCCTGAACCCG
CCGCCCTCCCCGGCCACGGACCCCTCCCTGTACAACATGGACATGTTCTACTCT
TCAAACATTCCGGCCACTGCGAGACCGTACAGGCCCTACATCATTCGAGGAA
TGGCGCCCCCGACGACGCCCTGCAGCACCGACGTGTGTGACAGCGACTACAGCG
CCAGCCGCTGGAAGGCCAGCAAGTACTACCTGGATTTGAACTCGGACTCAGA
CCCCTATCCACCCCCACCCACGCCCCACAGCCAGTACCTGTCGGCGGAGGACAG
CTGCCCGCCCTCGCCCGCCACCGAGAGGAGCTACTTCCATCTCTTCCCGCCCCTC
CGTCCCCCTGCACGGACTCATCCTGACCTCGGCCGGGCCACTCTGGCTTCTCTGT
GCCCTGTAAATAGTTTTAAATATGAACAAAGAAAAAAATATATTTTA
TGATTTAAAAAATAAATATAATTGGGATTTTAAAAACATGAGAAATGT
GAACTGTGATGGGGTGGGCAGGGCTGGGAGAACTTTGTACAGTGGAACAAA
TATTTATAAACTTAATTTTGTAAAACAG (SEQ ID NO: 31)
```

Figure 14(a)

```
GGCTGGTCTTGAACTCCTGGCCTGAGATGATCCTCTCTCCTCGGAAAGTGCTG
GGATTATAGCCTCGCCGCTCCTGCTATTTGCCAACCGCCGGGACGTACGGCTGG
TGGACGCCGGCGGAGTCAAGCTGGAGTCCACCATCGTGGTCAGCGGCCTGGAG
GATGCGGCCGCAGTGGACTTCCAGTTTTCCAAGGGAGCCGTGTACTGGACAG
ACGGAGCGAGGAGGCCATCAAGCAGACCTACCTGAACCAGACGGGGCCGCC
GTGCAGAACGTGGTCATCTCCGGCCTGGTCTCTCCCGACGGCCTCGCCTGCGACT
GGGTGGGCAAGAAGCTGTACTGGACGGACTCAGAGACCAACCGCATCGAGGT
GGCCAACCTCAATGGCACATCCCGGAAGGTGCTCTTCTGGCAGGACCTTGACC
AGCCGAGGGCCATCGCCTTGGACCCCGCTCACGGGTACATGTACTGGACAGAC
TGGGGTGAGACGCCCCGGATTGAGCGGGCAGGGATGGATGGCAGCACCCGGA
AGATCATTGTGGACTCGGACATTTACTGGCCCAATGGACTGACCATCGACCT
GGAGGAGCAGAAGCTCTACTGGGCTGACGCCAAGCTCAGCTTCATCCACCGTG
CCAACCTGGACGGCTCGTTCCGGCAGAAGGTGGTGGAGGGCAGCCTGACGCAC
CCCTTCGCCCTGACGCTCTCCGGGGACACTCTGTACTGGACAGACTGGCAGACC
CGCTCCATCCATGCCTGCAACAAGCGCACTGGGGGGAAGAGGAAGGAGATCC
TGAGTGCCCTCTACTCACCCATGGACATCCAGGTGCTGAGCCAGGAGCGGCAG
CCTTTCTTCCACACTCGCTGTGAGGAGGACAATGGCGGCTGCTCCCACCTGTGC
CTGCTGTCCCCAAGCGAGCCTTTCTACACATGCGCCTGCCCCACGGGTGTGCAG
CTGCAGGACAACGGCAGGACGTGTAAGGCAGGAGCCGAGGAGGTGCTGCTGC
TGGCCCGGCGGACGGACCTACGGAGGATCTCGCTGGACACGCCGGACTTTACCG
ACATCGTGCTGCAGGTGGACGACATCCGGCACGCCATTGCCATCGACTACGAC
CCGCTAGAGGGCTATGTCTACTGGACAGATGACGAGGTGCGGGCCATCCGCAG
GGCGTACCTGGACGGGTCTGGGGCGCAGACGCTGGTCAACACCGAGATCAACG
ACCCCGATGGCATCGCGGTCGACTGGGTGGCCCGAAACCTCTACTGGACCGAC
ACGGGCACGGACCGCATCGAGGTGACGCGCCTCAACGGCACCTCCCGCAAGAT
CCTGGTGTCGGAGGACCTGGACGAGCCCCGAGCCATCGCACTGCACCCCGTGAT
GGGCCTCATGTACTGGACAGACTGGGGAGAGAACCCTAAAATCGAGTGTGCC
AACTTGGATGGGCAGGAGCGGCGTGTGCTGGTCAATGCCTCCCTCGGGTGCCC
AACGGCCTGGCCCTGGACCTGCAGGAGGGGAAGCTCTACTGGGGAGACGCCA
AGACAGACAAGATCGAGGTGATCAATGTTGATGGGACGAAGAGGCGGACC
CTCCTGGAGGACAAGCTCCCGCACATTTTCGGGTTCACGCTGCTGGGGACTTC
ATCTACTGGACTGACTGGCAGCGCCGCAGCATCGAGCGGGTGCACAAGGTCA
AGGCCAGCCGGGACGTCATCATTGACCAGCTGCCCGACCTGATGGGGCTCAAA
GCTGTGAATGTGGCCAAGGTCGTCGGAACCAACCCGTGTGCGGACAGGAACG
GGGGGTGCAGCCACCTGTGCTTCTTCACACCCCACGCAACCCGGTGTGGCTGCCC
CATCGGCCT
GGAGCTGCTGAGTGACATGAAGACCTGCATCGTGCCTGAGGCCTTCTTGGTCT
TCACCAGCAGAGCCGCCATCCACAGGATCTCCCTCGAGACCAATAACAACGA
CGTGGCCATCCCGCTCACGGGCGTCAAGGAGGCCTCAGCCCTGGACTTTGATGT
```

Figure 14(a-1)

```
GTCCAACAACCACATCTACTGGACAGACGTCAGCCTGAAGACCATCAGCCGC
GCCTTCATGAACGGGAGCTCGGTGGAGCACGTGGTGGAGTTTGGCCTTGACTA
CCCCGAGGGCATGGCCGTTGACTGGATGGGCAAGAACCTCTACTGGGCCGACA
CTGGGACCAACAGAATCGAAGTGGCGCGGCTGGACGGGCAGTTCCGGCAAGT
CCTCGTGTGGAGGGACTTGGACAACCCGAGGTCGCTGGCCCTGGATCCCACCA
AGGGCTACATCTACTGGACCGAGTGGGGCGGCAAGCCGAGGATCGTGCGGGCC
TTCATGGACGGGACCAACTGCATGA
CGCTGGTGGACAAGGTGGGCCGGGCCAACGACCTCACCATTGACTACGCTGAC
CAGCGCCTCTACTGGACCGACCTGGACACCAACATGATCGAGTCGTCCAACA
TGCTGGGTCAGGAGCGGGTCGTGATTGCCGACGATCTCCCGCACCCGTTCGGTC
TGACGCAGTACAGCGATTATATCTACTGGACAGACTGGAATCTGCACAGCA
TTGAGCGGGCCGACAAGACTAGCGGCCGGAACCGCACCCTCATCCAGGGCCAC
CTGGACTTCGTGATGGACATCCTGGTGTTCCACTCCTCCCGCCAGGATGGCCTC
AATGACTGTATGCACAACAACGGGCAGTGTGGGCAGCTGTGCCTTGCCATCC
CCGGCGGCCACCGCTGCGGCTGCGCCTCACACTACACCCTGGACCCCAGCAGCCG
CAACTGCAGCCCGCCCACCACCTTCTTGCTGTTCAGCCAGAAATCTGCCATCA
GTCGGATGATCCCGGACGACCAGCACAGCCCGGATCTCATCCTGCCCCTGCATG
GACTGAGGAACGTCAAAGCCATCGACTATGACCCACTGGACAAGTTCATCT
ACTGGGTGGATGGGCGCCAGAACATCAAGCGAGCCAAGGACGACGGGACCCA
GCCCTTTGTTTTGACCTCTCTGAGCCAAGGCCAAAACCCAGACAGGCAGCCCC
ACGACCTCAGCATCGACATCTACAGCCGGACACTGTTCTGGACGTGCGAGGCC
ACCAATACCATCAACGTCCACAGGCTGAGCGGGGAAGCCATGGGGGTGGTGC
TGCGTGGGGACCGCGACAAGCCCAGGGCCATCGTCGTCAACGCGGAGCGAGGG
TACCTGTACTTCACCAACATGCAGGACCGGGCAGCCAAGATCGAACGCGCAG
CCCTGGACGGCACCGAGCGCGAGGTCCTCTTCACCACCGGCCTCATCCGCCCTGT
GGCCCTGGTGGTAGACAACACACTGGGCAAGCTGTTCTGGGTGGACGC
GGACCTGAAGCGCATTGAGAGCTGTGACCTGTCAGGGGCCAACCGCCTGACCC
TGGAGGACGCCAACATCGTGCAGCCTCTGGGCCTGACCATCCTTGGCAAGCAT
CTCTACTGGATCGACCGCCAGCAGCAGATGATCGAGCGTGTGGAGAAGACCA
CCGGGGACAAGCGGACTCGCATCCAGGGCCGTGTCGCCCACCTCACTGGCATCC
ATGCAGTGGAGGAAGTCAGCCTGGAGGAGTTCTCAGCCCACCCATGTGCCCGT
GACAATGGTGGCTGCTCCCACATCTGTATTGCCAAGGGTGATGGGACACCAC
GGTGCTCATGCCCAGTCCACCTCGTGCTCCTGCAGAACCTGCTGACCTGTGGAG
AGCCGCCCACCTGCTCCCCGGACCAGTTTGCATGTGCCACAGGGGAGATCGACT
GTATCCCCGGGGCCTGGCGCTGTGACGGCTTTCCCGAGTGCGATGACCAGAGCG
ACGAGGAGGGCTGCCCCGTGTGCTCCGCCGCCCAGTTCCCCTGCGCGCGGGTCA
GTGTGTGGACCTGCGCCTGCGCTGCGACGGCGAGGCAGACTGTCAGGACCGCTC
AGACGAGGCGGACTGTGACGCCATCTGCCTGCCCAACCAGTTCCGGTGTGCGA
GCGGCCAGTGTGTCCTCATCAAACAGCAGTGCGACTCCTTCCCCGACTGTATC
GACGGCTCCGACGAGCTCATGTGTGAAATCACCAAGCCGCCCTCAGACGACA
GCCCGGCCCACAGCAGTGCCATCGGGCCCGTCATTGGCATCATCCTCTCTCTCTT
```

Figure 14(a-2)

CGTCATGGGTGGTGTCTATTTTGTGTGCCAGCGCGTGGTGTGCCAGCGCTATGC
GGGGGCCAACGGGCCCTTCCCGCACGAGTATGTCAGCGGGACCCCGCACGTGCC
CCTCAATTTCATAGCCCCGGGCGGTTCCCAGCATGGCCCCTTCACAGGCATCGC
ATGCGGAAAGTCCATGATGAGCTCCGTGAGCCTGATGGGGGCCGGGGCGGGG
TGCCCCTCTACGACCGGAACCACGTCACAGGGGCCTCGTCCAGCAGCTCGTCCA
GCACGAAGGCCACGCTGTACCCGCCGATCCTGAACCCGCCGCCCTCCCCGGCCAC
GGACCCCTCCCTGTACAACATGGACATGTTCTACTCTTCAAACATTCCGGCCA
CTGTGAGACCGTACAGGCCCTACATCATTCGAGGAATGGCGCCCCGACGACG
CCCTGCAGCACCGACGTGTGTGACAGCGACTACAGCGCCAGCCGCTGGAAGGC
CAGCAAGTACTACCTGGATTTGAACTCGGACTCAGACCCCTATCCACCCCCAC
CCACGCCCCACAGCCAGTACCTGTCGGCGGAGGACAGCTGCCCGCCCTCGCCCGC
CACCGAGAGGAGCTACTTCCATCTCTTCCCGCCCCCTCCGTCCCCCTGCACGGAC
TCATCCTGACCTCGGCCGGGCCACTCTGGCTTCTCTGTGCCCCTGTAAATAGTT
TTAAATATGAACAAAGAAAAAAATATATTTTATGATTTAAAAAATAA
ATATAATTGGGATTTTAAAAACATGAGAAATGTGAACTGTGATGGGGTG
GGCAGGGCTGGGAGAACTTTGTACAGTGGAACAAATATTTATAAACTTAA
TTTTGTAAAACAG (SEQ ID NO: 32)

Figure 15(a)

AGGCTGGTCTCAAACTCCTGGCCTTAAGTGATCTGCCCGCCTCGGCCTCCCAAA
GTGCTGAGATGACAGGTGTGAGCCACCGTGCCCGGCCCAGAACTCTTTAATTC
CCACCTGAAACTTGCCGCCTTAAGCAGGTCCCCAGTCTCCCTCCCCTAGTCCCT
GGTCCCACCATTCTGCTTTCTGTCTCAATGAATTTGCCTACCCCTCGCCGCTCCT
GCTATTTGCCAACCGCCGGGACGTACGGCTGGTGGACGCCGGCGGAGTCAAGC
TGGAGTCCACCATCGTGGTCAGCGGCCTGGAGGATGCGGCCGCAGTGGACTTCC
AGTTTTCCAAGGGAGCCGTGTACTGGACAGACGTGAGCGAGGAGGCCATCA
AGCAGACCTACCTGAACCAGACGGGGGCCGCCGTGCAGAACGTGGTCATCTCC
GGCCTGGTCTCTCCCGACGGCCTCGCCTGCGACTGGGTGGGCAAGAAGCTGTAC
TGGACGGACTCAGAGACCAACCGCATCGAGGTGGCCAACCTCAATGGCACAT
CCCGGAAGGTGCTCTTCTGGCAGGACCTTGACCAGCCGAGGGCCATCGCCTTGG
ACCCCGCTCACGGGTACATGTACTGGACAGACTGGGGTGAGACGCCCCGGATT
GAGCGGGCAGGGATGGATGGCAGCACCCGGAAGATCATTGTGGACTCGGACA
TTTACTGGCCCAATGGACTGACCATCGACCTGGAGGAGCAGAAGCTCTACTG
GGCTGACGCCAAGCTCAGCTTCATCCACCGTGCCAACCTGGACGGCTCGTTCCG
GCAGAAGGTGGTGGAGGGCAGCCTGACGCACCCCTTCGCCCTGACGCTCTCCGG
GGACACTCTGTACTGGACAGACTGGCAGACCCGCTCCATCCATGCCTGCAACA
AGCGCACTGGGGGGAAGAGGAAGGAGATCCTGAGTGCCCTCTACTCACCCAT
GGACATCCAGGTGCTGAGCCAGGAGCGGCAGCCTTTCTTCCACACTCGCTGTG
AGGAGGACAATGGCGGCTGCTCCCACCTGTGCCTGCTGTCCCCAAGCGAGCCTT
TCTACACATGCGCCTGCCCCACGGGTGTGCAGCTGCAGGACAACGGCAGGACG
TGTAAGGCAGGAGCCGAGGAGGTGCTGCTGCTGGCCCGGCGGACGGACCTACG
GAGGATCTCGCTGGACACGCCGGACTTTACCGACATCGTGCTGCAGGTGGACG
ACATCCGGCACGCCATTGCCATCGACTACGACCCGCTAGAGGGCTATGTCTAC
TGGACAGATGACGAGGTGCGGGCCATCCGCAGGGCGTACCTGGACGGGTCTGG
GGCGCAGACGCTGGTCAACACCGAGATCAACGACCCCGATGGCATCGCGGTCG
ACTGGGTGGCCCGAAACCTCTACTGGACCGACACGGGCACGGACCGCATCGAG
GTGACGCGCCTCAACGGCACCTCCCGCAAGATCCTGGTGTCGGAGGACCTGGA
CGAGCCCCGAGCCATCGCACTGCACCCGTGATGGCCTCATGTACTGGACAG
ACTGGGGAGAGAACCCTAAAATCGAGTGTGCCAACTTGGATGGGCAGGAGC
GGCGTGTGCTGGTCAATGCCTCCCTCGGGTGGCCCAACGGCCTGGCCCTGGACCT
GCAGGAGGGGAAGCTCTACTGGGGAGACGCCAAGACAGACAAGATCGAGGT
GATCAATGTTGATGGGACGAAGAGGCGGACCCTCCTGGAGGACAAGCTCCCG
CACATTTTCGGGTTCACGCTGCTGGGGGACTTCATCTACTGGACTGACTGGCA
GCGCCGCAGCATCGAGCGGGTGCACAAGGTCAAGGCCAGCCGGGACGTCATCA
TTGACCAGCTGCCCGACCTGATGGGCTCAAAGCTGTGAATGTGGCCAAGGTC
GTCGGAACCAACCCGTGTGCGGACAGGAACGGGGGTGCAGCCACCTGTGCTT
CTTCACACCCCACGCAACCCGGTGTGGCTGCCCATCGGCCTGGAGCTGCTGAG
TGACATGAAGACCTGCATCGTGCCTGAGGCCTTCTTGGTCTTCACCAGCAGAG

Figure 15(a-1)

```
CCGCCATCCACAGGATCTCCCTCGAGACCAATAACAACGACGTGGCCATCCCG
CTCACGGGCGTCAAGGAGGCCTCAGCCCTGGACTTTGATGTGTCCAACAACCA
CATCTACTGGACAGACGTCAGCCTGAAGACCATCAGCCGCGCCTTCATGAAC
GGGAGCTCGGTGGAGCACGTGGTGGAGTTTGGCCTTGACTACCCCGAGGGCAT
GGCCGTTGACTGGATGGGCAAGAACCTCTACTGGGCCGACACTGGGACCAAC
AGAATCGAAGTGGCGCGGCTGGACGGGCAGTTCCGGCAAGTCCTCGTGTGGAG
GGACTTGGACAACCCGAGGTCGCTGGCCCTGGATCCCACCAAGGGCTACATCT
ACTGGACCGAGTGGGGCGGCAAGCCGAGGATCGTGCGGGCCTTCATGGACGGG
ACCAACTGCATGACGCTGGTGGACAAGGTGGGCCGGGCCAACGACCTCACCA
TTGACTACGCTGACCAGCGCCTCTACTGGACCGACCTGGACACCAACATGATC
GAGTCGTCCAACATGCTGGGTCAGGAGCGGGTCGTGATTGCCGACGATCTCCC
GCACCCGTTCGGTCTGACGCAGTACAGCGATTATATCTACTGGACAGACTGG
AATCTGCACAGCATTGAGCGGGCCGACAAGACTAGCGGCCGGAACCGCACCC
TCATCCAGGGCCACCTGGACTTCGTGATGGACATCCTGGTGTTCCACTCCTCCC
GCCAGGATGGCCTCAATGACTGTATGCACAACAACGGGCAGTGTGGGCAGCT
GTGCCTTGCCATCCCCGGCGGCCACCGCTGCGGCTGCGCCTCACACTACACCCTG
GACCCCAGCAGCCGCAACTGCAGCCCGCCCACCACCTTCTTGCTGTTCAGCCAG
AAATCTGCCATCAGTCGGATGATCCCGGACGACCAGCACAGCCCGGATCTCA
TCCTGCCCCTGCATGGACTGAGGAACGTCAAAGCCATCGACTATGACCCACTG
GACAAGTTCATCTACTGGGTGGATGGGCGCCAGAACATCAAGCGAGCCAAG
GACGACGGGACCCAGCCCTTTGTTTTGACCTCTCTGAGCCAAGGCCAAAACCC
AGACAGGCAGCCCCACGACCTCAGCATCGACATCTACAGCCGGACACTGTTCT
GGACGTGCGAGGCCACCAATACCATCAACGTCCACAGGCTGAGCGGGGAAGC
CATGGGGGTGGTGCTGCGTGGGGACCGCGACAAGCCCAGGGCCATCGTCGTCA
ACGCGGAGCGAGGGTACCTGTACTTCACCAACATGCAGGACCGGGCAGCCAA
GATCGAACGCGCAGCCCTGGACGGCACCGAGCGCGAGGTCCTCTTCACCACCGG
CCTCATCCGCCCTGTGGCCCTGGTGGTAGACAACACACTGGGCAAGCTGTTCTG
GGTGGACGCGGACCTGAAGCGCATTGAGAGCTGTGACCTGTCAGGGGCCAACC
GCCTGACCCTGGAGGACGCCAACATCGTGCAGCCTCTGGGCCTGACCATCCTTG
GCAAGCATCTCTACTGGATCGACCGCCAGCAGCAGATGATCGAGCGTGTGGA
GAAGACCACCGGGGACAAGCGGACTCGCATCCAGGGCCGTGTCGCCCACCTCA
CTGGCATCCATGCAGTGGAGGAAGTCAGCCTGGAGGAGTTCTCAGCCCACCCA
TGTGCCCGTGACAATGGTGGCTGCTCCCACATCTGTATTGCCAAGGGTGATGG
GACACCACGGTGCTCATGCCCAGTCCACCTCGTGCTCCTGCAGAACCTGCTGAC
CTGTGGAGAGCCGCCCACCTGCTCCCCGGACCAGTTTGCATGTGCCACAGGGGA
GATCGACTGTATCCCCGGGGCCTGGCGCTGTGACGGCTTTCCCGAGTGCGATGA
CCAGAGCGACGAGGAGGGCTGCCCCGTGTGCTCCGCCGCCCAGTTCCCCTGCGCG
CGGGGTCAGTGTGTGGACCTGCGCCTGCGCTGCGACGGCGAGGCAGACTGTCAG
GACCGCTCAGACGAGGCGGACTGTGACGCCATCTGCCTGCCCAACCAGTTCCGG
TGTGCGAGCGGCCAGTGTGTCCTCATCAAACAGCAGTGCGACTCCTTCCCCGA
CTGTATCGACGGCTCCGACGAGCTCATGTGTGAAATCACCAAGCCGCCCTCAG
```

Figure 15(a-2)

```
ACGACAGCCCGGCCCACAGCAGTGCCATCGGGCCCGTCATTGGCATCATCCTCT
CTCTCTTCGTCATGGGTGGTGTCTATTTTGTGTGCCAGCGCGTGGTGTGCCAGC
GCTATGCGGGGGCCAACGGGCCCTTCCCGCACGAGTATGTCAGCGGGACCCCGC
ACGTGCCCCTCAATTTCATAGCCCCGGGCGGTTCCCAGCATGGCCCCTTCACAG
GCATCGCATGCGGAAAGTCCATGATGAGCTCCGTGAGCCTGATGGGGGGCCGG
GGCGGGGTGCCCCTCTACGACCGGAACCACGTCACAGGGGCCTCGTCCAGCAGC
TCGTCCAGCACGAAGGCCACGCTGTACCCGCGGATCCTGAACCCGCCGCCCTCCC
CGGCCACGGACCCCTCCCTGTACAACATGGACATGTTCTACTCTTCAAACATT
CCGGCCACTGCGAGACCGTACAGGCCCTACATCATTCGAGGAATGGCGCCCCC
GACGACGCCCTGCAGCACCGACGTGTGTGACAGCGACTACAGCGCCAGCCGCT
GGAAGGCCAGCAAGTACTACCTGGATTTGAACTCGGACTCAGACCCCTATCC
ACCCCCACCCACGCCCCACAGCCAGTACCTGTCGGCGGAGGACAGCTGCCCGCCC
TCGCCCGCCACCGAGAGGAGCTACTTCCATCTCTTCCCGCCCCCTCCGTCCCCCTG
CACGGACTCATCCTGACCTCGGCCGGGCCACTCTGGCTTCTCTGTGCCCTGTAA
ATAGTTTTAAATATGAACAAAGAAAAAAATATATTTTATGATTTAAA
AAATAAATATAATTGGGATTTTAAAAACATGAGAAATGTGAACTGTGA
TGGGGTGGGCAGGGCTGGGAGAACTTTGTACAGTGGAACAAATATTTATA
AACTTAATTTTGTAAAACAG (SEQ ID NO: 33)
```

Figure 15(b)

CAATGTCCAGTTCCGCTGCAGTTATAACATCCCATTTTTTGATTTCTTTTTA
TTTTTTCCTTTTTCTTTTTGAGATGGAGTCTCGCTCTGTCACCCAGGCTGGAGT
GCAATGGG (SEQ ID NO: 34)

Figure 16(a)

```
GCCGCGGCGCCCGAGGCGGGAGCAAGAGGCGCCGGGAGCCGCGAGGATCCACCG
CCGCCGCGCGCCATGGAGCCCGAGTGAGCGCGCGGCGCTCCCGGCCGCCGGAC
GACATGGAAACGGCGCCGACCCGGGCCCCTCCGCCGCCGCCGCCGCCGCTGCTGC
TGCTGGTGCTGTACTGCAGCTTGGTCCCCGCCGCGGCCTCACCGCTCCTGTTGTT
TGCCAACCGCCGGGATGTGCGGCTAGTGGATGCCGGCGGAGTGAAGCTGGAGT
CCACCATTGTGGCCAGTGGCCTGGAGGATGCAGCTGCTGTAGACTTCCAGTTC
TCCAAGGGTGCTGTGTACTGGACAGATGTGAGCGAGGAGGCCATCAAACAG
ACCTACCTGAACCAGACTGGAGGTGCTGCACAGAACATTGTCATCTCGGGCC
TCGTGTCACCTGATGGCCTGGCCTGTGACTGGGTTGGCAAGAAGCTGTACTGG
ACGGACTCCGAGACCAACCGCATTGAGGTTGCCAACCTCAATGGGACGTCCCG
TAAGGTTCTCTTCTGGCAGGACCTGGACCAGCCAAGGGCCATTGCCCTGGATC
CTGCACATGGGTACATGTACTGGACTGACTGGGGGGAAGCACCCCGGATCGA
GCGGGCAGGGATGGATGGCAGTACCCGGAAGATCATTGTAGACTCCGACATT
TACTGGCCCAATGGGCTGACCATCGACCTGGAGGAACAGAAGCTGTACTGGG
CCGATGCCAAGCTCAGCTTCATCCACCGTGCCAACCTGGACGGCTCCTTCCGGC
AGAAGGTGGTGGAGGGCAGCCTCACTCACCCTTTTGCCCTGACACTCTCTGGG
GACACACTCTACTGGACAGACTGGCAGACCCGCTCCATCCACGCCTGCAACA
AGTGGACAGGGGAGCAGAGGAAGGAGATCCTTAGTGCTCTGTACTCACCCA
TGGACATCCAAGTGCTGAGCCAGGAGCGGCAGCCTCCCTTCCACACACCATGC
GAGGAGGACAACGGTGGCTGTTCCCACCTGTGCCTGCTGTCCCCGAGGGAGCCT
TTCTACTCCTGTGCCTGCCCCACTGGTGTGCAGTTGCAGGACAATGGCAAGAC
GTGCAAGACAGGGGCTGAGGAAGTGCTGCTGCTGGCTCGGAGGACAGACCTG
AGGAGGATCTCTCTGGACACCCCTGACTTCACAGACATAGTGCTGCAGGTGG
GCGACATCCGGCATGCCATTGCCATTGACTACGATCCCCTGGAGGGCTACGTG
TACTGGACCGATGATGAGGTGCGGGCTATCCGCAGGGCGTACCTAGATGGCTC
AGGTGCGCAGACACTTGTGAACACTGAGATCAATGACCCCGATGGCATTGCT
GTGGACTGGGTCGCCCGGAACCTCTACTGGACAGATACAGGCACTGACAGAA
TTGAGGTGACTCGCCTCAACGGCACCTCCCGAAAGATCCTGGTATCTGAGGAC
CTGGACGAACCGCGAGCCATTGTGTTGCACCCTGTGATGGCCTCATGTACTG
GACAGACTGGGGGGAGAACCCCAAAATCGAATGCGCCAACCTAGATGGGAG
AGATCGGCATGTCCTGGTGAACACCTCCCTTGGGTGGCCCAATGGACTGGCCC
TGGACCTGCAGGAGGGCAAGCTGTACTGGGGGGATGCCAAAACTGATAAAA
TCGAGGTGATCAACATAGACGGG (SEQ ID NO: 35)
```

Figure 16(b)

```
GCCGCGGCGCCCGAGGCGGGAGCAAGAGGCGCCGGGAGCCGCGAGGATCCACCG
CCGCCGCGCGCCATGGAGCCCGAGTGAGCGCGCGGCGCTCCCGGCCGCCGGAC
GACATGGAAACGGCGCCGACCCGGGCCCCTCCGCCGCCGCCGCCGCTGCTGC
TGCTGGTGCTGTACTGCAGCTTGGTCCCCGCCGCGG (SEQ ID NO: 36)
```

Figure 16(c)

ATGGAAACGGCGCCGACCCGGGCCCCTCCGCCGCCGCCGCCGCCGCTGCTGCTGCT
GGTGCTGTACTGCAGCTTGGTCCCCGCCGCGGCCTCACCGCTCCTGTTGTTTGCC.
AACCGCCGGGATGTGCGGCTAGTGGATGCCGGCGGAGTGAAGCTGGAGTCCAC
CATTGTGGCCAGTGGCCTGGAGGATGCAGCTGCTGTAGACTTCCAGTTCTCCA
AGGGTGCTGTGTACTGGACAGATGTGAGCGAGGAGGCCATCAAACAGACCT
ACCTGAACCAGACTGGAGGTGCTGCACAGAACATTGTCATCTCGGGCCTCGT
GTCACCTGATGGCCTGGCCTGTGACTGGGTTGGCAAGAAGCTGTACTGGACGG
ACTCCGAGACCAACCGCATTGAGGTTGCCAACCTCAATGGGACGTCCCGTAA
GGTTCTCTTCTGGCAGGACCTGGACCAGCCAAGGGCCATTGCCCTGGATCCTGC
ACATGGGTACATGTACTGGACTGACTGGGGGGAAGCACCCCGGATCGAGCGG
GCAGGGATGGATGGCAGTACCCGGAAGATCATTGTAGACTCCGACATTTAC
TGGCCCAATGGGCTGACCATCGACCTGGAGGAACAGAAGCTGTACTGGGCCG
ATGCCAAGCTCAGCTTCATCCACCGTGCCAACCTGGACGGCTCCTTCCGGCAG
AAGGTGGTGGAGGGCAGCCTCACTCACCCTTTTGCCCTGACACTCTCTGGGGA
CACACTCTACTGGACAGACTGGCAGACCCGCTCCATCCACGCCTGCAACAAGT
GGACAGGGGAGCAGAGGAAGGAGATCCTTAGTGCTCTGTACTCACCCATGG
ACATCCAAGTGCTGAGCCAGGAGCGGCAGCCTCCCTTCCACACACCATGCGAG
GAGGACAACGGTGGCTGTTCCCACCTGTGCCTGCTGTCCCCGAGGGAGCCTTTC
TACTCCTGTGCCTGCCCCACTGGTGTGCAGTTGCAGGACAATGGCAAGACGTG
CAAGACAGGGGCTGAGGAAGTGCTGCTGCTGGCTCGGAGGACAGACCTGAGG
AGGATCTCTCTGGACACCCCTGACTTCACAGACATAGTGCTGCAGGTGGGCG
ACATCCGGCATGCCATTGCCATTGACTACGATCCCCTGGAGGGCTACGTGTAC
TGGACCGATGATGAGGTGCGGGCTATCCGCAGGGCGTACCTAGATGGCTCAGG
TGCGCAGACACTTGTGAACACTGAGATCAATGACCCCGATGGCATTGCTGTG
GACTGGGTCGCCCGGAACCTCTACTGGACAGATACAGGCACTGACAGAATTG
AGGTGACTCGCCTCAACGGCACCTCCCGAAAGATCCTGGTATCTGAGGACCTG
GACGAACCGCGAGCCATTGTGTTGCACCCTGTGATGGGCCTCATGTACTGGAC
AGACTGGGGGGAGAACCCCAAAATCGAATGCGCCAACCTAGATGGGAGAG
ATCGGCATGTCCTGGTGAACACCTCCCTTGGGTGGCCCAATGGACTGGCCCTGG
ACCTGCAGGAGGGCAAGCTGTACTGGGGGATGCCAAAACTGATAAAATCG
AGGTGATCAACATAGACGGG (SEQ ID NO: 37)

Figure 16(d)

METAPTRAPPPPPPPLLLLVLYCSLVPAAASPLLLFANRRDVRLVDAGGVK
LESTIVASGLEDAAAVDFQFSKGAVYWTDVSEEAIKQTYLNQTGGAAQNIVI
SGLVSPDGLACDWVGKKLYWTDSETNRIEVANLNGTSRKVLFWQDLDQPRA
IALDPAHGYMYWTDWGEAPRIERAGMDGSTRKIIVDSDIYWPNGLTIDLEE
QKLYWADAKLSFIHRANLDGSFRQKVVEGSLTHPFALTLSGDTLYWTDWQT
RSIHACNKWTGEQRKEILSALYSPMDIQVLSQERQPPFHTPCEEDNGGCSHLCL
LSPREPFYSCACPTGVQLQDNGKTCKTGAEEVLLLARRTDLRRISLDTPDFTDI
VLQVGDIRHAIAIDYDPLEGYVYWTDDEVRAIRRAYLDGSGAQTLVNTEIND
PDGIAVDWVARNLYWTDTGTDRIEVTRLNGTSRKILVSEDLDEPRAIVLHP
VMGLMYWTDWGENPKIECANLDGRDRHVLVNTSLGWPNGLALDLQEGKLY
WGDAKTDKIEVINIDG (SEQ ID NO: 8)

Figure 17(a)

```
CCTCGCCGCTCCTGCTATTTGCCAACCGCCGGGACGTACGGCTGGTGGACGCCGG
CGGAGTCAAGCTGGAGTCCACCATCGTGGTCAGCGGCCTGGAGGATGCGGCCG
CAGTGGACTTCCAGTTTTCCAAGGGAGCCGTGTACTGGACAGACGTGAGCGA
GGAGGCCATCAAGCAGACCTACCTGAACCAGACGGGGGCCGCCGTGCAGAAC
GTGGTCATCTCCGGCCTGGTCTCTCCCGACGGCCTCGCCTGCGACTGGGTGGGCA
AGAAGCTGTACTGGACGGACTCAGAGACCAACCGCATCGAGGTGGCCAACCT
CAATGGCACATCCCGGAAGGTGCTCTTCTGGCAGGACCTTGACCAGCCGAGGG
CCATCGCCTTGGACCCCGCTCACGGGTACATGTACTGGACAGACTGGGGTGAG
ACGCCCCGGATTGAGCGGGCAGGGATGGATGGCAGCACCCGGAAGATCATTG
TGGACTCGGACATTTACTGGCCCAATGGACTGACCATCGACCTGGAGGAGCA
GAAGCTCTACTGGGCTGACGCCAAGCTCAGCTTCATCCACCGTGCCAACCTGG
ACGGCTCGTTCCGGCAGAAGGTGGTGGAGGGCAGCCTGACGCACCCCTTCGCCC
TGACGCTCTCCGGGGACACTCTGTACTGGACAGACTGGCAGACCCGCTCCATCC
ATGCCTGCAACAAGCGCACTGGGGGGAAGAGGAAGGAGATCCTGAGTGCCCT
CTACTCACCCATGGACATCCAGGTGCTGAGCCAGGAGCGGCAGCCTTTCTTCC
ACACTCGCTGTGAGGAGGACAATGGCGGCTGCTCCCACCTGTGCCTGCTGTCCC
CAAGCGAGCCTTTCTACACATGCGCCTGCCCCACGGGTGTGCAGCTGCAGGAC
AACGGCAGGACGTGTAAGGCAGGAGCCGAGGAGGTGCTGCTGCTGGCCCGGCG
GACGGACCTACGGAGGATCTCGCTGGACACGCCGGACTTTACCGACATCGTGC
TGCAGGTGGACGACATCCGGCACGCCATTGCCATCGACTACGACCCGCTAGAG
GGCTATGTCTACTGGACAGATGACGAGGTGCGGGCCATCCGCAGGGCGTACCT
GGACGGGTCTGGGGCGCAGACGCTGGTCAACACCGAGATCAACGACCCCGATG
GCATCGCGGTCGACTGGGTGGCCCGAAACCTCTACTGGACCGACACGGGCACG
GACCGCATCGAGGTGACGCGCCTCAACGGCACCTCCCGCAAGATCCTGGTGTCG
GAGGACCTGGACGAGCCCCGAGCCATCGCACTGCACCCCGTGATGGGCCTCATG
TACTGGACAGACTGGGGAGAGAACCCTAAAATCGAGTGTGCCAACTTGGAT
GGGCAGGAGCGGCGTGTGCTGGTCAATGCCTCCCTCGGGTGGCCCAACGGCCTG
GCCCTGGACCTGCAGGAGGGGAAGCTCTACTGGGGAGACGCCAAGACAGACA
AGATCGAGGTGATCAATGTTGATGGGACGAAGAGGCGGACCCTCCTGGAGG
ACAAGCTCCCGCACATTTTCGGGTTCACGCTGCTGGGGGACTTCATCTACTGG
ACTGACTGGCAGCGCCGCAGCATCGAGCGGGTGCACAAGGTCAAGGCCAGCCG
GGACGTCATCATTGACCAGCTGCCCGACCTGATGGGGCTCAAAGCTGTGAAT
GTGGCCAAGGTCGTCGGAACCAACCCGTGTGCGGACAGGAACGGGGGGTGCA
GCCACCTGTGCTTCTTCACACCCCACGCAACCCGGTGTGGCTGCCCATCGGCCT
GGAGCTGCTGAGTGACATGAAGACCTGCATCGTGCCTGAGGCCTTCTTGGTCT
TCACCAGCAGAGCCGCCATCCACAGGATCTCCCTCGAGACCAATAACAACGA
CGTGGCCATCCCGCTCACGGGCGTCAAGGAGGCCTCAGCCCTGGACTTTGATGT
GTCCAACAACCACATCTACTGGACAGACGTCAGCCTGAAGACCATCAGCCGC
GCCTTCATGAACGGGAGCTCGGTGGAGCACGTGGTGGAGTTTGGCCTTGACTA
CCCCGAGGGCATGGCCGTTGACTGGATGGGCAAGAACCTCTACTGGGCCGACA
```

Figure 17(a-1)

```
CTGGGACCAACAGAATCGAAGTGGCGCGGCTGGACGGGCAGTTCCGGCAAGT
CCTCGTGTGGAGGGACTTGGACAACCCGAGGTCGCTGGCCCTGGATCCCACCA
AGGGCTACATCTACTGGACCGAGTGGGGCGGCAAGCCGAGGATCGTGCGGCC
TTCATGGACGGGACCAACTGCATGACGCTGGTGGACAAGGTGGGCCGGGCCA
ACGACCTCACCATTGACTACGCTGACCAGCGCCTCTACTGGACCGACCTGGAC
ACCAACATGATCGAGTCGTCCAACATGCTGGGTCAGGAGCGGGTCGTGATTG
CCGACGATCTCCCGCACCCGTTCGGTCTGACGCAGTACAGCGATTATATCTAC
TGGACAGACTGGAATCTGCACAGCATTGAGCGGGCCGACAAGACTAGCGGCC
GGAACCGCACCCTCATCCAGGGCCACCTGGACTTCGTGATGGACATCCTGGTG
TTCCACTCCTCCCGCCAGGATGGCCTCAATGACTGTATGCACAACAACGGGCA
GTGTGGGCAGCTGTGCCTTGCCATCCCCGGCGGCCACCGCTGCGGCTGCGCCTCA
CACTACACCCTGGACCCCAGCAGCCGCAACTGCAGCCCGCCCACCACCTTCTTG
CTGTTCAGCCAGAAATCTGCCATCAGTCGGATGATCCCGGACGACCAGCACA
GCCCGGATCTCATCCTGCCCCTGCATGGACTGAGGAACGTCAAAGCCATCGAC
TATGACCCACTGGACAAGTTCATCTACTGGGTGGATGGGCGCCAGAACATCA
AGCGAGCCAAGGACGACGGGACCCAGCCCTTTGTTTTGACCTCTCTGAGCCAA
GGCCAAAACCCAGACAGGCAGCCCCACGACCTCAGCATCGACATCTACAGCC
GGACACTGTTCTGGACGTGCGAGGCCACCAATACCATCAACGTCCACAGGCT
GAGCGGGGAAGCCATGGGGGTGGTGCTGCGTGGGGACCGCGACAAGCCCAGGG
CCATCGTCGTCAACGCGGAGCGAGGGTACCTGTACTTCACCAACATGCAGGA
CCGGGCAGCCAAGATCGAACGCGCAGCCCTGGACGGCACCGAGCGCGAGGTCC
TCTTCACCACCGGCCTCATCCGCCCTGTGGCCCTGGTGGTAGACAACACACTGG
GCAAGCTGTTCTGGGTGGACGCGGACCTGAAGCGCATTGAGAGCTGTGACCTG
TCAGGGGCCAACCGCCTGACCCTGGAGGACGCCAACATCGTGCAGCCTCTGGGC
CTGACCATCCTTGGCAAGCATCTCTACTGGATCGACCGCCAGCAGCAGATGA
TCGAGCGTGTGGAGAAGACCACCGGGGACAAGCGGACTCGCATCCAGGGCCG
TGTCGCCCACCTCACTGGCATCCATGCAGTGGAGGAAGTCAGCCTGGAGGAGT
TCTCAGCCCACCCATGTGCCCGTGACAATGGTGGCTGCTCCCACATCTGTATTG
CCAAGGGTGATGGGACACCACGGTGCTCATGCCCAGTCCACCTCGTGCTCCTGC
AGAACCTGCTGACCTGTGGAGAGCCGCCCACCTGCTCCCCGGACCAGTTTGCAT
GTGCCACAGGGGAGATCGACTGTATCCCCGGGGCCTGGCGCTGTGACGGCTTTC
CCGAGTGCGATGACCAGAGCGACGAGGAGGGCTGCCCCGTGTGCTCCGCCGCCC
AGTTCCCCTGCGCGCGGGGTCAGTGTGTGGACCTGCGCCTGCGCTGCGACGGCGA
GGCAGACTGTCAGGACCGCTCAGACGAGGCGGACTGTGACGCCATCTGCCTGC
CCAACCAGTTCCGGTGTGCGAGCGGCCAGTGTGTCCTCATCAAACAGCAGTGC
GACTCCTTCCCCGACTGTATCGACGGCTCCGACGAGCTCATGTGTGAAATCAC
CAAGCCGCCCTCAGACGACAGCCCGGCCCACAGCAGTGCCATCGGGCCCGTCAT
TGGCATCATCCTCTCTCTCTTCGTCATGGGTGGTGTCTATTTTGTGTGCCAGCG
CGTGGTGTGCCAGCGCTATGCGGGGGCCAACGGGCCCTTCCCGCACGAGTATGT
CAGCGGGACCCCGCACGTGCCCCTCAATTTCATAGCCCCGGGCGGTTCCCAGCA
TGGCCCCTTCACAGGCATCGCATGCGGAAAGTCCATGATGAGCTCCGTGAGCC
```

Figure 17(a-2)

```
TGATGGGGGGCCGGGGCGGGGTGCCCCTCTACGACCGGAACCACGTCACAGGGG
CCTCGTCCAGCAGCTCGTCCAGCACGAAGGCCACGCTGTACCCGCCGATCCTGA
ACCCGCCGCCCTCCCCGGCCACGGACCCCTCCCTGTACAACATGGACATGTTCT
ACTCTTCAAACATTCCGGCCACTGTGAGACCGTACAGGCCCTACATCATTCG
AGGAATGGCGCCCCCGACGACGCCCTGCAGCACCGACGTGTGTGACAGCGACT
ACAGCGCCAGCCGCTGGAAGGCCAGCAAGTACTACCTGGATTTGAACTCGGA
CTCAGACCCCTATCCACCCCCACCCACGCCCCACAGCCAGTACCTGTCGGCGGA
GGACAGCTGCCCGCCCTCGCCCGCCACCGAGAGGAGCTACTTCCATCTCTTCCCG
CCCCCTCCGTCCCCCTGCACGGACTCATCCTGACCTCGGCCGGGCCACTCTGGCTT
CTCTGTGCCCCTGTAAATAGTTTTAAATATGAACAAAGAAAAAAATATA
TTTTATGATTTAAAAAATAAATATAATTGGGATTTTAAAAACATGAGA
AATGTGAACTGTGATGGGGTGGGCAGGGCTGGGAGAACTTTGTACAGTGGA
ACAAATATTTATAAACTTAATTTTGTAAAACAG (SEQ ID NO: 38)
```

Figure 17(b)

```
                              SPLLLFANRRDVRLVDAGGVKLESTIV
VSGLEDAAAVDFQFSKGAVYWTDVSEEAIKQTYLNQTGAAVQNVVISGLVSPDGLAC
DWVGKKLYWTDSETNRIEVANLNGTSRKVLFWQDLDQPRAIALDPAHGYMYWTDW
GETPRIERAGMDGSTRKIIVDSDIYWPNGLTIDLEEQKLYWADAKLSFIHRANLDGSFR
QKVVEGSLTHPFALTLSGDTLYWTDWQTRSIHACNKRTGGKRKEILSALYSPMDIQVLS
QERQPFFHTRCEEDNGGCSHLCLLSPSEPFYTCACPTGVQLQDNGRTCKAGAEEVLLL
ARRTDLRRISLDTPDFTDIVLQVDDIRHAIAIDYDPLEGYVYWTDDEVRAIRRAYLDGS
GAQTLVNTEINDPDGIAVDWVARNLYWTDTGTDRIEVTRLNGTSRKILVSEDLDEPRAI
ALHPVMGLMYWTDWGENPKIECANLDGQERRVLVNASLGWPNGLALDLQEGKLYW
GDAKTDKIEVINVDGTKRRTLLEDKLPHIFGFTLLGDFIYWTDWQRRSIERVHKVKASR
DVIIDQLPDLMGLKAVNVAKVVGTNPCADRNGGCSHLCFFTPHATRCGCPIGLELLSD
MKTCIVPEAFLVFTSRAAIHRISLETNNNDVAIPLTGVKEASALDFDVSNNHIYWTDVSL
KTISRAFMNGSSVEHVVEFGLDYPEGMAVDWMGKNLYWADTGTNRIEVARLDGQFR
QVLVWRDLDNPRSLALDPTKGYIYWTEWGGKPRIVRAFMDGTNCMTLVDKVGRAND
LTIDYADQRLYWTDLDTNMIESSNMLGQERVVIADDLPHPFGLTQYSDYIYWTDWNL
HSIERADKTSGRNRTLIQGHLDFVMDILVFHSSRQDGLNDCMHNNGQCGQLCLAIPGG
HRCGCASHYTLDPSSRNCSPPTTFLLFSQKSAISRMIPDDQHSPDLILPLHGLRNVKAIDY
DPLDKFIYWVDGRQNIKRAKDDGTQPFVLTSLSQGQNPDRQPHDLSIDIYSRTLFWTCE
ATNTINVHRLSGEAMGVVLRGDRDKPRAIVVNAERGYLYFTNMQDRAAKIERAALDG
TEREVLFTTGLIRPVALVVDNTLGKLFWVDADLKRIESCDLSGANRLTLEDANIVQPLG
LTILGKHLYWIDRQQQMIERVEKTTGDKRTRIQGRVAHLTGIHAVEEVSLEEFSAHPCA
RDNGGCSHICIAKGDGTPRCSCPVHLVLLQNLLTCGEPPTCSPDQFACATGEIDCIPGA
WRCDGFPECDDQSDEEGCPVCSAAQFPCARGQCVDLRLRCDGEADCQDRSDEADCD
AICLPNQFRCASGQCVLIKQQCDSFPDCIDGSDELMCEITKPPSDDSPAHSSAIGPVIGIIL
SLFVMGGVYFVCQRVVCQRYAGANGPFPHEYVSGTPHVPLNFIAPGGSQHGPFTGIAC
GKSMMSSVSLMGGRGGVPLYDRNHVTGASSSSSSSTKATLYPPILNPPPSPATDPSLYN
MDMFYSSNIPATVRPYRPYIIRGMAPPTTPCSTDVCDSDYSASRWKASKYYLDLNSDSD
PYPPPPTPHSQYLSAEDSCPPSPATERSYFHLFPPPPSPCTDSS (SEQ ID NO: 39)
```

Figure 18(a)

```
GCCGCGGCGCCCGAGGCGGGAGCAAGAGGCGCCGGGAGCCGCGAGGATCCACCGCCGCCG
CGCGCGCCATGGAGCCCGAGTGAGCGCGCGGCGCTCCCGGCCGCCGGACGACATGGAAAC
GGCGCCGACCCGGGCCCCTCCGCCGCCGCCGCCGCTGCTGCTGCTGGTGCTGTACTG
CAGCTTGGTCCCCGCCGCGGCCTCACCGCTCCTGTTGTTTGCCAACCGCCGGGATGTGCG
GCTAGTGGATGCCGGCGGAGTGAAGCTGGAGTCCACCATTGTGGCCAGTGGCCTGGAGGA
TGCAGCTGCTGTAGACTTCCAGTTCTCCAAGGGTGCTGTGTACTGGACAGATGTGAGCGA
GGAGGCCATCAAACAGACCTACCTGAACCAGACTGGAGCTGCTGCACAGAACATTGTCAT
CTCGGGCCTCGTGTCACCTGATGGCCTGGCCTGTGACTGGGTTGGCAAGAAGCTGTACTG
GACGGACTCCGAGACCAACCGCATTGAGGTTGCCAACCTCAATGGGACGTCCCGTAAGGT
TCTCTTCTGGCAGGACCTGGACCAGCCAAGGGCCATTGCCCTGGATCCTGCACATGGGTA
CATGTACTGGACTGACTGGGGGAAGCACCCCGGATCGAGCGGGCAGGGATGGATGGCAG
TACCCGGAAGATCATTGTAGACTCCGACATTTACTGGCCCAATGGGCTGACCATCGACCT
GGAGGAACAGAAGCTGTACTGGGCCGATGCCAAGCTCAGCTTCATCCACGTGCCAACCT
GGACGGCTCCTTCCGGCAGAAGGTGGTGGAGGGCAGCCTCACTCACCCTTTTGCCCTGAC
ACTCTCTGGGGACACACTCTACTGGACAGACTGGCAGACCCGCTCCATCCACGCCTGCAA
CAAGTGGACAGGGGAGCAGAGGAAGGAGATCCTTAGTGCTCTGTACTCACCCATGGACAT
CCAAGTGCTGAGCCAGGAGCGGCAGCCTCCCTTCCACACACCATGCGAGGAGGACAACGG
TGGCTGTTCCCACCTGTGCCTGCTGTCCCCGAGGGAGCCTTTCTACTCCTGTGCCTGCCC
CACTGGTGTGCAGTTGCAGGACAATGGCAAGACGTGCAAGACAGGGGCTGAGGAAGTGCT
GCTGCTGGCTCGGAGGACAGACCTGAGGAGGATCTCTCTGGACACCCCTGACTTCACAGA
CATAGTGCTGCAGGTGGGCGACATCCGGCATGCCATTGCCATTGACTACGATCCCCTGGA
GGGCTACGTGTACTGGACCGATGATGAGGTGCGGGCTATCCGCAGGGCGTACCTAGATGG
CTCAGGTGCGCAGACACTTGTGAACACTGAGATCAATGACCCCGATGGCATTGCTGTGGA
CTGGGTCGCCCGGAACCTCTACTGGACAGATACAGGCACTGACAGAATTGAGGTGACTCG
CCTCAACGGCACCTCCCGAAAGATCCTGGTATCTGAGGACCTGGACGAACCGCGAGCCAT
TGTGTTGCACCCTGTGATGGGCCTCATGTACTGGACAGACTGGGGGGAGAACCCCAAAAT
CGAATGCGCCAACCTAGATGGGAGAGATCGGCATGTCCTGGTGAACACCTCCCTTGGGTG
GCCCAATGGACTGGCCCTGGACCTGCAGGAGGGCAAGCTGTACTGGGGGGATGCCAAAAC
TGATAAAATCGAGGTGATCAACATAGACGGGACAAAGCGGAAGACCCTGCTTGAGGACAA
GCTCCCACACATTTTTGGGTTCACACTGCTGGGGGACTTCATCTACTGGACCGACTGGCA
GAGACGCAGTATTGAAAGGGTCCACAAGGTCAAGGCCAGCCGGGATGTCATCATTGATCA
ACTCCCCGACCTGATGGGACTCAAAGCCGTGAATGTGGCCAAGGTTGTCGGAACCAACCC
ATGTGCGGATGGAAATGGAGGGTGCAGCCATCTGTGCTTCTTCACCCCACGTGCCACCAA
GTGTGGCTGCCCCATTGGCCTGGAGCTGTTGAGTGACATGAAGACCTGCATAATCCCCGA
GGCCTTCCGGTATTCACCAGCAGAGCCACCATCCACAGGATCTCCCTGGAGACTAACAAC
AACGATGTGGCTATCCCACTCACGGGTGTCAAAGAGGCCTCTGCACTGGACTTTGATGTG
TCCAACAATCACATCTACTGGACTGATGTTAGCCTCAAGACGATCAGCCGAGCCTTCATG
AATGGGAGCTCAGTGGAGCACGTGATTGAGTTTGGCCTCGACTACCCTGAAGGAATGGCT
GTGGACTGGATGGGCAAGAACCTCTATTGGCGGACACAGGGACCAACAGGATTGAGGTG
GCCCGGCTGGATGGGCAGTTCCGGCAGGTGCTTGTGGAGAGACCTTGACAACCCCAGG
TCTCTGGCTCTGGATCCTACTAAAGGCTACATCTACTGGACTGAGTGGGGTGGCAAGCCA
AGGATTGTGCGGGCCTTCATGGATGGGACCAATTGTATGACACTGGTAGACAAGGTGGGC
CGGGCCAACGACCTCACCATTGATTATGCCGACCAGCGACTGTACTGGACTGACCTGGAC
ACCAACATGATTGAGTCTTCCAACATGCTGGGTCAGGAGCGCATGGTGATAGCTGACGAT
CTGCCCTACCCGTTTGGCCTGACTCAATATAGCGATTACATCTACTGGACTGACTGGAAC
CTGCATAGCATTGAACGGGCGGACAAGACCAGTGGGCGGAACCGCACCCTCATCCAGGGT
CACCTGGACTTCGTCATGGACATCCTGGTGTTCCACTCCTCCCGTCAGGATGGCCTCAAC
```

Figure 18(a-1)

```
GACTGCGTGCACAGCAATGGCCAGTGTGGGCAGCTGTGCCTCGCCATCCCCGGAGGCCAC
CGCTGTGGCTGTGCTTCACACTACACGCTGGACCCCAGCAGCCGCAACTGCAGCCCGCCC
TCCACCTTCTTGCTGTTCAGCCAGAAATTTGCCATCAGCCGGATGATCCCCGATGACCAG
CTCAGCCCGGACCTTGTCCTACCCCTTCATGGGCTGAGGAACGTCAAAGCCATCAACTAT
GACCCGCTGGACAAGTTCATCTACTGGGTGGACGGGCGCCAGAACATCAAGAGGGCCAAG
GACGACGGTACCCAGCCCTCCATGCTGACCTCTCCCAGCCAAAGCCTGAGCCCAGACAGA
CAGCCACACGACCTCAGCATTGACATCTACAGCCGGACACTGTTCTGGACCTGTGAGGCC
ACCAACACTATCAATGTCCACCGGCTGGATGGGGATGCCATGGGAGTGGTGCTTCGAGGG
GACCGTGACAAGCCAAGGGCCATTGCTGTCAATGCTGAGCGAGGGTACATGTACTTTACC
AACATGCAGGACCATGCTGCCAAGATCGAGCGAGCCTCCCTGGATGGCACAGAGCGGGAG
GTCCTCTTCACCACAGGCCTCATCCGTCCCGTGGCCCTTGTGGTGGACAATGCTCTGGGC
AAGCTCTTCTGGGTGGATGCCGACCTAAAGCGAATCGAAAGCTGTGACCTCTCTGGGGCC
AACCGCCTGACCCTGGAAGATGCCAACATCGTACAGCCAGTAGGTCTGACAGTGCTGGGC
AGGCACCTCTACTGGATCGACCGCCAGCAGCAGATGATCGAGCGCGTGGAGAAGACCACT
GGGGACAAGCGGACTAGGGTTCAGGGCCGTGTCACCCACCTGACAGGCATCCATGCCGTG
GAGGAAGTCAGCCTGGAGGAGTTCTCAGCCCATCCTTGTGCCCGAGACAATGGCGGCTGC
TCCCACATCTGTATCGCCAAGGGTGATGGAACACCGCGCTGCTCGTGCCCTGTCCACCTG
GTGCTCCTGCAGAACCTGCTGACTTGTGGTGAGCCTCCTACCTGCTCCCCTGATCAGTTT
GCATGTACCACTGGTGAGATCGACTGCATCCCCGGAGCCTGGCGCTGTGACGGCTTCCCT
GAGTGTGCTGACCAGAGTGATGAAGAAGGCTGCCCAGTGTGCTCCGCCTCTCAGTTCCCC
TGCGCTCGAGGCCAGTGTGTGGACCTGCGGTTACGCTGCGACGGTGAGGCCGACTGCCAG
GATCGCTCTGATGAAGTAACTGCGATGCTGTCTGTCTGCCCAATCAGTTCCGGTGCACCA
GCGGCCAGTGTGTCCTCATCAAGCAACAGTGTGACTCCTTCCCCGACTGTGCTGATGGGT
CTGATGAGCTCATGTGTGAAATCAACAAGCCACCCTCTGATGACATCCCAGCCCACAGCA
GTGCCATTGGGCCCGTCATTGGTATCATCCTCTCCCTCTTCGTCATGGGCGGGGTCTACT
TTGTCTGCCAGCGTGTGATGTGCCAGCGCTACACAGGGGCCAGTGGGCCCTTTCCCCACG
AGTATGTTGGTGGAGCCCCTCATGTGCCTCTCAACTTCATAGCCCCAGGTGGCTCACAGC
ACGGTCCCTTCCCAGGCATCCCGTGCAGCAAGTCCGTGATGAGCTCCATGAGCCTGGTGG
GGGGGCGCGGCAGCGTGCCCCTCTATGACCGGAATCACGTCACTGGGGCCTCATCCAGCA
GCTCGTCCAGCACAAAGGCCACACTATATCCGCCGATCCTGAACCCACCCCGTCCCCGG
CCACAGACCCCTCTCTCTACAACGTGGACGTGTTTTATTCTTCAGGCATCCCGGCCACCG
CTAGACCATACAGGCCCTACGTCATTCGAGGTATGGCACCCCAACAACACCGTGCAGCA
CAGATGTGTGTGACAGTGACTACAGCATCAGTCGCTGGAAGAGCAGCAAATACTACCTGG
ACTTGAATTCGGACTCAGACCCCTACCCCCCCCGCCCACCCCCACAGCCAGTACCTAT
CTGCAGAGGACAGCTGCCCACCCTCACCAGGCACTGAGAGGAGTTACTGCCACCTCTTCC
CGCCCCCACCGTCCCCCTGCACGGACTCGTCCTGACCTCGGCCGTCCACCCGGCCCTGCT
GCCTCCCTGTAAATATTTTAAATATGAACAAAGGAAAATATATTTTATGATTTAAAAA
ATAAATATAATTGGGGTTTTTAACAAGTGAGAAATGTGAGCGGTGAAGGGGTGGGCAGGG
CTGGGAAACTTTTCTAG (SEQ ID NO: 40)
```

Figure 18(b)

```
ATGGAAACGGCGCCGACCCGGGCCCCTCCGCCGCCGCCGCCGCTGCTGCTGCTGGTG
CTGTACTGCAGCTTGGTCCCCGCCGCGGCCTCACCGCTCCTGTTGTTTGCCAACCGCCGG
GATGTGCGGCTAGTGGATGCCGGCGGAGTGAAGCTGGAGTCCACCATTGTGGCCAGTGGC
CTGGAGGATGCAGCTGCTGTAGACTTCCAGTTCTCCAAGGGTGCTGTGTACTGGACAGAT
GTGAGCGAGGAGGCCATCAAACAGACCTACCTGAACCAGACTGGAGCTGCTGCACAGAAC
ATTGTCATCTCGGGCCTCGTGTCACCTGATGGCCTGGCCTGTGACTGGGTTGGCAAGAAG
CTGTACTGGACGGACTCCGAGACCAACCGCATTGAGGTTGCCAACCTCAATGGGACGTCC
CGTAAGGTTCTCTTCTGGCAGGACCTGGACCAGCCAAGGGCCATTGCCCTGGATCCTGCA
CATGGGTACATGTACTGGACTGACTGGGGGGAAGCACCCCGGATCGAGCGGGCAGGGATG
GATGGCAGTACCCGGAAGATCATTGTAGACTCCGACATTTACTGGCCCAATGGGCTGACC
ATCGACCTGGAGGAACAGAAGCTGTACTGGGCCGATGCCAAGCTCAGCTTCATCCACCGT
GCCAACCTGGACGGCTCCTTCCGGCAGAAGGTGGTGGAGGGCAGCCTCACTCACCCTTTT
GCCCTGACACTCTCTGGGGACACACTCTACTGGACAGACTGGCAGACCCGCTCCATCCAC
GCCTGCAACAAGTGGACAGGGGAGCAGAGGAAGGAGATCCTTAGTGCTCTGTACTCACCC
ATGGACATCCAAGTGCTGAGCCAGGAGCGGCAGCCTCCCTTCCACACACCATGCGAGGAG
GACAACGGTGGCTGTTCCCACCTGTGCCTGCTGTCCCCGAGGGAGCCTTTCTACTCCTGT
GCCTGCCCCACTGGTGTGCAGTTGCAGGACAATGGCAAGACGTGCAAGACAGGGGCTGAG
GAAGTGCTGCTGCTGGCTCGGAGGACAGACCTGAGGAGGATCTCTCTGGACACCCCTGAC
TTCACAGACATAGTGCTGCAGGTGGGCGACATCCGGCATGCCATTGCCATTGACTACGAT
CCCCTGGAGGGCTACGTGTACTGGACCGATGATGAGGTGCGGGCTATCCGCAGGGCGTAC
CTAGATGGCTCAGGTGCGCAGACACTTGTGAACACTGAGATCAATGACCCCGATGGCATT
GCTGTGGACTGGGTCGCCCGGAACCTCTACTGGACAGATACAGGCACTGACAGAATTGAG
GTGACTCGCCTCAACGGCACCTCCCGAAAGATCCTGGTATCTGAGGACCTGGACGAACCG
CGAGCCATTGTGTTGCACCCTGTGATGGGCCTCATGTACTGGACAGACTGGGGGGAGAAC
CCCAAAATCGAATGCGCCAACCTAGATGGGAGAGATCGGCATGTCCTGGTGAACACCTCC
CTTGGGTGGCCCAATGGACTGGCCCTGGACCTGCAGGAGGGCAAGCTGTACTGGGGGGAT
GCCAAAACTGATAAAATCGAGGTGATCAACATAGACGGGACAAAGCGGAAGACCCTGCTT
GAGGACAAGCTCCCACACATTTTTGGGTTCACACTGCTGGGGACTTCATCTACTGGACC
GACTGGCAGAGACGCAGTATTGAAAGGGTCCACAAGGTCAAGGCCAGCCGGGATGTCATC
ATTGATCAACTCCCCGACCTGATGGGACTCAAAGCCGTGAATGTGGCCAAGGTTGTCGGA
ACCAACCCATGTGCGGATGGAAATGGAGGGTGCAGCCATCTGTGCTTCTTCACCCCACGT
GCCACCAAGTGTGGCTGCCCCATTGGCCTGGAGCTGTTGAGTGACATGAAGACCTGCATA
ATCCCCGAGGCCTTCCTGGTATTCACCAGCAGAGCCACCATCCACAGGATCTCCCTGGAG
ACTAACAACAACGATGTGGCTATCCCACTCACGGGTGTCAAAGAGGCCTCTGCACTGGAC
TTTGATGTTCCAACAATCACATCTACTGGACTGATGTTAGCCTCAAGACGATCAGCCGAG
CCTTCATGAATGGGAGCTCAGTGGAGCACGTGATTGAGTTTGGCCTCGACTACCCTGAAG
GAATGGCTGTGGACTGGATGGGCAAGAACCTCTATTGGGCGGACACAGGGACCAACAGGA
TTGAGGTGGCCCGGCTGGATGGGCAGTTCCGGCAGGTGCTTGTGTGGAGAGACCTTGACA
ACCCCAGGTCTCTGGCTCTGGATCCTACTAAAGGCTACATCTACTGGACTGAGTGGGGTG
GCAAGCCAAGGATTGTGCGGGCCTTCATGGATGGGACCAATTGTATGACACTGGTAGACA
AGGTGGGCCGGGCCAACGACCTCACCATTGATTATGCCGACCAGCGACTGTACTGGACTG
ACCTGGACACCAACATGATTGAGTCTTCCAACATGCTGGGTCAGGAGCGCATGGTGATAG
CTGACGATCTGCCCTACCCGTTTGGCCTGACTCAATATAGCGATTACATCTACTGGACTG
ACTGGAACCTGCATAGCATTGAACGGCGGACAAGACCAGTGGGCGGAACCGCACCCTCA
TCCAGGGTCACCTGGACTTCGTCATGGACATCCTGGTGTTCCACTCCTCCCGTCAGGATG
GCCTCAACGACTGCGTGCACAGCAATGGCCAGTGTGGGCAGCTGTGCCTCGCCATCCCCG
GAGGCCACCGCTGTGGCTGTGCTTCACACTACACGCTGGACCCCAGCAGCCGCAACTGCA
```

Figure 18(b-1)

```
GCCCGCCCTCCACCTTCTTGCTGTTCAGCCAGAAATTTGCCATCAGCCGGATGATCCCCG
ATGACCAGCTCAGCCCGGACCTTGTCCTACCCCTTCATGGGCTGAGGAACGTCAAAGCCA
TCAACTATGACCCGCTGGACAAGTTCATCTACTGGGTGGACGGGCGCCAGAACATCAAGA
GGGCCAAGGACGACGGTACCCAGCCCTCCATGCTGACCTCTCCCAGCCAAAGCCTGAGCC
CAGACAGACAGCCACACGACCTCAGCATTGACATCTACAGCCGGACACTGTTCTGGACCT
GTGAGGCCACCAACACTATCAATGTCCACCGGCTGGATGGGGATGCCATGGGAGTGGTGC
TTCGAGGGGACCGTGACAAGCCAAGGGCCATTGCTGTCAATGCTGAGCGAGGGTACATGT
ACTTTACCAACATGCAGGACCATGCTGCCAAGATCGAGCGAGCCTCCCTGGATGGCACAG
AGCGGGAGGTCCTCTTCACCACAGGCCTCATCCGTCCCGTGGCCCTTGTGGTGGACAATG
CTCTGGGCAAGCTCTTCTGGGTGGATGCCGACCTAAAGCGAATCGAAAGCTGTGACCTCT
CTGGGGCCAACCGCCTGACCCTGGAAGATGCCAACATCGTACAGCCAGTAGGTCTGACAG
TGCTGGGCAGGCACCTCTACTGGATCGACCGCCAGCAGCAGATGATCGAGCGCGTGGAGA
AGACCACTGGGGACAAGCGGACTAGGGTTCAGGGCCGTGTCACCCACCTGACAGGCATCC
ATGCCGTGGAGGAAGTCAGCCTGGAGGAGTTCTCAGCCCATCCTTGTGCCCGAGACAATG
GCGGCTGCTCCCACATCTGTATCGCCAAGGGTGATGGAACACCGCGCTGCTCGTGCCCTG
TCCACCTGGTGCTCCTGCAGAACCTGCTGACTTGTGGTGAGCCTCCTACCTGCTCCCCTG
ATCAGTTTGCATGTACCACTGGTGAGATCGACTGCATCCCCGGAGCCTGGCGCTGTGACG
GCTTCCCTGAGTGTGCTGACCAGAGTGATGAAGAAGGCTGCCCAGTGTGCTCCGCCTCTC
AGTTCCCCTGCGCTCGAGGCCAGTGTGTGGACCTGCGGTTACGCTGCGACGGTGAGGCCG
ACTGCCAGGATCGCTCTGATGAAGCTAACTGCGATGCTGTCTGTCTGCCCAATCAGTTCC
GGTGCACCAGCGGCCAGTGTGTCCTCATCAAGCAACAGTGTGACTCCTTCCCCGACTGTG
CTGATGGGTCTGATGACTCATGTGTGAAATCAACAAGCCACCCTCTGATGACATCCCAGC
CCACAGCAGTGCCATTGGGCCCGTCATTGGTATCATCCTCTCCCTCTTCGTCATGGGCGG
GGTCTACTTTGTCTGCCAGCGTGTGATGTGCCAGCGCTACACAGGGGCCAGTGGGCCCTT
TCCCCACGAGTATGTTGGTGGAGCCCCTCATGTGCCTCTCAACTTCATAGCCCCAGGTGG
CTCACAGCACGGTCCCTTCCCAGGCATCCCGTGCAGCAAGTCCGTGATGAGCTCCATGAG
CCTGGTGGGGGGCGCGGCAGCGTGCCCCTCTATGACCGGAATCACGTCACTGGGGCCTC
ATCCAGCAGCTCGTCCAGCACAAAGGCCACACTATATCCGCCGATCCTGAACCCACCCCC
GTCCCCGGCCACAGACCCCTCTCTCTACAACGTGGACGTGTTTTATTCTTCAGGCATCCC
GGCCACCGCTAGACCATACAGGCCCTACGTCATTCGAGGTATGGCACCCCAACAACACC
GTGCAGCACAGATGTGTGTGACAGTGACTACAGCATCAGTCGCTGGAAGAGCAGCAAATA
CTACCTGGACTTGAATTCGGACTCAGACCCCTACCCCCCCCCGCCCACCCCCACAGCCA
GTACCTATCTGCAGAGGACAGCTGCCCACCCTCACCAGGCACTGAGAGGAGTTACTGCCA
CCTCTTCCCGCCCCCACCGTCCCCCTGCACGGACTCGTCCTGA  (SEQ ID NO: 41)
```

Figure 18(c)

```
   1  METAPTRAPP  PPPPPLLLLV  LYCSLVPAAA  SPLLLFANRR  DVRLVDAGGV
  51  KLESTIVASG  LEDAAAVDFQ  FSKGAVYWTD  VSEEAIKQTY  LNQTGAAAQN
 101  IVISGLVSPD  GLACDWVGKK  LYWTDSETNR  IEVANLNGTS  RKVLFWQDLD
 151  QPRAIALDPA  HGYMYWTDWG  EAPRIERAGM  DGSTRKIIVD  SDIYWPNGLT
 201  IDLEEQKLYW  ADAKLSFIHR  ANLDGSFRQK  VVEGSLTHPF  ALTLSGDTLY
 251  WTDWQTRSIH  ACNKWTGEQR  KEILSALYSP  MDIQVLSQER  QPPFHTPCEE
 301  DNGGCSHLCL  LSPREPFYSC  ACPTGVQLQD  NGKTCKTGAE  EVLLLARRTD
 351  LRRISLDTPD  FTDIVLQVGD  IRHAIAIDYD  PLEGYVYWTD  DEVRAIRRAY
 401  LDGSGAQTLV  NTEINDPDGI  AVDWVARNLY  WTDTGTDRIE  VTRLNGTSRK
 451  ILVSEDLDEP  RAIVLHPVMG  LMYWTDWGEN  PKIECANLDG  RDRHVLVNTS
 501  LGWPNGLALD  LQEGKLYWGD  AKTDKIEVIN  IDGTKRKTLL  EDKLPHIFGF
 551  TLLGDFIYWT  DWQRRSIERV  HKVKASRDVI  IDQLPDLMGL  KAVNVAKVVG
 601  TNPCADGNGG  CSHLCFFTPR  ATKCGCPIGL  ELLSDMKTCI  IPEAFLVFTS
 651  RATIHRISLE  TNNNDVAIPL  TGVKEASALD  FDVSNNHIYW  TDVSLKTISR
 701  AFMNGSSVEH  VIEFGLDYPE  GMAVDWMGKN  LYWADTGTNR  IEVARLDGQF
 751  RQVLVWRDLD  NPRSLALDPT  KGYIYWTEWG  GKPRIVRAFM  DGTNCMTLVD
 801  KVGRANDLTI  DYADQRLYWT  DLDTNMIESS  NMLGQERMVI  ADDLPYPFGL
 851  TQYSDYIYWT  DWNLHSIERA  DKTSGRNRTL  IQGHLDFVMD  ILVFHSSRQD
 901  GLNDCVHSNG  QCGQLCLAIP  GGHRCGCASH  YTLDPSSRNC  SPPSTFLLFS
 951  QKFAISRMIP  DDQLSPDLVL  PLHGLRNVKA  INYDPLDKFI  YWVDGRQNIK
1001  RAKDDGTQPS  MLTSPSQSLS  PDRQPHDLSI  DIYSRTLFWT  CEATNTINVH
1051  RLDGDAMGVV  LRGDRDKPRA  IAVNAERGYM  YFTNMQDHAA  KIERASLDGT
1101  EREVLFTTGL  IRPVALVVDN  ALGKLFWVDA  DLKRIESCDL  SGANRLTLED
1151  ANIVQPVGLT  VLGRHLYWID  RQQQMIERVE  KTTGDKRTRV  QGRVTHLTGI
1201  HAVEEVSLEE  FSAHPCARDN  GGCSHICIAK  GDGTPRCSCP  VHLVLLQNLL
1251  TCGEPPTCSP  DQFACTTGEI  DCIPGAWRCD  GFPECADQSD  EEGCPVCSAS
1301  QFPCARGQCV  DLRLRCDGEA  DCQDRSDEAN  CDAVCLPNQF  RCTSGQCVLI
1351  KQQCDSFPDC  ADGSDELMCE  INKPPSDDIP  AHSSAIGPVI  GIILSLFVMG
1401  GVYFVCQRVM  CQRYTGASGP  FPHEYVGGAP  HVPLNFIAPG  GSQHGPFPGI
1451  PCSKSVMSSM  SLVGGRGSVP  LYDRNHVTGA  SSSSSSSTKA  TLYPPILNPP
1501  PSPATDPSLY  NVDVFYSSGI  PATARPYRPY  VIRGMAPPTT  PCSTDVCDSD
1551  YSISRWKSSK  YYLDLNSDSD  PYPPPPTPHS  QYLSAEDSCP  PSPGTERSYC
1601  HLFPPPPSPC  TDSS        (SEQ ID NO: 42)
```

Figure 18(d)

```
  1 METAPTRAPPPPPPPLLLLVLYCSL.VPAAASPLLLFANRRDVRLVDAGG  49
    || ||   | |    ||||. |    ||||||||||||||||||||||||
  1 MEAAPPGPPWPLLLLLLLLLALCGCPAPAAASPLLLFANRRDVRLVDAGG  50

50 VKLESTIVASGLEDAAAVDFQFSKGAVYWTDVSEEAIKQTYLNQTGAAAQ  99
    ||||||||  |||||||||||||||||||||||||||||||||||||| |
 51 VKLESTIVVSGLEDAAAVDFQFSKGAVYWTDVSEEAIKQTYLNQTGAAVQ 100

100 NIVISGLVSPDGLACDWVGKKLYWTDSETNRIEVANLNGTSRKVLFWQDL 149
    |:||||||||||||||||||||||||||||||||||||||||||||||||
101 NVVISGLVSPDGLACDWVGKKLYWTDSETNRIEVANLNGTSRKVLFWQDL 150

150 DQPRAIALDPAHGYMYWTDWGEAPRIERAGMDGSTRKIIVDSDIYWPNGL 199
    ||||||||||||||||||||||| |||||||||||||||||||||||||
151 DQPRAIALDPAHGYMYWTDWGETPRIERAGMDGSTRKIIVDSDIYWPNGL 200

200 TIDLEEQKLYWADAKLSFIHRANLDGSFRQKVVEGSLTHPFALTLSGDTL 249
    ||||||||||||||||||||||||||||||||||||||||||||||||||
201 TIDLEEQKLYWADAKLSFIHRANLDGSFRQKVVEGSLTHPFALTLSGDTL 250

250 YWTDWQTRSIHACNKWTGEQRKEILSALYSPMDIQVLSQERQPPFHTPCE 299
    |||||||||||||| || .|||||||||||||||||||||||| ||| ||
251 YWTDWQTRSIHACNKRTGGKRKEILSALYSPMDIQVLSQERQPFFHTRCE 300

300 EDNGGCSHLCLLSPREPFYSCACPTGVQLQDNGKTCKTGAEEVLLLARRT 349
    ||||||||||||| ||||.|||||||||||||:||| |||||||||||||
301 EDNGGCSHLCLLSPSEPFYTCACPTGVQLQDNGRTCKAGAEEVLLLARRT 350

350 DLRRISLDTPDFTDIVLQVGDIRHAIAIDYDPLEGYVYWTDDEVRAIRRA 399
    |||||||||||||||||||| |||||||||||||||||||||||||||||
351 DLRRISLDTPDFTDIVLQVDDIRHAIAIDYDPLEGYVYWTDDEVRAIRRA 400

400 YLDGSGAQTLVNTEINDPDGIAVDWVARNLYWTDTGTDRIEVTRLNGTSR 449
    ||||||||||||||||||||||||||||||||||||||||||||||||||
401 YLDGSGAQTLVNTEINDPDGIAVDWVARNLYWTDTGTDRIEVTRLNGTSR 450

450 KILVSEDLDEPRAIVLHPVMGLMYWTDWGENPKIECANLDGRDRHVLVNT 499
    |||||||||||||| ||||||||||||||||||||||||||||.:| ||||
451 KILVSEDLDEPRAIALHPVMGLMYWTDWGENPKIECANLDGQERRVLVNA 500

500 SLGWPNGLALDLQEGKLYWGDAKTDKIEVINIDGTKRKTLLEDKLPHIFG 549
    |||||||||||||||||||||||||||||||:|||||:||||||||||||
501 SLGWPNGLALDLQEGKLYWGDAKTDKIEVINVDGTKRRTLLEDKLPHIFG 550

550 FTLLGDFIYWTDWQRRSIERVHKVKASRDVIIDQLPDLMGLKAVNVAKVV 599
    ||||||||||||||||||||||||||||||||||||||||||||||||||
551 FTLLGDFIYWTDWQRRSIERVHKVKASRDVIIDQLPDLMGLKAVNVAKVV 600
```

Figure 18(d-1)

```
600  GTNPCADGNGGCSHLCFFTPRATKCGCPIGLELLSDMKTCIIPEAFLVFT 649
     ||||||||  ||||||||||||  |::|||||||||||||||||:||||||||
601  GTNPCADRNGGCSHLCFFTPHATRCGCPIGLELLSDMKTCIVPEAFLVFT 650

650  SRATIHRISLETNNNDVAIPLTGVKEASALDFDVSNNHIYWTDVSLKTIS 699
     |||  ||||||||||||||||||||||||||||||||||||||||||||||
651  SRAAIHRISLETNNNDVAIPLTGVKEASALDFDVSNNHIYWTDVSLKTIS 700

700  RAFMNGSSVEHVIEFGLDYPEGMAVDWMGKNLYWADTGTNRIEVARLDGQ 749
     ||||||||||||:||||||||||||||||||||||||||||||||||||||
701  RAFMNGSSVEHVVEFGLDYPEGMAVDWMGKNLYWADTGTNRIEVARLDGQ 750

750  FRQVLVWRDLDNPRSLALDPTKGYIYWTEWGGKPRIVRAFMDGTNCMTLV 799
     ||||||||||||||||||||||||||||||||||||||||||||||||||
751  FRQVLVWRDLDNPRSLALDPTKGYIYWTEWGGKPRIVRAFMDGTNCMTLV 800

800  DKVGRANDLTIDYADQRLYWTDLDTNMIESSNMLGQERMVIADDLPYPFG 849
     |||||||||||||||||||||||||||||||||||||||·||||||:|||
801  DKVGRANDLTIDYADQRLYWTDLDTNMIESSNMLGQERVVIADDLPHPFG 850

850  LTQYSDYIYWTDWNLHSIERADKTSGRNRTLIQGHLDFVMDILVFHSSRQ 899
     ||||||||||||||||||||||||||||||||||||||||||||||||||
851  LTQYSDYIYWTDWNLHSIERADKTSGRNRTLIQGHLDFVMDILVFHSSRQ 900

900  DGLNDCVHSNGQCGQLCLAIPGGHRCGCASHYTLDPSSRNCSPPSTFLLF 949
     ||||||·|·|||||||||||||||||||||||||||||||||||·||||
901  DGLNDCMHNNGQCGQLCLAIPGGHRCGCASHYTLDPSSRNCSPPTTFLLF 950

950  SQKFAISRMIPDDQLSPDLVLPLHGLRNVKAINYDPLDKFIYWVDGRQNI 999
     |||  |||||||||  ||||:|||||||||||·||||||||||||||||
951  SQKSAISRMIPDDQHSPDLILPLHGLRNVKAIDYDPLDKFIYWVDGRQNI 1000

1000 KRAKDDGTQPSMLTSPSQSLSPDRQPHDLSIDIYSRTLFWTCEATNTINV 1049
     |||||||||  ·|||  ||·|||||||||||||||||||||||||||||
1001 KRAKDDGTQPFVLTSLSQGQNPDRQPHDLSIDIYSRTLFWTCEATNTINV 1050

1050 HRLDGDAMGVVLRGDRDKPRAIAVNAERGYMYFTNMQDHAAKIERASLDG 1099
     |||  |:|||||||||||||||  |||||:|||||||||  ||||·|||
1051 HRLSGEAMGVVLRGDRDKPRAIVVNAERGYLYFTNMQDRAAKIERAALDG 1100

1100 TEREVLFTTGLIRPVALVVDNALGKLFWVDADLKRIESCDLSGANRLTLE 1149
     ||||||||||||||||||||| |||||||||||||||||||||||||||
1101 TEREVLFTTGLIRPVALVVDNTLGKLFWVDADLKRIESCDLSGANRLTLE 1150

1150 DANIVQPVGLTVLGRHLYWIDRQQQMIERVEKTTGDKRTRVQGRVTHLTG 1199
     |||||||·|||:||:|||||||||||||||||||||||||:||||·||||
1151 DANIVQPLGLTILGKHLYWIDRQQQMIERVEKTTGDKRTRIQGRVAHLTG 1200
```

Figure 18(d-2)

```
1200 IHAVEEVSLEEFSAHPCARDNGGCSHICIAKGDGTPRCSCPVHLVLLQNL 1249
     ||||||||||||||||||||||||||||||||||||||||||||||||||
1201 IHAVEEVSLEEFSAHPCARDNGGCSHICIAKGDGTPRCSCPVHLVLLQNL 1250

1250 LTCGEPPTCSPDQFACTTGEIDCIPGAWRCDGFPECADQSDEEGCPVCSA 1299
     |||||||||||||| ||||||||||||||||| |||||||||||||
1251 LTCGEPPTCSPDQFACATGEIDCIPGAWRCDGFPECDDQSDEEGCPVCSA 1300

1300 SQFPCARGQCVDLRLRCDGEADCQDRSDEANCDAVCLPNQFRCTSGQCVL 1349
     .|||||||||||||||||||||||||||.|||:||||||| ||||||
1301 AQFPCARGQCVDLRLRCDGEADCQDRSDEADCDAICLPNQFRCASGQCVL 1350

1350 IKQQCDSFPDCADGSDELMCEINKPPSDDIPAHSSAIGPVIGIILSLFVM 1399
     ||||||||| ||||||||||||| |||||| ||||||||||||||||||
1351 IKQQCDSFPDCIDGSDELMCEITKPPSDDSPAHSSAIGPVIGIILSLFVM 1400

1400 GGVYFVCQRVMCQRYTGASGPFPHEYVGGAPHVPLNFIAPGGSQHGPFPG 1449
     |||||||||.|||| ||.|||||||| | ||||||||||||||||||| |
1401 GGVYFVCQRVVCQRYAGANGPFPHEYVSGTPHVPLNFIAPGGSQHGPFTG 1450

1450 IPCSKSVMSSMSLVGGRGSVPLYDRNHVTGASSSSSSSTKATLYPPILNP 1499
     | | ||.|||.||.|||| |||||||||||||||||||||||||||||||
1451 IACGKSMMSSVSLMGGRGGVPLYDRNHVTGASSSSSSSTKATLYPPILNP 1500

1500 PPSPATDPSLYNVDVFYSSGIPATARPYRPYVIRGMAPPTTPCSTDVCDS 1549
     |||||||||||.|.|||| |||| ||||||:||||||||||||||||||
1501 PPSPATDPSLYNMDMFYSSNIPATVRPYRPYIIRGMAPPTTPCSTDVCDS 1550

1550 DYSISRWKSSKYYLDLNSDSDPYPPPPTPHSQYLSAEDSCPPSPGTERSY 1599
     ||| ||||.||||||||||||||||||||||||||||||||| |||||
1551 DYSASRWKASKYYLDLNSDSDPYPPPPTPHSQYLSAEDSCPPSPATERSY 1600

1600 CHLFPPPPSPCTDSS 1614  (SEQ ID NO: 42)
     ||||||||||||||
1601 FHLFPPPPSPCTDSS 1615  (SEQ ID NO: 3)
```

Figure 18(e)

```
 25 CPAPAAASPLLLFANRRDVRLVDAGGVKLESTIVVSGLEDAAAVDFQFSK  74
    |||||||||||||||||||||||||||||||| |||||||||||||||||
 29 .....AASPLLLFANRRDVRLVDAGGVKLESTIVASGLEDAAAVDFQFSK  73

75 GAVYWTDVSEEAIKQTYLNQTGAAVQNVVISGLVSPDGLACDWVGKKLYW 124
    |||||||||||||||||||||||||| ||:|||||||||||||||||||
 74 GAVYWTDVSEEAIKQTYLNQTGAAAQNIVISGLVSPDGLACDWVGKKLYW 123

125 TDSETNRIEVANLNGTSRKVLFWQDLDQPRAIALDPAHGYMYWTDWGETP 174
    ||||||||||||||||||||||||||||||||||||||||||||||| |
124 TDSETNRIEVANLNGTSRKVLFWQDLDQPRAIALDPAHGYMYWTDWGEAP 173

175 RIERAGMDGSTRKIIVDSDIYWPNGLTIDLEEQKLYWADAKLSFIHRANL 224
    |||||||||||||||||||||||||||||||||||||||||||||||||
174 RIERAGMDGSTRKIIVDSDIYWPNGLTIDLEEQKLYWADAKLSFIHRANL 223

225 DGSFRQKVVEGSLTHPFALTLSGDTLYWTDWQTRSIHACNKRTGGKRKEI 274
    |||||||||||||||||||||||||||||||||||||||| || ·||||
224 DGSFRQKVVEGSLTHPFALTLSGDTLYWTDWQTRSIHACNKWTGEQRKEI 273

275 LSALYSPMDIQVLSQERQPFFHTRCEEDNGGCSHLCLLSPSEPFYTCACP 324
    ||||||||||||||||||| ||| |||||||||||||||| ||||·||||
274 LSALYSPMDIQVLSQERQPPFHTPCEEDNGGCSHLCLLSPREPFYSCACP 323

325 TGVQLQDNGRTCKAGAEEVLLLARRTDLRRISLDTPDFTDIVLQVDDIRH 374
    ||||||||:||| ||||||||||||||||||||||||||||||| ||||
324 TGVQLQDNGKTCKTGAEEVLLLARRTDLRRISLDTPDFTDIVLQVGDIRH 373

375 AIAIDYDPLEGYVYWTDDEVRAIRRAYLDGSGAQTLVNTEINDPDGIAVD 424
    |||||||||||||||||||||||||||||||||||||||||||||||||
374 AIAIDYDPLEGYVYWTDDEVRAIRRAYLDGSGAQTLVNTEINDPDGIAVD 423

425 WVARNLYWTDTGTDRIEVTRLNGTSRKILVSEDLDEPRAIALHPVMGLMY 474
    |||||||||||||||||||||||||||||||||||||||| ||||||||
424 WVARNLYWTDTGTDRIEVTRLNGTSRKILVSEDLDEPRAIVLHPVMGLMY 473

475 WTDWGENPKIECANLDGQERRVLVNASLGWPNGLALDLQEGKLYWGDAKT 524
    ||||||||||||||||·:| |||| ||||||||||||||||||||||||
474 WTDWGENPKIECANLDGRDRHVLVNTSLGWPNGLALDLQEGKLYWGDAKT 523

525 DKIEVINVDGTKRRTLLEDKLPHIFGFTLLGDFIYWTDWQRRSIERVHKV 574
    |||||||:|||||:|||||||||||||||||||||||||||||||||||
524 DKIEVINIDGTKRKTLLEDKLPHIFGFTLLGDFIYWTDWQRRSIERVHKV 573

575 KASRDVIIDQLPDLMGLKAVNVAKVVGTNPCADRNGGCSHLCFFTPHATR 624
    |||||||||||||||||||||||||||||||||| |||||||||||| |:
574 KASRDVIIDQLPDLMGLKAVNVAKVVGTNPCADGNGGCSHLCFFTPRATK 623
```

Figure 18(e-1)

```
625  CGCPIGLELLSDMKTCIVPEAFLVFTSRAAIHRISLETNNNDVAIPLTGV  674
     |||||||||||||||||:||||||||||| ||||||||||||||||||||
624  CGCPIGLELLSDMKTCIIPEAFLVFTSRATIHRISLETNNNDVAIPLTGV  673

675  KEASALDFDVSNNHIYWTDVSLKTISRAFMNGSSVEHVVEFGLDYPEGMA  724
     ||||||||||||||||||||||||||||||||||||||:|||||||||||
674  KEASALDFDVSNNHIYWTDVSLKTISRAFMNGSSVEHVIEFGLDYPEGMA  723

725  VDWMGKNLYWADTGTNRIEVARLDGQFRQVLVWRDLDNPRSLALDPTKGY  774
     |||||||||||||||||||||||||||||||||||||||||||||||||
724  VDWMGKNLYWADTGTNRIEVARLDGQFRQVLVWRDLDNPRSLALDPTKGY  773

775  IYWTEWGGKPRIVRAFMDGTNCMTLVDKVGRANDLTIDYADQRLYWTDLD  824
     |||||||||||||||||||||||||||||||||||||||||||||||||
774  IYWTEWGGKPRIVRAFMDGTNCMTLVDKVGRANDLTIDYADQRLYWTDLD  823

825  TNMIESSNMLGQERVVIADDLPHPFGLTQYSDYIYWTDWNLHSIERADKT  874
     ||||||||||||||.|||||||:||||||||||||||||||||||||||
824  TNMIESSNMLGQERMVIADDLPYPFGLTQYSDYIYWTDWNLHSIERADKT  873

875  SGRNRTLIQGHLDFVMDILVFHSSRQDGLNDCMHNNGQCGQLCLAIPGGH  924
     |||||||||||||||||||||||||||||||||.|.|||||||||||||
874  SGRNRTLIQGHLDFVMDILVFHSSRQDGLNDCVHSNGQCGQLCLAIPGGH  923

925  RCGCASHYTLDPSSRNCSPPTTFLLFSQKSAISRMIPDDQHSPDLILPLH  974
     |||||||||||||||||||.||||||||| |||||||||| ||||:||||
924  RCGCASHYTLDPSSRNCSPPSTFLLFSQKFAISRMIPDDQLSPDLVLPLH  973

975  GLRNVKAIDYDPLDKFIYWVDGRQNIKRAKDDGTQPFVLTSLSQGQNPDR  1024
     |||||||.|||||||||||||||||||||||||||.|||.||.|||
974  GLRNVKAINYDPLDKFIYWVDGRQNIKRAKDDGTQPSMLTSPSQSLSPDR  1023

1025 QPHDLSIDIYSRTLFWTCEATNTINVHRLSGEAMGVVLRGDRDKPRAIVV  1074
     ||||||||||||||||||||||||||||||:|||||||||||||||| |
1024 QPHDLSIDIYSRTLFWTCEATNTINVHRLDGDAMGVVLRGDRDKPRAIAV  1073

1075 NAERGYLYFTNMQDRAAKIERAALDGTEREVLFTTGLIRPVALVVDNTLG  1124
     ||||||:|||||||| |||||||.|||||||||||||||||||||| ||
1074 NAERGYMYFTNMQDHAAKIERASLDGTEREVLFTTGLIRPVALVVDNALG  1123

1125 KLFWVDADLKRIESCDLSGANRLTLEDANIVQPLGLTILGKHLYWIDRQQ  1174
     ||||||||||||||||||||||||||||||||.|||:||:|||||||||
1124 KLFWVDADLKRIESCDLSGANRLTLEDANIVQPVGLTVLGRHLYWIDRQQ  1173

1175 QMIERVEKTTGDKRTRIQGRVAHLTGIHAVEEVSLEEFSAHPCARDNGGC  1224
     |||||||||||||||:|||| ||||||||||||||||||||||||||||
1174 QMIERVEKTTGDKRTRVQGRVTHLTGIHAVEEVSLEEFSAHPCARDNGGC  1223
```

Figure 18(e-2)

```
1225 SHICIAKGDGTPRCSCPVHLVLLQNLLTCGEPPTCSPDQFACATGEIDCI 1274
     |||||||||||||||||||||||||||||||||||||||||| |||||||
1224 SHICIAKGDGTPRCSCPVHLVLLQNLLTCGEPPTCSPDQFACTTGEIDCI 1273

1275 PGAWRCDGFPECDDQSDEEGCPVCSAAQFPCARGQCVDLRLRCDGEADCQ 1324
     ||||||||||||| |||||||||||||.||||||||||||||||||||||
1274 PGAWRCDGFPECADQSDEEGCPVCSASQFPCARGQCVDLRLRCDGEADCQ 1323

1325 DRSDEADCDAICLPNQFRCASGQCVLIKQQCDSFPDCIDGSDELMCEITK 1374
     ||||||.|||:||||||||| |||||||||||||||| |||||||||| |
1324 DRSDEANCDAVCLPNQFRCTSGQCVLIKQQCDSFPDCADGSDELMCEINK 1373

1375 PPSDDSPAHSSAIGPVIGIILSLFVMGGVYFVCQRVVCQRYAGANGPFPH 1424
     ||||| |||||||||||||||||||||||||||||||.|||| ||.||||
1374 PPSDDIPAHSSAIGPVIGIILSLFVMGGVYFVCQRVMCQRYTGASGPFPH 1423

1425 EYVSGTPHVPLNFIAPGGSQHGPFTGIACGKSMMSSVSLMGGRGGVPLYD 1474
     ||| | ||||||||||||||||||| || | ||.|||.||.|||| |||||
1424 EYVGGAPHVPLNFIAPGGSQHGPFPGIPCSKSVMSSMSLVGGRGSVPLYD 1473

1475 RNHVTGASSSSSSSTKATLYPPILNPPPSPATDPSLYNMDMFYSSNIPAT 1524
     |||||||||||||||||||||||||||||||||||||||.|.|||| ||||
1474 RNHVTGASSSSSSSTKATLYPPILNPPPSPATDPSLYNVDVFYSSGIPAT 1523

1525 VRPYRPYIIRGMAPPTTPCSTDVCDSDYSASRWKASKYYLDLNSDSDPYP 1574
     ||||||:|||||||||||||||||||||| ||||.|||||||||||||||
1524 ARPYRPYVIRGMAPPTTPCSTDVCDSDYSISRWKSSKYYLDLNSDSDPYP 1573

1575 PPPTPHSQYLSAEDSCPPSPATERSYFHLFPPPPSPCTDSS 1615 (SEQ ID NO: 43)
     ||||||||||||||||||| ||||| ||||||||||||||||
1574 PPPTPHSQYLSAEDSCPPSPGTERSYCHLFPPPPSPCTDSS 1614 (SEQ ID NO: 44)
```

RECEPTOR

This application claims benefit of U.S. Provisional Application Nos. 60/043,553 and 60/048,740, filed Apr. 15, 1997 and Jun. 5, 1997, respectively.

FIELD OF THE INVENTION

The present invention relates to nucleic acids, polypeptides, oligonucleotide probes and primers, methods of diagnosis or prognosis, and other methods relating to and based on the identification of a gene, which is characterised as a member of the LDL-receptor family and for which there are indications that some alleles are associated with susceptibility to insulin-dependent diabetes mellitus ("IDDM"), also known as type 1 diabetes.

More particularly, the present invention is based on cloning and characterisation of a gene which the present inventors have termed "LDL-receptor related protein-5 (LRP5)" (previously "LRP-3"), based on characteristics of the encoded polypeptide which are revealed herein for the first time and which identify it as a member of the LDL receptor family. Furthermore, experimental evidence is included herein which provides indication that LRP5 is the IDDM susceptibility gene IDDM4.

BACKGROUND OF THE INVENTION

Diabetes, the dysregulation of glucose homeostasis, affects about 6% of the general population. The most serious form, type 1 diabetes, which affects up to 0.4% of European-derived population, is caused by autoimmune destruction of the insulin producing β-cells of the pancreas, with a peak age of onset of 12 years. The β-cell destruction is irreversible, and despite insulin replacement by injection patients suffer early mortality, kidney failure and blindness (Bach, 1994; Tisch and McDevitt, 1996). The major aim, therefore, of genetic research is to identify the genes predisposing to type 1 diabetes and to use this information to understand disease mechanisms and to predict and prevent the total destruction of β-cells and the disease.

The mode of inheritance of type 1 diabetes does not follow a simple Mendelian pattern, and the concordance of susceptibility genotype and the occurrence of disease is much less than 100%, as evidenced by the 30–70% concordance of identical twins (Matsuda and Kuzuya, 1994; Kyvik et al, 1995). Diabetes is caused by a number of genes or polygenes acting together in concert, which makes it particularly difficult to identify and isolate individual genes.

The main IDDM locus is encoded by the major histocompatibility complex (MHC) on chromosome 6p21 (IDDM1). The degree of familial clustering at this locus, $\lambda s=2.5$, where $\lambda s=P$ expected [sharing of zero alleles at the locus identical-by-descent (IBD)]/P observed [sharing of zero alleles IBD] (Risch 1987; Todd, 1994), with a second locus on chromosome 11p15, IDDM2, the insulin minisatellite $\lambda s=1.25$ (Bell et al, 1984; Thomson et al, 1989; Owerbach et al, 1990; Julier et al, 1991; Bain et al, 1992; Spielman et al, 1993; Davies et al, 1994; Bennett et al, 1995). These loci were initially detected by small case control association studies, based on their status as functional candidates, which were later confirmed by further case-control, association and linkage studies.

These two loci, however, cannot account for all the observed clustering of disease in families ($\lambda s=15$), which is estimated from the ratio of the risk for siblings of patients and the population prevalence (6%/0.4%) (Risch, 1990). We initiated a positional cloning strategy in the hope of identifying the other loci causing susceptibility to type 1 diabetes, utilising the fact that markers linked to a disease gene will show excess of alleles shared identical-by-descent in affected sibpairs (Penrose, 1953; Risch, 1990; Holmans, 1993).

The initial genome-wide scan for linkage utilising 289 microsatellite markers, in 96 UK sibpair families, revealed evidence of linkage to an additional eighteen loci (Davies et al, 1994). Confirmation of linkage to two of these loci was achieved by analysis of two additional family sets (102 UK families and 84 USA families), IDDM4 on chromosome 11q13 (MLS 1.3, P=0.003 at FGF3) and IDDM5 on chromosome 6q (MLS 1.8 at ESR). At IDDM4 the most significant linkage was obtained in the subset of families sharing 1 or 0 alleles IBD at HLA (MLS=2.8; P=0.001; $\lambda s=1.2$) (Davies et al, 1994). This linkage was also observed by Hashimoto et al (1994) using 251 affected sibpairs, obtaining P=0.0008 in all sibpairs. Combining these results, with 596 families, provides substantial support for IDDM4 (P=1.5×10-6) (Todd and Farrall, 1996; Luo et al, 1996).

BRIEF DESCRIPTION OF THE INVENTION

The present inventors now disclose for the first time a gene encoding a novel member of the LDL-receptor family, which they term "LRP5" (previously "LRP-3"). Furthermore, evidence indicates that the gene represents the IDDM susceptibility locus IDDM4, the identification and isolation of which is a major scientific breakthrough.

Over the last 10 years many genes for single gene or monogenic diseases, which are relatively rare in the population, have been positioned by linkage analysis in families, and localised to a small enough region to allow identification of the gene. The latter sublocalisation and fine mapping can be carried out in single gene rare diseases because recombinations within families define the boundaries of the minimal interval beyond any doubt. In contrast, in common diseases such as diabetes or asthma the presence of the disease mutation does not always coincide with the development of the disease: disease susceptibility mutations in common disorders provide risk of developing of the disease, and this risk is usually much less than 100%. Hence, susceptibility genes in common diseases cannot be localised using recombination events within families, unless tens of thousands of families are available to fine map the locus. Because collections of this size are impractical, investigators are contemplating the use of association mapping, which relies on historical recombination events during the history of the population from which the families came from.

Association mapping has been used in over a dozen examples of rare single gene traits, and particularly in genetically isolated populations such as Finland to fine map disease mutations. Nevertheless, association mapping is fundamentally different from straight forward linkage mapping because even though the degree of association between two markers or a marker and a disease mutation is proportional to the physical distance along the chromosome this relationship can be unpredictable because it is dependent on the allele frequencies of the markers, the history of the population and the age and number of mutations at the disease locus. For rare, highly penetrant single gene diseases there is usually one major founder chromosome in the population under study, making it relatively feasible to locate an interval that is smaller than one that can be defined by standard recombination events within living families. The resolution of this method in monogenic diseases in which there is one main founder chromosome is certainly less than 2cM, and in certain examples the resolution is down to 100 kb of DNA (Hastbacka et al. (1994) Cell 78,1–20).

In common diseases like type 1 diabetes, which are caused by a number of genes or polygenes acting together in concert the population frequency of the disease allele may be very high, perhaps exceeding 50%, and there are likely to be several founder chromosomes, all of which impart risk, and not a 100% certainty of disease development. Because association mapping is dependent on unpredictable parameters, and because founder chromosomes will be several and common in frequency in the general population, the task of fine mapping polygenes is currently one of some controversy, and many doubt the feasibility at all of a systematic genetic approach using a combination of linkage and association mapping. Recently, Risch and Marakandis have provided some mathematical background to the feasibility of association mapping in complex diseases (Science 273 1516–1517, 1996) but they did not take into account the effect of multiple founder chromosomes.

As a result of these uncertainties, extremely large numbers of diabetic families are required for genotyping, with a large number of markers across a specific region, giving a linkage disequilibrium curve which may have several peaks. The question is, which peak identifies the aetiological mutation, and in what ways can we establish this? To our knowledge, the linkage disequilibrium curves and haplotype association maps shown in FIGS. 3, 4, 19 and 20 are the first of their kind for any complex polygenic disease for any locus. Curves of this nature have not been published yet in the literature, even for the well-established IDDM1/MHC locus. In this respect the work described here is entirely novel and at the cutting edge of research into the genetics of polygenes.

BRIEF DESCRIPTION OF THE FIGURES

FIG. 5(a) shows DNA sequence of the LRP5 isoform 1 cDNA (SEQ ID NO:1).

FIG. 5(b) shows the DNA sequence of the longest open reading frame present in the LRP5 cDNA (SEQ ID NO:2).

FIG. 5(c) amino acid sequence translation (in standard single letter code) of the open reading frame in FIG. 5(b) (SEQ ID NO:3).

FIG. 5(d) motifs of LRP5 isoform 1 (SEQ ID NO:3), encoded by the open reading frame contained in FIG. 5(b) (SEQ ID NO:2). Symbols: Underlined residues 1–24 contain a signal for protein export and cleavage, ▼ indicates the position of an intron/exon boundary, * indicates a putative N-linked glycosylation site in the proposed extracellular portion of the receptor. The EGF-binding motifs are shaded light gray, LDL-receptor ligand motifs are shaded a darker gray. The spacer regions are indicated by the underlined four amino acids with high similarity to the YWTD motif. A putative transmembrane spanning domain is underlined with a heavy line. Areas shaded in the cytoplasmic domain (1409 to end) may be involved in endocytosis.

FIG. 5(e) amino acid sequence of the mature LRP5 protein (SEQ ID NO:4).

FIG. 5(f) shows the comparison of the nucleotide sequence of the first 432 nucleotides of the 5' end of the human isoform1 cDNA sequence (FIG. 5(a) (SEQ ID NO:1)) on the upper line (SEQ ID NO:5) with the first 493 nucleotides of the 5' end of the mouse Lrp5 cDNA sequence (FIG. 16(a) (SEQ ID NO:35)) on the lower line (SEQ ID NO:6). The comparison was performed using the GCG algorithm GAP (Genetics Computer Group, Madison, Wis.).

FIG. 5(g) shows the comparison of the first 550 amino acids of human LRP5 isoform 1 (SEQ ID NO:7) with the first 533 amino acids of mouse Lrp5 (SEQ ID NO:8) using the GCG algorithm GAP (Genetics Computer Group, Madison, Wis.).

FIG. 6(a) shows the amino acid sequence of LRP5 motifs (SEQ ID NOS:9 to 22). A comparison was made using the program crossmatch (obtained from Dr. Phil Green, University of Washington) between the motifs present in LRP1 and the LRP5 amino acid sequence. The best match for each LRP5 motif is shown. For each motif, the top line is the LRP5 isoform 1 amino acid sequence, the middle line is amino acids that are identical in the two motifs, the lower line is the amino acid sequence of the best match LRP1 motif. Of particular note are the conserved cysteine (C) residues that are the hallmark of both the EGF-precursor and LDL-receptor ligand binding motifs(SEQ ID NOS:9–22).

FIG. 6(b) illustrates the motif organization of the LDL-receptor and LRP5. The LDL-receptor ligand binding motif are represented by the light gray boxes, the EGFlike motifs are represented by the dark gray boxes. The YWTD spacer motifs are indicated by the vertical lines. The putative transmembrane domains are represented by the black box.

FIG. 11(a) shows the DNA sequence of the isoform 2 cDNA (SEQ ID NO:23).

FIG. 11(b) shows the longest open reading frame of isoform 2 (also isoform 4,5,6) (SEQ ID NO:24).

FIG. 11(c) shows the amino acid sequence of isoform 2 (also isoform 4,5,6) (SEQ ID NO:25), encoded by the open reading frame of FIG. 12(b).

FIG. 12(a) shows the DNA sequence of isoform 3 cDNA (SEQ ID NO:26).

FIG. 12(b) shows sequence obtained by GRAIL and a putative extension of isoform 3 (SEQ ID NO:27).

FIG. 12(c) shows a putative open reading frame for isoform 3 (SEQ ID NO:28).

FIG. 12(d) shows the amino acid sequence of isoform 3 (SEQ ID NO:29).

FIG. 12(e) shows the GRAIL predicted promoter sequence for isoform 3 (SEQ ID NO:30).

FIG. 13 shows the DNA sequence of the isoform 4 cDNA (SEQ ID NO:31), which contains an open reading frame encoding isoform 2 (FIG. 11(b)).

FIG. 14 shows the DNA sequence of the present in cDNA isoform 5 (SEQ ID NO:32), which contains an open reading frame encoding isoform 2 (FIG. 11(b)).

FIG. 15(a) shows the DNA sequence of isoform 6 (SEQ ID NO:33), which contains an open reading frame encoding isoform 2(FIG. 11 (b)).

FIG. 15(b) shows the GRAIL predicted promoter sequence associated with isoform6 (SEQ ID NO:34).

FIG. 16(a) shows the DNA sequence of a portion of the mouse Lrp5 cDNA (SEQ ID NO:35).

FIG. 16(b) shows the DNA sequence of the 5' extension of the mouse clone (SEQ ID NO:36).

FIG. 16(c) shows the DNA sequence of a portion of the open reading frame of mouse Lrp5 (SEQ ID NO:37).

FIG. 16(d) show the amino acid sequence of the open reading frame encoding a portion of mouse Lrp5 (SEQ ID NO:8).

FIG. 17(a) shows DNA sequence of exons A to V (SEQ ID NO:38).

FIG. 17(b) shows the amino acid sequence (SEQ ID NO:39) encoded by an open reading frame contained in FIG. 17(a).

FIG. 18(a) shows the nucleotide sequence of the full length mouse Lrp5 cDNA (SEQ ID NO:40).

FIG. 18(b) shows the nucleotide sequence for the longest open reading frame present in the mouse Lrp5 cDNA (SEQ ID NO:41).

FIG. 18(c) shows the amino acid sequence translation (in single letter code) of the open reading frame in FIG. 18(b) (SEQ ID NO:42).

FIG. 18(d) shows an alignment of the amino acid sequence of the human LRP5 protein and the mouse Lrp5 protein (SEQ ID NOS:3,42) program using the GCG algorithm GAP (Genetics Computer Group, Madison, Wis.).

FIG. 18(e) shows an alignment of the amino acid sequence of the mature human LRP5 protein with the mature mouse LRP5 (SEQ ID NOS:43,44) program using the GCG algorithm GAP (Genetics Computer Group, Madison, Wis.).

LRP5 Gene Structure

Figure 7:
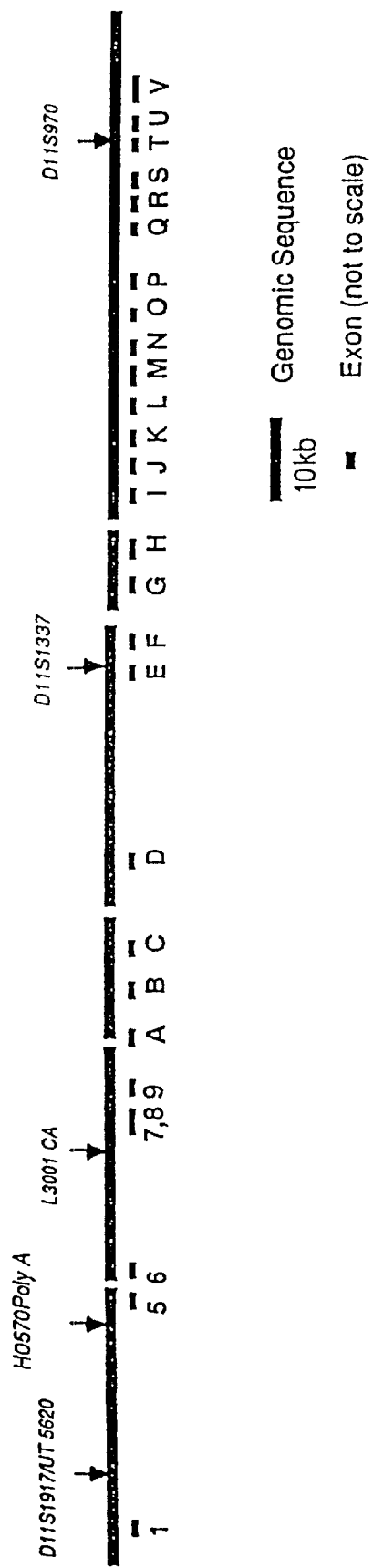
FIG. 7 shows LRP5 gene structure. The DNA sequence of contiguous pieces of genomic DNA is represented by the heavy lines and are according to the indicated scale. The position of the markers D11S1917(UT5620), H0570POLYA, L3001CA, D11S1337, and D11S970 are indicated. The exons are indicated by the small black boxes with their numerical or alphabetical name below, the size of the exons is not to scale.

The gene identified contains 22 exons, termed A–V, which encode most of the mature LRP5 protein. The 22 exons account for 4961 nucleotides of the LRP5 gene transcript (FIG. 5(a) (SEQ ID NO: 1) and are located in an approximately 110 kb of genomic DNA. The genomic DNA containing these exons begins downstream of the genetic marker L3001CA and includes the genetic markers D11S1337, 141ca5, and D11S970 (FIG. 7). Several different 5' ends of the LRP5 transcript have been identified. Of particular interest is isoform 1 with a 5' end encoding a signal peptide sequence for protein export (secretory leader peptide) across the plasma membrane. As discussed below the LRP5 protein is likely to contain a large extracellular domain, therefore it would be anticipated that this protein would have a signal sequence. The exon encoding the signal sequence, termed exon 6, lies near the genetic marker H0570POLYA. This exon is 35 kb upstream of exon A and thus extends the genomic DNA comprising the LRP5 gene to at least 160 kb.

Figure 8:
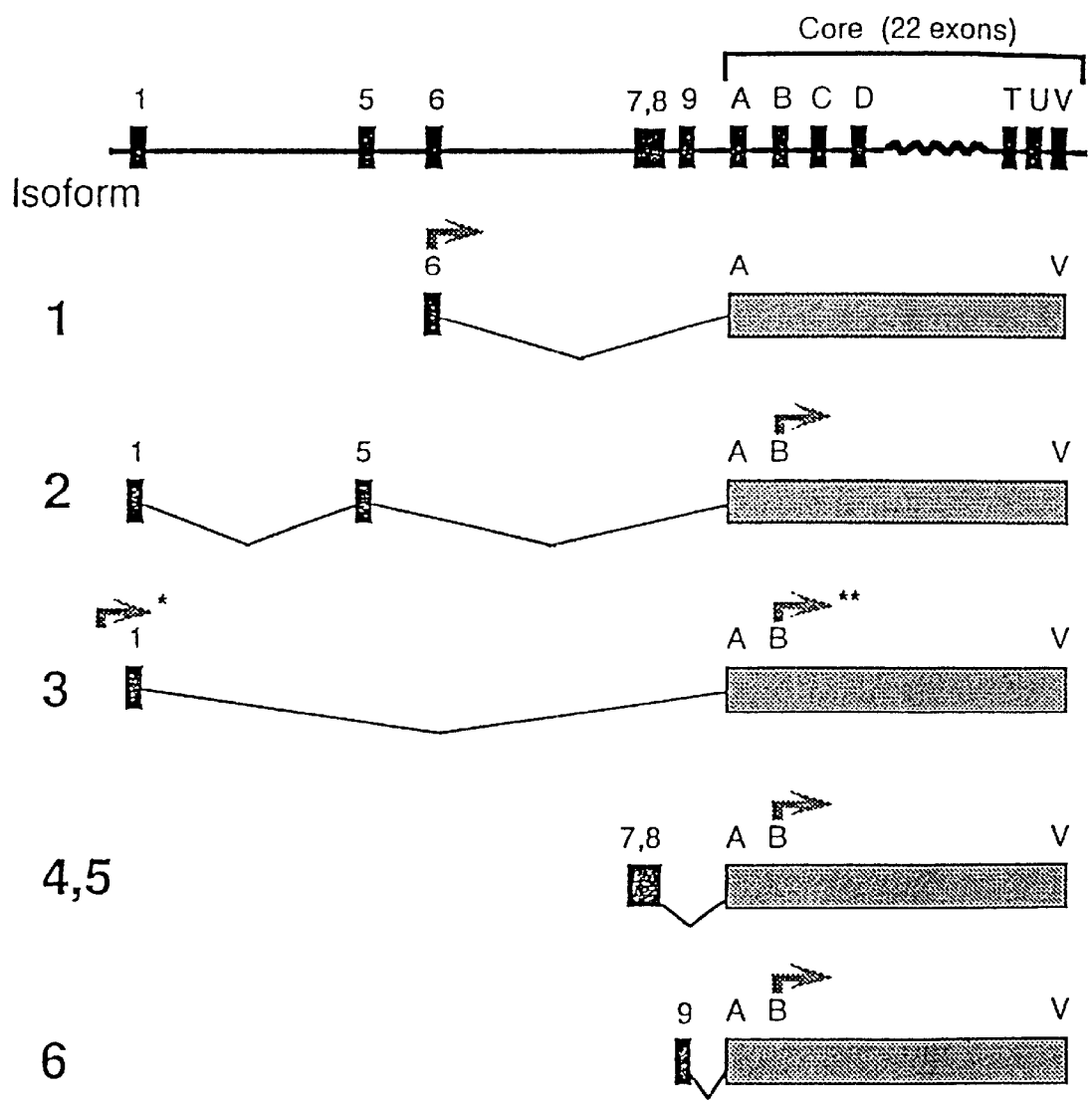
FIG. 8 illustrates different LRP5 gene isoforms. Alternatively spliced 5' ends of the LRP5 gene are indicated with the isoform number for each alternatively spliced form. The light gray arrow indicates the start of translation which occurs in exon 6 in isoform 1, may occur upstream of exon 1 in isoform 3 and occurs in exon B in isoforms 2, 4, 5, and 6. The core 22 exons (A to V) are represented by the box.

Several additional isoforms of the LRP5 gene that arise from alternative splicing of the 5' end have been identified by PCR (FIG. 8). The functional relevance of these additional isoforms is not clear. Two of these LRP5 transcripts contain exon 1 which is located upstream of the genetic marker D11S1917(UT5620) and expands the LRP5 gene to approximately 180 kb of genomic DNA. The transcript termed isoform 3 consists of exon 1 spliced directly to exon A. The reading frame is open at the 5' end and thus there is the potential for additional coding information present in exons upstream of exon 1. Alternatively, centromeric extension of exon 1 to include all of the open reading frame associated with this region yields the open reading frame for isoform 3.

The second transcript that contains exon 1 also contains exon 5, which is located near the genetic marker H0570POLYA. The open reading frame for this isoform, isoform 2, begins in exon B and thus encodes a truncated LRP5 protein which lacks any predicted secretory leader peptide in the first 100 amino acids. There are three additional transcripts each with an open reading frame beginning in exon B and with 5' ends near the genetic marker L3001CA.

Expression Profile of LRP5

Northern blot analysis indicates that the major mRNA transcript for the LRP5 gene is approximately 5 to 5.5 kb and is most highly expressed in liver, pancreas, prostate, and placenta. Expression is also detected in skeletal muscle, kidney, spleen, thymus, ovary, lung, small intestine, and colon. Minor bands both larger and smaller than 5 kb are detected and may represent alternative splicing events or related family members.

LRP5 is a Member of the LDL-receptor Family

The gene identified in the IDDM4 locus, lrp5, is a member of the LDL-receptor family. This family of proteins has several distinguishing characteristics, a large extracellular domain containing cysteine rich motifs which are involved in ligand binding, a single transmembrane spanning domain, and an "NPXY" (SEQ ID NO:45) internalization motif (Krieger and Herz (1994) Ann. Rev. Biochem. 63: 601–637). The functional role of the members of this family is the clearance of their ligands by the mechanism of receptor mediated endocytosis. This is illustrated by the most highly characterized member of the family, the LDL-receptor which is responsible for the clearance of LDL cholesterol from plasma (Goldstein, et. al. (1985) Ann. Rev. Cell Biol. 1: 1–39).

LRP5 is most closely related to the LDL-receptor related protein (LRP) which is also know as the alpha2-macroglobulin receptor. Translation of the open reading frame (ORF) of isoform 1 yields the LRP5 protein. Comparison of the LRP5 protein to human LRP1 using the algorithm GAP (Genetics Computer Group, Madison, Wis.) reveals an overall amino acid similarity of 55% and 34% identity to the region of the human LRP1 protein from amino acids 1236 to 2934. The DNA of this ORF is 45% identical to LRP1 encoding DNA as indicated by GAP. A slightly lower but significant level of similarity is seen with the megalin receptor also termed LRP2 and gp330 (Saito, et al. (1994) Proc. Natl. Acad. Sci. 91: 9725–9729), as well as the Drosophilla vitellogenin receptor (Schonboum et. al. (1995) Proc. Natl. Acad. Sci. 92: 1485–1489). Similarity is also observed with other members of the LDL-receptor family including the LDL-receptor (Suedhof et. al. (1985) Science 228: 815–822) and the VLDL receptor (Oka et. al. (1994) Genomics 20: 298–300). Due to the presence of EGF-like motifs in LRP5 similarity is also observed with the EGF precursor and nidogen precursor which are not members of the LDL-receptor family.

Properties and Motifs of LRP5

The N-terminal portion of LRP5 likely has the potential for a signal sequence cleavage site. Signal sequences are frequently found in proteins that are exported across the plasma membrane (von Heijne (1994) Ann. Rev. Biophys. Biomol. Struc. 23: 167–192). In addition, other members of the LDL-receptor family contain a signal sequence for protein export.

The presence of a signal sequence cleavage site was initially identified by a comparison of the human LRP5 with a mouse cDNA sequence that we obtained. The initial mouse partial cDNA sequence that we obtained, 1711 nucleotides (FIG. 16(a) (SEQ ID NO:35)), is 87% identical over an approximately 1500 nucleotide portion to the human LRP5 cDNA and thus is likely to be the mouse ortholog (Lrp5) of the human LRP5. The cloned portion of the mouse cDNA contains an open reading frame (FIG. 16(c) (SEQ ID NO:37)) encoding 533 amino acids. The initiating codon has consensus nucleotides for efficient translation at both the −3 (purine) and +4 (G nucleotide) positions (Kozak, M. 1996, Mamalian Genome 7:563–574). A 500 amino acid of the portion of the mouse Lrp5 (FIG. 5(g) and FIG. 16(d) (SEQ ID NO:8)) is 96% identical to human LRP5, further supporting the proposal that this is the mouse ortholog of LRP5.

Significantly, the first 200 nucleotides of the mouse cDNA have very little similarity to the 5' extensions present in isoforms 2–6 discussed below. By contrast this sequence is 75% identical with the human sequence for exon 6 that comprises the 5' end of isoform 1. Thus isoform 1 which encodes a signal peptide for protein export likely represents the most biologically relevant form of LRP5.

Importantly, both the human LRP5 and mouse Lrp5 open reading frames encodes a peptide with the potential to act as a eukaryotic signal sequence for protein export (von Heijne, 1994, Ann. Rev. Biophys. Biomol. Struc. 23:167–192). The highest score for the signal sequence as determined by using the SigCleave program in the GCG analysis package (Genetics Computer Group, Madison Wis.) generates a mature peptide beginning at residue 25 of human LRP5 and residue 29 of mouse Lrp5 (FIGS. 5(d and g)). Additional sites that may be utilized produce mature peptides in the human LRP5 beginning at amino acid residues 22, 23, 23, 26, 27, 28, 30 or 32. Additional cleavage sites in the mouse Lrp5 result in mature peptides beginning at amino acid residue 31, 32, 33, or 38 (FIG. 5(g) (SEQ ID NO:8)). The mature human LRP5 protein is show in FIG. 5(e) (SEQ ID NO:4).

The other alternative isoforms of LRP5 lack a signal sequence near the N-terminus of the encoded protein. The functional relevance of these additional isoforms is not known, however there are several exported proteins which lack a signal sequence and are transported by a signal peptide independent mechanism (Higgins, C. F. (1992) Ann. Rev. Cell Biol. 8: 67–113). Thus it is possible that the putative extracellular domain of these isoforms is translocated across the plasma membrane.

The extracellular domain of members of the LDL receptor family contains multiple motifs containing six cysteine residues within an approximately 40 amino acid region. (Krieger and Herz (1994) Ann. Rev. Biochem. 63: 601–637). Several classes of these cysteine rich motifs have been defined based on the spacing of the cysteine residues and the nature of other conserved amino acids within the motif. The LDL-receptor ligand binding (class A) motif is distinguished by a cluster of acidic residues in the C-terminal portion of the motif which includes a highly conserved SDE sequence. The importance of this acidic region in ligand binding has been demonstrated by mutagenesis studies (Russell et. al. (1989) J. Biol. Chem. 264: 21682–21688). Three LDL-receptor ligand binding motifs are found in the LRP5 protein (FIG. 6(a) (SEQ ID NOS:9 to 22)). The EGF-like (class B) motif lacks the cluster of acidic residues present in the LDL-receptor ligand binding motif. In addition, the spacing of the cysteine residues differs in the EGF-like motifs relative to the LDL-receptor ligand binding motif. The LRP5 protein contains 4 EGF-precursor (B.2) motifs, which have the property of an NGGCS motif between the first and second cysteine residue (FIG. 6(a) (SEQ ID NOS:9 to 22)).

The size of the members of the LDL receptor family and the number of the cysteine-rich repeats in the extracellular domain varies greatly. LRP1 is a large protein of 4544 amino acids and contains 31 LDL-receptor ligand binding motifs (class A) and 22 EGF-like motifs (class B) (Herz et. al., (1988) EMBO 7: 4119–4127). Similarly the megalin receptor, LRP2, is a protein of 4660 amino acids and consists of 36 LDL-receptor ligand binding motifs and 17 EGF-like motifs (Saito et. al. (1994) PNAS 91: 9725–9729). In contrast, the LDL receptor is a relatively small protein of 879 amino acids which contains 7 LDL-ligand binding motifs and 3 EGF-like motifs. The predicted size of the mature LRP5 protein, 1591 amino acids, is intermediate between LRP1 and the LDL receptor. As indicated above the LRP5 protein contains four EGF-like motifs and three LDL-ligand binding motifs. It has been postulated that the multiple motif units, particularly evident in LRP1 and LRP2, account for the ability of these proteins to bind multiple lipoprotein and protein ligands (Krieger and Herz (1994) Ann. Rev. Biochem. 63: 601–637).

The arrangement of the LDL-receptor ligand binding and EGF-like motifs relative to each other is similar in both the LDL receptor, LRP1, and LRP2. In each of these proteins multiple LDL-ligand binding motifs are grouped together and followed by at least one EGF-like motif (Herz et. al., (1988) EMBO 7: 4119–4127, 1988). By contrast, in the LRP5 protein an EGF-like motif precedes the group of three LDL-ligand binding motifs (FIG. 6(b)). An additional property unique to LRP5 is that the LDL-ligand binding motifs in LRP5 are followed by the putative transmembrane domain. The different arrangement of the motifs may define LRP5 as a member of a new subfamily within the LDL-receptor related protein family.

LRP5 has a signal peptide for protein export at the N-terminus of the protein. Signal peptide cleavage yields a mature LRP5 protein which begins with an EGF precursor spacer domain from amino acids 31–297 (amino acid residue numbers are based upon the LRP5 precursor). The EGF precursor spacer domain is composed of five approximately 50 amino acid repeats that each contain the characteristic sequence motif Tyr-Trp-Thr-Asp (YWTD) (SEQ ID NO:46). There are three additional spacer domains from amino acids 339–602, 643–903, and 944–1214. Each spacer domain is followed by an EGF repeat from amino acids 297–338 (egf1), 603–642 (egf2), 904–943 (egf3), and 1215–1255 (egf4). The EGF repeats contain six conserved cysteine residues and are of the B.2 class which has an Asn-Gly-Gly-Cys (NGGC) (SEQ ID NO:47) motif as a feature (Herz et al. 1988, EMBO J 7:4119–27) (FIG. 6(a) (SEQ ID NO:9 to 22)). A single unit defined as an EGF precursor spacer domain and an EGF repeat, is repeated four times in LRP5. The last EGF repeat is adjacent to three consecutive LDLR repeats from amino acids 1257–1295 (ldlr1), 1296–1333 (ldlr2), and 1334–1372 (ldlr3). The LDLR repeats have the conserved cysteine residues, as well as, the motif Ser-Asp-Glu (SDE) as a characteristic feature (FIG. 6(a) (SEQ ID NOS:9 to 22)). There are thirteen amino acids separating the LDLR repeats from the putative transmembrane spanning domain of 23 amino acids from 1386–1408. The putative extracellular domain of LRP5 has six potential sites for N-linked glycosylation at amino acid residues 93, 138, 446, 499, 705, and 878 (FIG. 5(d) (SEQ ID NO:3)).

The intracellular domain of LRP5 is comprised of 207 amino acids which is longer than most members of the family but similar in size to LRP2 (Saito et. al. (1994) PNAS 91:9725–9729). It does not exhibit similarity to the LDL-receptor family, nor is it similar to any other known proteins. The cytoplasmic domain of LRP5 is comprised of 16% proline and 15% serine residues (FIG. 5(d) (SEQ ID NO:3)). Most members of the LDL-receptor family contain a conserved NPXY motif in the cytoplasmic domain which has been implicated in endocytosis by coated pits (Chen et. al. (1990) J. Biol. Chem. 265: 3116–3123). Mutagenesis studies have indicated that the critical residue for recognition by components of the endocytotic process is the tyrosine residue (Davis, et al. (1987) Cell 45: 15–24). Replacement of the tyrosine residue by phenylalanine or tryptophan is tolerated, thus the minimal requirement for this residue appears to be that it is aromatic amino acid (Davis, et al. (1987) Cell 45: 15–24). Structural studies have indicated that the critical function of the NP residues is to provide a beta-turn that presents the aromatic residue (Bansal and Gierasch (1991) Cell 67: 1195–1201).

Although the cytoplasmic domain of LRP5 does not contain an NPXY motif, there are several aromatic residues in the LRP5 cytoplasmic domain that lie in putative turn regions (FIG. 5(d) (SEQ ID NO:3)) and thus may be involved in facilitating endocytosis. In particular tyrosine 1473 which occurs in the sequence VPLY (SEQ ID NOS:48) motif has the proline and tyrosine in the correct position, relative to the consensus motif. Although the NPXY motif has been implicated in endocytosis in several proteins it is not an absolute requirement as there are proteins that lack the NPXY motif, e.g. the transferrin receptor, that undergo endocytosis by coated pits (Chen, et. al. (1990) J. Biol. Chem. 265: 3116–3123). In any event, we anticipate that the primary function of this protein will be receptor mediated endocytosis of its ligand.

Potential Roles of LRP5

The ability of members of the LDL-receptor family to bind multiple ligands suggests that LRP5 may function to bind one or more ligands. Moreover, in a fashion analogous to other members of the family, once bound the LRP5 receptor ligand complex would endocytose resulting in clearance of the ligand from the extracellular milieu. The nature of the LRP5 ligand may be a lipid, a protein, a protein complex, or a lipoprotein and may possess a variety of functions. Although the physiological function of the most closely related member of the LDL-receptor family, LRP1, is uncertain, it does possess a number of biochemical activities. LRP1 binds to alpha-2 macroglobulin. Alpha-2 macroglobulin is a plasma complex that contains a "bait" ligand for a variety of proteinases e.g. trypsin, chymotrypsin, pancreatic elastase and plasma kallikrein (Jensen (1989) J. Biol. Chem. 20:11539–11542). Once the proteinase binds and enzymatically cleaves the "bait" alpha-2 macroglobulin undergoes a conformational change and "traps" the proteinase. The proteinase:alpha-2 macroglobulin complex is rapidly cleared by LRP. This mechanism scavenges proteinases that have the potential to mediate a variety of biological functions e.g. antigen processing and proteinase secretion (Strickland et. al. (1990) J. Biol. Chem. 265: 17401–17404). The importance of this function is evidenced by the prenatal death of Lrp1 knockout mice (Zee et. al. (1994) Genomics 23: 256–259).

Antigen presentation is a critical component in the development of IDDM as is evidenced by the pivotal role of MHC haplotypes in conferring disease susceptibility (Tisch and McDivitt (1996) Cell 85: 291–297). By analogy with LRP1, LRP5 may play a role in antigen presentation in which case polymorphisms within this gene could affect the development of autoimmunity in the type 1 diabetic patient.

The alpha-2 macroglobulin complex also binds cytokines and growth factors such as interleukin-1 beta, interleukin 2, interleukin 6, transforming growth factor-beta, and fibroblast growth factor (Moestrup and Gliemann (1991) J. Biol. Chem. 266: 14011–14017). Thus the alpha-2 macroglobulin receptor has the potential to play a role in the clearance of cytokines and growth factors. The role of cytokines in mediating immune and inflammatory responses is well established. For example, the interleukin-2 gene is a strong candidate gene for the Idd3 locus in the non-obese diabetic mouse, an animal model for type 1 diabetes (Denny et. al. (1977) Diabetes 46:695–700). If LRP5 binds alpha-2 macroglobulin or related complexes then it may play a role in the immune response by mediating cytokine clearance. For example, the LRP5 which is expressed in pancreas, the target tissue of IDDM, may play a role in clearing cytokines from the inflammatory infiltrate (insulitis) that is ongoing in the disease. A polymorphism in LRP5 that reduces the ability of LRP5 to clear cytokines may increase an individuals susceptibility to developing IDDM. Furthermore an individual with a polymorphism that increases the ability of LRP5 to clear cytokines may be protected from developing IDDM. Conversely, certain cytokines counteract other cytokines and thus removal of certain beneficial cytokines by LRP5 may confer disease susceptibility and thus a polymorphism that reduces LRP5 activity may confer protection from developing the disease.

Increases of free fatty acids (FFA) have been shown to reduce insulin secretion in animals (Boden et. al. (1997) Diabetes 46: 3–10). In addition, ApoE which is a ligand for the LDL-receptor, has been associated with an antioxidant activity (Miyata and Smith (1996) Nature Genet. 14: 55–61) and oxidative damage is a central pathogenic mechanism in pancreatic β-cell destruction in type 1 diabetes (Bac (1994) Endocrin. Rev. 15: 516–542). Thus alterations in the ability of LRP5 to bind ApoE and related lipoproteins may influence the susceptibility to oxidative damage in pancreatic β-cells. Transfection of forms of LRP5 into β-cells may facilitate resistance of β cells to damage by the immune system in autoimmunity and in transplantation.

A pharmacological entity termed the lipolysis-stimulated receptor (LSR) which binds and endocytoses chylomicron remnants in the presence of FFA has been described (Mann et. al. (1995) Biochemistry 34: 10421–10431. One possible role for the LRP5 gene product is that it is responsible for this activity.

Another member of the LRP family is LRP2, also known as megalin and gp330, this protein has been implicated in Heymann's nephritis, an autoimmune disease of the kidney in rats (Saito et. al. (1994) PNAS 91: 9725–9729). Heymann's nephritis is a model of glomerularnephritis and is characterized by the development of autoantibodies to the alpha-2 macroglobulin receptor associated protein, also known as the Heymann nephritis antigen. The Heymann nephritis antigen binds to LRP2 (Strickland et. al. (1991) J. Biol. Chem. 266: 13364–13369). LRP2 may play a role in this disease by clearance of this pathogenic protein. In an analogous manner the function of LRP5 may be to bind and clear proteins in the pancreas to which the IDDM patient has generated autoantibodies. Alternatively LRP5 itself may be an autoantigen in the IDDM patient.

LRP1 has been identified as the receptor for certain bacterial toxins (Krieger and Herz (1994) Ann. Rev. Biochem. 63: 601–637) and the human rhinovirus (Hofer et. al. (1994) Proc. Natl. Acad. Sci. 91: 1839–42). It is possible that a viral infection alters an individuals susceptibility to IDDM (Epstein (1994) N. Eng. J. Med. 331: 1428–1436). If certain viruses utilize LRP5 as a mode of entry into the cell then polymorphisms in LRP5 may alter the individuals susceptibility to type 1 diabetes.

Alterations in LRP5 may participate in the pathogenesis of other diseases. LRP1 binds lipoproteins such as apoE and C-apolipoproteins. The clearance of lipoproteins such as apoE and apoB by the LDL receptor is its primary role, mutations in the LDL receptor lead to hypercholesterolemia (Chen et. al. (1990) J. Biol. Chem. 265: 3116–3123). Therefore mutations in LRP5 that decrease the ability of the protein to scavenge lipoproteins may cause an elevation in cholesterol. Variations in LRP5 could predispose to the development of macrovascular complications in diabetics, the major cause of death. In type 2 diabetics, pancreatic pathology is characterised by the deposition of amyloid. Amyloid deposition may decrease pancreatic β-cell function. LRP5 could function in the metabolism of islet amyloid and influence susceptibility to type 2 diabetes as well as type 1 diabetes. The role of ApoE in Alzheimer's disease indicates that proteins such as LRP1 and possibly LRP5 have the potential to contribute to the pathogenesis of this disease.

Polymorphism in genes involved in the development of osteoporosis-pseudoglioma syndrome have been mapped to a 3-cM region of chromosome 11 which includes the gene encoding LRP5 (Gong et. al. (1996) Am. J. Hum. Genet. 59: 146–151). The pathogenic mechanism of this disease is unknown but is believed to involve a regulatory role, patients with have aberrant vascular growth in the viteroretina. The potential role of LRP5 in the clearance of fibroblast growth factor, a mediator of angiogenesis, and the chromosomal location of the gene suggests that it may play a role in this disease. This proposed function could also be connected with the development of retinopathy in diabetes.

Polymoorphisms in the LRP5 Gene

The exons of the LRP5 gene are being scanned for polymorphisms. There are several polymorphisms that change an amino acid in LRP5 that have been identified in IDDM patients (Table 5). Of particular interest is a C to T transition, which changes an Ala codon to Val, in one of the three conserved LDL receptor ligand binding motifs. In addition to this polymorphism described above, a C to T transition was identified in the codon for $Asn^{709}$ (with no effect on the encoded amino acid), and three polymorphisms were identified in intronic sequences flanking the exons. An additional set of polymorphisms has been identified by comparing experimentally derived cDNA sequences with the genomic DNA sequence (Table 5). Some of these polymorphism will be analyzed in a large number of IDDM patients and control individuals to determine their association with IDDM.

Figure 9:
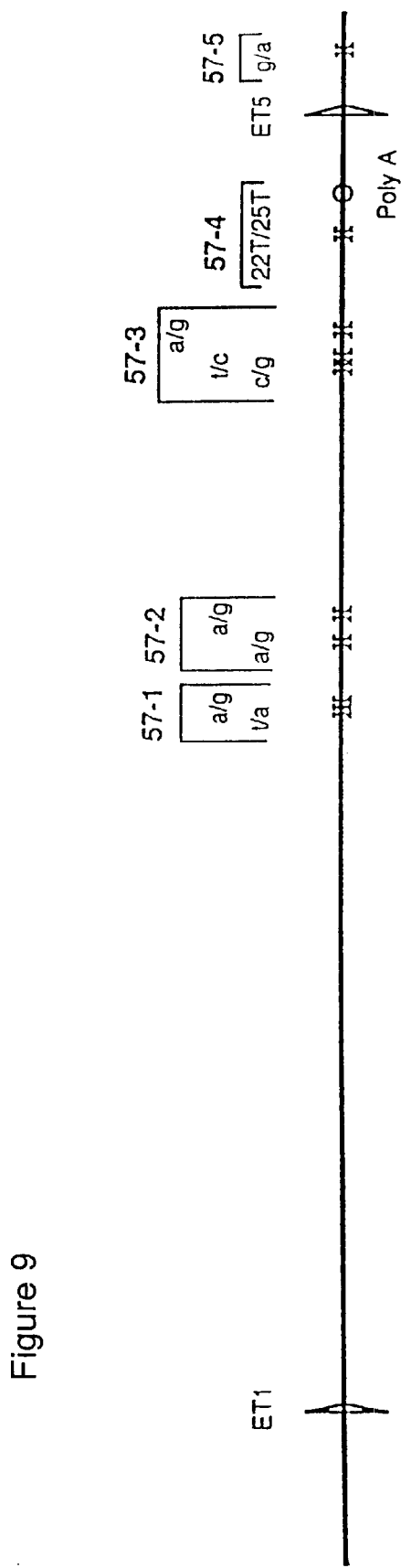
FIG. 9 is a SNP map of Contig 57. Polymorphisms were identified by the comparison of the DNA sequence of BAC 14-1-15 with cosmids EO 864 and BO 7185. Corresponding Table 6 indicates a PCR amplicon that includes the site of the polymorphism, the nature of the single nucleotide polymorphis (SNP), its location and the restriction site that is altered, if any. The line represents the contiguous genomic DNA with the relative location of the polymorphisms and the amplicons used to detect them. The large thin triangles represent the site of putative exons. The marker H0570POLYA is indicated.
Figure 10:
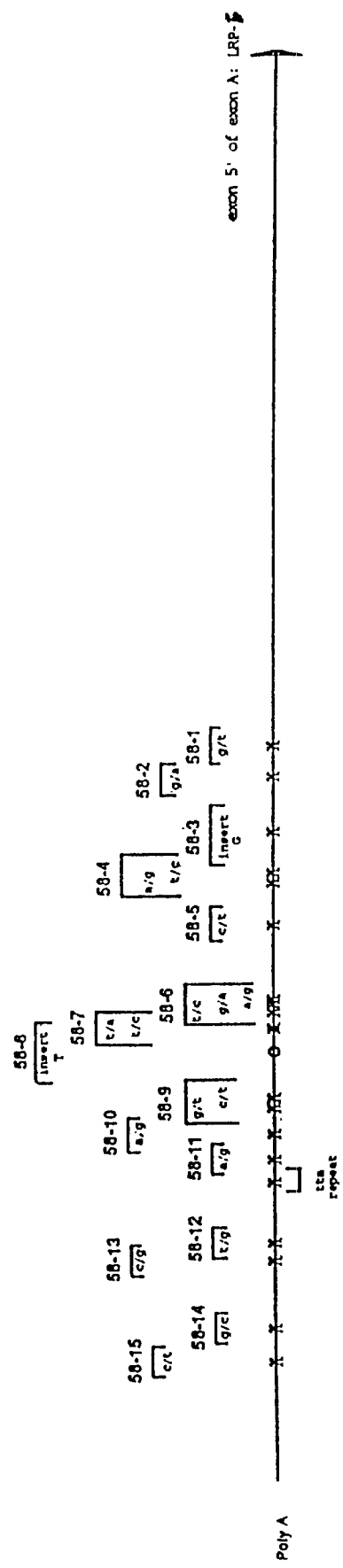
FIG. 10 is a SNP map of Contig 58. Polymorphisms were identified by the comparison of the DNA sequence of BAC 14-1-15 with cosmid BO 7185. Corresponding Table 6 indicates a PCR amplicon that includes the site of the polymorphism, the nature of the single nucleotide polymorphism (SNP), its location and the restriction site that is altered, if any. The line represents the contiguous genomic DNA with the relative location of the polymorphisms and the amplicons used to detect them. The large thin triangle at the very end of the line represents exon A of LRP5.

A number of (approximately 30) single nucleotide polymorphisms (SNPs) were identified in the genomic DNA sequences of overlapping BAC and cosmid clones surrounding the genetic marker poly A. The contiguous genomic sequences containing these polymorphism have been termed contig 57 (FIG. 9), which contains exons 1 and 5 along with the genetic markers poly A and D11S1917(UT5620), and contig 58 (FIG. 10) which contains the genetic marker L3001ca and part of exon A.

Additional Experimental Evidence

A region of identity-by-descent associated with type 1 diabetes has been identified in the 5' portion of the LRP5 gene. By combining data from SNPs and microsatellite markers we have identified a region identical-by-descent in susceptible haplotypes, the minimal region consists of 25 kb which contains the putative regulatory regions of LRP5 and the first exon. This strengthens the genetic evidence for LRP5 being a diabetes risk gene. Therefore therapies that affect LRP5 may be useful in the prevention and treatment of type 1 diabetes.

Overexpression of LRP5 in mice provides evidence for LRP5 affecting lipoprotein metabolism. Statistically significant evidence for modulation of triglycerides by LRP5 has been obtained. Thus therapies that affect LRP5 may be useful in the treatment of cardiovascular disease and conditions where serum triglycerides are elevated.

Suggestive evidence was obtained for LRP5 reducing serum cholesterol when it is above normal. There is also evidence for the ability of LRP5 to interact with very low-density lipoprotein particles and reduce their levels in serum. Therefore therapies that affect LRP-5 may be useful in the treatment of cardiovascular disease and conditions where serum cholesterol levels are elevated.

Biochemical studies indicate that LRP5 has the capacity to function in the uptake of low-density lipoprotein (LDL) particles. Thus therapies that affect LRP5 may be useful in the treatment of cardiovascular disease where LDL levels are elevated.

Overexpression of LRP5 in mice provided statistically significant evidence for a reduction in serum alkaline phosphatase. A reduction in serum alkaline phosphatase is consistent with LRP5 playing a role in modulation of the immune response. This provides evidence for LRP5 participating in the pathogenesis of type 1 diabetes. Therefore therapies that affect LRP5 may be useful in the treatment of autoimmune diseases.

Cellular localization of LRP5 indicates that it is expressed in a particular subtype, the phagocytic macrophages, of mature tissue macrophages. Evidence from the literature indicates that this class of macrophages is involved in autoimmune disease, supporting a role for LRP5 in autoimmune disease and type 1 diabetes. Therefore therapies that affect LRP5 may be useful in the treatment of autoimmune diseases.

Full length cDNAs for both human and mouse LRP5 have been obtained. Antibodies directed against LRP5 have been developed. These reagents provide tools to further analyze the biological function of LRP5.

Irrespective of LRP5's actual mode of action and involvement in IDDM and other diseases, the experimental work described herein establishes and supports the practical applications which are disclosed as aspects and embodiments of the present invention.

According to one aspect of the present invention there is provided a nucleic acid molecule which has a nucleotide sequence encoding a polypeptide which includes the amino acid sequence shown in FIG. 5(c) (SEQ ID NO:3), FIG. 5(d) (SEQ ID NO:3) or FIG. 5(e) (SEQ ID NO:4). The amino acid sequence of FIG. 5(c) (SEQ ID NO:3) includes that of FIG. 5(e) (SEQ ID NO:4) and a signal sequence.

The coding sequence may be that shown included in FIG. 5(a) (SEQ ID NO: 1) or FIG. 5(b) (SEQ ID NO:2) or it may be a mutant, variant, derivative or allele of the sequence shown. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in FIG. 5(a) (SEQ ID NO: 1) or FIG. 5(b) (SEQ ID NO:2) yet encode a polypeptide with the same amino acid sequence. The amino acid sequence shown in FIG. 5(c) (SEQ ID NO:3) consists of 1615 residues.

On the other hand the encoded polypeptide may comprise an amino acid sequence which differs by one or more amino acid residues from the amino acid sequence shown in FIG. 5(c) (SEQ ID NO:3). Nucleic acid encoding a polypeptide which is an amino acid sequence mutant, variant, derivative or allele of the sequence shown in FIG. 5(c) (SEQ ID NO:3) is further provided by the present invention. Such polypeptides are discussed below. Nucleic acid encoding such a polypeptide may show at the nucleotide sequence and/or encoded amino acid level greater than about 60% homology with the coding sequence shown in FIG. 5(a) (SEQ ID NO: 1) and/or the amino acid sequence shown in FIG. 5(c) (SEQ ID NO:3), greater than about 70% homology, greater than about 80% homology, greater than about 90% homology or greater than about 95% homology. For amino acid "homology", this may be understood to be similarity (according to the established principles of amino acid similarity, e.g. as determined using the algorithm GAP (Genetics Computer Group, Madison, Wis.) or identity. GAP uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found below.

The present invention extends to nucleic acid that hybridizes with any one or more of the specific sequences disclosed herein under stringent conditions. Suitable conditions include, e.g. for detection of sequences that are about 80–90% identical such as detection of mouse LRP5 with a human probe or vice versa, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

The coding sequence may be included within a nucleic acid molecule which has the sequence shown in FIG. 5(a) (isoform 1) (SEQ ID NO: 1) or FIG. 5(b) (SEQ ID NO:2) and encode the full polypeptide of isoform 1 (FIG. 5(c) (SEQ ID NO:3)). Mutants, variants, derivatives and alleles of these sequences are included within the scope of the present invention in terms analogous to those set out in the preceding paragraph and in the following disclosure.

Also provided by the present invention in various aspects and embodiments is a nucleic acid molecule encoding a polypeptide which includes the amino acid sequence shown in FIG. 17(b) (SEQ ID NO:39). This sequence forms a substantial part of the amino acid sequence shown in FIG. 5(e) (SEQ ID NO:4). Nucleic acid encoding a polypeptide which includes the amino acid sequence shown in FIG. 17(b) (SEQ ID NO:39) may include the coding sequence shown in FIG. 17(b) (SEQ ID NO:39), or an allele, variant, mutant or derivative in similar terms to those discussed above and below for other aspects and embodiments of the present invention.

According to various aspects of the present invention there are also provided various isoforms of the LRP5 polypeptide and gene. The gene of FIG. 5 is known as isoform 1. Included within the present invention is a nucleic acid molecule which has a nucleotide sequence encoding a polypeptide which includes the amino acid sequence of a polypeptide shown in FIG. 11(c) (isoform 2) (SEQ ID NO:25). The coding sequence may be as shown in FIG. 11(b) (SEQ ID NO:24) (which may be included within a molecule which has the sequence shown in FIG. 11(a) (isoform 2) (SEQ ID NO:23) or the sequence shown in FIG. 12(a) (isoform 3) (SEQ ID NO:26)), FIG. 13 (isoform 4) (SEQ ID NO:31), FIG. 14 (isoform 5) (SEQ ID NO:32) and FIG. 15 (isoform 6) (SEQ ID NO:33). Mutants, derivatives, variants and alleles of these sequences are also provided by the present invention, as disclosed.

Further nucleic acid molecules according to the present invention include the nucleotide sequence of any of FIG. 5(a) (SEQ ID NO: 1), FIG. 12(b) (SEQ ID NO:27), FIG. 12(e) (SEQ ID NO:30), FIG. 15(b) (SEQ ID NO:34), FIG. 16(a) (SEQ ID NO:35) and FIG. 16(b) (SEQ ID NO:36) and nucleic acid encoding the amino acid sequences encoded by FIG. 5(a) (SEQ ID NO: 1), FIG. 11(b) (SEQ ID NO:24), FIG. 12(c) (SEQ ID NO:28) or FIG. 16(c) (SEQ ID NO:37), along with mutants, alleles, variants and derivatives of these sequences. Further included are nucleic acid molecules encoding the amino acid sequence of FIG. 18(c) (SEQ ID NO:42), particularly including the coding sequence shown in FIG. 18(b) (SEQ ID NO:41).

Particular alleles according to the present invention have sequences have a variation indicated in Table 5 or Table 6. One or more of these may be associated with susceptibility to IDDM or other disease. Alterations in a sequence according to the present invention which are associated with IDDM or other disease may be preferred in accordance with embodiments of the present invention. Implications for screening, e.g. for diagnostic or prognostic purposes, are discussed below.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. The coding sequence shown herein is a DNA sequence. Where nucleic acid according to the invention includes RNA, reference to the sequence shown should be construed as encompassing reference to the RNA equivalent, with U substituted for T.

Nucleic acid may be provided as part of a replicable vector, and also provided by the present invention are a vector including nucleic acid as set out above, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as E. coli. This is discussed further below.

The nucleic acid sequence provided in accordance with the present invention is useful for identifying nucleic acid of interest (and which may be according to the present invention) in a test sample. The present invention provides a method of obtaining nucleic acid of interest, the method including hybridisation of a probe having the sequence shown in any of FIGS. 5(a), 11(a), 11(b), 12(a), 12(b), 12(c), 12(e), 13, 14, 15, 15(b) 16(a), 16(b), and 16(c), or a complementary sequence, to target nucleic acid. Hybridisation is generally followed by identification of successful hybridisation and isolation of nucleic acid which has hybridised to the probe, which may involve one or more steps of PCR. It will not usually be necessary to use a probe with the complete sequence shown in any of these figures. Shorter fragments, particularly fragments with a sequence encoding the conserved motifs (FIG. 5(c,d), and FIG. 6(a) (SEQ ID NOS:9 to 22)) may be used.

Nucleic acid according to the present invention is obtainable using one or more oligonucleotide probes or primers designed to hybridise with one or more fragments of the nucleic acid sequence shown in any of the figures, particularly fragments of relatively rare sequence, based on codon usage or statistical analysis. A primer designed to hybridise with a fragment of the nucleic acid sequence shown in any of the figures may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with a sequence shown and a primer which hybridises to the oligonucleotide linker.

Such oligonucleotide probes or primers, as well as the full-length sequence (and mutants, alleles, variants and derivatives) are also useful in screening a test sample containing nucleic acid for the presence of alleles, mutants and variants, with diagnostic and/or prognostic implications as discussed in more detail below.

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643–1650, (1991)). PCR comprises steps of denaturation of template nucleic acid (if double-stranded), annealing of primer to target, and polymerisation. The nucleic acid probed or used as template in the amplification reaction may be genomic DNA, cDNA or RNA. Other specific nucleic acid amplification techniques include strand displacement activation, the QB replicase system, the repair chain reaction, the ligase chain reaction and ligation activated transcription. For convenience, and because it is generally preferred, the term PCR is used herein in contexts where other nucleic acid amplification techniques may be applied by those skilled in the art. Unless the context requires otherwise, reference to PCR should be taken to cover use of any suitable nucleic acid amplification reaction available in the art.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on. On the basis of amino acid sequence information, oligonucleotide probes or primers may be designed, taking into account the degeneracy of the genetic code, and, where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but need not be than 18–20. Those skilled in the art are well versed in the design of primers for use processes such as PCR. Various techniques for synthesizing oligonucleotide primers are well known in the art, including phosphotriester and phosphodiester synthesis methods.

Preferred amino acid sequences suitable for use in the design of probes or PCR primers may include sequences conserved (completely, substantially or partly) encoding the motifs present in LRP5 (FIG. 5(d) (SEQ ID NO:3)).

A further aspect of the present invention provides an oligonucleotide or polynucleotide fragment of the nucleotide sequence shown in any of the figures herein providing nucleic acid according to the present invention, or a complementary sequence, in particular for use in a method of obtaining and/or screening nucleic acid. Some preferred oligonucleotides have a sequence shown in Table 2 (SEQ ID NOS:49–54), Table 4 (SEQ ID NOS:83–317), Table 7 (SEQ ID NOS:, Table 8 (SEQ ID NOS:318–333) or Table 9 (SEQ ID NOS:49–74, 334–402), or a sequence which differs from any of the sequences shown by addition, substitution, insertion or deletion of one or more nucleotides, but preferably without abolition of ability to hybridise selectively with nucleic acid in accordance with the present invention, that is wherein the degree of similarity of the oligonucleotide or polynucleotide with one of the sequences given is sufficiently high.

In some preferred embodiments, oligonucleotides according to the present invention that are fragments of any of the sequences shown, or any allele associated with IDDM or other disease susceptibility, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of IDDM or other disease susceptibility.

Methods involving use of nucleic acid in diagnostic and/or prognostic contexts, for instance in determining susceptibility to IDDM or other disease, and other methods concerned with determining the presence of sequences indicative of IDDM or other disease susceptibility are discussed below.

Further embodiments of oligonucleotides according to the present invention are anti-sense oligonucleotide sequences based on the nucleic acid sequences described herein. Anti-sense oligonucleotides may be designed to hybridise to the complementary sequence of nucleic acid, pre-mRNA or mature mRNA, interfering with the production of polypeptide encoded by a given DNA sequence (e.g. either native polypeptide or a mutant form thereof), so that its expression is reduce or prevented altogether. Anti-sense techniques may be used to target a coding sequence, a control sequence of a gene, e.g. in the 5' flanking sequence, whereby the antisense oligonucleotides can interfere with control sequences. Anti-sense oligonucleotides may be DNA or RNA and may be of around 14–23 nucleotides, particularly around 15–18 nucleotides, in length. The construction of antisense sequences and their use is described in Peyman and Ulman, Chemical Reviews, 90:543–584, (1990), and Crooke, Ann. Rev. Pharmacol. Toxicol., 32:329–376, (1992).

Nucleic acid according to the present invention may be used in methods of gene therapy, for instance in treatment of individuals with the aim of preventing or curing (wholly or partially) IDDM or other disease. This may ease one or more symptoms of the disease. This is discussed below.

Nucleic acid according to the present invention, such as a full-length coding sequence or oligonucleotide probe or primer, may be provided as part of a kit, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled. A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile).

According to a further aspect, the present invention provides a nucleic acid molecule including a LRP5 gene promoter.

In another aspect, the present invention provides a nucleic acid molecule including a promoter, the promoter including the sequence of nucleotides shown in FIG. 12(e) (SEQ ID NO:30) or FIG. 15(b) (SEQ ID NO:34). The promoter may comprise one or more fragments of the sequence shown in FIG. 12(e) (SEQ ID NO:30) or FIG. 15(b) (SEQ ID NO:34), sufficient to promote gene expression. The promoter may comprise or consist essentially of a sequence of nucleotides 5' to the LRP5 gene in the human chromosome, or an equivalent sequence in another species, such as the mouse.

Any of the sequences disclosed in the figures herein may be used to construct a probe for use in identification and isolation of a promoter from a genomic library containing a genomic LRP5 gene. Techniques and conditions for such probing are well known in the art and are discussed elsewhere herein. To find minimal elements or motifs responsible for tissue and/or developmental regulation, restriction enzyme or nucleases may be used to digest a nucleic acid molecule, followed by an appropriate assay (for example using a reporter gene such as luciferase) to determine the sequence required. A preferred embodiment of the present invention provides a nucleic acid isolate with the minimal nucleotide sequence shown in FIG. 12(e) (SEQ ID NO:30) or FIG. 15(b) (SEQ ID NO:34) required for promoter activity.

As noted, the promoter may comprise one or more sequence motifs or elements conferring developmental and/or tissue-specific regulatory control of expression. Other regulatory sequences may be included, for instance as identified by mutation or digest assay in an appropriate expression system or by sequence comparison with available information, e.g. using a computer to search on-line databases.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

The present invention extends to a promoter which has a nucleotide sequence which is allele, mutant, variant or derivative, by way of nucleotide addition, insertion, substitution or deletion of a promoter sequence as provided herein. Preferred levels of sequence homology with a provided sequence may be analogous to those set out above for encoding nucleic acid and polypeptides according to the present invention. Systematic or random mutagenesis of nucleic acid to make an alteration to the nucleotide sequence may be performed using any technique known to those skilled in the art. One or more alterations to a promoter sequence according to the present invention may increase or decrease promoter activity, or increase or decrease the magnitude of the effect of a substance able to modulate the promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production.

Further provided by the present invention is a nucleic acid construct comprising a LRP5 promoter region or a fragment, mutant, allele, derivative or variant thereof able to promoter transcription, operably linked to a heterologous gene, e.g. a coding sequence. A "heterologous" or "exogenous" gene is generally not a modified form of LRP5. Generally, the gene may be transcribed into mRNA which may be translated into a peptide or polypeptide product which may be detected and preferably quantitated following expression. A gene whose encoded product may be assayed following expression is termed a "reportergene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectro-photometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Nucleic acid constructs comprising a promoter (as disclosed herein) and a heterologous gene (reporter) may be employed in screening for a substance able to modulate activity of the promoter. For therapeutic purposes, e.g. for treatment of IDDM or other disease, a substance able to up-regulate expression of the promoter may be sought. A method of screening for ability of a substance to modulate activity of a promoter may comprise contacting an expression system, such as a host cell, containing a nucleic acid construct as herein disclosed with a test or candidate substance and determining expression of the heterologous gene.

The level of expression in the presence of the test substance may be compared with the level of expression in the absence of the test substance. A difference in expression in the presence of the test substance indicates ability of the substance to modulate gene expression. An increase in expression of the heterologous gene compared with expression of another gene not linked to a promoter as disclosed herein indicates specificity of the substance for modulation of the promoter.

A promoter construct may be introduced into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed then analysed.

Following identification of a substance which modulates or affects promoter activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of promoter activity, in accordance with what is disclosed herein, but also a pharmaceutical composition, medicament, drug or other composition comprising such a substance, a method comprising administration of such a composition to a patient, e.g. for increasing LRP5 expression for instance in treatment (which may include preventative treatment) of IDDM or other disease, use of such a substance in manufacture of a composition for administration, e.g. for increasing LRP5 expression for instance in treatment of IDDM or other disease, and a method of making a pharmaceutical composition comprising admixing such a substance with a pharmaceutically acceptable excipient, vehicle or carrier, and optionally other ingredients.

A further aspect of the present invention provides a polypeptide which has the amino acid sequence shown in FIG. 5(c) (SEQ ID NO:3), which may be in isolated and/or purified form, free or substantially free of material with which it is naturally associated, such as other polypeptides or such as human polypeptides other than that for which the amino acid sequence is shown in FIG. 5(c) (SEQ ID NO:3), or (for example if produced by expression in a prokaryotic cell) lacking in native glycosylation, e.g. unglycosylated. Further polypeptides according to the present invention have an amino acid sequence selected from that shown in the polypeptide shown in FIG. 11(c) (SEQ ID NO:25), that shown in 12(d), and the partial polypeptide shown in FIG. 16(d) (SEQ ID NO:8).

Polypeptides which are amino acid sequence variants, alleles, derivatives or mutants are also provided by the present invention. A polypeptide which is a variant, allele, derivative or mutant may have an amino acid sequence which differs from that given in a figure herein by one or more of addition, substitution, deletion and insertion of one or more amino acids. Preferred such polypeptides have LRP5 function, that is to say have one or more of the following properties: immunological cross-reactivity with an antibody reactive the polypeptide for which the sequence is given in a figure herein; sharing an epitope with the polypeptide for which the amino acid sequence is shown in a figure herein (as determined for example by immunological cross-reactivity between the two polypeptides; a biological activity which is inhibited by an antibody raised against the polypeptide whose sequence is shown in a figure herein; ability to reduce serum triglyceride; ability to reduce serum cholesterol; ability to interact with and/or reduce serum levels of very low-density lipoprotein particles; ability to affect serum alkaline phosphatase levels. Alteration of sequence may change the nature and/or level of activity and/or stability of the LRP5 protein.

A polypeptide which is an amino acid sequence variant, allele, derivative or mutant of the amino acid sequence shown in a figure herein may comprise an amino acid sequence which shares greater than about 35%. sequence identity with the sequence shown, greater than about 40%, greater than about 50%, greater than about 60%, greater than about 70%, greater than about 80%, greater than about 90% or greater than about 95%. The sequence may share greater than about 60% similarity, greater than about 70% similarity, greater than about 80% similarity or greater than about 90% similarity with the amino acid sequence shown in the relevant figure. Amino acid similarity is generally defined with reference to the algorithm GAP (Genetics Computer Group, Madison, Wis.) as noted above, or the TBLASTN program, of Altschul et al. (1990) J. Mol. Biol. 215: 403–10. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from that shown in a figure herein by insertion, addition, substitution or deletion of 1 amino acid, 2, 3, 4, 5–10, 10–20 20–30, 30–50, 50–100, 100–150, or more than 150 amino acids.

Sequence comparison may be made over the full-length of the relevant sequence shown herein, or may more preferably be over a contiguous sequence of about or greater than about 20, 25, 30, 33, 40, 50, 67, 133, 167, 200, 233, 267, 300, 333, 400, 450, 500, 600, 700, 800, 900, 1000, 1100, 1200, 1300, 1400, 1500, 1600, or more amino acids or nucleotide triplets, compared with the relevant amino acid sequence or nucleotide sequence as the case may be.

The present invention also includes active portions, fragments, derivatives and functional mimetics of the polypeptides of the invention. An "active portion" of a polypeptide means a peptide which is less than said full length polypeptide, but which retains a biological activity, such as a biological activity selected from binding to ligand, involvement in endocytosis. Thus an active portion of the LRP5 polypeptide may, in one embodiment, include the transmembrane domain and the portion of the cytoplasmic tail involved in endocytosis. Such an active fragment may be included as part of a fusion protein, e.g. including a binding portion for a different ligand. In different embodiments, combinations of LDL and EGF motifs may be included in a molecule to confer on the molecule different binding specificities.

A "fragment" of a polypeptide generally means a stretch of amino acid residues of at least about five contiguous amino acids, often at least about seven contiguous amino acids, typically at least about nine contiguous amino acids, more preferably at least about 13 contiguous amino acids, and, more preferably, at least about 20 to 30 or more contiguous amino acids. Fragments of the LRP5 polypeptide sequence may include antigenic determinants or epitopes useful for raising antibodies to a portion of the amino acid sequence. Alanine scans are commonly used to find and refine peptide motifs within polypeptides, this involving the systematic replacement of each residue in turn with the amino acid alanine, followed by an assessment of biological activity.

Preferred fragments of LRP5 include those with any of the following amino acid sequences:

| | |
|---|---|
| SYFHLFPPPPSPCTDSS | (SEQ ID NOS:403) |
| VDGRQNIKRAKDDGT | (SEQ ID NOS:404) |
| EVLFTTGLIRPVALVVDN | (SEQ ID NOS:405) |
| IQGHLDFVMDILVFHS, | (SEQ ID NOS:406) | which may be used for instance in raising or isolating antibodies. Variant and derivative peptides, peptides which have an amino acid sequence which differs from one of these sequences by way of addition, insertion, deletion or substitution of one or more amino acids are also provided by the present invention, generally with the proviso that the variant or derivative peptide is bound by an antibody or other specific binding member which binds one of the peptides whose sequence is shown. A peptide which is a variant or derivative of one of the shown peptides may compete with the shown peptide for binding to a specific binding member, such as an antibody or antigen-binding fragment thereof.

A "derivative" of a polypeptide or a fragment thereof may include a polypeptide modified by varying the amino acid sequence of the protein, e.g. by manipulation of the nucleic acid encoding the protein or by altering the protein itself. Such derivatives of the natural amino acid sequence may involve one or more of insertion, addition, deletion or substitution of one or more amino acids, which may be without fundamentally altering the qualitative nature of biological activity of the wild type polypeptide. Also encompassed within the scope of the present invention are functional mimetics of active fragments of the LRP5 polypeptides provided (including alleles, mutants, derivatives and variants). The term "functional mimetic" means a substance which may not contain an active portion of the relevant amino acid sequence, and probably is not a peptide at all, but which retains in qualitative terms biological activity of natural LRP5 polypeptide. The design and screening of candidate mimetics is described in detail below.

Sequences of amino acid sequence variants representative of preferred embodiments of the present invention are shown in Table 5 and Table 6. Screening for the presence of one or more of these in a test sample has a diagnostic and/or prognostic use, for instance in determining IDDM or other disease susceptibility, as discussed below.

Other fragments of the polypeptides for which sequence information is provided herein are provided as aspects of the present invention, for instance corresponding to functional domains. One such functional domain is the putative extracellular domain, such that a polypeptide fragment according to the present invention may include the extracellular domain of the polypeptide of which the amino acid sequence is shown in FIG. 5(*e*) (SEQ ID NO:4) or FIG. 5(*c*) (SEQ ID NO:3). This runs to amino acid 1385 of the precursor sequence of FIG. 5(*c*) (SEQ ID NO:3). Another useful LRP5 domain is the cytoplasmic domain, 207 amino acids shown in FIG. 5(*d*) (SEQ ID NO:3). This may be used in targeting proteins to move through the endocytotic pathway.

A polypeptide according to the present invention may be isolated and/or purified (e.g. using an antibody) for instance after production by expression from encoding nucleic acid (for which see below). Thus, a polypeptide may be provided free or substantially free from contaminants with which it is naturally associated (if it is a naturally-occurring polypeptide). A polypeptide may be provided free or substantially free of other polypeptides. Polypeptides according to the present invention may be generated wholly or partly by chemical synthesis. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide, peptide fragment, allele, mutant, derivative or variant according to the present invention may be used as an immunogen or otherwise in obtaining specific antibodies. Antibodies are useful in purification and other manipulation of polypeptides and peptides, diagnostic screening and therapeutic contexts. This is discussed further below.

A polypeptide according to the present invention may be used in screening for molecules which affect or modulate its activity or function, e.g. binding to ligand, involvement in endocytosis, movement from an intracellular compartment to the cell surface, movement from the cell surface to an intracellular compartment. Such molecules may interact with the ligand binding portion of LRP5, the cytoplasmic portion of LRP5, or with one or more accessory molecules e.g. involved in movement of vesicles containing LRP5 to and from the cell surface, and may be useful in a therapeutic (possibly including prophylactic) context.

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility. Such means for screening for substances potentially useful in treating or preventing IDDM or other disease is provided by polypeptides according to the present invention. Substances identified as modulators of the polypeptide represent an advance in the fight against IDDM and other diseases since they provide basis for design and investigation of therapeutics for in vivo use. Furthermore, they may be useful in any of a number of conditions, including autoimmune diseases, such as glomerulonephritis, diseases and disorders involving disruption of endocytosis and/or antigen presentation, diseases and disorders involving cytokine clearance and/or inflammation, viral infection, pathogenic bacterial toxin contamination, elevation of free fatty acids or hypercholesterolemia, type 2 diabetes, osteoporosis, and Alzheimer's disease, given the functional indications for LRP5, discussed elsewhere herein. As noted elsewhere, LRP5, fragments thereof, and nucleic acid according to the invention may also be useful in combatting any of these diseases and disorders.

A method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology (Schultz, J S (1996) Biotechnol. Prog. 12:729–743) provides an efficient way of testing a potentially vast number of different substances for ability to modulate activity of a polypeptide. Prior to or as well as being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified as a modulator of polypeptide activity, in accordance with what is disclosed herein, but also a pharmaceutical composition, medicament, drug or other composition comprising such a substance, a method comprising administration of such a composition to a patient, e.g. for treatment (which may include preventative treatment) of IDDM or other disease, use of such a substance in manufacture of a composition for administration, e.g. for treatment of IDDM or other disease, and a method of making a pharmaceutical composition comprising admixing such a substance with a pharmaceutically acceptable excipient, vehicle or carrier, and optionally other ingredients.

A substance identified using as a modulator of polypeptide or promoter function may be peptide or non-peptide in nature. Non-peptide "small molecules" are often preferred for many in vivo pharmaceutical uses. Accordingly, a mimetic or mimick of the substance (particularly if a peptide) may be designed for pharmaceutical use. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Mimetics of substances identified as having ability to modulate LRP5 polypeptide or promoter activity using a screening method as disclosed herein are included within the scope of the present invention. A polypeptide, peptide or substance able to modulate activity of a polypeptide according to the present invention may be provided in a kit, e.g. sealed in a suitable container which protects its contents from the external environment. Such a kit may include instructions for use.

A convenient way of producing a polypeptide according to the present invention is to express nucleic acid encoding it, by use of the nucleic acid in an expression system. Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid may take place in vivo by ay of gene therapy, as discussed below. A host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

Thus, in various further aspects, the present invention provides a non-human animal with a human LRP5 transgene within its genome. The transgene may have the sequence of any of the isoforms identified herein or a mutant, derivative, allele or variant thereof as disclosed. In one preferred embodiment, the heterologous human LRP5 sequence replaces the endogenous animal sequence. In other preferred embodiments, one or more copies of the human LRP5 sequence are added to the animal genome.

Preferably the animal is a rodent, and most preferably mouse or rat.

This may have a therapeutic aim. (Gene therapy is discussed below.) The presence of a mutant, allele or variant sequence within cells of an organism, particularly when in place of a homologous endogenous sequence, may allow the organism to be used as a model in testing and/or studying the role of the LRP5 gene or substances which modulate activity of the encoded polypeptide and/or promoter in vitro or are otherwise indicated to be of therapeutic potential.

An animal model for LRP5 deficiency may be constructed using standard techniques for introducing mutations into an animal germ-line. In one example of this approach, using a mouse, a vector carrying an insertional mutation within the LRP5 gene may be transfected into embryonic stem cells. A selectable marker, for example an antibiotic resistance gene such as neoR, may be included to facilitate selection of clones in which the mutant gene has replaced the endogenous wild type homologue. Such clones may be also be identified or further investigated by Southern blot hybridisation. The clones may then be expanded and cells injected into mouse blastocyst stage embryos. Mice in which the injected cells have contributed to the development of the mouse may be identified by Southern blotting. These chimeric mice may then be bred to produce mice which carry one copy of the mutation in the germ line. These heterozygous mutant animals may then be bred to produce mice carrying mutations in the gene homozygously. The mice having a heterozygous mutation in the LRP5 gene may be a suitable model for human individuals having one copy of the gene mutated in the germ line who are at risk of developing IDDM or other disease.

Animal models may also be useful for any of the various diseases discussed elsewhere herein.

Instead of or as well as being used for the production of a polypeptide encoded by a transgene, host cells may be used as a nucleic acid factory to replicate the nucleic acid of interest in order to generate large amounts of it. Multiple copies of nucleic acid of interest may be made within a cell when coupled to an amplifiable gene such as dihyrofolate reductase (DHFR), as is well known. Host cells transformed with nucleic acid of interest, or which are descended from host cells into which nucleic acid was introduced, may be cultured under suitable conditions, e.g. in a fermentor, taken from the culture and subjected to processing to purifiy the nucleic acid. Following purification, the nucleic acid or one or more fragments thereof may be used as desired, for instance in a diagnostic or prognostic assay as discussed elsewhere herein.

The provision of the novel LRP-5 polypeptide isoforms and mutants, alleles, variants and derivatives enables for the first time the production of antibodies able to bind these molecules specifically.

Accordingly, a further aspect of the present invention provides an antibody able to bind specifically to the polypeptide whose sequence is given in a figure herein. Such an antibody may be specific in the sense of being able to distinguish between the polypeptide it is able to bind and other human polypeptides for which it has no or substantially no binding affinity (e.g. a binding affinity of about 1000× less). Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Suitable peptides for use in immunising an animal and/or isolating anti-LRP5 antibody include any of the following amino acid sequences:

| | |
|---|---|
| SYFHLFPPPPSPCTDSS | (SEQ ID NOS:403) |
| VDGRQNIKRAKDDGT | (SEQ ID NOS:404) |
| EVLFTTGLIRPVALVVDN | (SEQ ID NOS:405) |
| IQGHLDFVMDILVFHS. | (SEQ ID NOS:406) |

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge. Particular embodiments of antibodies according to the present invention include antibodies able to bind and/or which bind specifically, e.g. with an affinity of at least $10^{-7}$ M, to one of the following peptides:

| | |
|---|---|
| SYFHLFPPPPSPCTDSS | (SEQ ID NOS:403) |
| VDGRQNIKRAKDDGT | (SEQ ID NOS:404) |
| EVLFTTGLIRPVALVVDN | (SEQ ID NOS:405) |
| IQGHLDFVMDILVFHS. | (SEQ ID NOS:406) |

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

The identification of the LRP5 gene and indications of its association with IDDM and other diseases paves the way for aspects of the present invention to provide the use of materials and methods, such as are disclosed and discussed above, for establishing the presence or absence in a test sample of an variant form of the gene, in particular an allele or variant specifically associated with IDDM or other disease. This may be for diagnosing a predisposition of an individual to IDDM or other disease. It may be for diagnosing IDDM of a patient with the disease as being associated with the IDDM4 gene.

This allows for planning of appropriate therapeutic and/or prophylactic treatment, permitting stream-lining of treatment by targeting those most likely to benefit.

A variant form of the gene may contain one or more insertions, deletions, substitutions and/or additions of one or more nucleotides compared with the wild-type sequence (such as shown in Table 5 or Table 6) which may or may not disrupt the gene function. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce expression from the gene or affect the processing or stability of the mRNA transcript. For instance, a sequence alteration may affect alternative splicing of mRNA. As discussed, various LRP5 isoforms resulting from alternative splicing are provided by the present invention.

There are various methods for determining the presence or absence in a test sample of a particular nucleic acid sequence, such as the sequence shown in any figure herein, or a mutant, variant or allele thereof, e.g. including an alteration shown in Table 5 or Table 6.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RN'ases. Nucleic acid in a test sample may be sequenced and the sequence compared with the sequence shown in any of the figures herein, to determine whether or not a difference is present. If so, the difference can be compared with known susceptibility alleles (e.g. as shown in Table 5 or Table 6) to determine whether the test nucleic acid contains one or more of the variations indicated, or the difference can be investigated for association with IDDM or other disease.

Since it will not generally be time- or labour-efficient to sequence all nucleic acid in a test sample or even the whole LRP5 gene, a specific amplification reaction such as PCR using one or more pairs of primers may be employed to amplify the region of interest in the nucleic acid, for instance the LRP5 gene or a particular region in which polymorphisms associated with IDDM or other disease susceptibility occur. The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the LRP5 gene, or its complement, containing a sequence alteration known to be associated with IDDM or other disease susceptibility. Under suitably stringent conditions, specific hybridisation of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the polymorphism on a denaturing polyacrylamide DNA sequencing gel, with specific bands that are linked to the gene variants being selected.

SSCP heteroduplex analysis may be used for screening DNA fragments for sequence variants/mutations. It generally involves amplifying radiolabelled 100–300 bp fragments of the gene, diluting these products and denaturing at 95° C. The fragments are quick-cooled on ice so that the DNA remains in single stranded form. These single stranded fragments are run through acrylamide based gels. Differences in the sequence composition will cause the single stranded molecules to adopt difference conformations in this gel matrix making their mobility different from wild type fragments, thus allowing detecting of mutations in the fragments being analysed relative to a control fragment upon exposure of the gel to X-ray film. Fragments with altered mobility/conformations may be directly excised from the gel and directly sequenced for mutation.

Sequencing of a PCR product may involve precipitation with isopropanol, resuspension and sequencing using a TaqFS+ Dye terminator sequencing kit. Extension products may be electrophoresed on an ABI 377 DNA sequencer and data analysed using Sequence Navigator software.

A further possible screening approach employs a PTT assay in which fragments are amplified with primers that contain the consensus Kozak initiation sequences and a T7 RNA polymerase promoter. These extra sequences are incorporated into the 5' primer such that they are in frame with the native coding sequence of the fragment being analysed. These PCR products are introduced into a coupled transcription/translation system. This reaction allows the production of RNA from the fragment and translation of this RNA into a protein fragment. PCR products from controls make a protein product of a wild type size relative to the size of the fragment being analysed. If the PCR product analysed has a frame-shift or nonsense mutation, the assay will yield a truncated protein product relative to controls. The size of the truncated product is related to the position of the mutation, and the relative region of the gene from this patient may be sequenced to identify the truncating mutation.

An alternative or supplement to looking for the presence of variant sequences in a test sample is to look for the presence of the normal sequence, e.g. using a suitably specific oligonucleotide probe or primer. Use of oligonucleotide probes and primers has been discussed in more detail above.

Allele- or variant-specific oligonucleotide probes or primers according to embodiments of the present invention may be selected from those shown in Table 4 (SEQ ID NOS:83–317), Table 7 (SEQ ID NOS:240–317) or Table 8 (SEQ ID NOS:318–333).

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid.

Thus, an oligonucleotide probe that has the sequence of a region of the normal LRP5 gene (either sense or anti-sense strand) in which mutations associated with IDDM or other disease susceptibility are known to occur (e.g. see Table 5 and Table 6) may be annealed to test nucleic acid and the presence or absence of a mis-match determined. Detection of the presence of a mis-match may indicate the presence in the test nucleic acid of a mutation associated with IDDM or other disease susceptibility. On the other hand, an oligonucleotide probe that has the sequence of a region of the gene including a mutation associated with IDDM or other disease susceptibility may be annealed to test nucleic acid and the presence or absence of a mis-match determined. The presence of a mis-match may indicate that the nucleic acid in the test sample has the normal sequence (the absence of a mis-match indicating that the test nucleic acid has the mutation). In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene shown in a figure herein or a variant or allele, e.g. as containing an alteration shown in Table 5 or Table 6 is digested with the same enzyme or enzymes.

The presence or absence of a lesion in a promoter or other regulatory sequence may also be assessed by determining the level of mRNA production by transcription or the level of polypeptide production by translation from the mRNA. Determination of promoter activity has been discussed above.

A test sample of nucleic acid may be provided for example by extracting nucleic acid from cells or biological tissues or fluids, urine, saliva, faeces, a buccal swab, biopsy or preferably blood, or for pre-natal testing from the amnion, placenta or foetus itself.

There are various methods for determining the presence or absence in a test sample of a particular polypeptide, such as the polypeptide with the amino acid sequence shown in any figure herein or an amino acid sequence mutant, variant or allele thereof.

A sample may be tested for the presence of a binding partner for a specific binding member such as an antibody (or mixture of antibodies), specific for one or more particular variants of the polypeptide shown in a figure herein. A sample may be tested for the presence of a binding partner for a specific binding member such as an antibody (or mixture of antibodies), specific for the polypeptide shown in a figure herein. In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the polypeptide whose sequence is disclosed herein, or if it is a mutant or variant form. Amino acid sequence is routine in the art using automated sequencing machines.

A test sample containing one or more polypeptides may be provided for example as a crude or partially purified cell or cell lysate preparation, e.g. using tissues or cells, such as from saliva, faeces, or preferably blood, or for pre-natal testing from the amnion, placenta or foetus itself.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering an agent directly, it may be be produced in target cells by expression from an encoding gene introduced into the cells, e.g. in a viral vector (see below). The vector may be targeted to the specific cells to be treated, or it may contain regulatory elements which are switched on more or less selectively by the target cells. Viral vectors may be targeted using specific binding molecules, such as a sugar, glycolipid or protein such as an antibody or binding fragment thereof. Nucleic acid may be targeted by means of linkage to a protein ligand (such as an antibody or binding fragment thereof) via polylysine, with the ligand being specific for a receptor present on the surface of the target cells.

An agent may be administered in a precursor form, for conversion to an active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

Nucleic acid according to the present invention, e.g. encoding the authentic biologically active LRP-5 polypeptide or a functional fragment thereof, may be used in a method of gene therapy, to treat a patient who is unable to synthesize the active polypeptide or unable to synthesize it at the normal level, thereby providing the effect provided by the wild-type with the aim of treating and/or preventing one or more symptoms of IDDM and/or one or more other diseases.

Vectors such as viral vectors have been used to introduce genes into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see e.g. U.S. Pat. No. 5,252, 479 and WO 93/07282. In particular, a number of viruses have been used as gene transfer vectors, including adenovirus, papovaviruses, such as SV40, vaccinia virus, herpesviruses, including HSV and EBV, and retroviruses, including gibbon ape leukaemia virus, Rous Sarcoma Virus, Venezualian equine enchephalitis virus, Moloney murine leukaemia virus and murine mammary tumourvirus. Many gene therapy protocols in the prior art have used disabled murine retroviruses.

Disabled virus vectors are produced in helper cell lines in which genes required for production of infectious viral particles are expressed. Helper cell lines are generally missing a sequence which is recognised by the mechanism which packages the viral genome and produce virions which contain no nucleic acid. A viral vector which contains an intact packaging signal along with the gene or other sequence to be delivered (e.g. encoding the LRP5 polypeptide or a fragment thereof) is packaged in the helper cells into infectious virion particles, which may then be used for the gene delivery.

Other known methods of introducing nucleic acid into cells include electroporation, calcium phosphate co-precipitation, mechanical techniques such as microinjection, transfer mediated by liposomes and direct DNA uptake and receptor-mediated DNA transfer. Liposomes can encapsulate RNA, DNA and virions for delivery to cells. Depending on factors such as pH, ionic strength and divalent cations being present, the composition of liposomes may be tailored for targeting of particular cells or tissues. Liposomes include phospholipids and may include lipids and steroids and the composition of each such component may be altered. Targeting of liposomes may also be achieved using a specific binding pair member such as an antibody or binding fragment thereof, a sugar or a glycolipid.

The aim of gene therapy using nucleic acid encoding the polypeptide, or an active portion thereof, is to increase the amount of the expression product of the nucleic acid in cells in which the level of the wild-type polypeptide is absent or present only at reduced levels. Such treatment may be therapeutic or prophylactic, particularly in the treatment of individuals known through screening or testing to have an IDDM4 susceptibility allele and hence a predisposition to the disease.

Similar techiques may be used for anti-sense regulation of gene expression, e.g. targeting an antisense nucleic acid molecule to cells in which a mutant form of the gene is expressed, the aim being to reduce production of the mutant gene product. Other approaches to specific down-regulation of genes are well known, including the use of ribozymes designed to cleave specific nucleic acid sequences. Ribozymes are nuceic acid molecules, actually RNA, which specifically cleave single-stranded RNA, such as mRNA, at defined sequences, and their specificity can be engineered. Hammerhead ribozymes may be preferred because they recognise base sequences of about 11–18 bases in length, and so have greater specificity than ribozymes of the Tetrahymena type which recognise sequences of about 4 bases in length, though the latter type of ribozymes are useful in certain circumstances. References on the use of ribozymes include Marschall, et al. Cellular and Molecular Neurobiology, 1994. 14(5): 523; Hasselhoff, Nature 334: 585 (1988) and Cech, J. Amer. Med. Assn., 260: 3030 (1988).

Aspects of the present invention will now be illustrated with reference to the accompanying figures described already above and experimental exemplification, by way of example and not limitation. Further aspects and embodiments will be apparent to those of ordinary skill in the art. All documents mentioned in this specification are hereby incorporated herein by reference.

EXAMPLE 1

Cloning of LRP5

As noted above, confirmation of linkage to two of the 18 potential loci for IDDM predisposition was achieved by analysis of two family sets (102 UK families and 84 USA families), IDDM4 on chromosome 11q13 (MLS 1.3, P=0.01 at FGF3) and IDDM5 on chromosome 6q (MLS 1.8 P=0.003 at ESR). At IDDM4 the most significant linkage was obtained in the subset of families sharing 1 or 0 alleles IBD at HLA (MLS=2.8; P=0.0002; ls=1.2) (Davies et al, 1994). This linkage was also observed by Hashimoto et al (1994) using 251 affected sibpairs, obtaining P=0.0008 in all sibpairs. Combining these results, with 596 families, provides substantial support for IDDM4 (P=1.5×10$^{-6}$) (Todd and Farrall, 1996; Luo et al, 1996).

Figure 1:
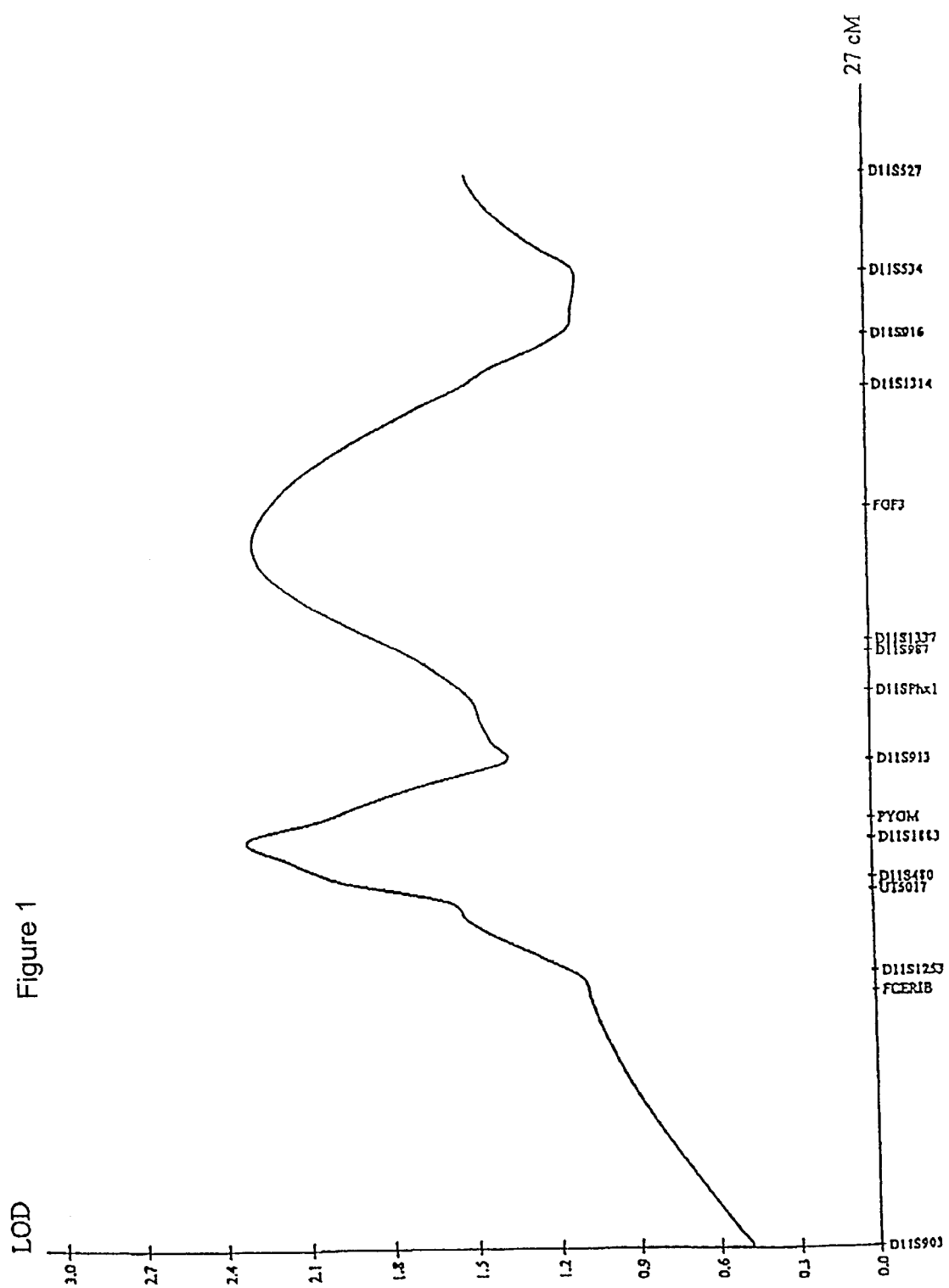
FIG. 1 illustrates approximate localisation of IDDM4 on chromosome 11q13. Multipoint linkage map of maximum likelihood IBD in a subgroup of HLA 1:0 sharers in 150 families. MLS of 2.3 at FGF3 and D11S1883 ($\lambda$s=1.19) were obtained (Davies et al (1994) Nature 371: 130–136).

Multipoint analysis with other markers in the FGF3 region produced an MLS of 2.3 at FGF3 and D11S1883 (ls=1.19), and delineated the interval to a 27cM region, flanked by the markers D11S903 and D11S527 (FIG. 1).

Multipoint linkage analysis cannot localise the gene to a small region unless several thousand multiplex families are available. Instead, association mapping has been used for rare single gene diseases which can narrow the interval containing the disease gene to less than 2cM or 2M bases. Nevertheless, this method is highly unpredictable and has not previously been used to locate a polygene for a common disease. Association mapping has been used to locate the IDDM2/INS polygene but this relied on the selection of a functional candidate polymorphism/gene and was restricted to a very small (<30kb) region. Linkage disequilibrium (LD) or association studies were carried out in order to delineate the IDDM4 region to less than 2cM. In theory, association of a particular allele very close to the founder mutation will be detected in populations descended from that founder. The transmission disequilibrium test (TDT, Spielman et al, 1993) measures association by assessing the deviation from 50% of the transmission of alleles from a marker locus from parents to affected children. The detection of association is dependent on the ancestry of each population studied to be as homogeneous as possible, in order to reduce the possiblity that the presence of several founder-chromosomes, decreasing the power to detect the association. These parameters are highly unpredictable.

Figure 2:
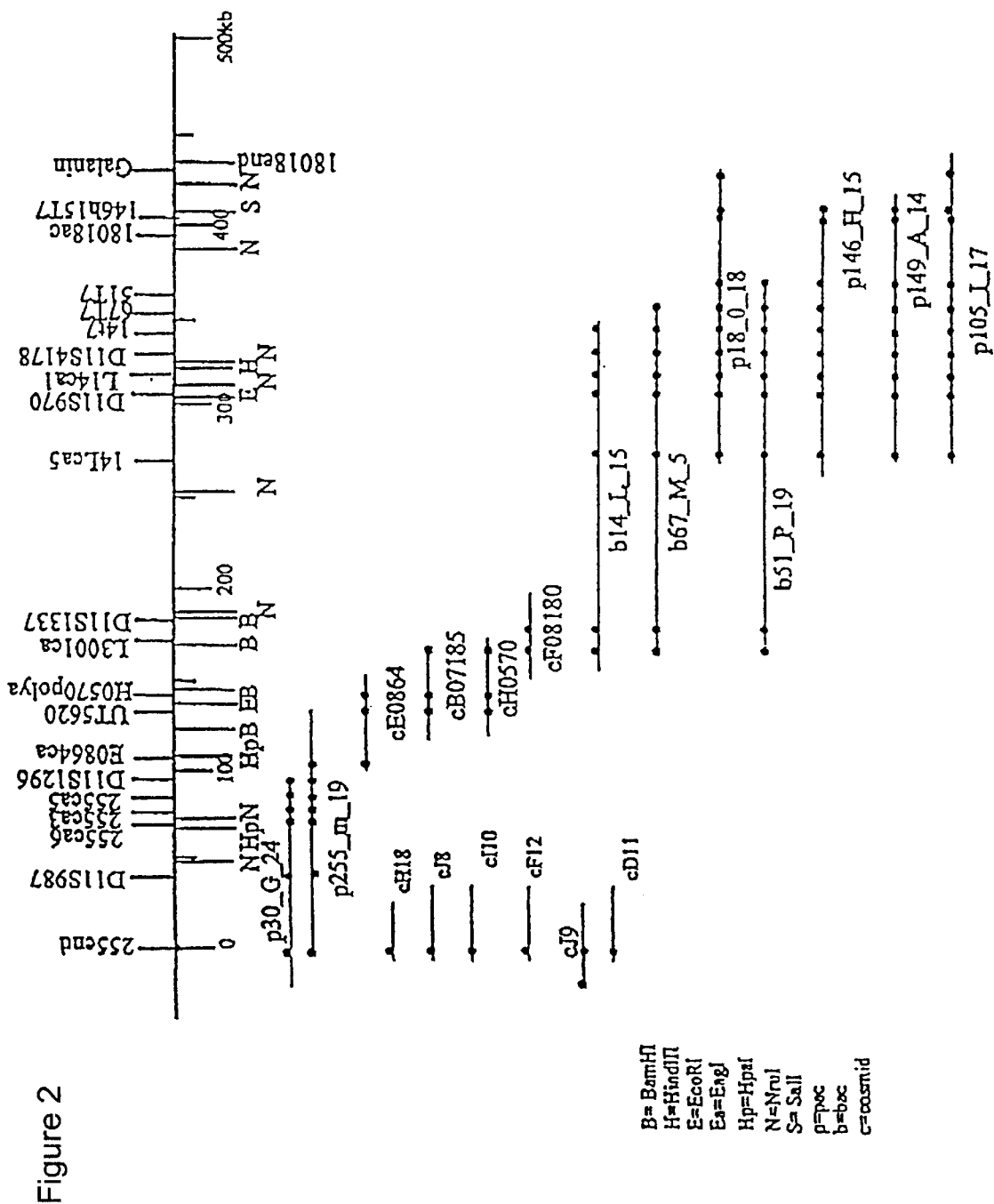
FIG. 2 shows a physical map of the region D11S987—Galanin on chromosome 11q13. The interval was cloned in pacs, bacs and cosmids, and restriction mapped using a range of restriction enzymes to determine the physical distance between each marker.

Analysis of markers spanning the IDDM4 linkage interval, LD was detected at D11S1917(UT5620) in 554 families, P=0.01. A physical map of this region, comprising approximately 500 kb, was achieved by constructing a pac, bac and cosmid contig (FIG. 2). The region was physically mapped by hybridisation of markers onto restriction-enzyme digested clones resolved through agarose, and Southern blotted.

Figure 3:
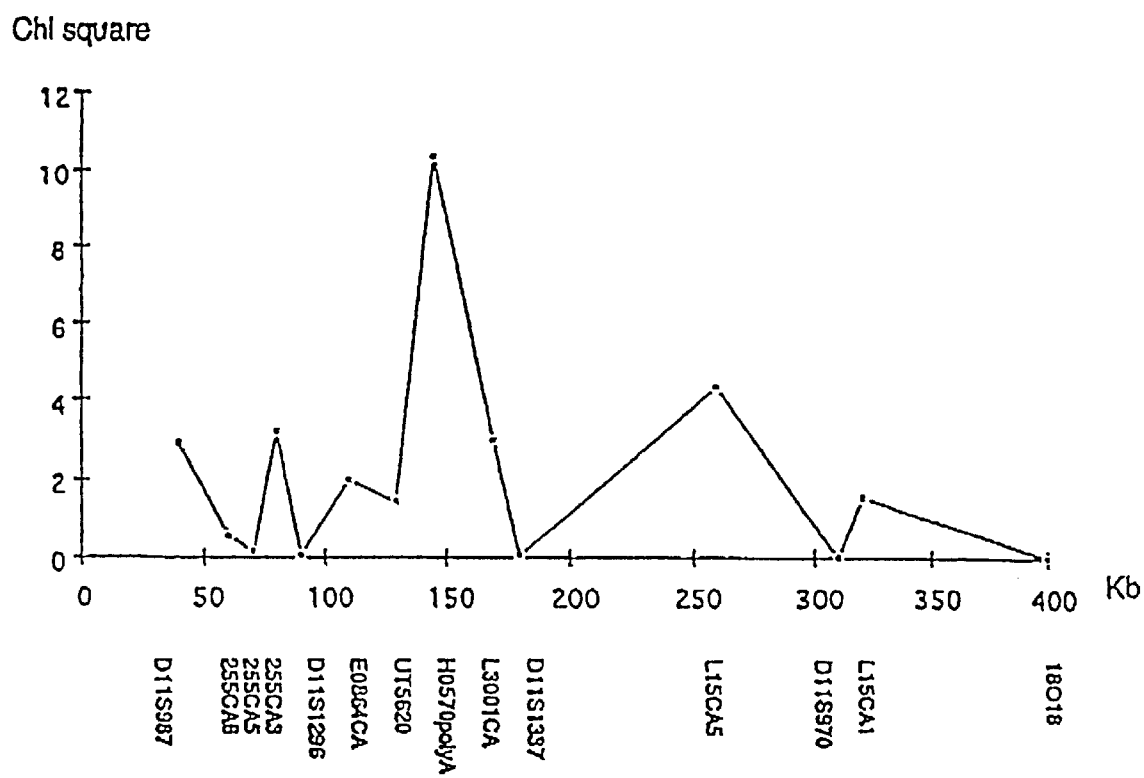
FIG. 3 shows a single-point linkage disequilibrium curve at the IDDM4 region. 1289 families were analysed by TDT, with a peak at H0570POLYA,) P=0.001. x-axis: physical distance in kb; y-axis: TDT $\chi^2$ statistic (tdf).

Further microsatellites (both published, and those isolated from the clones by microsatellite rescue) were analysed within 1289 families, from four different populations (UK, USA, Sardinia and Norway). A LD graph was constructed, with a peak at H0570POLYA, P=0.001, flanked by the markers D11S987 and 18018AC (FIG. 3). The LD detected at a polymorphic marker is influenced by allele frequency, and whether the mutation causing susceptibility to type 1 diabetes arose on a chromosome where the allele in LD is the same allele as that on protective or neutral chromosomes. In the case where the marker being analysed has the same allele in LD with both susceptible and protective genotypes, these will remain undetected by single point analysis, in effect cancelling each other out, and showing little or no evidence for LD with the disease locus. Unpredictability of the method arising from this has been noted already above.

Figure 4:
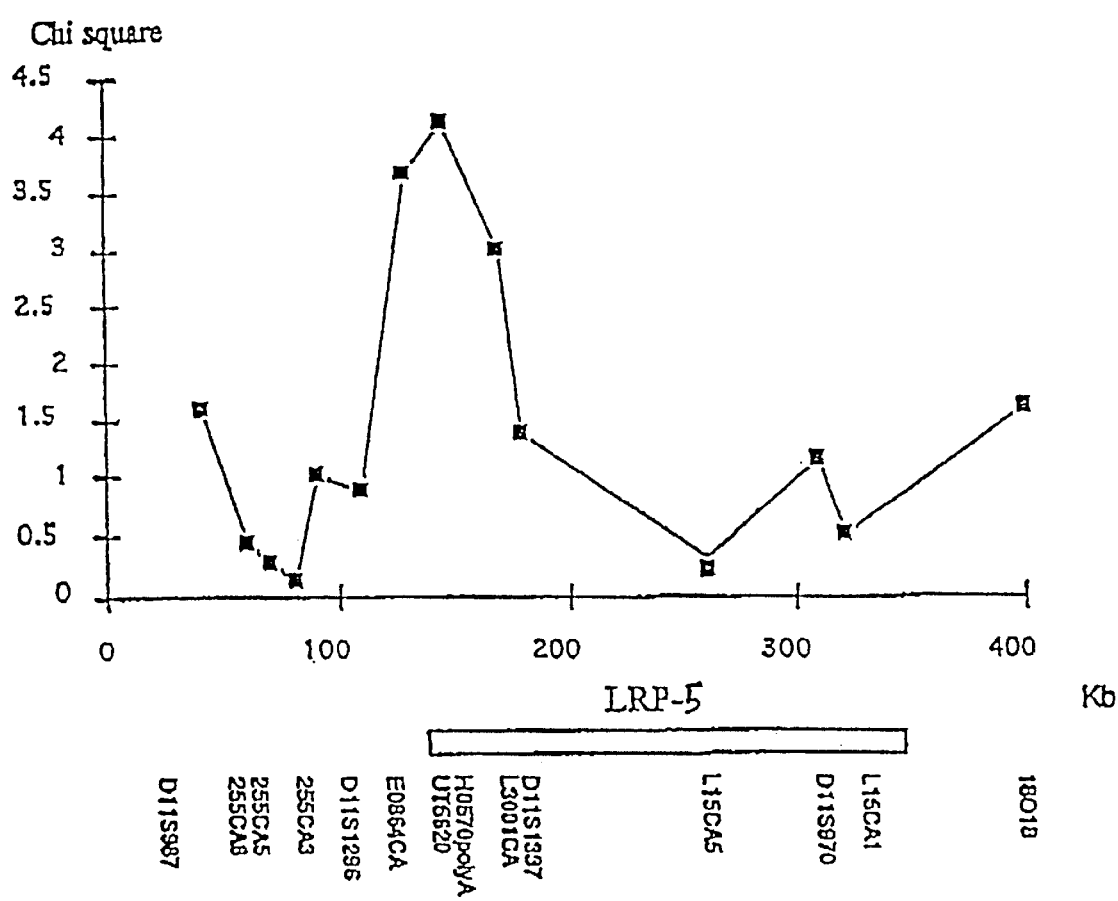
FIG. 4 shows a three-point rolling linkage disequilibrium curve at IDDM4, with 1289 families, from four different populations (UK, USA, Sardinia and Norway). In order to minimise the effects of variation in allele frequency at each polymorphism, the TDT data was obtained at three consecutive markers, and expressed as an average of the three. x-axis: physical distance in kb; y-axis: TDT $\chi^2$ statistic.

In order to maximise the information obtained with each marker, a three point rolling LD curve was produced with the IDDM4 markers (FIG. 4). In this case the percentage transmission (% T) was calculated from a marker, and its two immediate flanking markers, and averaged between them to minimise the effects of fluctuating allele frequency. This also produced a peak at H0570POLYA, with P=0.04, and indicates that the IDDM4 mutation is more likely to be in the interval E0864CA-D11S1337 (75 kb).

By the identification of this 75 kb interval which shows association with type 1 diabetes, disease associated haplotypes were identified. These are derived from the original founder chromosomes on which the diabetes mutation or mutations IDDM4 arose. In order to identify the mutation causing susceptibility to type 1 diabetes, a refined linkage disequilibrium curve, based on single nucleotide polymorphisms (SNPS) and haplotypes, is constructed. SNPs are identified by sequencing individuals with specific haplotypes which have been identified from the microsatellite analysis: homozygous susceptible to type 1 diabetes, homozygous protective for type 1 diabetes, and controls. One of these SNPs may be the etiological mutation IDDM4, or may be in very strong linkage disequilibrium with the primary disease locus, and hence be at a peak of the refined curve. Cross-match analysis further reduces the number of candidate SNPs, as shown by the localisation of the IDDM2 mutation by this method (Bennett et al, 1995; Bennett and Todd, 1996). This requires identification of distinct haplotypes or founder chromosomes, which have a different arrangement of alleles from the main susceptible or protective haplotypes, so that association or transmission of candidate SNP alleles can be tested in different haplotype backgrounds. The candidate mutations can be assessed for effects on gene function or regulation.

In different populations different IDDM4 mutations may have arisen in the same gene. We are sequencing several putative founder chromosome or disease associated haplotypes from several unrelated individuals from different populations to identify candidate mutations for IDDM4, and which cluster in the same gene.

To carry out an extensive search for DNA mutations or polymorphisms, the entire region and flanking regions of the associated region was sequenced (the 75 kb core region and 125 kb of flanking DNA). The DNA sequence also aids in gene identification and is complementary to other methods of gene identification such as cDNA selection or gene identification by DNA sequencing and comparative analysis of homologous mouse genomic DNA.

Various strategies were used in the hope of identifying potential coding sequences within this region: sequencing, computer prediction of putative exons and promoters, and cDNA selection, to try to increase the likelihood of identifying all the genes within this interval.

Construction of Libraries for Shotgun Sequencing

DNA was prepared from either cosmids, BACs (Bacterial Artificial Chromosomes), or PACs (P1 Artificial Chromosomes). Cells containing the vector were streaked on Luria-Bertani (LB) agar plates supplemented with the appropriate antibiotic. A single colony was used to inoculate 200 ml of LB media supplemented with the appropriate antibiotic and grown overnight at 37° C. The cells were pelleted by centrifugation and plasmid DNA was prepared by following the QIAGEN (Chatsworth, Calif.) Tip500 Maxi plasmid/cosmid purification protocol with the following modifications; the cells from 100 ml of culture were used for each Tip500 column, the NaCl concentration of the elution buffer was increased from 1.25M to 1.7M, and the elution buffer was heated to 65° C.

Purified BAC and PAC DNA was digested with Not I restriction endonuclease and then subjected to pulse field gel electrophoresis using a BioRad CHEF Mapper system. (Richmond, Calif.). The digested DNA was electrophoresed overnight in a 1% low melting temperature agarose (BioRad, Richmond Calif.) gel that was prepared with 0.5×Tris Borate EDTA (10×stock solution, Fisher, Pittsburg, Pa.). The CHEF Mapper autoalgorithm default settings were used for switching times and voltages. Following electrophoresis the gel was stained with ethidium bromide (Sigma, St. Louis, Mo.) and visualized with a ultraviolet transilluminator. The insert band(s) was excised from the gel. The DNA was eluted from the gel slice by beta-Agarase (New England Biolabs, Beverly Mass.) digestion according to the manufacturer's instructions. The solution containing the DNA and digested agarose was brought to 50 mM Tris pH 8.0, 15 mM MgCl2, and 25% glycerol in a volume of 2 ml and placed in a AERO-MIST nebulizer (CIS-US, Bedford Mass.). The nebulizer was attatched to a nitrogen gas source and the DNA was randomly sheared at 10 psi for 30 sec. The sheared DNA was ethanol precipitated and resuspended in TE (10 mM Tris, 1 mM EDTA). The ends were made blunt by treatment with Mung Bean Nuclease (Promega, Madison, Wis.) at 30° C. for 30 min, followed by phenol/chloroform extraction, and treatment with T4 DNA polymerase (GIBCO/BRL, Gaithersburg, Md.) in multicore buffer (Promega, Madison, Wis.) in the presence of 40 uM dNTPs at 16° C. To facilitate subcloning of the DNA fragments, BstX I adapters (Invitrogen, Carlsbad, Calif.) were ligated to the fragments at 14° C. overnight with T4 DNA ligase (Promega, Madison Wis.). Adapters and DNA fragments less than 500 bp were removed by column chromatography using a cDNA sizing column (GIBCO/BRL, Gaithersburg, Md.) according to the instructions provided by the manufacturer. Fractions containing DNA greater than 1 kb were pooled and concentrated by ethanol precipitation. The DNA fragments containing BstX I adapters were ligated into the BstX I sites of PSHOT II which was constructed by subcloning the BstX I sites from pcDNA II (Invitrogen, Carlsbad, Calif.) into the BssH II sites of pBlueScript (Stratagene, La Jolla, Calif.). PSHOT II was prepared by digestion with BstX I restriction endonuclease and purified by agarose gel electrophoresis. The gel purified vector DNA was extracted from the agarose by following the Prep-A-Gene (BioRad, Richmond, Calif.) protocol. To reduce ligation of the vector to itself, the digested vector was treated with calf intestinal phosphatase (GIBCO/BRL, Gaithersburg, Md.). Ligation reactions of the DNA fragments with the cloning vector were transformed into ultracompetent XL-2 Blue cells (Stratagene, La Jolla, Calif.), and plated on LB agar plates supplemented with 100 ug/ml ampicillin. Individual colonies ere picked into a 96 well plate containing 100 ul/well of LB broth supplemented with ampicillin and grown overnight at 37° C. Approximately 25 ul of 80% sterile glycerol was added to each well and the cultures stored at −80° C.

Preparation of Plasmiid DNA

Glycerol stocks were used to inoculate 5 ml of LB broth supplemented with 100 ug/ml ampicillin either manually or by using a Tecan Genesis RSP 150 robot (Tecan AG, Hombrechtikon, Switzerland) programmed to inoculate 96 tubes containing 5 ml broth from the 96 wells. The cultures were grown overnight at 37° C. with shaking to provide aeration. Bacterial cells were pelleted by centrifugation, the supernatant decanted, and the cell pellet stored at −20° C. Plasmid DNA was prepared with a QIAGEN Bio Robot 9600 (QIAGEN, Chatsworth Calif.) according to the Qiawell Ultra protocol. To test the frequency and size of inserts plasmid DNA was digested with the restriction endonuclease Pvu II. The size of the restriction endonuclease products was examined by agarose gel electrophoresis with the average insert size being 1 to 2 kb.

DNA Sequence Analysis of Shotgun Clones

DNA sequence analysis was performed using the ABI PRISM™ dye terminator cycle sequencing ready reaction kit with AmpliTaq DNA polymerase, FS (Perkin Elmer, Norwalk, Conn.). DNA sequence analysis was performed with M13 forward and reverse primers. Following amplification in a Perkin-Elmer 9600 the extension products were purified and analyzed on an ABI PRISM 377 automated sequencer (Perkin Elmer, Norwalk, Conn.). Approximately 12 to 15 sequencing reactions were performed per kb of DNA to be examined e.g. 1500 reactions would be performed for a PAC insert of 100 kb.

Assembly of DNA Sequences

Phred/Phrap was used for DNA sequences assembly. This program was developed by Dr. Phil Green and licensed from the University of Washington (Seattle, Wash.). Phred/Phrap consists of the following programs: Phred for base-calling, Phrap for sequence assembly, Crossmatch for sequence comparisons, Consed and Phrapview for visualization of data, and Repeatmasker for screening repetitive sequences. Vector and *E. coli* DNA sequences were identified by Crossmatch and removed from the DNA sequence assembly process. DNA sequence assembly was on a SUN Enterprise 4000 server running Solaris 2.51 operating system (Sun Microsystems Inc., Mountain View, Calif.) using default Phrap parameters. The sequence assemblies were further analyzed using Consed and Phrapview.

BioInformatic Analysis of Assembled DNA Sequences

When the assembled DNA sequences approached five to six fold coverage of the region of interest the exon and promoter prediction abilities of the program GRAIL (ApoCom, Oak Ridge) were utilized to aid in gene identification. ApoCom GRAIL is a commercial version of the Department of Energy developed GRAIL Gene Characterization Software licensed to ApoCom Inc. by Lockheed Martin Energy Research Corporation and ApoCom Client Tool for Genomics (ACTG) TM.

The DNA sequences at various stages of assembly were queried against the DNA sequences in the GenBank database (subject) using the BLAST algorithm (S.F. Altschul, et al. (1990) J. Mol. Biol. 215, 403–410), with default parameters. When examining large contiguous sequences of DNA repetitive elements were masked following identification by crossmatch with a database of mammalian repetitive elements. Following BLAST analysis the results were compiled by a parser program written by Dr. Guochun Xie (Merck Research Lab). The parser provided the following information from the database for each DNA sequence having a similarity with a P value greater than $10^{-6}$; the annotated name of the sequence, the database from which it was derived, the length and percent identity of the region of similarity, and the location of the similarity in both the query and the subject.

The BLAST analysis identified a high degree of similarities (90–100% identical) over a length of greater than 100 bp between DNA sequences we obtained and a number of human EST sequences present in the database. These human EST sequences clustered into groups that are represented by accession numbers; R73322, R50627, F07016. In general, each EST cluster is presumed to represent a single gene. The DNA sequences in R73322 cluster of 424 nucleotides had a lower but significant degree of DNA sequence similarity to the gene encoding the LDL receptor related protein (GenBank accession number X13916) and several other members of the LDL receptor family. Therefore it was concluded that the sequences that were highly similar to EST R73322 encoded a member of the LDL receptor family.

Members of each EST cluster were assembled using the program Sequencher (Perkin Elmer, Norwalk Conn.). To increase the accuracy of the EST sequence data extracted from the database relevent chromatogram trace files from the genomic DNA sequences obtained from shotgun sequencing were included in the assembly. The corrected EST sequences were reanalyzed by BLAST and BLASTX. For EST cluster 3, represented by accession number R50627 analysis of the edited EST assembly revealed that this cluster was similar to members of the LDL receptor family. This result suggested the possibility that these two EST clusters were components of the same gene.

Experimentally derived cDNA sequences were assembled using the program Sequencher (Perkin Elmer, Norwalk Conn.). Genomic DNA sequences and cDNA sequences were compared by using the program Crossmatch which allowed for a rapid and sensitive detection of the location of exons. The identification of intron/exon boundaries was then accomplished by manually comparing the genomic and cDNA sequences by using the program GeneWorks (Intelligenetics Inc., Campbell Calif.).

Northern Blot Analysis

Primers 256F and 622R ((SEQ ID NOS:51,52) Table 2) were used to amplify a PCR product of 366 bp from a fetal brain cDNA library. This product was purified on an agarose gel, the DNA extracted, and subcloned into pCR2.1 (Invitrogen, Carlsbad, Calif.). The 366 bp probe was labeled by random priming with the Amersham Rediprime kit (Arlington Heights, Ill.) in the presence of 50–100 uCi of 3000 Ci/mmole [alpha $^{32}$P]dCTP (Dupont/NEN, Boston, Mass.). Unincorporated nucleotides were removed with a ProbeQuant G-50 spin column (Pharmacia/Biotech, Piscataway, N.J.). The radiolabeled probe at a concentration of greater than $1 \times 10^6$ cpm/ml in rapid hybridization buffer (Clontech, Palo Alto, Calif.) was incubated overnight at 65° C. with human multiple tissue Northern's I and II (Clontech, Palo Alto, Calif.). The blots were washed by two 15 min incubations in 2×SSC, 0.1SDS (prepared from 20×SSC and 20% SDS stock solutions, Fisher, Pittsburg, Pa.) at room temperature, followed by two 15 min incubations in 1×SSC, 0.1% SDS at room temperature, and two 30 min incubations in 0.1×SSC, 0.1% SDS at 60° C. Autoradiography of the blots was done to visualize the bands that specifically hybridized to the radiolabeled probe.

The probe hybridized to an approximately 5–5.5 kb mRNA transcript that is most highly expressed in placenta, liver, pancreas, and prostate. It is expressed at an intermediate level in lung, skeletal muscle, kidney, spleen, thymus, ovary, small intestine, and colon. The message is expressed at a low level in brain, testis, and leukocytes. In tissues where the transcript is highly expressed, e.g. liver and pancreas, additional bands of 7 kb and 1.3 kb are observed.

Isolation of Full Length cDNAs

PCR based techniques were used to extend regions that were highly similar to ESTs and regions identified by exon prediction software (GRAIL). The one technique utilized is a variation on Rapid Amplification of cDNA Ends (RACE) termed Reduced Complexity cDNA Analysis (RCCA) similar procedures are reported by Munroe et. al. (1995) PNAS 92: 2209–2213 and Wilfinger et. al. (1997) BioTechniques 22: 481–486. This technique relies upon a PCR template that is a pool of approximately 20,000 cDNA clones, this reduces the complexity of the template and increases the probability of obtaining longer PCR extensions. A second technique that was used to extend cDNAs was PCR between regions that were identified in the genomic sequence of having the potential to be portions of a gene e.g. sequences that were very similar to ESTs or sequences that were identified by GRAIL. These PCR reactions were done on cDNA prepared from approximately 5 ug of mRNA (Clontech, Palo Alto, Calif.) with the SuperScript™ choice system (Gibco/BRL, Gaithersburg, Md.). The first strand cDNA synthesis was primed using 1 ug of oligo(dT)$_{12-18}$ primer and 25 ng of random hexamers per reaction. Second strand cDNA synthesis was performed according to the manufacturer's instructions.

Identification of Additional Exons Related to EST Cluster 1

We scanned 96 wells of a human fetal brain plasmid library, 20,000 clones per well, by amplifying a 366 bp PCR product using primers 256F and 622R. The reaction mix consisted of 4 ul of plasmid DNA (0.2 ng/ml), 10 mM Tris-HCl pH 8.3, 50 mM KCl, 10% sucrose, 2.5 mM MgCl$_2$, 0.1% Tetrazine, 200 mM dNTP's, 100 ng of each primer and 0.1 ul of Taq Gold (Perkin-Elmer, Norwalk, Conn.). A total reaction volume of 11 ul was incubated at 95° C. for 12 min followed by 32 cycles of 95° C. for 30 sec. 60° C., for 30 sec and 72° C. for 30 sec. Approximately 20 wells were found to contain the correct 366 bp fragment by PCR analysis. 5' and 3' RACE was subsequently performed on several of the positive wells containing the plasmid cDNA library using a vector specific primer and a gene specific primer. The vector specific primers, PBS 543R and PBS 873F were both used in combination with gene specific primers 117F and 518R because the orientation of the insert was not known. PCR amplification conditions consisted of 1×TaKaRa Buffer LA, 2.5 mM MgCl$_2$, 500 mM dNTP's, 0.2 ul of TaKaRa LA Taq Polymerase (PanVera, Madison Wis.), 100 ng of each primer and 5 ul of the plasmid library at 0.2 ng/ml. In a total reaction volume of 20 ml, the thermal cycling conditions were as follows: 92° C. for 30 sec, followed by 32 cycles of 92° C. for 30 sec, 1 min at 60° C. and 10 min at 68° C. After the initial PCR amplification, a nested or semi-nested PCR reaction was performed using nested vector primers PBS 578R and PBS 838F and various gene specific primers (256F, 343F, 623R and 657R). The PCR products were separated from the unincorporated dNTP's and primers using QIAGEN, QIAquick PCR purification spin columns using standard protocols and resuspended in 30 ul of water. The amplification conditions for the nested and semi-nested PCR were the same as the initial PCR amplification except that 3 ul of the purified PCR fragment was used as template and that the cycling conditions were for only 20 cycles. Products obtained from this PCR amplification were analyzed on 1% agarose gels, excised fragments were purified using QIAGEN QIAquick spin columns and sequenced using ABI dye-terminator sequencing kits. The products were analyzed on ABI 377 sequencers according to standard protocols.

Connection of EST Clusters 1-3

As discussed above it is possible that each EST cluster represents a single gene, alternatively the EST clusters may be portions of the same gene. To distinguish between these two possiblities, primers were designed to the two other EST clusters in the region represented by EST accession numbers F07016 (cluster 2, containing 272 nucleotides) and R50627 (cluster 3, containing 1177 nucleotides). Primers from cluster 1 (117F and 499F) were paired with a primer from EST cluster 3 (4034R) in a PCR reaction. A 50 ul reaction was performed using the Takara LA Taq polymerase (Panvera, Madison, Wis.) in the reaction buffer supplied by the manufacturer with the addition of 0.32 mM dNTPs, primers, and approximately 30ng of lymph node cDNA. PCR products were amplified for 35 cycles of 94° C. for 30 sec, 60° C. for 30 sec, and 72° C. for 4 minutes. Products were electrophoresed on a 1% agarose gel and bands of 2.5 to 3 kb were excised, subcloned into pCR 2.1 (Invitrogen, Carlsbad, Calif.), and plasmid DNA was prepared for DNA sequence analysis.

The primary reaction described above generated by a primer in EST cluster 1 (638F) and EST cluster 3 (4173R) was utilized as the template for a reaction with a primer from EST cluster 1 (638F) and from EST cluster 2 (3556R). This semi-nested PCR reaction was performed with Takara LA Taq polymerase as described in the previous paragraph. An approximately 2 kb product was generated and subcloned for DNA sequence analysis. The assembly of the DNA sequence results of these PCR products indicated that EST clusters 1 to 3 were part of the same gene and established their orientation relative to each other in the mRNA transcript produced by this gene.

PCR reactions were also performed between EST clusters 2 and 3. Amplification from liver cDNA using Takara LA Taq polymerase (Panvera, Madison, Wis.) with the primers 2519F, 3011F, or 3154F (EST cluster 2) in combination with 5061R (EST cluster 3) was done for 35 cyles of 95° C. for 30 sec, 60° C. for 60 sec, and 72° C. for 3 minutes. The PCR products were gel purified, subcloned, and the DNA sequence was determined. The DNA sequence analysis of the ends of all these PCR products resulted in most of the cDNA sequence however to provide for complete DNA sequence of both strands oligonucleotide primers were designed and used for DNA sequencing (FIG. 5(a) (SEQ ID NO: 1)).

Extension of the 5' End

RCCA analysis was utilized to obtain a number of clones extended 5' by using the internal gene specific primers as described previously. Several clonal extensions were isolated however most of the clones analyzed stopped within exon A. One clone extended past the 5' end of exon A but the sequence was contiguous with genomic DNA, since a body of evidence indicates an intron/exon boundary at the 5' end of exon A it appeared likely that this extension is a result of unprocessed intronic sequence. A second clone h10 extended past this point but diverged from the genomic DNA sequence. It was concluded that this represented a chimeric clone that was present in the original fetal brain cDNA library.

Identification of 5' end of Isoform 1

As described above results from RCCA experiments yielded a number of independent clones that terminated at the 5' end of exon A. This suggested that the human LRP5 gene contains a region that the reverse transcriptase has difficulty transcribing. To circumvent this problem we decided to isolate the mouse ortholog of LRP5, since subtle differences in DNA sequence content can alter the ability of an enzyme to transcribe a region. To increase the probability of isolating the 5' portion of the mouse gene a human probe of 366 nucleotides, described above and derived from exons A and B was used.

A cDNA library was constructed from mouse liver mRNA purchased from Clontech (Palo Alto, Calif.). cDNA was prepared using the SuperScript Choice system (Gibco/BRL Gaithersburg, Md.) according to the manufacturer's instructions. Phosphorylated Bst XI adapters (Invitrogen, San Diego, Calif.) were ligated to approximately 2 ug of mouse liver cDNA. The ligation mix was diluted and size-fractionated on a cDNA sizing column (Gibco/BRL Gaithersburg, Md.). Drops from the column were collected and the eluted volume from the column determined as described for the construction of shotgun libraries. The size-fractionated cDNA with the Bst XI linkers was ligated into the vector pSHOT II, described above, cut with the restriction endonuclease Bst XI, gel purified, and dephosphorylated with calf intestinal phosphatase (Gibco/BRL, Gaithersburg, Md.). The ligation containing approximately 10–20 ng of cDNA and approximately 100 ng of vector was incubated overnight at 14° C. The ligation was transformed into XL-2 Blue Ultracompetent cells (Stratagene, La Jolla, Calif.). The transformed cells were spread on twenty 133 mm Colony/Plaque Screen filters (Dupont/NEN, Boston, Mass.) at a density of approximately 30,000 colonies per plate on Luria Broth agar plates supplemented with 100 ug/ml ampicillin (Sigma, St. Louis, Mo.). The colonies were grown overnight and then replica plated onto two duplicate filters. The replica filters were grown for several hours at 37° C. until the colonies were visible and processed for in situ hybridization of colonies according to established procedures (Maniatis, Fritsch and Sambrook, 1982). A Stratalinker (Stratagene, La Jolla, Calif.) was used to crosslink the DNA to the filter. The filters were hybridized overnight with greater than 1,000,000 cpm/ml probe in 1×hybridization buffer (Gibco/BRL, Gaithersburg, Md.) containing 50%. formamide at 42° C. The probe was generated from a PCR product derived from the human LRP5 cDNA using primers 512F and 878R. This probe was random prime labeled with the Amersham Rediprime kit (Arlington Heights, IL) in the presence of 50–100 uCi of 3000 Ci/mmole [alpha 32P]dCTP (Dupont/NEN, Boston, Mass.) and purified using a ProbeQuant G-50 spin column (Pharmacia/Biotech, Piscataway, N.J.). The filters were washed with 0.1×SSC, 0.1% SDS at 42° C. Following autoradiography individual regions containing hybridization positive colonies were excised from the master filter and placed into 0.5 ml Luria Broth plus 20% glycerol. Each positive was replated at a density of approximate 50–200 colonies per 100 mm plate and screened by hybridization as described above. Single colonies were isolated and plasmid DNA was prepared for DNA sequence analysis.

Three clones were isolated from the mouse cDNA library the assembled sequence of the clones (FIG. 16(*a*) (SEQ ID NO:35)) that had a high degree of similarity (87% identical over an approximately 1700 nucleotide portion) with the human LRP5 gene and thus likely represent the mouse ortholog of LRP5. The 500 amino acid of the portion of the mouse LRP5 (FIG. 16(*d*) (SEQ ID NO:8)) that we initially obtained is 96%. identical to human LRP5. Significantly two of these clones had sequence that was 5' of the region corresponding to exon A, clone 19a contained an additional 200 bp and clone 9a contained an additional 180 bp (FIG. 16(*b*) (SEQ ID NO:36)). The additional 200 bp contains an open reading frame that begins at bp 112 (FIG. 16(*c*) (SEQ ID NO:37)). The initiating codon has consensus nucleotides for efficient initiation of translation at both the −3 (purine) and +4 (G nucleotide) positions (Kozak, M. 1996, Mamalian Genome 7:563–574). This open reading frame encodes a peptide with the potential to act as a eukaryotic signal sequence for protein export (von Heijne, 1994, Ann. Rev. Biophys. Biomol. Struc. 23:167–192). The highest score for the signal sequence as determined by using the SigCleave program in the GCG analysis package (Genetics Computer Group, Madison Wis.) generates a mature peptide beginning at residue 29 of isoform 1. Additional sites that may be utilized produce mature peptides beginning at amino acid residue 31 (the first amino acid encoded by exon A) or amino acid residues 32, 33, or 38.

Molecular Cloning of the Full Length Mouse Lrp3 cDNA

The mouse cDNA clones isolated by nucleic acid hybridization contain 1.7 Kb of the 5' end of the Lrp3 cDNA (FIG. 16(*a*) (SEQ ID NO:35)). This accounts for approximately one-third of the full length cDNA when compared to the human cDNA sequence. The remainder of the mouse Lrp3 cDNA was isolated using PCR to amplify products from mouse liver cDNA. PCR primers, Table 9 (SEQ ID NOS:49–74,334–402), were designed based upon DNA sequences identified by the sequence skimming of mouse genomic clones, BACs 53-d-8 and 131-p-15, which contain the mouse Lrp3 gene. BAC 53-d-8 was mapped by FISH analysis to mouse chromosome 19 which is syntenic with 11q13. Sequence skimming of these clones identified DNA sequences that corresponded to the coding region of human LRP5 as well as the 3' untranslated region. This strategy resulted in the determination of a mouse cDNA sequence of 5059 nucleotides (FIG. 18(*a*) (SEQ ID NO:40)) which contains an open reading frame of 4842 nucleotides (FIG. 18(*b*) (SEQ ID NO:41)) that encodes a protein of 1614 amino acids (FIG. 18(*c*) (SEQ ID NO:42)). The putative ATG is in a sequence context favorable for initiation of translation (Kozak, M. 1996, Mamalian Genome 7:563–574).

Comparison of Human and Mouse LRP5

The cDNA sequences of human and mouse LRP5 display 87% identity. The open reading frame of the human LRP5 cDNA encodes a protein of 1615 amino acids (SEQ ID NO:3) that is 94% identical to the 1614 amino acid protein encoded by mouse Lrp3 (SEQ ID NOS:42) (FIG. 18(*d*)). The difference in length is due to a single amino acid deletion in the mouse Lrp3 signal peptide sequence. The signal peptide sequence is not highly conserved being less than 50% identical between human and mouse. The location of the putative signal sequence cleavage site is at amino acid residue 25 in the human and amino acid 29 in the mouse. Cleavage at these sites would result in mature human and mouse proteins of 1591 and 1586 amino acids, respectively, which are 95°. identical (FIG. 18(*e*) (SEQ ID NOS:43,44)). The high degree of overall sequence similarity argues strongly that the identified sequences are orthologs of the LRP5 gene. This hypothesis is further supported by the results of genomic Southern experiments (data not shown).

Identification of Human Signal Peptide Exon for Isoform 1

The human exon encoding a signal peptide was isolated from liver cDNA by PCR. The forward primer 1F (SEQ ID NO:51) (Table 9) was used in combination with one of the following reverse primers: 218R, 265R, 318R, and 361R (SEQ ID NOS:50,52,53,54) in a PCR reaction using Taq Gold polymerase (Perkin-Elmer, Norwalk, Conn.) and supplemented with either 3, 5, or 7% DMSO. Products were amplified for 40 cycles of 30 sec 95° C., 30 sec 58° C., and 1 min 72° C. The products were analyzed on an agarose gel and some of the reactions containing bands of the predicted size were selected for DNA sequence analysis and subcloning into pCR2.1 (Invitrogen, San Diego, Calif.).

The derived DNA sequence of 139 nucleotides upstream of exon 2 (also known as exon A) contains an ATG that is in a context for efficient initiation of translation: an adenine (A) residue at the −3 position and a guanine (G) residue at the +4 position (Kozak, M. 1996, Mamalian Genome 7:563–574). The open reading frame for this ATG continues for 4854 nucleotides (FIG. 5(b)) (SEQ ID NO:2) which encodes a polypeptide of 1615 amino acids (FIG. 5(c) (SEQ ID NO:3)).

The sequence following the initiator ATG codon encodes a peptide with the potential to act as a signal for protein export. The highest score for the signal sequence (15.3) indicated by the SigCleave program in the GCG analysis package (Genetics Computer Group, Madison Wis.) generates a mature polypeptide beginning at amino acid residue 25 (FIG. 5(d,e). Additional putative cleavage sites that may be utilized to produce a mature LRP5 protein are predicted for residues 23, 24, 26, 27, 28, 30 and 32 (the first amino acid encoded by exon A).

Determination of the Genomic DNA Sequence Containing and Flanking the Signal Peptide Exon The region that contained genomic DNA sequence identical to the cDNA sequence encoding a signal peptide was in a gap between two stretches of contiguous genomic DNA sequence known as contigs 57 and 58. To close this gap four clones were chosen from the shotgun library that were determined to span this gap according to analysis by the program Phrapview licensed from Dr. Phil Green of the University of Washington (Seattle, Wash.). Direct DNA sequencing of these clones was unsuccessful, i.e. high GC content significantly reduced the efficiency of the cycle sequencing. To circumvent this problem PCR products were generated by incorporating 7-deaza-dGTP (Pharmacia, Pharmacia Biotech, Piscataway, N.J.). The conditions for these reactions consisted of a modification of the Klentaq Advantage-GC polymerase kit (Clontech, Palo Alto, Calif.). The standard reaction protocol was modified by supplementing the reaction mix with 200 uM 7-deaza-dGTP. Inserts were amplified with M13 forward and reverse primers for 32 cycles of 30 sec at 92° C., 1 min at 60° C., and 5 min at 68° C. Products were gel purified using Qiaquick gel extraction kit (Qiagen Inc., Santa Clarita, Calif.) and sequenced as described previously. Assembly of the resulting sequences closed the gap and generated a contiguous sequence of approximately 78,000 bp of genomic DNA.

Extension of Isoforms 2 and 3

The software package GRAIL (supra) predicts exons and promoter sequences from genomic DNA sequence. One region identified by GRAIL is an exon originally designated G1 and subsequently termed exon 1 that is approximately 55 kb upstream of the beginning of exon A (FIG. 12(c) (SEQ ID NO:28)). Three primers designated G1 1f to 3f were designed based on this sequence. This exon was of particular interest because GRAIL also predicted a promoter immediately upstream of the exonic sequence (FIG. 12 (e)). Furthermore one of the open reading frames in G1 encoded a peptide that had the characteristics of a eukaryotic signal sequence.

To determine whether the G1 predicted exon was part of the LRP5 gene, reverse transcriptase (RT) PCR was performed using the Taqara RNA PCR kit (Panvera, Madison Wis.). Human liver mRNA (50 ng) was used as the template for a 10 ul reverse transcriptase reaction. The reverse transcriptase reaction using one of the LRP5 specific primers (622R, 361R, or 318R) was incubated at 60° C. for 30 min, followed by 99° C. for 5 min, and then the sample was placed on ice. One of the forward primers, Table 2, (G1 1f, 2f, or 3f) (SEQ ID NOS:75,76,77) was added along with the reagents for PCR amplification and the reaction was amplified for 30 cycles of 30 sec at 94° C., 30 sec at 60° C., and 2 min at 72° C. This primary PCR reaction was then diluted 1:2 in water and 1 ul of the reaction was used in a second 20 ul reaction using nested primers. The reaction conditions for the second round of amplification were 30 cycles of 94° C. for 30 sec, 60° C. for 30 sec and 72° C. for 2 min. The products were separated on an agarose gel and excised. The purified fragments were subcloned into pCR 2.1 (Invitrogen, Carlsbad, Calif.), plasmid DNA was prepared, and the DNA sequence was determined.

The DNA sequence of these products indicated that G1 (exon 1) was present on at least a portion of the LRP5 transcripts. Two different isoforms were identified. The first, isoform 2 (FIG. 11(a) (SEQ ID NO:23)), identified in this experiment consists of exon 1 followed by an exon that we have given the designation exon 5. This splice variant has an open reading frame that initiates in exon B nucleotide 402 (FIG. 11(a)), the initiator methionine at this location does not conform to the consensus sequences for translation initiation (Kozak, M. (1996) Mamalian Genome 7:563–574). A second potential initiator methionine is present at nucleotide 453, this codon is in a context for efficient initiation of translation initiation (Kozak, M. (1996) Mamalian Genome 7:563–574). The longest potential open reading frame for isoform 2 (FIG. 11(c)) encodes a splice variant contains a eukaryotic signal sequence at amino acid 153. The mature peptide generated by this splice variant would be lacking the first five spacer domains and a portion of the first EGF-like motif.

The second isoform (isoform 3) consists of exon 1 followed by exon A (FIG. 12(a)). It is not known whether exon 1 is the first exon of isoform 2. However the location of a GRAIL predicted promoter upstream of G1 suggests the possibility that exon 1 is the first exon. Futhermore there is an open reading frame that extends past the 5' intron/exon boundary postulated by GRAIL (FIG. 12(b)). Therefore we have examined the possiblity of incorporating this extended open reading frame into the LRPS transcript. The resulting open reading frame (FIG. 12(c)) encodes a 1639 amino acid protein (FIG. 12(d). The initiator methionine codon does not contain either of the consensus nucleotides that are thought to be important for efficient translation (Kozak, M. 1996, Mamalian Genome 7:563–574). Nor does the predicted protein contain a predicted eukaryotic signal sequence within the first 100 amino acids. Alternatively there may be additional exons upstream of exon 1 which provide the initiator methionine codon and/or a potential signal sequence.

RACE Extension of the 5' End of lrp5: Isoforms 4 and 5

RACE is an established protocol for the analysis of cDNA ends. This procedure was performed using the Marathon RACE template purchased from Clontech (Palo Alto, Calif.). This was performed according to instructions using Clontech "Marathon" cDNA from fetal brain and mammary tissue. Two "nested" PCR amplifications were performed using the ELONGASE™ long-PCR enzyme mix & buffer from Gibco-BRL (Gaithersburg, Md.).

Marathon Primers

AP1: CCATCCTAATACGACTCACTATAGGGC (SEQ ID NOS:407)

AP2: ACTCACTATAGGGCTCGAGCGGC (SEQ ID NOS:408)

First round PCR used 2 microliters Marathon placenta cDNA template and 10 pmoles each of primers L217 and AP1. Thermal cycling was: 94° C. 30 sec, 68° C. 6 min, 5 cycles; 94° C. 30 sec, 64° C. 30 sec, 68° C. 4 min, 5 cycles; 94° C. 30 sec, 62° C. 30 sec, 68° C. 4 min, 30 cycles. One microliter from a 1/20 dilution of this reaction was added to a second PCR reaction as DNA template. This PCR reaction also differed from the first PCR reaction in that nested primers L120 and AP2 were used. Two products of approximately 1600 bp and 300 bp were observed and cloned into pCR2.1 (Invitrogen, Carlsbad Calif.). The DNA sequence of these clones indicated that they were generated by splicing of sequences to exon A. The larger 1.6 kb fragment (FIG. 13 (SEQ ID NO:31)) identified a region approximately 4365 nucleotides upstream of exon A and appeared to be contiguous with genomic DNA for 1555 base pairs. The sequence identified by the 300 bp fragment was approximately 5648 nucleotides upstream of exon A (FIG. 14 (SEQ ID NO:32)). This sequence had similarity to Alu repeats. The region identified by the 300 bp fragment was internal to the region identified by the 1.6 kb fragment. The open reading frame for these isoforms designated 4 and 5 is the same as described for isoform 2 (FIG. 11(b)).

Extension of Isoform 6

GRAIL (supra) analysis was used to predict potential promoter regions for the gene. Primers were designed to the isoform 6 promoter sequence (FIG. 15(b)) which was defined by GRAIL and is approximately 4 kb centromeric of exon A. This region was designated GRAIL promoter-1 (Gp-1).

The PCR primer Gp 1f (SEQ ID NO:78) (Table 2) was used in a PCR reaction with primer 574r and 599r using the polymerase Taq Gold in the reaction buffer supplied by the manufacturer (Perkin Elmer, Norwalk, Conn.). The reaction conditions were 12 min at 95° C. followed by 35 cycles of 95° C. for 30 sec, 60° C. for 30 sec, and 72° C. for 1 min 30 sec with approximately long of liver cDNA per 20 ul reaction. The primary reactions were diluted 20 fold in water and a second round of PCR using primer Gp 1f in combination with either 474r or 521r was done. Products were analyzed on a 2% agarose gel and bands of approximately 220 to 400 bp were subcloned into pCR 2.1 (Invitrogen, Carlsbad, Calif.) and analyzed by DNA sequence analysis. The open reading frame present in isoform 4 is the same as described for isoform 2 above (FIG. 11(b)).

Microsatellite Rescue

A vectorette library was made from each clone by restricting each clone and ligating on a specific bubble linker (Munroe, D. J. et al. (1994) Genomics 19, 506). PCR was carried out beween a primer (Not 1-A) specific for the linker, and a repeat motif (AC)11N, (where N is not A), at an annealing temperature of 65° C. The PCR products were gel purified and sequenced using the ABI PRISM dye terminator cycle sequencing kit as previously described. From this sequence, a primer was designed, which was used in PCR with the Not 1-A primer. This was also sequenced, and a second PCR primer designed, (Table 8 (SEQ ID NOS:318–333)) so that both primers flanked the repeat motif, and were used for genotyping.

Mutation Scanning

Single nucleotide polymorphisms (SNP's) were identified in type 1 diabetic patients using a sequencing scanning approach (Table 5).

Primers were designed to specifically amplify genomic fragments, approximately 500 to 800 bp in length, containing specific regions of interest (i.e. regions that contained LRP5 exons, previously identified SNP's or GRAIL predicted exons). To facilitate fluorescent dye primer sequencing, forward and reverse primer pairs were tailed with sequences that correspond to the M13 Universal primer (5'-TGTAAAACGACGGCCAGT-3') (SEQ ID NO:409) and a modified M13 reverse primer (5'-GCTATGACCATGATTACGCC-3') (SEQ ID NO:410), respectively. PCR products produced using the primer sets, mentioned above, were amplified in 50 ul reactions consisting of Perkin-Elmer 10×PCR Buffer, 200 mM dNTP's, 0.5 ul of Taq Gold (Perkin-Elmer Corp., Foster City, Calif.), 50 ng of patient DNA and 20 pmol/ml of forward and reverse primers. Cycling conditions were 95° C. for 12 min; 35 cycles of 95° C. for 30 sec, 57° C. for 30 sec and 68° C. for 2 min, followed by an extension of 72° C. for 6 min and a 4° C. hold.

Conditions were optimized so that only single DNA fragments were produced by these reaction. The PCR products were then purified for sequencing using QiaQuick strips or QiaQuick 96 well plates on the Qiagen robot (Qiagen Inc., Santa Clarita, Calif.). This purification step removes the unincorporated primers and nucleotides.

Direct BODIPY dye primer cycle sequencing was the method used to analyze the PCR products (Metzker et. al. (1996) Science 271, 1420–1422). A Tecan robot (Tecan, Research Triangle Park, N.C.) carried out the sequencing reactions using standard dye primer sequencing protocols (ABI Dye Primer Cycle Sequencing with AmpliTaq DNA Polymerase FS, Perkin-Elmer Corp., Foster City, Calif.). The reactions were generated using the following cycling conditions on a DNA Engine thermal cycler (M.J. Research Inc., Watertown, Mass.), 15 cycles of 95° C. for 4 sec, 55° C. for 10 sec, and 70° C. for 60 sec; followed by 15 cycles of 95° C. for 4 sec, and 70° C. for 60 sec. After cycling, samples were pooled, precipitated and dried down. The samples were resuspended in 3 ul of loading buffer and 2 ml were run on an ABI 377 Automated DNA sequencer.

Once SNP's have been identified, scanning technologies are employed to evaluate their informativeness as markers to assist in the determination of association of the gene with disease in the type 1 diabetic families. We are using restriction fragment length polymorphisms (RFLP's) to assess SNP's that change a restriction endonuclease site. Furthermore, we are using forced RFLP PCR (Li and Hood (1995) Genomics 26, 199–206; Haliassos et.al. (1989) Nuc. Acids Res. 17, 3608) and ARMS (Gibbs et.al. (1989) Nuc. Acids Res. 17, 2437–2448; Wu et. al. (1989) Proc. Natl. Acad. Sci. USA 86, 2757–2760) to evaluate SNP's that do not change a restriction endonuclease site. We are also trying to scan larger regions of the locus by developing fluorescent based Cleavase (CFLP) (Life Technologies, Gaithersburg, Md.) and Resolvase, (Avitech Diagnostics, Malvern, Pa.) assays.

Haplotype Analysis at IDDM4

Haplotype mapping (or identity-by-descent mapping) has been used in conjunction with association mapping to identify regions of identity-by-descent (IBD) in founder populations, where (some) of the affected individuals in a founder population share not only the mutation, but also a quite large genomic haplotype (hence identical piece of DNA) surrounding the disease locus. Recombinant haplotypes can be utilised to delineate the region containing the mutation. These methods have been used to map the genes of the recessive disorders: Wilson's disease, Batten's disease, Hirschsprung's disease and hereditary haemochromatosis (Tanzi, R., et al. (1993) *Nature Genet* 5, 344–350; The International Batten Disease Consortium. (1995) *Cell* 82, 949–957; Puffenberger, E., et al. (1994) *Hum Mol Genet* 3, 1217–1225; and Feder, J., et al. (1996) *Nature Genet* 13, 399–408). Similarly, in type 1 diabetes, for IDDM1, comparative MHC haplotype mapping between specific Caucasian and haplotypes of African origin identified both HLA-DQA1 and HLA-DQB1 as susceptibility loci for this disorder (Todd, J. et al (1989) *Nature* 338, 587–589; and Todd, J. et al (1987) *Nature* 329, 599–604).

On chromosome 11q13 haplotype analysis was undertaken in conjunction with association analysis in order to identify regions of IBD between haplotypes which are transmitted more often than expected, hence contain a susceptible allele at the aetiological locus; in contrast protective haplotypes will be transmitted less often than expected and contain a different (protective) allele at the aetiological locus. Evidence for a deviation in the expected transmission of alleles was shown with the two polymorphic markers D11S1917 and H0570POLYA. In 2042 type 1 diabetic families from the UK, USA, Norway, Sardinia, Romania, Finland, Italy and Denmark, transmission of D11S1917-H0570POLYA haplotype 3-2 to affected offspring was negative (46%), with a 2×2 test of heterogeneity between affected and unaffected transmissions produced $\chi^2=23$, df=1, $p<1.5\times10^{-6}$, providing good evidence that this is a protective haplotype. In contrast, the 2-3 haplotype was more transmitted to affected than non-affected offspring (% T=51.3; 2×2 contingency test; $\chi^2=5.5$, df=1, p<0.02), indicating that this was a susceptible (or possibly neutral) chromosome. A further haplotype, which is rare, has been identified which appears to be susceptible to type 1 diabetes (D11S1917-H0570POLYA, 3-3, % T affecteds=62.4, 2×2 contingency test, affecteds vs non-affecteds;chi$^2$=6.7, df=1, p<0.009). Therefore, analysis of association in this region has produced evidence for a haplotype which contains an allele protective against type 1 diabetes, as it is significantly less transmitted to the affected offspring in comparison to the unaffected offspring, and evidence for two non-protective haplotypes, which have a neutral or susceptible effect on type 1 diabetes.

Figure 19:
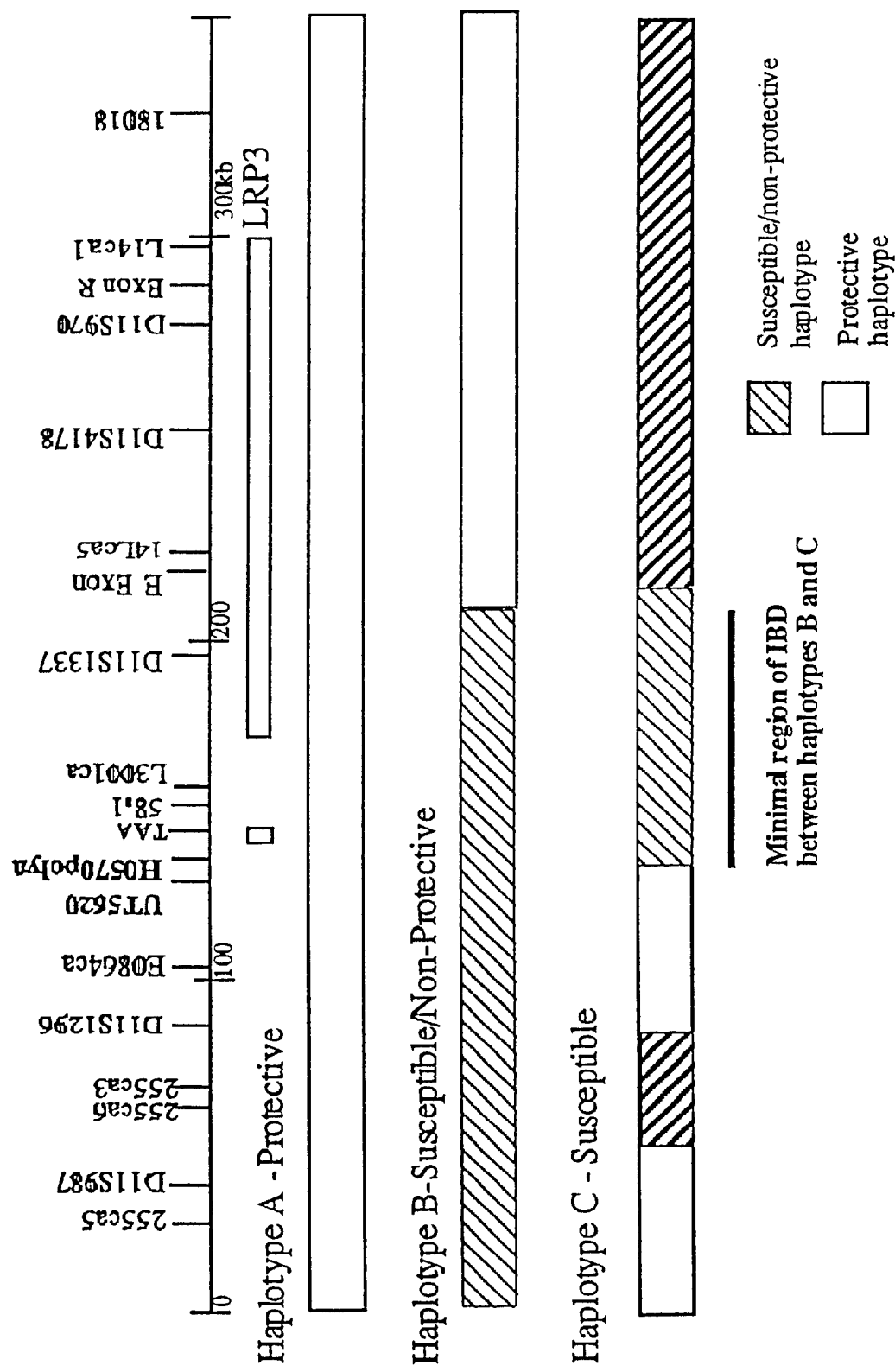
FIG. 19 shows a schematic representation of haplotypes across the IDDM4 region. Three distinct haplotypes are shown. Haplotype A is protective against IDDM whereas haplotypes B and C are susceptible/non-protective for IDDM.
Figure 20:
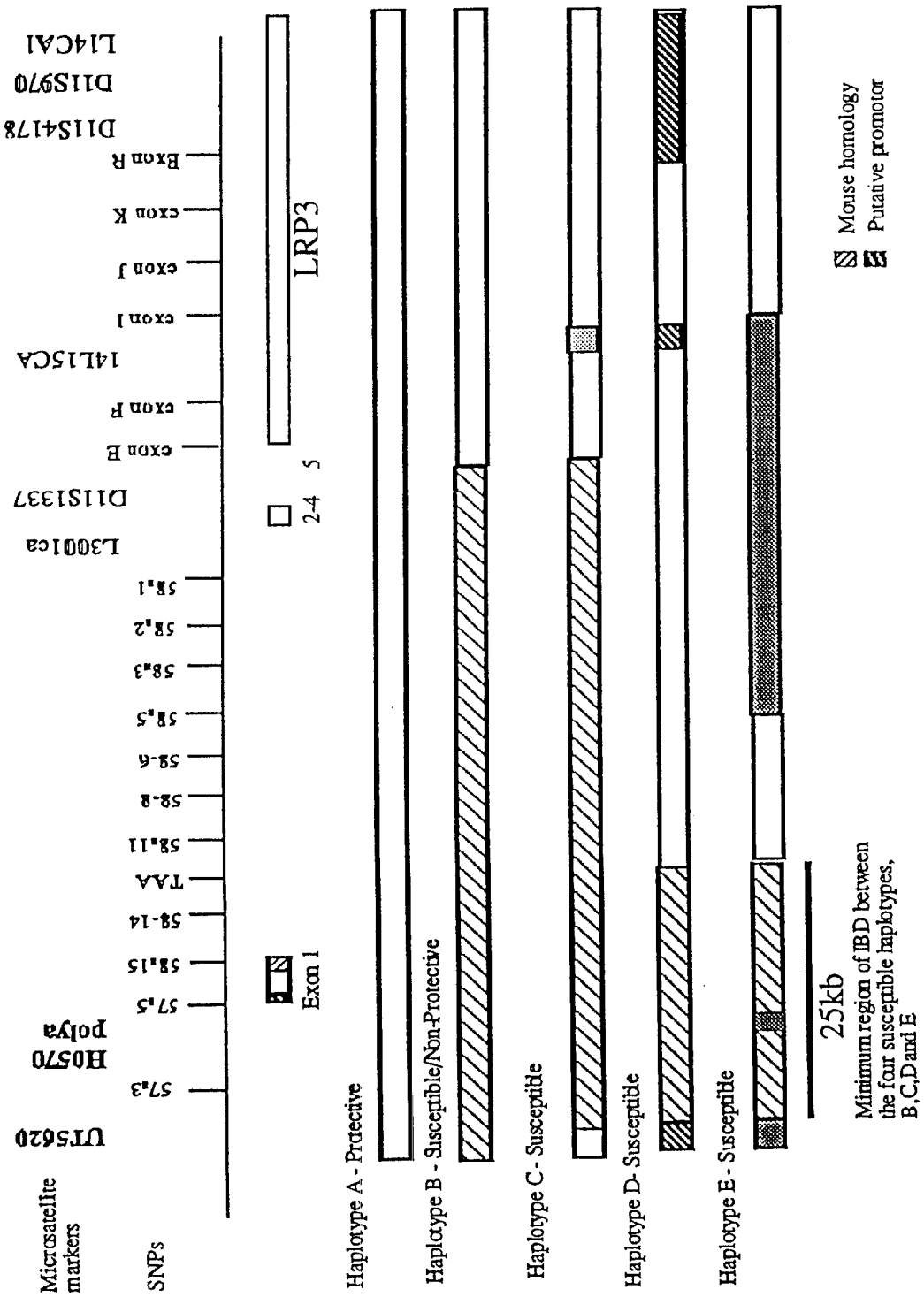
FIG. 20 shows a schematic representation of single nucleotide polymorphism (SNP) haplotypes across the IDDM4 region. Haplotype A is protective whereas haplotypes B, C, D, and E are susceptible/non-protective. A minimal region of 25 kb which is Identical By Descent (IBD) for the four susceptible haplotypes is indicated. The SNP designations, e.g. 57-3, are as described in Table 6 and FIGS. 9 and 10.

Extending this haplotype analysis to include the 14 flanking microsatellite markers 255ca5, D11S987, 255ca6, 255ca3, D11S1296, E0864CA, TAA, L3001CA, D11S1337, 14LCA5, D11S4178, D11S970, 14LCA1, 18O18, as well as the single nucleotide polymorphisms (SNPs) 58-1, Exon E (intronic, 8bp 3' of exon 6) and Exon R (Ala$^{1330}$, exon 18) (FIG. 19), revealed highly conserved haplotypes within this interval in the diabetic individuals. A distinct protective haplotype (A) has been identified (encompassing the 3-2 haplotype at D11S1917-H0570POLYA), as well as a distinct susceptible haplotype (B) (encompassing the 2-3 haplotype at D11S1917-H0570POLYA). The susceptible haplotype is IBD with the protective haplotype, 3' of marker D11S1337, indicating that the aetiological variant playing a role in type 1 diabetes does not lie within the identical region, localising it 5' of Exon E of the LRP-5 gene. This region that is IBD between the protective, and susceptible haplotypes prevents association analysis being undertaken, as no deviation in transmission to affected offspring would be detected. The rare susceptible haplotype (C), 3-3 at D11S1917-H0570POLYA, can also be identified. Haplotype analysis with the additional markers in the region reveals that this rare susceptible haplotype is identical to the susceptible haplotype between UT5620 and 14L15CA, potentially localising the aetiological variant between UT5620 and Exon E, which is approximately 100 kb. Therefore, the susceptible and rare susceptible haplotypes may carry an allele (or separate alleles) which confers a susceptible effect on type 1 diabetes, whereas the protective haplotype contains an allele protective against IDDM. The 5' region of the LRP5 gene lies within this interval, encompassing the 5' regulatory regions of the LRP5 gene and exons 1 to 6.

Analysis of the Italian and Sardinian haplotypes revealed an additional two susceptible haplotypes. At D11S1917-H0570POLYA in the Italian families haplotype 1-3, 63% T, 2×2 affected verses non-affecteds p=0.03 (haplotype D). At H0570POLYA -L3001 in the Sardinian families haplotype 1-2 58% T, 2×2 affected verses non-affecteds, p=0.05 (haplotype E).

Samples containing the above five haplotypes were genotyped with SNPs from the IDDM4 region in order to investigate regions of IBD (FIG. B). These SNPs confirmed the region of IBD between the susceptible haplotypes B and C between UT5620 and 14L15CA. It also confirmed the region of IBD between the protective and susceptible haplotypes A and B 3' of marker D11S1337, excluding this region from containing the aetiological variant. The SNP analysis also revealed a potential region of IBD between UT5620 and TAA, between the susceptible haplotypes B, C, D and E, which is distinct from the protective haplotype A (a 25 kb region). The marker H0570POLYA lies within this interval, and is not identical in haplotype E compared to the other susceptible haplotypes; possibly this is due to mutation at this polymorphism, or it delineates a boundary within this region and the aetiological variant is either 5' or 3' of this marker. Further analysis of additional SNPs within this interval will be necessary.

Therefore haplotype mapping within the IDDM4 region has identified a region of IBD between the susceptible haplotypes B and C of 100 kb, in the 51 region of the LRP5 gene. SNP haplotype mapping has possibly further delineated this to a 25 kb interval encompassing the 5' region of LRP5 which includes possible regulatory sequences for this gene; a putative promoter, and regions of homology with the mouse syntenic region (Table 12), as well as exon 1 of LRP5.

Construction of Adenovirus Vectors Containing LRP5

The full-length human LRP5 gene was cloned into the adenovirus transfer vector pdelE1sp1A-CMV-bGHPA containing the human Cytomegalovirus immediate early promoter and the bovine growth hormone polyadenylation signal to create pdehlrp3. This vector was used to construct an adenovirus containing the LRP5 gene inserted into the E1 region of the virus directed towards the 5' ITR. In order to accommodate a cDNA of this length, the E3 region has been completely deleted from the virus as it has been described for pBHG10 (Bett at al.1994 Proc Natl Acad Sci 91: 8802–8806) An identical strategy was used to construct an adenoviral vector containing the full-length mouse Lrp5 gene.

A soluble version of mouse Lrp5 was constructed in which a His tag and a translational stop signal replaced the putative transmembrane spanning domain (primers listed in Table 9 (SEQ ID NOS:49–74,334–402)). This should result in the secretion of the extracellular domain of Lrp5 and facilitate the biochemical characterization of the putative ligand binding domain of Lrp5. Similarly a soluble version of human LRP5 can be constructed using primers shown in Table 9 (SEQ ID NOS:49–74,334–402). The extracellular domain runs to amino acid 1385 of the precursor (immature) protein sequence.

Identification of LRP5 Ligands

LRP5 demonstrates the ablility to bind and take up LDL (see below), but this activity is not a high level. Therefore, it is likely that LRP5 has the capacity to bind additional ligand(s). To identify LRP5 ligands the extracellular domain consisting of the first 1399 amino acids of human LRP5, or the corresponding region of mouse Lrp5 will be purified. A number of expression systems can be used these include plasmid based systems in Drosophila S2 cells, yeast and $E.$ $coli$ and viral based systems in mammalian cells and SF9 insect cells. A histidine tag will be used to purify LRP5 on a nickel column (Novagen, Madison Wis.). A variety of resins may be used in column chromatography to further enrich soluble LRP5. LRP5 will be attached to a solid support e.g. a nickel column. Solutions containing ligands from serum fractions, urine fractions, or fractions from tissue extracts will be fractionated over the LRP5 column. LRP5 complexed with bound ligand will be eluted from the nickel column with imidazole. The nature of the ligand(s) bound to LRP5 will be characterized by gel electrophoresis, amino acid sequence, amino acid composition, gas chromatography, and mass spectrophotometer.

Attachment of purified LRP5 to a BiaCore 2000 (BiaCore, Uppsula Sweden) chip will be used to determine whether ligands that bind to LRP5 are present in test solutions. Once ligands for LRP5 are identified the LRP5 chip will be used to characterize the kinetics of the LRP5 ligand interaction.

Adenoviral vectors containing soluble versions of LRP5 will be used to infect animals, isolation of ligand/LRP5 complexes from serum or liver extracts will be facilitated by the use of a histidine tag and antibodies directed against this portion of LRP5.

Treatment of Animals with LRP5 Virus

A wide range of species may be treated with adenovirus vectors carrying a transgene. Mice are the preferred species for performing experiments due to the availability of a number of genetically altered strains of mice, i.e. knockout, transgenic and inbred mice. However larger animals e.g. rats or rabbits may be used when appropriate. A preferred animal model to test the ability of LRP5 to modify the development of type 1 diabetes is the non-obese diabetic (NOD) mouse. Preferred animal models for examination of a potential role for LRP5 in lipoprotein metabolism are mice in which members of the LDL-receptor family have been disrupted, e.g. the LDL-receptor (LDLR), or in which genes involved in lipoprotein metabolism, e.g. Apo-E, have been disrupted.

Adenoviruses are administered by injecting approximately $1 \times 10^9$ plaque forming units into the tail vein of a mouse. Based on previous studies this form of treatment results in the infection of hepatocytes at a relatively high frequency. Three different adenovirus treatments were prepared, 1.) adenovirus containing no insert (negative control), 2.) adenovirus containing human LDLR (positive control) or 3.) adenovirus containing human LRP5. Each of these viruses were used to infect five C57 wild type and five C57 LDLR knockout mice. A pretreatment bleed, 8 days prior to injection of the virus was used to examine serum chemistry values prior to treatment. The animals were injected with virus. On day five following administration of the virus a second (treatment) bleed was taken and the animals were euthanized for collection of serum for lipoprotein fractionation. In addition tissues were harvested for in situ analysis, immuno-histochemistry, and histopathology.

Throughout the experiment, animals were maintained in a standard light/dark cycle and given a regular chow diet. The animals were fasted prior to serum collection. In certain experimental conditions it may be desirable to give animals a high fat diet.

Standard clinical serum chemistry assays were performed to determine; serum triglycerides, total cholesterol, alkaline phosphatase, aspartate aminotransferase, alanine aminotransferase, urea nitrogen, and creatinine. Hematology was performed to examine the levels of circulating leukocytes, neutrophils, the percent lymphocytes, monocytes, and eosinophils, erythrocytes, platelets, hemoglobin, and percent hematocrit.

Serum lipoproteins were fractionated into size classes using a Superose 6 FPLC sizing column and minor modifications of the procedure described by Gerdes et al. (Clin. Chim. Acta 205:1–9 (1992)), the most significant difference from the Gerdes procedure being that only one column was used. Column fractions were collected and analyzed for cholesterol and triglyceride. The "area under the curve" was calculated for each lipoprotein class. The approximate peak fractions that correspond to each of the classes defined by density are: fraction 24 for VLDL, fraction 36 for LDL and fraction 51 for HDL.

LRP5 Overexpression Affects Serum Triglycerides and Lipoproteins

Statistical analysis of serum chemistry data indicated that relative to control virus there was a 300 decrease, p value= 0.025, in triglyceride levels in animals treated with LRP5 containing virus (Table 10). This decrease in triglycerides occurred at a similar level in both wild type and KO mice. By comparison, the LDLR virus reduced serum triglycerides approximately 55%, relative to the contol virus. This result indicates that LRP5 has the potential to modulate serum triglyceride levels.

The serum lipoprotein profile indicated that the VLDL particle class was decreased in wild type mice treated with LRP5 virus. Although the number of samples analyzed was not sufficient for statistical analyses, this result is consistent with the observed decrease in serum triglycerides. These results suggest that LRP5 has the potential to bind and internalize lipid rich particles, causing the decrease in serum triglycerides and VLDL particles. Therefore treatment with LRP5 or with therapeutic agents that increase the expression of LRP5 or the biological activity of LRP5 may be useful in reducing lipid rich particles and triglycerides in patients with diseases that increase triglyceride levels, e.g. type 2 diabetes and obesity.

Although not statistically significant there was an observed trend towards a reduction in serum cholesterol levels as a consequence of LRP5 treatment (28%, p=0.073) in mice that have a high level of serum cholesterol (approximately 220 mg/dL), due to a disruption (knockout) of the LDL-receptor (Table 10). An opposite trend, in that LRP5 treatment elevated serum cholesterol (30%, p=0.08) was not observed in wild type mice which have a relatively low level of serum cholesterol (approximately 70 mg/dL). The small treatment groups, n=4, in these data sets limits the interpretation of these results and indicates that further experimentation is necessary. Nevertheless, these results suggest that in a state of elevated cholesterol an increase in the activity of LRP5 might reduce serum cholesterol levels. Therefore treatment with LRP5 or with therapeutic agents that increase either the expression of LRP5 or the biological activity of LRP5 may be useful in reducing cholesterol in patients with hypercholesterolemia.

LRP5 Overexpression may Affect Serum Alkaline Phosphatase Levels

Serum alkaline phosphatase levels can be dramatically elevated, e.g. 20 fold increase, as a consequence of an obstruction of the bile duct (Jaffe, M. S. and McVan, B., 1997, *Davis's laboratory and diagnostic test handbook*. pub. F. A. Davis Philadelphia Pa.). However, lower levels, up to a three fold increase of alkaline phosphatase can result from the inflammatory response that take place in response to an infectious agent in the liver, e.g. adenovirus. In animals treated with a control virus there was an approximately 2-fold increase in alkaline phosphatase levels. In contrast, there was only a slight increase in alkaline phophatase levels in animals treated with the LRP5 virus. Relative to the control the alkaline phosphatase level was reduced 49% in the LRP5 treated animals, p value=0.001 (Table 10).

The increase in alkaline phosphatase levels may be a consequence of the level of infection with the adenovirus, therefore, a possible explanation for the decrease in the animals treated with the LRP5 virus may simply be due to less virus in this treatment group. An indicator of the level of the viral infection is the appearance in the serum of the liver enzymes aspartate aminotransferase and alanine aminotransferase. These enzymes are normally found in the cytoplasm of cells and elevated in the serum when cellular damage occurs (Jaffe, M. S. and McVan, B., 1997, *Davis's laboratory and diagnostic test handbook*. pub. F. A. Davis Philadelphia Pa.). Therefore these enzymes serve as markers for the level of toxicity that is a consequence of the adenoviral infection. These enzymes are present at a normally low level prior to the infection and in animals that did not receive virus. Importantly, the levels of aspartate aminotransferase and alanine aminotransferase are higher in the animals given the LRP5 virus indicating that these animals have more cellular damage and thus a more extensive infection than the animals given the control virus (Table 11). Therefore, it is unlikely that the reduced level of alkaline phosphatase is simply owing to less LRP5 virus being administered. A second possible explanation is that LRP5 modifies the nature of the inflammatory response resulting from the adenovirus infection. A possible role for LRP5 in modulating the inflammatory response is consistent with the genetic data indicating that this gene is associated with risk for developing type 1 diabetes. Chronic insulitis or inflammation is a precursor to clinical onset of type 1 diabetes therefore LRP5 treatment or treatment with therapeutic agents that either increase the transcription of LRP5 may be of utility in preventing type 1 diabetes. Type 1 diabetes is an autoimmune disease, therefore treatment with LRP5 or with therapeutics agents that either increase the expression of LRP5 or the biological activity of LRP5 may be useful in treating other autoimmune diseases.

Expression of LRP5 in Cell Lines

Overexpression of LRP5 under the control of a heterologous promoter can be accomplished either by infection with an adenovirus containing LRP5 or by transfection with a plasmid vector containing LRP5. Transfection with a plasmid vector can lead to either transient or a stable expression of the transgene.

Endogenous LDL-receptors reduce the ability to detect the uptake of LDL by other members of the LDL-receptor family. To study lipoprotein uptake in the absence of the LDL-receptor, primary cell lines from human patients with familial hypercholesterolemia (FH) were used. These FH cell lines lack any endogenous LDL-receptor. FH fibroblasts were infected at an MOI of 500 plaque forming units per cell for 24 hours at 37° C. Following infection, cells were incubated with 40 $\mu$g/ml $^{125}$I-LDL at 37° C. After 4 hours, cells were washed and uptake of LDL measured. A modest (approximately 60%) increase in the level of LDL uptake was observed. By comparison, the infection of FH cells with an adenovirus containing the LDL-receptor resulted in a 20-fold increase in LDL uptake (p<0.0001, n=3). To determine whether this modest level of activity mediated by LRP5 was statistically significant, 24 individual wells were infected with LRP5 virus and analyzed. Statistical analysis of this experiment indicated that the increase in LDL uptake was highly signficant, p<0.0001. Therefore LRP5 can mediate LDL uptake. However, based on the modest level of activity, relative to the LDL-receptor, it does not appear that the primary activity of LRP5 is to mediate the uptake of LDL.

Additional cell lines exist that lack either the LDL-receptor or other members of the LDL-receptor family. The PEA-13 cell line (ATCC 2216-CRL) lacks the LRP1 receptor. Mutant CHO cells lacking the LDL receptor have been described by Kingsley and Krieger (Proceedings National Academy Sciences USA (1984) 81:5454). This cell line, known as ldlA7, is particularly useful for the creation of stable transfectant cell lines expressing recombinant LRP5.

Anti-LRP5 Antibodies
Western Blot Analysis

| SYFHLFPPPPSPCTDSS | (SEQ ID NOS:403) |
| VDGRQNIKRAKDDGT | (SEQ ID NOS:404) |
| EVLFTTGLIRPVALVVDN | (SEQ ID NOS:405) |
| IQGHLDFVMDILVFHS | (SEQ ID NOS:406) | were evaluated by Western blot analysis.

COS cells were infected with an adenovirus containing human LRP5 cDNA. Three days after the infection the cells were harvested by scraping into phosphate buffered saline (Gibco/BRL Gaithersburg, Md.) containing the protease inhibitors PMSF (100 ug/ml), aprotinin (2 ug/ml), and pepstatin A (1 ug/ml). The cells were pelleted by a low speed spin, resuspended in phosphate buffered saline containing protease inhibitors and lysed by Dounce homogenization. Nuclei were removed with a low speed spin, 1000 rpm for 5 min in a Beckman J-9 rotor. The supernatant was collected and centrifuged at high speed, 100,000×g for 3 hours, to pellet the membranes. Membranes were resuspended in SDS-sample buffer (Novex, San Diego Calif.).

Membrane proteins were fractionated by electrophoresis on a 10% Tris-glycine acrylamide gel (Novex, San Diego Calif.). The fractionated proteins were transferred to PVDF paper (Novex, San Diego Calif.) according to the manufacturer's instructions. Standard Western blot analysis was performed on the membrane with the primary antibody being a 1:200 dilution of crude antisera and the secondary antibody a 1:3000 dilution of antirabbit IgG HRP conjugate (Amersham, Arlington Heights, Ill.). ECL reagents (Amersham, Arlington Heights, Ill.) were used to visualize proteins recognized by the antibodies present in the sera.

A band of approximately 170–180 kD was detected by sera from a rabbit immunized with the peptide SYFHLFPPPPSPCTDSS (SEQ ID NO:403). This band was only detected in the cells that were infected with the adenovirus containing human LRP5 and was not present in cells that were infected with a control virus. Furthermore, the detection of this 170 kD band was blocked by preadsorbing a 1:500 dilution of the sera with 0.1 ug/ml of the peptide SYFHLFPPPPSPCTDSS (SEQ ID NO:403) but not with 0.1 ug/ml of the peptide VDGRQNIKRAKDDGT (SEQ ID NOS:404). Therefore this protein band of approximately 170 kD detected by the antibody directed against the peptide SYFHLFPPPPSPCTDSS (SEQ ID NO:403) is human LRP5. The predicted size of the mature human LRP5 protein is 176 kD.

The antisera from a rabbit immunized with the peptide SYFHLFPPPPSPCTDSS (SEQ ID NO:403) was affinity purified with an Affigel 10 column (BioRad, Hercules Calif.) to which the MAP peptide SYFHLFPPPPSPCTDSS (SEQ ID NO:403) was covalently attatched. This results in antisera with greater specificity for LRP5.

The antisera from a rabbit immunized with the peptide IQGHLDFVMDILVFHS (SEQ ID NOS:406) is able to detect a band of approximately 170 kD that is present in cells infected with an LRP5 containing virus but not cells infected with a control virus. This antibody recognizes a peptide that is present in the putative extracellular domain of LRP5 and thus will be useful in detecting the soluble version of LRP5. However, there is greater background observed when using this antisera relative to that from the rabbit immunized with the peptide SYFHLFPPPPSPCTDSS (SEQ ID NO:403).

LRP5 is Expressed in Tissue Macrophages

The crude and affinity purified antisera to the LRP5 peptide SYFHLFPPPPSPCTDSS (SEQ ID NO:403) was used for immunocytochemistry studies in human liver. The antibody recognized tissue macrophages, termed Kupfer cells in the liver, that stained positive for LRP5 and positive for the marker RFD7 (Harlan Bioproducts, Indianapolis Ind.) which recognizes mature tissue phagocytes and negative for an MHC class II marker, RFD1 (Harlan Bioproducts, Indianapolis Ind.). This pattern of staining (RFD1–RFD7+) identifies a subpopulation of macrophages, the effector phagocytes. This class of macrophages has been implicated in the progression of disease in a model for autoimmune disease, experimental autoimmune neuritis (Jung. S. et al., 1993, J Neurol Sci 119: 195–202). The expression in phagocytic tissue macrophages supports a role for LRP3 in modulating the inflammatory component of the immune response. This result is consistent with the proposed role based on the differences observed in alkaline phoshatase levels in animals treated with LRP5 virus and the genetic data indicating that LRP5 is a diabetes risk gene.

Determination of Additional Conserved Regions of the LRP5 Gene

High throughput DNA sequencing of shotgun libraries prepared from mouse BAC clones 131-p-15 and 53-d-8 was used to identify regions of the LRP5 gene that are conserved between mouse and man. To identify these regions the mouse genomic DNA, either unassembled sequences or assembled contigs, was compared against an assembly of human genomic DNA. The comparison was done by using the BLAST algorithm with a cutoff of 80%. This analysis resulted in the identification of a majority of the exons of the LRP5 gene and identified a number of patches of conserved sequences at other locations in the gene (Table 12).

There are sequences conserved between human and mouse located 4.3 kb and 168 bp upstream of the putative ATG. These sequences may represent 5' untranslated sequences of the mRNA transcript or promoter elements.

Within the putative first intron of 36 kb there are twelve patches that exhibit a degree of DNA sequence conservation. Some of these regions, e.g. 41707–41903, are quite extensive and have a high degreee of sequence conservation, similar to that observed for the exons of the LRP5 gene. Since these regions do not appear to be transcribed it is likely that these conserved regions play a role in regulating either the transcription of the LRP5 gene or the processing of the LRP5 mRNA transcript. Regardless of exact nature of their role these newly identified regions represent areas where sequence polymorphism may affect the biological activity of LRP5.

The BAC clone 131-p-15 which contains the first two exons of LRP5 was sequenced extensively, i.e. approximately 6× coverage. BAC clone 53-d-8 contains sequences from exon D to exon V, however the level of sequence coverage of this clone was only approximately 1× (skim sequencing). The skim sequencing of mouse BAC 53-d-8 resulted in 76% of the exons being detected, however in some instances only a portion of an exon was present in the mouse sequence data. In addition to the exons, there were three patches in the BAC 53-d-8 sequences that exhibited a degree of sequence conservation with the human sequences (Table 12). All of these were located in the large 20 kb intron between exons D and E. These sequences may represent regions that are important for the processing of this large intron and thus polymorphisms in these sequences may affect the expression level of LRP5.

Determination of Relative Abundance of Alternatively Spliced LRP5 MnPNA Transcripts Several techniques may be used to determine the relative abundance of the different alternatively spliced isoforms of LRP5.

Northern blot analysis of probes derived from specific transcripts is used to survey tissues for the abundance of a particular transcript. More sensitive techniques such as RNase protection assays will be performed. Reagents from commercially available kits (Ambion, Inc. Austin Tex.) are used to prepare probes. The relative abundance of transcript that hybridizes to a probe radiolabeled with [alpha]32P-UTP is analyzed by native and denaturing acrylamide gels (Novex Inc., San Diego, Calif.). Primer extension assays are performed according to established procedures (Sambrook et. al. (1989) Molecular Cloning, Cold Spring Harbour Press, NY) using reverse primers derived from the 5' portion of the transcript.

Isolation of Other Species Homologs of LRP5 Gene

The LRP5 gene from different species, e.g. rat, dog, are isolated by screening of a cDNA library with portions of the gene that have been obtained from cDNA of the species of interest using PCR primers designed from the human LRP5 sequence. Degenerate PCR is performed by designing primers of 17–20 nucleotides with 32–128 fold degeneracy by selecting regions that code for amino acids that have low codon degeneracy e.g. Met and Trp. When selecting these primers preference is given to regions that are conserved in the protein e.g. the motifs shown in FIG. 6b. PCR products are analyzed by DNA sequence analysis to confirm their similarity to human LRP5. The correct product is used to screen cDNA libraries by colony or plaque hybridization at high stringency. Alternatively probes derived directly from the human LRP5 gene are utilized to isolate the cDNA sequence of LRP5 from different species by hybridization at reduced stringency. A cDNA library is generated as described above.

REFERENCES

1. Bach, J.-F (1994). Endocrine. Rev. 15: 516–542.
2. Bain, S., et al. (1992). Diabetes 41: 91A.
3. Bell, G. I., et al. (1984). Diabetes 33: 176–83.
4. Bennett, S. T., et al. (1995). Nature Genet. 9: 284–292.
5. Bennett, S. T. and Todd, J. A (1996). Annu. Rev. Genet.30: 343–370.
6. Buckler, A. et al. (1991). P.N.A.S USA 88: 4005–4009.
7. Davies, J. L., et al. (1994). Nature 371: 130–136.
8. Doria, A., et al (1996). Diabetologia 39: 594–599.
9. Hashimoto, L., et al. (1994). Nature 371: 161–164.
10. Holmans, P. (1993). Am. J. Hum. Genet. 52: 362–374.
11. Julier, C., et al. (1991a). Nature 354: 155–159.
12. Kennedy, G. C., et al. (1995). Nature Genet. 9: 293–298.
13. Kyvik, K. O., et al. (1995). Brit. Med. J. 311: 913–917.

14. Lucassen, A., et al. (1993). Nature Genet. 4: 305–310.
15. Lucassen, A., et al. (1995). Hum. Mol. Genet. 4: 501–506.
16. Luo, D.-F., et al. (1996). Hum. Mol. Genet. 5: 693–698.
17. Matsuda, A. and Kuzuya, T. (1994). Diab. Res. Clin. Pract. 24: Suppl., S63–S67.
18. Risch (1987). Am. J. Hum. Genet. 40: 1–14.
19. Owerbach, D., et al. (1990). Diabetes 39: 1504–1509.
20. Parimoo, S., et al. (1991). P.N.A.S. USA 88: 9623–9627.
21. Penrose, L. S. (1953). Acta. Genet. Stat. Med. 4: 257–265.
22. Risch, S. S. (1990). Diabetes 39: 1315–19.
23. Spielman, R., et al. (1993). Am. J. Hum. Genet. 52: 506–516.
24. Thomson, G., et al. (1989). Genet. Epidemiol. 6: 155–160.
25. Tisch, R. and McDevitt, H. O. (1996). Cell 85: 291–297.
26. Todd, J. A. (1994). Diabetic Med. 11: 6–16.
27. Todd, J. A., et al. (1987). Nature 329: 599–604.
28. Todd, J. A. and Farrall, M. (1996). Hum. Mol. Genet. 5: 1443–1448.
29. Todd, J. A., et al. (1989). Nature 338: 587–589.
30. Vafiadis, P., et al. (1996). J. Autoimmunity 9: 397–403.

TABLE 1

Haplotype analysis at D11S1917 (UT5620) - H057OPOLYA, within 2582 families from UK, USA, Norway and Sardinia. Susceptible, protective and neutral alleles were identified at each polymorphism, and transmission of recombinant haplotypes to diabetic offspring was calculated (t = transmission, nt = non transmission) Significant transmission of the haplotype 332-104 was detected (P = 0.005), as well as significant non-transmission of the haplotype 328-103 (P = 0.03)

|  | D11S1917 (UT5620) | H057OPOLYA | t | nt | P |
| --- | --- | --- | --- | --- | --- |
|  | 328 | 104 | 539 | 474 |  |
| Protective | 332 | 103 | 427 | 521 | 0.002 |
| Susceptible | 332 | 104 | 60 | 33 | 0.005 |
| Protective | 328 | 103 | 16 | 31 | 0.03 |

TABLE 2

PCR Primers for obtaining LRP5 cDNA
Primers located within LRP5 cDNA:
The primers are numbered beginning at
nucleotide 1 in FIG. 5(a) (SEQ ID NO: 1).

| | | |
| --- | --- | --- |
| 1F (muex 1f): | ATGGAGCCCGAGTGAGC | (SEQ ID NO:49) |
| 218R (27R): | ATGGTGGACTCCAGCTTGAC | (SEQ ID NO:50) |
| 256F (1F): | TTCCAGTTTTCCAAGGGAG | (SEQ ID NO:51) |

TABLE 2-continued

PCR Primers for obtaining LRP5 cDNA
Primers located within LRP5 cDNA:
The primers are numbered beginning at
nucleotide 1 in FIG. 5(a) (SEQ ID NO: 1).

| | | |
| --- | --- | --- |
| 265R (26R): | AAAACTGGAAGTCCACTGCG | (SEQ ID NO:52) |
| 318R (4R): | GGTCTGCTTGATGGCCTC | (SEQ ID NO:53) |
| 343F (2F): | GTGCAGAACGTGGTCATCT | (SEQ ID NO:54) |
| Vector Primers for RCCA | | |
| 361R (21R): | GTGCAGAACGTGGTCATCT | (SEQ ID NO:54) |
| 622R (2R): | AGTCCACAATGATCTTCCGG | (SEQ ID NO:55) |
| 638F (4F): | CCAATGGACTGACCATCGAC | (SEQ ID NO:56) |
| 657R (1R): | GTCGATGGTCAGTCCATTGG | (SEQ ID NO:57) |
| 956R (22R): | TTGTCCTCCTCACAGCGAG | (SEQ ID NO:58) |
| 1713F (21F): | GGACTTCATCTACTGGACTG | (SEQ ID NO:59) |
| 1481R (23R): | CAGTCGTCCAGTACATGAG | (SEQ ID NO:60) |
| 1981F (22F): | GCCTTCTTGGTCTTCACCAG | (SEQ ID NO:61) |
| 2261F (23F): | GGACCAACAGAATCGAAGTG | (SEQ ID NO:62) |
| 2484R (5R): | GTCAATGGTGAGGTCGT | (SEQ ID NO:63) |
| 2519F (5F): | ACACCAACATGATCGAGTCG | (SEQ ID NO:64) |
| 3011F (24F): | ACAAGTTCATCTACTGGGTG | (SEQ ID NO:65) |
| 3154F (25F): | CGGACACTGTTCTGGACGTG | (SEQ ID NO:66) |
| 3173R (25R): | CACGTCCAGAACAGTGTCCG | (SEQ ID NO:67) |
| 3556R (3R): | TCCAGTAGAGATGCTTGCCA | (SEQ ID NO:68) |
| Vector Primers for RCCA | | |
| 3577F (3F): | ATCGAGCGTGTGGAGAAGAC | (SEQ ID NO:69) |
| 4094F (30F): | TCCTCATCAAACAGCAGTGC | (SEQ ID NO:70) |
| 4173R (6R): | CGGCTTGGTGATTTCACAC | (SEQ ID NO:71) |
| 4687F (6F): | GTGTGTGACAGCGACTACAGC | (SEQ ID NO:72) |
| 4707R (30R): | GCTGTAGTCGCTGTCACACAC | (SEQ ID NO:73) |
| 5061R (7R): | GTACAAAGTTCTCCCAGCCC | (SEQ ID NO:74) |
| PCR primers in Sequences identified by GRAIL | | |
| G1 1F: | TCTTCTCCAGAGGATGCAGC | (SEQ ID NO:75) |
| G1 2F: | TTCGTCTTGAACTTCCCAGC | (SEQ ID NO:76) |
| G1 3F: | TCTTCTTCTCCAGAGGATGCA | (SEQ ID NO:77) |
| Gp1 1F: | AGGCTGGTCTCAAACTCCTG | (SEQ ID NO:78) |
| PBS.543R: | GGGGATGTGCTGCAAGGCGA | (SEQ ID NO:79) |
| PBS.578R: | CCAGGGTTTTCCCAGTCACGAC | (SEQ ID NO:80) |
| PBS.838F: | TTGTGTGGAATTGTGAGCGGATAAC | (SEQ ID NO:81) |
| PBS.873F: | CCCAGGCTTTACACTTTATGCTTCC | (SEQ ID NO:82) |

TABLE 3

Intron-Exon Organization of Human LRP-5

| 3' Acceptor Sequence | | Exon | Exon Size | 5' Donor Sequence | Intron Number & |
| --- | --- | --- | --- | --- | --- |
| Intron | Exon | Number | (bp) | Exon  Intron | Size (bp) |
| ccgggtcaac/ATGGAG (SEQ ID NO: 411) | | Ex 1 (6) | (91) | CCGCGG/gtaggtgggc | 1 (35051) (SEQ ID NO: 412) |
| tgccccacag/CCTCGC (SEQ ID NO: 413) | | Ex 2 (A) | (391) | TCACGG/gtaaaccctg | 2 (9408) (SEQ ID NO: 414) |
| cccgtcacag/GTACAT (SEQ ID NO: 415) | | Ex 3 (B) | (198) | GTTCCG/gtaggtaccc | 3 (6980) (SEQ ID NO: 416) |
| ctgactgcag/GCAGAA | | Ex 4 (C) | (197) | CTTTCT/gtgagtgccg | 4 (1640) |

TABLE 3-continued

Intron-Exon Organization of Human LRP-5

| 3' Acceptor Sequence Intron | Exon | Exon Number | Exon Size (bp) | 5' Donor Sequence Exon | Intron | Intron Number & Size (bp) |
|---|---|---|---|---|---|---|
| (SEQ ID NO: 417) | | | | | | (SEQ ID NO: 418) |
| gttttcccag/TCCACA | Ex 5 | (D) | (132) | AGGCAG/ | gtgaggcggt | 5 (20823) |
| (SEQ ID NO: 419) | | | | | | (SEQ ID NO: 420) |
| gtctccacag/GAGCCG | Ex 6 | (E) | (397) | GATGGG/ | gtaagacggg | 6 (3213) |
| (SEQ ID NO: 421) | | | | | | (SEQ ID NO: 422) |
| tcttctccag/CCTCAT | Ex 7 | (F) | (172) | ATCGAG/ | gtgaggctcc | 7 (13445) |
| (SEQ ID NO: 423) | | | | | | (SEQ ID NO: 424) |
| cgtcctgcag/GTGATC | Ex 8 | (G) | (217) | TCGTCG/ | gtgagtccgg | 8 (2826) |
| (SEQ ID NO: 425) | | | | | | (SEQ ID NO: 426) |
| tcgcttccag/GAACCA | Ex 9 | (H) | (290) | CTGAAG/ | gtagcgtggg | 9 (5000+) |
| (SEQ ID NO: 427) | | | | | | (SEQ ID NO: 428) |
| ctgctgccag/ACCATC | Ex 10 | (I) | (227) | CAAGGG/ | gtaagtgttt | 10 (1295) |
| (SEQ ID NO: 429) | | | | | | (SEQ ID NO: 430) |
| tgcctttccag/CTACAT | Ex 11 | (J) | (185) | TGCTGG/ | gtgagggccg | 11 (2068) |
| (SEQ ID NO: 431) | | | | | | (SEQ ID NO: 432) |
| gttcatgcag/GTCAGG | Ex 12 | (K) | (324) | GCAGCC/ | gtaagtgcct | 12 (2005) |
| (SEQ ID NO: 433) | | | | | | (SEQ ID NO: 434) |
| cctcctctag/CGCCCA | Ex 13 | (L) | (200) | ACCCAG/ | gcaggtgccc | 13 (6963) |
| (SEQ ID NO: 435) | | | | | | (SEQ ID NO: 436) |
| tgtcttacag/CCCTTT | Ex 14 | (M) | (209) | GCGAGG/ | gtaggaggcc | 14 (1405) |
| (SEQ ID NO: 437) | | | | | | (SEQ ID NO: 438) |
| cctcccgcag/GTACCT | Ex 15 | (N) | (191) | TGTCAG/ | gtaaggggcc | 15 (686) |
| (SEQ ID NO: 439) | | | | | | (SEQ ID NO: 440) |
| ctgcttgcag/GGGCCA | Ex 16 | (O) | (210) | AGTTCT/ | gtacgtgggg | 16 (3894) |
| (SEQ ID NO: 441) | | | | | | (SEQ ID NO: 442) |
| gtctttgcag/CAGCCC | Ex 17 | (P) | (126) | GTGGAG/ | gtaggtgtga | 17 (3903) |
| (SEQ ID NO: 443) | | | | | | (SEQ ID NO: 444) |
| cctcccccag/AGCCGC | Ex 18 | (Q) | (237) | GTGACG/ | gtgaggccct | 18 (3042) |
| (SEQ ID NO: 445) | | | | | | (SEQ ID NO: 446) |
| tcccttgcag/CCATCT | Ex 19 | (R) | (111) | TGTGTG/ | gtgagccagc | 19 (1448) |
| (SEQ ID NO: 447) | | | | | | (SEQ ID NO: 448) |
| tctctggcag/AAATCA | Ex 20 | (S) | (237) | TCACAG/ | gtaaggagcc | 20 (1095) |
| (SEQ ID NO: 449) | | | | | | (SEQ ID NO: 450) |
| tccctgccag/GCATCG | Ex 21 | (T) | (140) | CCGCCG/ | gtgaggggcg | 21 (6514) |
| (SEQ ID NO: 451) | | | | | | (SEQ ID NO: 452) |
| ctctcctcag/ATCCTG | Ex 22 | (U) | (98) | GTACAG/ | gtaggacatc | 22 (2275) |
| (SEQ ID NO: 453) | | | | | | (SEQ ID NO: 454) |
| tcccttttcag/GCCCTA | Ex 23 | (V) | (>262) | | | 23 (19985) |
| (SEQ ID NO: 455) | | | | | | |

TABLE 4

LRP-5 Exon primers

| (SEQ ID NO: 83) | E1x1 1f | CAGGGTTTCATCCTTTGTGG |
|---|---|---|
| (SEQ ID NO: 84) | E1x1 1fU | TGTAAAACGACGGCCAGTCAGGGTTTCATCCTTTGTGG |
| (SEQ ID NO: 85) | E1x1 1fR | GCTATGACCATGATTACGCCCAGGGTTTCATCCTTTGTGG |
| (SEQ ID NO: 86) | E1x1 1r | TGACGGGAAGAGTTCCTCAG |
| (SEQ ID NO: 87) | E1x1 1rR | GCTATGACCATGATTACGCCTGACGGGAAGAGTTCCTCAG |
| (SEQ ID NO: 88) | E1x5 1f | TCTGCTCTTCCTGAACTGCC |
| (SEQ ID NO: 89) | E1x5 1fU | TGTAAAACGACGGCCAGTTCTGCTCTTCCTGAACTGCC |
| (SEQ ID NO: 90) | E1x5 1r | TTGAGTCCTTCAACAAGCCC |
| (SEQ ID NO: 91) | E1x5 1rR | GCTATGACCATGATTACGCCTTGAGTCCTTCAACAAGCCC |
| (SEQ ID NO: 92) | E1x6 1fU | TGTAAAACGACGGCCAGTTTCCCCACTCATAGAGGCTC |
| (SEQ ID NO: 93) | E1x6 1rR | GCTATGACCATGATTACGCCGCTCCCAACTCGCCAAGT |
| (SEQ ID NO: 94) | E1x6a 1fU | TGTAAAACGACGGCCAGTGGTCAACATGGAGGCAGC |
| (SEQ ID NO: 95) | E1x6a 1rR | GCTATGACCATGATTACGCCCAGGTGTCAGTCCGCTTG |
| (SEQ ID NO: 96) | E1x6b 1fU | TGTAAAACGACGGCCAGTGCAGAGAAGTTCTGAGC |
| (SEQ ID NO: 97) | E1x6b 1rR | GCTATGACCATGATTACGCCCTTGGCCAGCCATACTC |
| (SEQ ID NO: 98) | E1x6c 1fU | TGTAAAACGACGGCCAGTCAAGCAAGCCTCTTGCTACC |
| (SEQ ID NO: 99) | E1x6c 1rR | GCTATGACCATGATTACGCCACTGCAATGAGGTGAAAGGC |
| (SEQ ID NO: 100) | E1x6d 1fU | TGTAAAACGACGGCCAGTCAGGTGAGAACAAGTGTCCG |
| (SEQ ID NO: 101) | E1x6d 1rR | GCTATGACCATGATTACGCCGCTGCCTCCATGTTGACC |
| (SEQ ID NO: 102) | E1x6e 1fU | TGTAAAACGACGGCCAGTTGTGCTGGGTGAGATTCT |
| (SEQ ID NO: 103) | E1x6e 1rR | GCTATGACCATGATTACGCCTGTGGAGCCTCTATGAGTGG |
| (SEQ ID NO: 104) | E1x6f 1fU | TGTAAAACGACGGCCAGTGGGTGACAGGTGGCAGTAG |
| (SEQ ID NO: 105) | E1x6f 1rR | GCTATGACCATGATTACGCCGGAAGGAAGGACACTTGAGC |
| (SEQ ID NO: 106) | E1x6g 1fU | TGTAAAACGACGGCCAGTCCTGGTGTGTTTGAGAACCC |
| (SEQ ID NO: 107) | E1x6g 1rR | GCTATGACCATGATTACGCCCAATGGGAAGCCAGGCTAG |

TABLE 4-continued

| | | |
|---|---|---|
| (SEQ ID NO: 108) | E1xA 1f | ATCTTGCTGGCTTAGCCAGT |
| (SEQ ID NO: 109) | E1xA 1fU | TGTAAAACGACGGCCAGTATCTTGCTGGCTTAGCCAGT |
| (SEQ ID NO: 110) | E1xA 1fR | GCTATGACCATGATTACGCCATCTTGCTGGCTTAGCCAGT |
| (SEQ ID NO: 111) | E1xA 1r | GCTCATGAAATTCGAGAGAG |
| (SEQ ID NO: 112) | E1xA 1rR | GCTATGACCATGATTACGCCGCTCATGCAAATTCGAGAGAG |
| (SEQ ID NO: 113) | E1xB 1f | CCTGTTGGTTATTTCCGATGG |
| (SEQ ID NO: 114) | E1xB 1fU | TGTAAAACGACGGCCAGTCCTGTTGGTTATTTCCGATGG |
| (SEQ ID NO: 115) | E1xB 1fR | GCTATGACCATGATTACGCCCCTGTTGGTTATTTCCGATGG |
| (SEQ ID NO: 116) | E1xB 1r | CCTGAGTTAAGAAGGAACGCC |
| (SEQ ID NO: 117) | E1xB 1rR | GCTATGACCATGATTACGCCCCTGAGTTAAGAAGGAACGCC |
| (SEQ ID NO: 118) | E1xC 1f | AATTGGGTCAGCAGCAATG |
| (SEQ ID NO: 119) | E1xC 1fR | GCTATGACCATGATTACGCCAATTGGGTCAGCAGCAATG |
| (SEQ ID NO: 120) | E1xC 2f | AATTGGGTCAGCAGCAATG |
| (SEQ ID NO: 121) | E1xC 2fU | TGTAAAACGACGGCCAGTAATTGGGTCAGCAGCAATG |
| (SEQ ID NO: 119) | E1xC 2fR | GCTATGACCATGATTACGCCAATTGGGTCAGCAGCAATG |
| (SEQ ID NO: 122) | E1xC 1r | TTGGATCGCTAGAGATTGGG |
| (SEQ ID NO: 123) | E1xC 1rR | GCTATGACCATGATTACGCCTTGGATCGCTAGAGATTGGG |
| (SEQ ID NO: 124) | E1xC 2r | GCACCCTAATTGGCACTCA |
| (SEQ ID NO: 125) | E1xC 2rR | GCTATGACCATGATTACGCCGCACCCTAATTGGCACTCA |
| (SEQ ID NO: 126) | E1xD 1f | TGACGGTCCTCTTCTGGAAC |
| (SEQ ID NO: 127) | E1xD 1fR | GCTATGACCATGATTACGCCTGACGGTCCTCTTCTGGAAC |
| (SEQ ID NO: 128) | E1xD 2f | CGAGGCAGGATGTGACTCAT |
| (SEQ ID NO: 129) | E1xD 2fU | TGTAAAACGACGGCCAGTCGAGGCAGGATGTGACTCAT |
| (SEQ ID NO: 130) | E1xD 2fR | GCTATGACCATGATTACGCCCGAGGCAGGATGTGACTCAT |
| (SEQ ID NO: 131) | E1xD 1r | AGTGGATCATTTCGAACGG |
| (SEQ ID NO: 132) | E1xD 1rR | GCTATGACCATGATTACGCCAGTGGATCATTTCGAACGG |
| (SEQ ID NO: 133) | E1xD 2r | CCAACTCAGCTTCCCGAGTA |
| (SEQ ID NO: 134) | E1xD 2rR | GCTATGACCATGATTACGCCCCAACTCAGCTTCCCGAGTA |
| (SEQ ID NO: 135) | E1xE 1f | TGGCTGAGTATTTCCCTTGC |
| (SEQ ID NO: 136) | E1xE 1fU | TGTAAAACGACGGCCAGTTGGCTGAGTATTTCCCTTGC |
| (SEQ ID NO: 137) | E1xE 1fR | GCTATGACCATGATTACGCCTGGCTGAGTATTTCCCTTGC |
| (SEQ ID NO: 138) | E1xE 1r | TTTAACAAGCCCTCCTCCG |
| (SEQ ID NO: 139) | E1xE 1rR | GCTATGACCATGATTACGCCTTTAACAAGCCCTCCTCCG |
| (SEQ ID NO: 140) | E1xF 1f | CAACGCCAGCATCTACTGA |
| (SEQ ID NO: 141) | E1xF 1fU | TGTAAAACGACGGCCAGTCAACGCCAGCATCTACTGA |
| (SEQ ID NO: 142) | E1xF 1fR | GCTATGACCATGATTACGCCCAACGCCAGCATCTACTGA |
| (SEQ ID NO: 143) | E1xF 1r | CAAATAGCAGAGCACAGGCA |
| (SEQ ID NO: 144) | E1xF 1rR | GCTATGACCATGATTACGCCCAAATAGCAGAGCACAGGCA |
| (SEQ ID NO: 145) | E1xG 1f | TGAAGTTGCTGCTCTTGGG |
| (SEQ ID NO: 146) | E1xG 1fU | TGTAAAACGACGGCCAGTTGAAGTTGCTGCTCTTGGG |
| (SEQ ID NO: 147) | E1xG 1fR | GCTATGACCATGATTACGCCTGAAGTTGCTGCTCTTGGG |
| (SEQ ID NO: 148) | E1xG 1r | CACTTCCTCCTCATGCAAGTC |
| (SEQ ID NO: 149) | E1xG 1rR | GCTATGACCATGATTACGCCCACTTCCTCCTCATGCAAGTC |
| (SEQ ID NO: 150) | E1xH 1f | AGACTGGAGCCTCTGTGTTCG |
| (SEQ ID NO: 151) | E1xH 1fU | TGTAAAACGACGGCCAGTAGACTGGAGCCTCTGTGTTCG |
| (SEQ ID NO: 152) | E1xH 1fR | GCTATGACCATGATTACGCCAGACTGGAGCCTCTGTGTTCG |
| (SEQ ID NO: 153) | E1xH 1r | TGTGTGTCTACCGGACTTGC |
| (SEQ ID NO: 154) | E1xH 1rR | GCTATGACCATGATTACGCCTGTGTGTCTACCGGACTTGC |
| (SEQ ID NO: 155) | E1xH 2r | GAACAGAGGCAAGGTTTTCCC |
| (SEQ ID NO: 156) | E1xH 2rR | GCTATGACCATGATTACGCCGAACAGAGGCAAGGTTTTCCC |
| (SEQ ID NO: 157) | E1xI 1f | AGAATCGCTTGAACCCAGG |
| (SEQ ID NO: 158) | E1xI 1fR | GCTATGACCATGATTACGCCAGAATCGCTTGAACCCAGG |
| (SEQ ID NO: 159) | E1xI 2f | GCTGGTTCCTAAAATGTGGC |
| (SEQ ID NO: 160) | E1xI 2fU | TGTAAAACGACGGCCAGTGCTGGTTCCTAAAATGTGGC |
| (SEQ ID NO: 161) | E1xI 2fR | GCTATGACCATGATTACGCCGCTGGTTCCTAAAATGTGGC |
| (SEQ ID NO: 162) | E1xI 1r | CATACGAGGTGAACACAAGGAC |
| (SEQ ID NO: 163) | E1xI 1rR | GCTATGACCATGATTACGCCCATACGAGGTGAACACAAGGAC |
| (SEQ ID NO: 164) | E1xJ 1f | TGAAGAGGTGGGGACAGTTG |
| (SEQ ID NO: 165) | E1xJ 1fR | GCTATGACCATGATTACGCCTGAAGAGGTGGGGACAGTTG |
| (SEQ ID NO: 166) | E1xJ 2f | CTTGTGCCTTCCAGCTACATC |
| (SEQ ID NO: 167) | E1xJ 2fU | TGTAAAACGACGGCCAGTCTTGTGCCTTCCAGCTACATC |
| (SEQ ID NO: 168) | E1xJ 2fR | GCTATGACCATGATTACGCCCTTGTGCCTTCCAGCTACATC |
| (SEQ ID NO: 169) | E1xJ 1r | AGTCCTGGCACAGGGATTAG |
| (SEQ ID NO: 170) | E1xJ 1rR | GCTATGACCATGATTACGCCAGTCCTGGCACAGGGATTAG |
| (SEQ ID NO: 171) | E1xJ 2r | ATAACTGCAGCAAAGGCACC |
| (SEQ ID NO: 172) | E1xJ 2rR | GCTATGACCATGATTACGCCATAACTGCAGCAAAGGCACC |
| (SEQ ID NO: 173) | E1xK 1f | GCTTCAGTGGATCTTGCTGG |
| (SEQ ID NO: 174) | E1xK 1fU | TGTAAAACGACGGCCAGTGCTTCAGTGGATCTTGCTGG |
| (SEQ ID NO: 175) | E1xK 1fR | GCTATGACCATGATTACGCCGCTTCAGTGGATCTTGCTGG |
| (SEQ ID NO: 176) | E1xK 1r | TGTGCAGTGCACAACCTACC |
| (SEQ ID NO: 177) | E1xK 1rR | GCTATGACCATGATTACGCCTGTGCAGTGCACAACCTACC |
| (SEQ ID NO: 178) | E1xL 1f | GTTGTCGAGTGGCGTGCTAT |
| (SEQ ID NO: 179) | E1xL 1fU | TGTAAAACGACGGCCAGTGTTGTCGAGTGGCGTGCTAT |
| (SEQ ID NO: 180) | E1xL 1fR | GCTATGACCATGATTACGCCGTTGTCGAGTGGCGTGCTAT |
| (SEQ ID NO: 181) | E1xL 1r | AAAAGTCCTGTGGGGTCTGA |
| (SEQ ID NO: 182) | E1xL 1rR | GCTATGACCATGATTACGCCAAAAGTCCTGTGGGGTCTGA |
| (SEQ ID NO: 183) | E1xM 1f | AGAAGTGTGGCCTCTGCTGT |
| (SEQ ID NO: 184) | E1xM 1fU | TGTAAAACGACGGCCAGTAGAAGTGTGGCCTCTGCTGT |
| (SEQ ID NO: 185) | E1xM 1fR | GCTATGACCATGATTACGCCAGAAGTGTGGCCTCTGCTGT |

TABLE 4-continued

| | | |
|---|---|---|
| (SEQ ID NO: 186) | E1xM 1r | GTGAAAGAGCCTGTGTTTGCT |
| (SEQ ID NO: 187) | E1xM 1rR | GCTATGACCATGATTACGCCGTGAAAGAGCCTGTGTTTGCT |
| (SEQ ID NO: 188) | E1xN 1f | AGACCCTGCTTCCAAATAAGC |
| (SEQ ID NO: 189) | E1xN 1fU | TGTAAAACGACGGCCAGTAGACCCTGCTTCCAAATAAGC |
| (SEQ ID NO: 190) | E1xN 1fR | GCTATGACCATGATTACGCCAGACCCTGCTTCCAAATAAGC |
| (SEQ ID NO: 191) | E1xN 1r | ACTCATTTTCTGCCTGCC |
| (SEQ ID NO: 192) | E1xN 1rR | GCTATGACCATGATTACGCCACTCATTTTCTGCCTCTGCC |
| (SEQ ID NO: 193) | E1xO 1f | TGGCAGTCCTGTCAACCTCT |
| (SEQ ID NO: 194) | E1xO 1fU | TGTAAAACGACGGCCAGTTGGCAGTCCTGTCAACCTCT |
| (SEQ ID NO: 195) | E1xO 1fR | GCTATGACCATGATTACGCCTGGCAGTCCTGTCAACCTCT |
| (SEQ ID NO: 196) | E1xO 1r | CACACAGGATCTTGCACTGG |
| (SEQ ID NO: 197) | E1xO 1rR | GCTATGACCATGATTACGCCCACACAGGATCTTGCACTGG |
| (SEQ ID NO: 198) | E1xP 1f | AGGGCCAGTTCTCATGAGTT |
| (SEQ ID NO: 199) | E1xP 1fU | TGTAAAACGACGGCCAGTAGGGCCAGTTCTCATGAGTT |
| (SEQ ID NO: 200) | E1xP 1fR | GCTATGACCATGATTACGCCAGGGCCAGTTCTCATGAGTT |
| (SEQ ID NO: 201) | E1xP 1r | GGGCAAAGGAAGACACAATC |
| (SEQ ID NO: 202) | E1xP 1rR | GCTATGACCATGATTACGCCGGGCAAAGGAAGACACAATC |
| (SEQ ID NO: 203) | E1xQ 1f | CAACTTCTGCTTTGAAGCCC |
| (SEQ ID NO: 204) | E1xQ 1fU | TGTAAAACGACGGCCAGTCAACTTCTGCTTTGAAGCCC |
| (SEQ ID NO: 205) | E1xQ 1fR | GCTATGACCATGATTACGCCCAACTTCTGCTTTAAGCCC |
| (SEQ ID NO: 206) | E1xQ 1r | GACAGACTTGGCAATCTCCC |
| (SEQ ID NO: 207) | E1xQ 1rR | GCTATGACCATGATTACGCCGACAGACTTGGCAATCTCCC |
| (SEQ ID NO: 208) | E1xR 1f | TCTGCTCTCTGTTTGGAGTCC |
| (SEQ ID NO: 209) | E1xR 1fU | TGTAAAACGACGGCCAGTTCTGCTCTCTGTTTGGAGTCC |
| (SEQ ID NO: 210) | E1xR 1fR | GCTATGACCATGATTACGCCTCTGCTCTCTGTTTGGAGTCC |
| (SEQ ID NO: 211) | E1xR 1r | CCCTAAACTCCACGTTCCTG |
| (SEQ ID NO: 212) | E1xR 1rR | GCTATGACCATGATTACGCCCCCTAAACTCCACGTTCCTG |
| (SEQ ID NO: 213) | E1xS 1f | GGGTTAATGTTGGCCACATC |
| (SEQ ID NO: 214) | E1xS 1fR | GCTATGACCATGATTACGCCGGGTTAATGTTGGCCACATC |
| (SEQ ID NO: 215) | E1xS 2f | TTGGCAGGGATGTGTTGAG |
| (SEQ ID NO: 216) | E1xS 2fU | TGTAAAACGACGGCCAGTTTGGCAGGGATGTGTTGAG |
| (SEQ ID NO: 217) | E1xS 2fR | GCTATGACCATGATTACGCCTTGGCAGGGATGTGTTGAG |
| (SEQ ID NO: 218) | E1xS 1r | GTCTGCCACATGTGCAAGAG |
| (SEQ ID NO: 219) | E1xS 1rR | GCTATGACCATGATTACGCCGTCTGCCACATGTGCAAGAG |
| (SEQ ID NO: 220) | E1xT 1f | TGGTCTGAGTCTCGTGGGTA |
| (SEQ ID NO: 221) | E1xT 1fU | TGTAAAACGACGGCCAGTTGGTCTGAGTCTCGTGGGTA |
| (SEQ ID NO: 222) | E1xT 1fR | GCTATGACCATGATTACGCCTGGTCTGAGTCTCGTGGGTA |
| (SEQ ID NO: 223) | E1xT 1r | GAGGTGGATTTGGGTGAGATT |
| (SEQ ID NO: 224) | E1xT 1rR | GCTATGACCATGATTACGCCGAGGTGGATTTGGGTGAGATT |
| (SEQ ID NO: 225) | E1xU 1f | AGCCCTCTCTGCAAGGAAAG |
| (SEQ ID NO: 226) | E1xU 1fU | TGTAAAACGACGGCCAGTAGCCCTCTCTGCAAGGAAAG |
| (SEQ ID NO: 227) | E1xU 1fR | GCTATGACCATGATTACGCCAGCCCTCTCTGCAAGGAAAG |
| (SEQ ID NO: 228) | E1xU 1r | CAGAACGTGGAGTTCTGCTG |
| (SEQ ID NO: 229) | E1xU 1rR | GCTATGACCATGATTACGCCCAGAACGTGGAGTTCTGCTG |
| (SEQ ID NO: 230) | E1xV 1f | TACCGAATCCCACTCCTCTG |
| (SEQ ID NO: 231) | E1xV 1fU | TGTAAAACGACGGCCAGTTACCGAATCCCACTCCTCTG |
| (SEQ ID NO: 232) | E1xV 1fR | GCTATGACCATGATTACGCCTACCGAATCCCACTCCTCTG |
| (SEQ ID NO: 233) | E1xV 2f | CATGGTAGAGGTGGGACCAT |
| (SEQ ID NO: 234) | E1xV 2fU | TGTAAAACGACGGCCAGTCATGGTAGAGGTGGGACCAT |
| (SEQ ID NO: 235) | E1xV 2fR | GCTATGACCATGATTACGCCCATGGTAGAGGTGGGACCAT |
| (SEQ ID NO: 236) | E1xV 1r | GATATCCACCTCTGCCCAAG |
| (SEQ ID NO: 237) | E1xV 1rR | GCTATGACCATGATTACGCCGATATCCACCTCTGCCCAAG |
| (SEQ ID NO: 238) | E1xV 2r | TTACAGGGGCACAGAGAAGC |
| (SEQ ID NO: 239) | E1xV 2rR | GCTATGACCATGATTACGCCTTACAGGGGCACAGAGAAGC |
| | SNP primers | |
| (SEQ ID NO: 240) | 57-1 1f | GCAACAGAGCAAGACCCTGT |
| (SEQ ID NO: 241) | 57-1 1fR | GCTATGACCATGATTACGCCGCAACAGAGCAAGACCCTGT |
| (SEQ ID NO: 242) | 57-1 1r | AAATTAGCCAGGCATGGTG |
| (SEQ ID NO: 243) | 57-1 1rR | GCTATGACCATGATTACGCCAAATTAGCCAGGCATGGTG |
| (SEQ ID NO: 244) | 57-1 1fU | TGTAAAACGACGGCCAGTGCAACAGAGCAAGACCCTGT |
| (SEQ ID NO: 245) | 57-2 1f | CCTGCAGAAGGAAACCTGAC |
| (SEQ ID NO: 246) | 57-2 1fR | GCTATGACCATGATTACGCCCCTGCAGAAGGAAACCTGAC |
| (SEQ ID NO: 247) | 57-2 1r | CTGCATCTTTGCCACCATG |
| (SEQ ID NO: 248) | 57-2 1rR | GCTATGACCATGATTACGCCCTGCATCTTTGCCACCATG |
| (SEQ ID NO: 249) | 57-2 1fU | TGTAAAACGACGGCCAGTCCTGCAGAAGGAAACCTGAC |
| (SEQ ID NO: 250) | 57-3 1f | TTCCCAGGAGGCAAGTTATG |
| (SEQ ID NO: 251) | 57-3 1fR | GCTATGACCATGATTACGCCTTCCCAGGAGGCAAGTTATG |
| (SEQ ID NO: 252) | 57-3 1r | TGGGCTTAGGTGATCCTCAC |
| (SEQ ID NO: 253) | 57-3 1rR | GCTATGACCATGATTACGCCTGGGCTTAGGTGATCCTCAC |
| (SEQ ID NO: 254) | 57-3 1fU | TGTAAAACGACGGCCAGTTTCCCAGGAGGCAAGTTATG |
| (SEQ ID NO: 255) | 57-4 1f | ACCAAGCCCAACTAATCAGC |
| (SEQ ID NO: 256) | 57-4 1fR | GCTATGACCATGATTACGCCACCAAGCCCAACTAATCAGC |
| (SEQ ID NO: 257) | 57-4 1r | ATGCCTGTAATCCCAGCACT |
| (SEQ ID NO: 258) | 57-4 1rR | GCTATGACCATGATTACGCCATGCCTGTAATCCCAGCACT |
| (SEQ ID NO: 259) | 57-4 1fU | TGTAAAACGACGGCCAGTACCAAGCCCAACTAATCAGC |
| (SEQ ID NO: 260) | 57-5 1f | ACTGCAAGCCCTCTCTGAAC |
| (SEQ ID NO: 261) | 57-5 1r | CGAAGACTGCGAAACAGACA |
| (SEQ ID NO: 262) | 58-1 1f | CTAGTGCCGTGCAGAATGAG |

TABLE 4-continued

| | | |
|---|---|---|
| (SEQ ID NO: 263) | 58-1 1r | GGCCACTGCAATGAGATACA |
| (SEQ ID NO: 264) | 58-2 1f | GAGAAACAGTTCCAGGGTGG |
| (SEQ ID NO: 265) | 58-2 1fR | GCTATGACCATGATTACGCCGAGAAACAGTTCCAGGGTGG |
| (SEQ ID NO: 266) | 58-2 1r | AAACTGAGGCTGGGAGAGGT |
| (SEQ ID NO: 267) | 58-2 1rR | GCTATGACCATGATTACGCCAAACTGAGGCTGGGAGAGGT |
| (SEQ ID NO: 268) | 58-3 1f | TGTTCTTCCTCACAGGGAGG |
| (SEQ ID NO: 269) | 58-3 1fR | GCTATGACCATGATTACGCCTGTTCTTCCTCACAGGGAGG |
| (SEQ ID NO: 270) | 58-3 1r | TCCCCAAATCTGTCCAGTTC |
| (SEQ ID NO: 271) | 58-3 1rR | GCTATGACCATGATTACGCCTCCCCAAATCTGTCCAGTTC |
| (SEQ ID NO: 272) | 58-4 1f | CATACCTGGAGGGATGCTTG |
| (SEQ ID NO: 273) | 58-4 1fR | GCTATGACCATGATTACGCCCATACCTGGAGGGATGCTTG |
| (SEQ ID NO: 274) | 58-4 1r | TAGGTTGCTGTGTGGCTTCA |
| (SEQ ID NO: 275) | 58-4 1rR | GCTATGACCATGATTACGCCTAGGTTGCTGTGTGGCTTCA |
| (SEQ ID NO: 276) | 58-5 1f | CTTCTGACAAAGCAGAGGCC |
| (SEQ ID NO: 277) | 58-5 1fR | GCTATGACCATGATTACGCCCTTCTGACAAAGCAGAGGCC |
| (SEQ ID NO: 278) | 58-5 1r | GCTGTTAGGGTTACCATCGC |
| (SEQ ID NO: 279) | 58-5 1rR | GCTATGACCATGATTACGCCGCTGTTAGGGTTACCATCGC |
| (SEQ ID NO: 280) | 58-6 1f | CCACAGGGTGATATGCTGTC |
| (SEQ ID NO: 281) | 58-6 1fR | GCTATGACCATGATTACGCCCCACAGGGTGATATGCTGTC |
| (SEQ ID NO: 282) | 58-6 1r | CGCCTGGCTACTTTGGTACT |
| (SEQ ID NO: 283) | 58-6 1rR | GCTATGACCATGATTACGCCCGCCTGGCTACTTTGGTACT |
| (SEQ ID NO: 284) | 58-7 1f | CCAAATGAACCTGGGCAAC |
| (SEQ ID NO: 285) | 58-7 1fR | GCTATGACCATGATTACGCCCCAAATGAACCTGGGCAAC |
| (SEQ ID NO: 286) | 58-7 1r | GTCTTGGCTCACTGCAACCT |
| (SEQ ID NO: 287) | 58-7 1rR | GCTATGACCATGATTACGCCGTCTTGGCTCACTGCAACCT |
| (SEQ ID NO: 288) | 58-8 1f | GCCAAGACTGTGCTACTGCA |
| (SEQ ID NO: 289) | 58-8 1r | CAGGGAGCAGATCTTACCCA |
| (SEQ ID NO: 290) | 58-9 1f | TGGGATTAACTAGGGAGGGG |
| (SEQ ID NO: 291) | 58-9 1fR | GCTATGACCATGATTACGCCTGGGATTAACTAGGGAGGGG |
| (SEQ ID NO: 292) | 58-9 1r | TGCTGCTGTCTCCATCTCTG |
| (SEQ ID NO: 293) | 58-9 1rR | GCTATGACCATGATTACGCCTGCTGCTGTCTCCATCTCTG |
| (SEQ ID NO: 294) | 58-10 1f | ACAGACCAGCAGTGAAACCTG |
| (SEQ ID NO: 295) | 58-10 1fR | GCTATGACCATGATTACGCCACAGACCAGCAGTGAAACCTG |
| (SEQ ID NO: 296) | 58-10 1r | GTTCACTGCAACCTCTGCCT |
| (SEQ ID NO: 297) | 58-10 1rR | GCTATGACCATGATTACGCCGTTCACTGCAACCTCTGCCT |
| (SEQ ID NO: 298) | 58-11 1f | GTTCTCGTAGATGCTTGCAGG |
| (SEQ ID NO: 299) | 58-11 1fR | GCTATGACCATGATTACGCCGTTCTCGTAGATGCTTGCAGG |
| (SEQ ID NO: 300) | 58-11 1r | GAGGCAGGAGGATCACTTGA |
| (SEQ ID NO: 301) | 58-11 1rR | GCTATGACCATGATTACGCCGAGGCAGGAGGATCACTTGA |
| (SEQ ID NO: 302) | 58-12 1f | TGAGCTGAGATCACACCGCT |
| (SEQ ID NO: 303) | 58-12 1fR | GCTATGACCATGATTACGCCTGAGCTGAGATCACACCGCT |
| (SEQ ID NO: 304) | 58-12 1r | AGTTGACACTTTGCTGGCCT |
| (SEQ ID NO: 305) | 58-12 1rR | GCTATGACCATGATTACGCCAGTTGACACTTTGCTGGCCT |
| (SEQ ID NO: 306) | 58-13 1f | CTCTGCATGGCTTAGGGACA |
| (SEQ ID NO: 307) | 58-13 1fR | GCTATGACCATGATTACGCCCTCTGCATGGCTTAGGGACA |
| (SEQ ID NO: 308) | 58-13 1r | GGCTGCTCTCTGCATTCTCT |
| (SEQ ID NO: 309) | 58-13 1rR | GCTATGACCATGATTACGCCGGCTGCTCTCTGCATTCTCT |
| (SEQ ID NO: 310) | 58-14 1f | CTGGCTTTAGCTTGCATTTCC |
| (SEQ ID NO: 311) | 58-14 1fR | GCTATGACCATGATTACGCCCTGGCTTTAGCTTGCATTTCC |
| (SEQ ID NO: 312) | 58-14 1r | TGCCTCAGTTTTCTCACCTGT |
| (SEQ ID NO: 313) | 58-14 1rR | GCTATGACCATGATTACGCCTGCCTCAGTTTTCTCACCTGT |
| (SEQ ID NO: 314) | 58-15 1f | CAAACAGCCACTGAGCATGT |
| (SEQ ID NO: 315) | 58-15 1fR | GCTATGACCATGATTACGCCCAAACAGCCACTGAGCATGT |
| (SEQ ID NO: 316) | 58-15 1r | TCCTCCTGTAGATGCCCAAG |
| (SEQ ID NO: 317) | 58-15 1rR | GCTATGACCATGATTACGCCTCCTCCTGTAGATGCCCAAG |

TABLE 5

LRP-5 exon SNPs

| Exon | Polymorphism | Amino Acid Change | Location |
|---|---|---|---|
| exon E | G to A | Intronic | 10 bp 3' of exon E |
| exon E | C to T | none | Phe$^{331}$, exon E |
| exon F | G to A | Intronic | 50 bp 5' of exon F |
| exon G | C to T | none | Phe$^{518}$, exon G |
| exon I | C to T | none | Asn$^{709}$, exon I |
| exon P | C to T | Intronic | 82 bp 5' of exon P |
| exon N | C to T | none | Asp$^{1068}$, exon N |
| exon N | A to G | none | Val$^{1088}$, exon N |
| exon Q | C to T | Ala$^{1299}$ to Val | Ala$^{1299}$, exon Q |
| exon U | T to C | Val$^{1494}$ to Ala | Val$^{1494}$, exon U |

TABLE 6

SNP's Identified in the IDDM 4 Locus
List of PCR Fragments and available RFLP Sites for Analysis:

| PCR Product | SNP | Location | Enzyme |
|---|---|---|---|
| Contig 57 | | | |
| 57-1 | a/t | 13363 | none |
| 57-1 | a/g | 13484 | Bst XI |
| 57-2 | a/g | 14490 | none |
| 57-2 | a/g | 14885 | none |
| 57-3 | c/g | 18776 | Mae II |
| 57-3 | t/c | 18901 | Msp I |
| 57-3 | a/g | 19313 | Afl II |
| 57-4 | 22T/25T | 20800 | none |

TABLE 6-continued

SNP's Identified in the IDDM 4 Locus
List of PCR Fragments and available RFLP Sites for Analysis:

| PCR Product | SNP | Location | Enzyme |
|---|---|---|---|
| 57-5 | g/a | 23713 | Msp I |
| Contig 58 | | | |
| 58-15 | c/t | 3015 | none |
| 58-14 | g/c | 3897 | Pfl MI |
| 58-13 | c/g | 5574 | Eco NI |
| 58-12 | t/g | 6051 | none |
| 58-11 | a/g | 8168 | none |
| 58-10 | a/g | 8797 | none |
| 58-9 | g/t | 9445 | none |
| 58-9 | c/t | 9718 | none |
| 58-8 | insert T | 10926 | Pst I |
| 58-7 | t/a | 11449 | Bst XI |
| 58-7 | t/c | 11468 | none |
| 58-6 | t/c | 11878 | none |
| 58-6 | g/a | 12057 | none |
| 58-6 | a/g | 12180 | Hga I |
| 58-5 | c/t | 14073 | none |
| 58-4 | a/g | 15044 | Mae II |
| 58-4 | t/c | 15354 | none |
| 58-3 | insert G | 16325 | none |
| 58-2 | g/a | 17662 | none |
| 58-1 | g/t | 18439 | Bgl II |

TABLE 7

SNP primers

| | | |
|---|---|---|
| (SEQ ID NO: 240) 57-1 1f | GCAACAGAGCAAGACCCTGT |
| (SEQ ID NO: 241) 57-1 1fR | GCTATGACCATGATTACGCCGCAACAGAGCAAGACCCTGT |
| (SEQ ID NO: 242) 57-1 1r | AAATTAGCCAGGCATGGTG |
| (SEQ ID NO: 243) 57-1 1rR | GCTATGACCATGATTACGCCAAATTAGCCAGGCATGGTG |
| (SEQ ID NO: 244) 57-1 1fU | TGTAAAACGACGGCCAGTGCAACAGAGCAAGACCCTGT |
| (SEQ ID NO: 245) 57-2 1f | CCTGCAGAAGGAAACCTGAC |
| (SEQ ID NO: 246) 57-2 1fR | GCTATGACCATGATTACGCCCCTGCAGGAAGGAAACCTGAC |
| (SEQ ID NO: 247) 57-2 1r | CTGCATCTTTGCCACCATG |
| (SEQ ID NO: 248) 57-2 1rR | GCTATGACCATGATTACGCCCTGCATCTTTGCCACCATG |
| (SEQ ID NO: 249) 57-2 1fU | TGTAAAACGACGGCCAGTCCTGCAGAAGGAAACCTGAC |
| (SEQ ID NO: 250) 57-3 1f | TTCCCAGGAGGCAAGTTATG |
| (SEQ ID NO: 251) 57-3 1fR | GCTATGACCATGATTACGCCTTCCCAGGAGGCAAGTTATG |
| (SEQ ID NO: 252) 57-3 1r | TGGGCTTAGGTGATCCTCAC |
| (SEQ ID NO: 253) 57-3 1rR | GCTATGACCATGATTACGCCTGGGCTTAGGTGATCCTCAC |
| (SEQ ID NO: 254) 57-3 1fU | TGTAAAACGACGGCCAGTTTCCCAGGAGGCAAGTTATG |
| (SEQ ID NO: 255) 57-4 1f | ACCAAGCCCAACTAATCAGC |
| (SEQ ID NO: 256) 57-4 1fR | GCTATGACCATGATTACGCCACCAAGCCCAACTAATCAGC |
| (SEQ ID NO: 257) 57-4 1r | ATGCCTGTAATCCCAGCACT |
| (SEQ ID NO: 258) 57-4 1rR | GCTATGACCATGATTACGCCATGCCTGTAATCCCAGCACT |
| (SEQ ID NO: 259) 57-4 1fU | TGTAAAACGACGGCCAGTACCAAGCCCAACTAATCAGC |
| (SEQ ID NO: 260) 57-5 1f | ACTGCAAGCCCTCTCTGAAC |
| (SEQ ID NO: 261) 57-5 1r | CGAAGACTGCGAAACAGACA |
| (SEQ ID NO: 262) 58-1 1f | CTAGTGCCGTGCAGAATGAG |
| (SEQ ID NO: 263) 58-1 1r | GGCCACTGCAATGAGATACA |
| (SEQ ID NO: 264) 58-2 1f | GAGAAACAGTTCCAGGGTGG |
| (SEQ ID NO: 265) 58-2 1fR | GCTATGACCATGATTACGCCGAGAAACAGTTCCAGGGTGG |
| (SEQ ID NO: 266) 58-2 1r | AAACTGAGGCTGGGAGAGGT |
| (SEQ ID NO: 267) 58-2 1rR | GCTATGACCATGATTACGCCAAACTGAGGCTGGGAGAGGT |
| (SEQ ID NO: 268) 58-3 1f | TGTTCTTCCTCACAGGGAGG |
| (SEQ ID NO: 269) 58-3 1fR | GCTATGACCATGATTACGCCTGTTCTTCCTCACAGGGAGG |
| (SEQ ID NO: 270) 58-3 1r | TCCCCAAATCTGTCCAGTTC |
| (SEQ ID NO: 271) 58-3 1rR | GCTATGACCATGATTACGCCTCCCCAAATCTGTCCAGTTC |
| (SEQ ID NO: 272) 58-4 1f | CATACCTGGAGGGATGCTTG |
| (SEQ ID NO: 273) 58-4 1fR | GCTATGACCATGATTACGCCCATACCTGGAGGGATGCTTG |
| (SEQ ID NO: 274) 58-4 1r | TAGGTTGCTGTGTGGCTTCA |
| (SEQ ID NO: 275) 58-4 1rR | GCTATGACCATGATTACGCCTAGGTTGCTGTGTGGCTTCA |
| (SEQ ID NO: 276) 58-5 1f | CTTCTGACAAAGCAGAGGCC |
| (SEQ ID NO: 277) 58-5 1fR | GCTATGACCATGATTACGCCCTTCTGACAAAGCAGAGGCC |
| (SEQ ID NO: 278) 58-5 1r | GCTGTTAGGGTTACCATCGC |
| (SEQ ID NO: 279) 58-5 1rR | GCTATGACCATGATTACGCCGCTGTTAGGGTTACCATCGC |
| (SEQ ID NO: 280) 58-6 1f | CCACAGGGTGATATGCTGTC |
| (SEQ ID NO: 281) 58-6 1fR | GCTATGACCATGATTACGCCCCACAGGGTGATATGCTGTC |
| (SEQ ID NO: 282) 58-6 1r | CGCCTGGCTACTTTGGTACT |
| (SEQ ID NO: 283) 58-6 1rR | GCTATGACCATGATTACGCCCGCCTGGCTACTTTGGTACT |

TABLE 7-continued

SNP primers

| | | | |
|---|---|---|---|
| (SEQ ID NO: 284) | 58-7 1f | CCAAATGAACCTGGGCAAC | |
| (SEQ ID NO: 285) | 58-7 1fR | GCTATGACCATGATTACGCCCCAAATGAACCTGGGCAAC | |
| (SEQ ID NO: 286) | 58-7 1r | GTCTTGGCTCACTGCAACCT | |
| (SEQ ID NO: 287) | 58-7 1rR | GCTATGACCATGATTACGCCGTCTTGGCTCACTGCAACCT | |
| (SEQ ID NO: 288) | 58-8 1f | GCCAAGACTGTGCTACTGCA | |
| (SEQ ID NO: 289) | 58-8 1r | CAGGGAGCAGATCTTACCCA | |
| (SEQ ID NO: 290) | 58-9 1f | TGGGATTAACTAGGGAGGGG | |
| (SEQ ID NO: 291) | 58-9 1fR | GCTATGACCATGATTACGCCTGGGATTAACTAGGGAGGGG | |
| (SEQ ID NO: 292) | 58-9 1r | TGCTGCTGTCTCCATCTCTG | |
| (SEQ ID NO: 293) | 58-9 1rR | GCTATGACCATGATTACGCCTGCTGCTGTCTCCATCTCTG | |
| (SEQ ID NO: 294) | 58-10 1f | ACAGACCAGCAGTGAAACCTG | |
| (SEQ ID NO: 295) | 58-10 1fR | GCTATGACCATGATTACGCCACAGACCAGCAGTGAAACCTG | |
| (SEQ ID NO: 296) | 58-10 1r | GTTCACTGCAACCTCTGCCT | |
| (SEQ ID NO: 297) | 58-10 1rR | GCTATGACCATGATTACGCCGTTCACTGCAACCTCTGCCT | |
| (SEQ ID NO: 298) | 58-11 1f | GTTCTCGTAGATGCTTGCAGG | |
| (SEQ ID NO: 299) | 58-11 1fR | GCTATGACCATGATTACGCCGTTCTCGTAGATGCTTGCAGG | |
| (SEQ ID NO: 300) | 58-11 1r | GAGGCAGGAGGATCACTTGA | |
| (SEQ ID NO: 301) | 58-11 1rR | GCTATGACCATGATTACGCCGAGGCAGGAGGATCACTTGA | |
| (SEQ ID NO: 302) | 58-12 1f | TGAGCTGAGATCACACCGCT | |
| (SEQ ID NO: 303) | 58-12 1fR | GCTATGACCATGATTACGCCTGAGCTGAGATCACACCGCT | |
| (SEQ ID NO: 304) | 58-12 1r | AGTTGACACTTTGCTGGCCT | |
| (SEQ ID NO: 305) | 58-12 1rR | GCTATGACCATGATTACGCCAGTTGACACTTTGCTGGCCT | |
| (SEQ ID NO: 306) | 58-13 1f | CTCTGCATGGCTTAGGGACA | |
| (SEQ ID NO: 307) | 58-13 1fR | GCTATGACCATGATTACGCCCTCTGCATGGCTTAGGGACA | |
| (SEQ ID NO: 308) | 58-13 1r | GGCTGCTCTCTGCATTCTCT | |
| (SEQ ID NO: 309) | 58-13 1rR | GCTATGACCATGATTACGCCGGCTGCTCTCTGCATTCTCT | |
| (SEQ ID NO: 310) | 58-14 1f | CTGGCTTTAGCTTGCATTTCC | |
| (SEQ ID NO: 311) | 58-14 1fR | GCTATGACCATGATTACGCCCTGGCTTTAGCTTGCATTTCC | |
| (SEQ ID NO: 312) | 58-14 1r | TGCCTCAGTTTTCTCACCTGT | |
| (SEQ ID NO: 313) | 58-14 1rR | GCTATGACCATGATTACGCCTGCCTCAGTTTTCTCACCTGT | |
| (SEQ ID NO: 314) | 58-15 1f | CAAACAGCCACTGAGCATGT | |
| (SEQ ID NO: 315) | 58-15 1fR | GCTATGACCATGATTACGCCCAAACAGCCACTGAGCATGT | |
| (SEQ ID NO: 316) | 58-15 1r | TCCTCCTGTAGATGCCCAAG | |
| (SEQ ID NO: 317) | 58-15 1rR | GCTATGACCATGATTACGCCTCCTCCTGTAGATGCCCAAG | |

TABLE 8

Primers designed by microsatellite rescue for genotyping and restriction mapping of the IDDM4 region on chromosome 11q13. The other primers used are published, and are also in the Genome Database.

| | | |
|---|---|---|
| 255CA3F | GCCGAGAATTGTCATCTTAACT | (SEQ ID NO: 318) |
| 255CA3R | GGATTGAAAGCTGCAAACTACA | (SEQ ID NO: 319) |
| 255CA5F | GGAGCCACCACATCCAGTTA | (SEQ ID NO: 320) |
| 255CA5R | TGGAGGGATTGCTTGAGG | (SEQ ID NO: 321) |
| 255CA6F | AGGTGTACACCACCATGCCT | (SEQ ID NO: 322) |
| 255CA6R | TGGTGCCAATTATTGCTGC | (SEQ ID NO: 323) |
| 14LCA5F | AGATCTTATACACATGTGCGCG | (SEQ ID NO: 324) |
| 14LCA5R | AGGTGACATCACTTACAGCGG | (SEQ ID NO: 325) |
| L15CA1F | ATTACCCAGGCATGGTGC | (SEQ ID NO: 326) |
| L15CA1R | CAGGCACTTCTTCCAGGTCT | (SEQ ID NO: 327) |
| 18018ACF | AGGGTTACACTGGAGTTTGC | (SEQ ID NO: 328) |
| 18018ACR | AAACCTTCAATGTGTTCATTAAAAC | (SEQ ID NO: 329) |
| E0864CAF | TCAACTTTATTGGGGGTTTA | (SEQ ID NO: 330) |
| E0864CAR | AAGGTAAAAGTCCAAAATGG | (SEQ ID NO: 331) |
| H0570POLYAF | GGACAGTCAGTTATTGAAATG | (SEQ ID NO: 332) |
| H0560POLYAR | TTTCCTCTCTGGGAGTCTCT | (SEQ ID NO: 333) |

E0864CA was obtained from the cosmid E0864
H0570POLYA was obtained from the cosmid H0570
255CA5, 255CA3 and 255CA6 were obtained from the PAC2S5_m_19
14LCA5 and L15CA1 were obtained from the BAC 14_1_15
18018AC was obtained from the PAC 18_o_18

TABLE 9

| PCR Primers for obtaining LRP-3 cDNA | |
|---|---|
| A.) Primers located within humanLRP-3 cDNA: The primers are numbered beginning at nucleotide 1 in FIG. 17 (a) | |
| 1F (muex 1f) ATGGAGCCCGAGTGAGC | (SEQ ID NO: 49) |
| 200f TCAAGCTGGAGTCCACCATC | (SEQ ID NO: 334) |
| 218R (27R) ATGGTGGACTCCAGCTTGAC | (SEQ ID NO: 50) |
| 256F (1F) TTCCAGTTTTCCAAGGGAG | (SEQ ID NO: 51) |
| 265R (26R) AAAACTGGAAGTCCACTGCG | (SEQ ID NO: 52) |
| 318R (4R) GGTCTGCTTGATGGCCTC | (SEQ ID NO: 53) |
| 343F (2F) GTGCAGAACGTGGTCATCT | (SEQ ID NO: 54) |
| 361R (21R) GTGCAGAACGTGGTCATCT | (SEQ ID NO: 54) |
| 622R (2R) AGTCCACAATGATCTTCCGG | (SEQ ID NO: 55) |
| 638F (4F) CCAATGGACTGACCATCGAC | (SEQ ID NO: 56) |
| 657R (1R) GTCGATGGTCAGTCCATTGG | (SEQ ID NO: 57) |
| 936f CACTCGCTGTGAGGAGGAC | (SEQ ID NO: 335) |
| 956R (22R) TTGTCCTCCTCACAGCGAG | (SEQ ID NO: 58) |
| 1040f (51f) ACAACGGCAGGACGTGTAAG | (SEQ ID NO: 336) |
| 1174f (40f) ATTGCCATCGACTACGACC | (SEQ ID NO: 337) |
| 1277f (52f) TGGTCAACACCGAGATCAAC | (SEQ ID NO: 338) |
| 1333f AACCTCTACTGGACCGACAC | (SEQ ID NO: 339) |
| 1462f (41f) CTCATGTACTGGACAGACT | (SEQ ID NO: 340) |
| 1481R (23R) CAGTCTGTCCAGTACATGAG | (SEQ ID NO: 60) |
| 1607f (50f) GAGACGCCAAGACAGACAAG | (SEQ ID NO: 341) |
| 1713F (21F) GGACTTCATCTACTGGACTG | (SEQ ID NO: 59) |
| 1732r (40r) CAGTCCAGTAGATGAAGTCC | (SEQ ID NO: 342) |
| 1904r (k275r) GTGAAGAAGCACAGGTGGCT | (SEQ ID NO: 343) |
| 1960r TCATGTCACTCAGCAGCTCC | (SEQ ID NO: 344) |
| 1981F (22F) GCCTTCTTGGTCTTCACCAG | (SEQ ID NO: 61) |
| 2261F (23F) GGACCAACAGAATCGAAGTG | (SEQ ID NO: 62) |
| 2484R (5R) GTCAATGGTGAGGTCGT | (SEQ ID NO: 63) |
| 2519F (5F) ACACCAACATGATCGAGTCG | (SEQ ID NO: 64) |
| 2780r CCGTTGTTGTGCATACAGTC | (SEQ ID NO: 345) |
| 3011F (24F) ACAAGTTCATCTACTGGGTG | (SEQ ID NO: 65) |
| 3154F (25F) CGGACACTGTTCTGGACGTG | (SEQ ID NO: 66) |
| 3173R (25R) CACGTCCAGAACAGTGTCCG | (SEQ ID NO: 67) |
| 3556R (3R) TCCAGTAGAGATGCTTGCCA | (SEQ ID NO: 68) |
| 3577F (3F) ATCGAGCGTGTGGAGAAGAC | (SEQ ID NO: 69) |
| 3851r GTGGCACATGCAAACTGGTC | (SEQ ID NO: 346) |
| 4094F (30F) TCCTCATCAAACAGCAGTGC | (SEQ ID NO: 70) |
| 4173R (6R) CGGCTTGGTGATTTCACAC | (SEQ ID NO: 71) |
| 4687F (6F) | (SEQ ID NO: 72) |

TABLE 9-continued

PCR Primers for obtaining LRP-3 cDNA

```
GTGTGTGACAGCGACTACAGC
4707R (30R)                                  (SEQ ID NO: 73)
GCTGTAGTCGCTGTCACACAC
5061R (7R)                                   (SEQ ID NO: 74)
GTACAAAGTTCTCCCAGCCC
3' end with XbaI site                        (SEQ ID NO: 347)
5069r
GCTCTAGAGTACAAAGTTCTCCCAGCCC
Soluble/HSV/His primers                      (SEQ ID NO: 348)
HLRP3_His_primer1 (4203r)
ATCCTCGGGGTCTTCCGGGGCGAGTTCTGGCTGGCTACTGCTGTGGGCCGGGCT
HLRP3_His_primer2                            (SEQ ID NO: 349)
TGGATATCTCAGTGGTGGTGGTGGTGGTGCTCGACATCCTCGGGGTCTTCCGG
G
HLRP3_5'_primer (49f)                        (SEQ ID NO: 350)
TAGAATTCGCCGCCACCATGGAGGCAGCGCCGCCC
B.) Mouse Lrp-3 cDNA primers.
The primers are numbered beginning at nucleotide 1 in FIG. 18(a).
13f(mulrp3 5f)                               (SEQ ID NO: 351)
GAGGCGGGAGCAAGAGG
68f(MucD 1f)                                 (SEQ ID NO: 352)
GC Hind 3 CATGGAGCCCGAGTGAGC
69f(muex 1f)                                 (SEQ ID NO: 353)
ATGGAGCCCGAGTGAGC
83r(muex 1r)                                 (SEQ ID NO: 354)
TCACTCGGGCTCCATGG
171f(MucD 2f)                                (SEQ ID NO: 355)
TGCTGTACTGCAGCTTGGTC
300f(MucD 10F)                               (SEQ ID NO: 356)
ATGCAGCTGCTGTAGACTTCC
378r(mulrp3 3r)                              (SEQ ID NO: 357)
GTCTGTTTGATGGCCTCCTC
414r(MucD 7R)                                (SEQ ID NO: 358)
ATGTTCTGTGCAGCACCTCC
445r(mulrp3 4r)                              (SEQ ID NO: 359)
GCCATCAGGTGACACGAG
536f(MucD 11F)                               (SEQ ID NO: 360)
AAGGTTCTCTTCTGGCAGGAC
619r(MucD 12R)                               (SEQ ID NO: 361)
CCAGTCAGTCCAGTACATG
714f(museq 1f)                               (SEQ ID NO: 362)
TCGACCTGGAGGAACAGAAG
752f(mulrpAb 1f)                             (SEQ ID NO: 363)
AAGCTCAGCTTCATCCACCG
765r(MucD 8R)                                (SEQ ID NO: 364)
ATGAAGCTGAGCTTGGCATC
915f(MucD 12F)                               (SEQ ID NO: 365)
AGCAGAGGAAGGAGATCCTTAG
957r(MucD 9R)                                (SEQ ID NO: 366)
TCCATGGGTGAGTACAGAGC
1105r(museq 1r)                              (SEQ ID NO: 367)
ATTGTCCTGCAACTGCACAC
1232f(MucD 13F)                              (SEQ ID NO: 368)
GCCATTGCCATTGACTACG
1254r(MucD 10R)                              (SEQ ID NO: 369)
GGATCGTAGTCAATGGCAATG
1425f(MucD 14F)                              (SEQ ID NO: 370)
GAATTGAGGTGACTCGCCTC
1433r(MucD 18R)                              (SEQ ID NO: 371)
CCTCAATTCTGTAGTGCCTG
1501f(muxt 4f)                               (SEQ ID NO: 372)
TGTGTTGCACCCTGTGATG
1579r(MucD 11R)                              (SEQ ID NO: 373)
ATCTAGGTTGGCGCATTCG
1610r(MucD 13R)                              (SEQ ID NO: 374)
AGGTGTTCACCAGGACATG
1710r(mulrpAb 1r)                            (SEQ ID NO: 375)
GCGAGCTCCCGTCTATGTTGATCACCTCG
1868f(MucD 3f)                               (SEQ ID NO: 376)
GACCTGATGGGACTCAAAGC
2062r(MucD 2r)                               (SEQ ID NO: 377)
GCTGGTGAATACCAGGAAGG
2103f(MucD 4f)                               (SEQ ID NO: 378)
```

TABLE 9-continued

PCR Primers for obtaining LRP-3 cDNA

ACGATGTGGCTATCCCACTC
2422r(MucD 14R) (SEQ ID NO: 379)
AGTAGGATCCAGAGCCAGAG
2619f(MucD 5f) (SEQ ID NO: 380)
AGCGCATGGTGATAGCTGAC
2718r(MucD 3r) (SEQ ID NO: 381)
CGTTCAATGCTATGCAGGTTC
2892f(MucD 15F) (SEQ ID NO: 382)
GTGCTTCACACTACACGCTG
2959f(MucD 6f) (SEQ ID NO: 383)
CAGCCAGAAATTTGCCATC
3218r(MucD 4r) (SEQ ID NO: 384)
TCCGGCTGTAGATGTCAATG
3237f(MucD 7f) (SEQ ID NO: 385)
AGGCCACCAACACTATCAATG
3348r(MucD 52R) (SEQ ID NO: 386)
TACCCTCGCTCAGCATTGAC
3554f(MucD 8f) (SEQ ID NO: 387)
CTGGAAGATGCCAACATCG
3684r(MucD 5r) (SEQ ID NO: 388)
TGAACCCTAGTCCGCTTGTC
3848f(MucD 18F) (SEQ ID NO: 389)
CTGCAGAACCTGCTGACTTG
3973f(MucD 19F) (SEQ ID NO: 390)
CCAGAGTGATGAAGAAGGCTG
3981r(MucD 15R) (SEQ ID NO: 391)
TCACTCTGGTCAGCACACTC
4079f(MucD 16F) (SEQ ID NO: 392)
CAGGATCGCTCTGATGAAGC
4105r(MucD 53R) (SEQ ID NO: 393)
GCAGTTAGCTTCATCAGAGCG
4234f(MucD 9f) (SEQ ID NO: 394)
ACCCTCTGATGACATCCCAG
4270r(MucD 16R) (SEQ ID NO: 395)
AATGGCACTGCTGTGGGC
4497r(MucD 6r) (SEQ ID NO: 396)
AGGCTCATGGAGCTCATCAC
4589r(MucD 54R) (SEQ ID NO: 397)
ATAGTGTGGCCTTTGTGCTG
4703f(MucD 17F) (SEQ ID NO: 398)
GTCATTCGAGGTATGGCACC
4799r(MucD 17R) (SEQ ID NO: 399)
GGTAGTATTTGCTGCTCTTCC
5114r(MucD 1r) (SEQ ID NO: 400)
GC Xba I AAAGTTTCCCAGCCCTGCC
Soluble/adeno primers
3554f(MsolF) (SEQ ID NO: 401)
CTGGAAGATGCCAACATCG
4264r(MHiSR) (SEQ ID NO: 402)
GCTCTAGACTAGTGATGGTGATGGTGATGACTGCTGTGGGCTGGGATGTCATC
AGAGGGTGG

TABLE 10

Summary of Serum Chemistry Comparison of LRP3 treatment vs control

| Variable | Mouse Type | Treatment (% diff ± SE) | p-value (Treatment) |
|---|---|---|---|
| triglycerides | WT + KO | −30±14 | 0.025 |
| alkaline phosphatase# | WT + KO | −49±15 | 0.001 |
| total cholesterol | KO only | −28±15 | 0.073 |
| total cholesterol | WT only | 30±13 | 0.080 |
| AST# | WT + KO | 8±66 | 0.912 |
| ALT# | WT + KO | −34±51 | 0.431 |
| BUN | WT + KO | −19±15 | 0.195 | statistically significantly higher baseline values for controls.

TABLE 11

Summary for Blood Chemistry Variables Pooled over Knockout and Wild-Type Mice

| Variable | Treat Group | Animal Type | n | baseline (mean ± % CV) | post-treat (mean ± % CV) t | change | % change (95% CI) | p-value (% chg) |
|---|---|---|---|---|---|---|---|---|
| trigly (mg/dL) | Control | POOLED | 10 | 86 ± 13% | 186 ± 35% | 100 | 115% (61, 189) | <0.001 |
| trigly (mg/dL) | LDL | POOLED | 9 | 92 ± 31% | 81 ± 55% | -12 | -13% (-35, 17) | 0.321 |
| trigly (mg/dL) | LRP3 | POOLED | 8 | 99 ± 24% | 128 ± 36% | 29 | 30% (-10, 86) | 0.133 |
| alkphos (U/L) | Control | POOLED | 10 | 190 ± 19% | 374 ± 30% | 184 | 97% (68, 130) | <0.001 |
| alkphos (U/L) | LDL | POOLED | 9 | 162 ± 12% | 193 ± 29% | 31 | 19% (-1, 43) | 0.061 |
| alkphos (U/L) | LRP3 | POOLED | 8 | 154 ± 13% | 146 ± 35% | -8 | -5% (-24, 19) | 0.604 |
| totchol (mg/dL) | Control | POOLED | 10 | 116 ± 69% | 176 ± 86% | 60 | 51% (21, 89) | 0.002 |
| totchol (mg/dL) | LDL | POOLED | 9 | 124 ± 58% | 87 ± 68% | -37 | -30% (-41, -17) | 0.001 |
| totchol (mg/dL) | LRP3 | POOLED | 8 | 127 ± 62% | 166 ± 57% | 39 | 30% (9, 56) | 0.009 |
| AST (U/L) | Control | POOLED | 9 | 41 ± 22% | 821 ± 69% | 780 | 1894% (1142, 3101) | <0.001 |
| AST (U/L) | LDL | POOLED | 8 | 41 ± 25% | 362 ± 61% | 320 | 772% (369, 1520) | <0.001 |
| AST (U/L) | LRP3 | POOLED | 8 | 33 ± 21% | 989 ± 129% | 955 | 2888% (953, 8380) | <0.001 |
| ALT (U/L) | Control | POOLED | 10 | 33 ± 15% | 624 ± 59% | 591 | 1798% (1203, 2665) | <0.001 |
| ALT (U/L) | LDL | POOLED | 8 | 32 ± 36% | 331 ± 42% | 299 | 938% (447, 1872) | <0.001 |
| ALT (U/L) | LRP3 | POOLED | 8 | 25 ± 35% | 1020 ± 157% | 994 | 3944% (861, 16921) | <0.001 |
| BUN (U/L) | Control | POOLED | 8 | 29 ± 12% | 23 ± 11% | -5 | -19% (-29, -7) | 0.008 |
| BUN (U/L) | LDL | POOLED | 9 | 28 ± 19% | 25 ± 14% | -3 | -12% (-22, 1) | 0.062 |
| BUN (U/L) | LRP3 | POOLED | 8 | 28 ± 12% | 19 ± 41% | -9 | -31% (-53, 2) | 0.058 |

Note means given are geometric means.
p-value is from a 2-sided paired t-test.

TABLE 12

Regions of Sequence Similarity Between Human and Mouse LRP-3

| Location in Human Sequence | Nucleotide Length | Percent Identity | BLAST Score | Exon Name |
|---|---|---|---|---|
| Contig 31 | | | | |
| 20235–20271 | 37 | 86 | 140 | |
| 24410–24432 | 23 | 86 | 88 | |
| 24464–24667 | 204 | 82 | 168,223 | 6 |
| 24904–24995 | 52 | 82 | 179 | |
| 25489–25596 | 108 | 81 | 360 | |
| 26027–26078 | 52 | 80 | 170 | |
| 26192–26261 | 70 | 84 | 251 | |
| 26385–26486 | 102 | 87 | 393 | |
| 28952–28993 | 42 | 85 | 156 | |
| 41707–41903 | 197 | 90 | 823 | |
| 42827–42898 | 66 | 81 | 222 | |
| 43468–43585 | 117 | 85 | 316 | |
| 50188–50333 | 146 | 86 | 550 | |
| 54455–54494 | 40 | 80 | 128 | |
| 54718–54750 | 33 | 87 | 129 | |
| 59713–60123 | 411 | 87 | 1587 | A |
| 78536–78680 | 145 | 80 | 473 | D |
| 87496–87548 | 53 | 88 | 211 | |
| 87598–87717 | 120 | 84 | 429 | |
| 90772–90819 | 48 | 85 | 177 | |
| 99457–99795 | 339 | 83 | 1182 | E |
| 103094–103281 | 188 | 83 | 661 | F |
| 116659–116954 | 296 | 81 | 985 | G |
| 119754–120089 | 336 | 83 | 1167 | H |
| Contig 30 | | | | |
| 8920–9256 | 337 | 89 | 1026 | K |
| 11238–11353 | 116 | 84 | *418 | L |
| 18394–18648 | 255 | 80 | 825 | M |
| 20020–20224 | 205 | 84 | 746 | N |
| 20926–21153 | 228 | 83 | 807 | O |
| 24955–25155 | 201 | 82 | 672 | P |
| 29126–19288 | 163 | 74 | *437 | Q |
| 33874–34033 | 160 | 85 | *593 | S |
| 35205–35340 | 136 | 86 | 509 | T |
| 41911—41911 | 55 | 80 | *176 | U |
| 44629–44681 | 53 | 73 | *249 | V |

What is claimed is:

1. An isolated nucleic acid molecule encoding a polypeptide which comprises the amino acid sequence shown in FIG. 5(e)(SEQ ID NO:4).

2. A nucleic acid molecule encoding a polypeptide which comprises the amino acid sequence shown in FIG. 5(c)(SEQ ID NO:3).

3. A nucleic acid molecule according to claim 1 comprising the coding sequence shown in FIG. 5(a)(SEQ ID NO:1).

4. An isolated nucleic acid molecule encoding a polypeptide which binds and takes up low density lipoprotein, said nucleic acid hybridizing under stringent conditions to nucleic acid according to claim 3, said stringent conditions comprising hybridization overnight at 42° C. in 0.25M Na$_2$HPO$_4$, pH 7.2, 6.5% SDS, 10% dextran sulphate and washing at 55° C. in 0.1×SSC, 0.1% SDS.

5. An oligonucleotide fragment of a nucleic acid molecule according to claim 3 of at least 14 nucleotides.

6. An oligonucleotide consisting of a nucleotide sequence of any one of SEQ ID NOs: 49–52, 54–57, 59–62, 64–69, 72–74, 238, and 334–346.

7. A method of producing the polypeptide shown in FIG. 5(c)(SEQ ID NO: 3) which comprises introducing a nucleic acid encoding the polypeptide into a host cell, causing or allowing expression of the nucleic acid and isolating and/or purifying the polypeptide produced thereby.

8. A method according to claim 7 further comprising formulating the polypeptide into a composition which includes at least one additional component.

9. An isolated nucleic acid molecule encoding a polypeptide which binds and takes up low density lipoprotein, said polypeptide comprising an amino acid sequence which shows greater than 90% homology with the amino acid sequence shown in FIG. 5(e)(SEQ ID NO:4).

10. A composition comprising a nucleic acid molecule which encodes a polypeptide which is selected from the group consisting of polypeptides shown in FIGS. 5(e)(SEQ ID NO:4) and 5(c)(SEQ ID NO:3), and a physiologically acceptable excipient.

* * * * *

SEQUENCE LISTING (1) GENERAL INFORMATION:

(iii) NUMBER OF SEQUENCES: 455

(2) INFORMATION FOR SEQ ID NO:1:

(i) SEQUENCE CHARACTERISTICS:
        (A) LENGTH: 5098 base pairs
        (B) TYPE: nucleic acid
        (C) STRANDEDNESS: single
        (D) TOPOLOGY: linear (xi) SEQUENCE DESCRIPTION: SEQ ID NO:1:

```
ATGGAGCCCG AGTGAGCGCG GCGCGGGCCC GTCCGGCCGC CGGACAACAT GGAGGCAGCG     60

CCGCCCGGGC CGCCGTGGCC GCTGCTGCTG CTGCTGCTGC TGCTGCTGGC GCTGTGCGGC    120

TGCCCGGCCC CCGCCGCGGC CTCGCCGCTC CTGCTATTTG CCAACCGCCG GGACGTACGG    180

CTGGTGGACG CCGGCGGAGT CAAGCTGGAG TCCACCATCG TGGTCAGCGG CCTGGAGGAT    240

GCGGCCGCAG TGGACTTCCA GTTTTCCAAG GGAGCCGTGT ACTGGACAGA CGTGAGCGAG    300

GAGGCCATCA AGCAGACCTA CCTGAACCAG ACGGGGCCG CCGTGCAGAA CGTGGTCATC     360

TCCGGCCTGG TCTCTCCCGA CGGCCTCGCC TGCGACTGGG TGGGCAAGAA GCTGTACTGG    420

ACGGACTCAG AGACCAACCG CATCGAGGTG GCCAACCTCA ATGGCACATC CCGGAAGGTG    480

CTCTTCTGGC AGGACCTTGA CCAGCCGAGG GCCATCGCCT TGGACCCCGC TCACGGGTAC    540

ATGTACTGGA CAGACTGGGG TGAGACGCCC CGGATTGAGC GGGCAGGGAT GGATGGCAGC    600

ACCCGGAAGA TCATTGTGGA CTCGGACATT TACTGGCCCA ATGGACTGAC CATCGACCTG    660

GAGGAGCAGA AGCTCTACTG GGCTGACGCC AAGCTCAGCT TCATCCACCG TGCCAACCTG    720

GACGGCTCGT TCCGGCAGAA GGTGGTGGAG GGCAGCCTGA CGCACCCCTT CGCCCTGACG    780

CTCTCCGGGG ACACTCTGTA CTGGACAGAC TGGCAGACCC GCTCCATCCA TGCCTGCAAC    840

AAGCGCACTG GGGGAAGAG GAAGGAGATC CTGAGTGCCC TCTACTCACC CATGGACATC     900

CAGGTGCTGA GCCAGGAGCG GCAGCCTTTC TTCCACACTC GCTGTGAGGA GGACAATGGC    960

GGCTGCTCCC ACCTGTGCCT GCTGTCCCCA AGCGAGCCTT TCTACACATG CGCCTGCCCC   1020

ACGGGTGTGC AGCTGCAGGA CAACGGCAGG ACGTGTAAGG CAGGAGCCGA GGAGGTGCTG   1080

CTGCTGGCCC GGCGGACGGA CCTACGGAGG ATCTCGCTGG ACACGCCGGA CTTTACCGAC   1140

ATCGTGCTGC AGGTGGACGA CATCCGGCAC GCCATTGCCA TCGACTACGA CCCGCTAGAG   1200

GGCTATGTCT ACTGGACAGA TGACGAGGTG CGGGCCATCC GCAGGGCGTA CCTGGACGGG   1260

TCTGGGGCGC AGACGCTGGT CAACACCGAG ATCAACGACC CCGATGGCAT CGCGGTCGAC   1320

TGGGTGGCCC GAAACCTCTA CTGGACCGAC ACGGGCACGG ACCGCATCGA GGTGACGCGC   1380

CTCAACGGCA CCTCCCGCAA GATCCTGGTG TCGGAGGACC TGGACGAGCC CCGAGCCATC   1440

GCACTGCACC CCGTGATGGG CCTCATGTAC TGGACAGACT GGGGAGAGAA CCCTAAAATC   1500

GAGTGTGCCA ACTTGGATGG GCAGGAGCGG CGTGTGCTGG TCAATGCCTC CCTCGGGTGG   1560

CCCAACGGCC TGGCCCTGGA CCTGCAGGAG GGGAAGCTCT ACTGGGGAGA CGCCAAGACA   1620

GACAAGATCG AGGTGATCAA TGTTGATGGG ACGAAGAGGG GGACCCTCCT GGAGGACAAG   1680

CTCCCGCACA TTTTCGGGTT CACGCTGCTG GGGGACTTCA TCTACTGGAC TGACTGGCAG   1740

CGCCGCAGCA TCGAGCGGGT GCACAAGGTC AAGGCCAGCC GGGACGTCAT CATTGACCAG   1800

CTGCCCGACC TGATGGGGCT CAAAGCTGTG AATGTGGCCA AGGTCGTCGG AACCAACCCG   1860

TGTGCGGACA GGAACGGGGG GTGCAGCCAC CTGTGCTTCT TCACACCCCA CGCAACCCGG   1920

TGTGGCTGCC CCATCGGCCT GGAGCTGCTG AGTGACATGA AGACCTGCAT CGTGCCTGAG   1980

GCCTTCTTGG TCTTCACCAG CAGAGCCGCC ATCCACAGGA TCTCCCTCGA GACCAATAAC   2040

AACGACGTGC ATCCCGCTC ACGGGCGTCA AGGAGGCCTC AGCCCTGGAC TTTGATGTGT    2100
```

-continued

```
CCAACAACCA CATCTACTGG ACAGACGTCA GCCTGAAGAC CATCAGCCGC GCCTTCATGA    2160

ACGGGAGCTC GGTGGAGCAC GTGGTGGAGT TTGGCCTTGA CTACCCCGAG GGCATGGCCG    2220

TTGACTGGAT GGGCAAGAAC CTCTACTGGG CCGACACTGG GACCAACAGA ATCGAAGTGG    2280

CGCGGCTGGA CGGGCAGTTC CGGCAAGTCC TCGTGTGGAG GGACTTGGAC AACCCGAGGT    2340

CGCTGGCCCT GGATCCCACC AAGGGCTACA TCTACTGGAC CGAGTGGGGC GGCAAGCCGA    2400

GGATCGTGCG GGCCTTCATG ACGGGACCA  ACTGCATGAC GCTGGTGGAC AAGGTGGGCC    2460

GGGCCAACGA CCTCACCATT GACTACGCTG ACCAGCGCCT CTACTGGACC GACCTGGACA    2520

CCAACATGAT CGAGTCGTCC AACATGCTGG GTCAGGAGCG GGTCGTGATT GCCGACGATC    2580

TCCCGCACCC GTTCGGTCTG ACGCAGTACA GCGATTATAT CTACTGGACA GACTGGAATC    2640

TGCACAGCAT TGAGCGGGCC GACAAGACTA GCGGCCGGAA CCGCACCCTC ATCCAGGGCC    2700

ACCTGGACTT CGTGATGGAC ATCCTGGTGT TCCACTCCTC CCGCCAGGAT GGCCTCAATG    2760

ACTGTATGCA CAACAACGGG CAGTGTGGGC AGCTGTGCCT TGCCATCCCC GGCGGCCACC    2820

GCTGCGGCTG CGCCTCACAC TACACCCTGG ACCCCAGCAG CCGCAACTGC AGCCCGCCCA    2880

CCACCTTCTT GCTGTTCAGC CAGAAATCTG CCATCAGTCG GATGATCCCG GACGACCAGC    2940

ACAGCCCGGA TCTCATCCTG CCCCTGCATG GACTGAGGAA CGTCAAAGCC ATCGACTATG    3000

ACCCACTGGA CAAGTTCATC TACTGGGTGG ATGGGCGCCA GAACATCAAG CGAGCCAAGG    3060

ACGACGGGAC CCAGCCCTTT GTTTTGACCT CTCTGAGCCA AGGCCAAAAC CCAGACAGGC    3120

AGCCCCACGA CCTCAGCATC GACATCTACA GCCGGACACT GTTCTGGACG TGCGAGGCCA    3180

CCAATACCAT CAACGTCCAC AGGCTGAGCG GGGAAGCCAT GGGGGTGGTG CTGCGTGGGG    3240

ACCGCGACAA GCCCAGGGCC ATCGTCGTCA ACGCGGAGCG AGGGTACCTG TACTTCACCA    3300

ACATGCAGGA CCGGGCAGCC AAGATCGAAC GCGCAGCCCT GGACGGCACC GAGCGCGAGG    3360

TCCTCTTCAC CACCGGCCTC ATCCGCCCTG TGGCCCTGGT GGTAGACAAC ACACTGGGCA    3420

AGCTGTTCTG GGTGGACGCG GACCTGAAGC GCATTGAGAG CTGTGACCTG TCAGGGGCCA    3480

ACCGCCTGAC CCTGGAGGAC GCCAACATCG TGCAGCCTCT GGGCCTGACC ATCCTTGGCA    3540

AGCATCTCTA CTGGATCGAC CGCCAGCAGC AGATGATCGA GCGTGTGGAG AAGACCACCG    3600

GGGACAAGCG GACTCGCATC CAGGGCCGTG TCGCCCACCT CACTGGCATC CATGCAGTGG    3660

AGGAAGTCAG CCTGGAGGAG TTCTCAGCCC ACCCATGTGC CCGTGACAAT GGTGGCTGCT    3720

CCCACATCTG TATTGCCAAG GGTGATGGGA CACCACGGTG CTCATGCCCA GTCCACCTCG    3780

TGCTCCTGCA GAACCTGCTG ACCTGTGGAG AGCCGCCCAC CTGCTCCCCG GACCAGTTTG    3840

CATGTGCCAC AGGGGAGATC GACTGTATCC CCGGGGCCTG GCGCTGTGAC GGCTTTCCCG    3900

AGTGCGATGA CCAGAGCGAC GAGGAGGGCT GCCCCGTGTG CTCCGCCGCC CAGTTCCCCT    3960

GCGCGCGGGG TCAGTGTGTG GACCTGCGCC TGCGCTGCGA CGGCGAGGCA GACTGTCAGG    4020

ACCGCTCAGA CGAGGCGGAC TGTGACGCCA TCTGCCTGCC CAACCAGTTC CGGTGTGCGA    4080

GCGGCCAGTG TGTCCTATCA AACAGCAGTG CGACTCCTTC CCCGACTGTA TCGACGGCTC    4140

CGACGAGCTC ATGTGTGAAA TCACCAAGCC GCCCTCAGAC GACAGCCCGG CCCACAGCAG    4200

TGCCATCGGG CCCGTCATTG GCATCATCCT CTCTCTCTTC GTCATGGGTG GTGTCTATTT    4260

TGTGTGCCAG CGCGTGGTGT GCCAGCGCTA TGCGGGGGCC AACGGGCCCT TCCCGCACGA    4320

GTATGTCAGC GGGACCCCGC ACGTGCCCCT CAATTTCATA GCCCCGGGCG GTTCCCAGCA    4380

TGGCCCCTTC ACAGGCATCG CATGCGGAAA GTCCATGATG AGCTCCGTGA GCCTGATGGG    4440

GGGCCGGGGC GGGGTGCCCC TCTACGACCG GAACCACGTC ACAGGGGCCT CGTCCAGCAG    4500
```

-continued

| | |
|---|---|
| CTCGTCCAGC ACGAAGGCCA CGCTGTACCC GCCGATCCTG AACCCGCCGC CCTCCCCGGC | 4560 |
| CACGGACCCC TCCCTGTACA ACATGGACAT GTTCTACTCT TCAAACATTC CGGCCACTGT | 4620 |
| GAGACCGTAC AGGCCCTACA TCATTCGAGG AATGGCGCCC CCGACGACGC CCTGCAGCAC | 4680 |
| CGACGTGTGT GACAGCGACT ACAGCGCCAG CCGCTGGAAG GCCAGCAAGT ACTACCTGGA | 4740 |
| TTTGAACTCG GACTCAGACC CCTATCCACC CCCACCCACG CCCCACAGCC AGTACCTGTC | 4800 |
| GGCGGAGGAC AGCTGCCCGC CCTCGCCCGC CACCGAGAGG AGCTACTTCC ATCTCTTCCC | 4860 |
| GCCCCCTCCG TCCCCCTGCA CGGACTCATC CTGACCTCGG CCGGGCCACT CTGGCTTCTC | 4920 |
| TGTGCCCCTG TAAATAGTTT TAAATATGAA CAAAGAAAAA AATATATTTT ATGATTTAAA | 4980 |
| AAATAAATAT AATTGGGATT TTAAAAACAT GAGAAATGTG AACTGTGATG GGGTGGGCAG | 5040 |
| GGCTGGGAGA ACTTTGTACA GTGGAACAAA TATTTATAAA CTTAATTTTG TAAAACAG | 5098 |

(2) INFORMATION FOR SEQ ID NO:2:

(i) SEQUENCE CHARACTERISTICS:
        (A) LENGTH: 4843 base pairs
        (B) TYPE: nucleic acid
        (C) STRANDEDNESS: single
        (D) TOPOLOGY: linear (xi) SEQUENCE DESCRIPTION: SEQ ID NO:2:

| | |
|---|---|
| ATGGAGGCAG CGCCGCCCGG GCCGCCGTGG CCGCTGCTGC TGCTGCTGCT GCTGCTGCTG | 60 |
| GCGCTGTGCG GCTGCCCGGC CCCCGCCGCG GCCTCGCCGC TCCTGCTATT TGCCAACCGC | 120 |
| CGGGACGTAC GGCTGGTGGA CGCCGGCGGA GTCAAGCTGG AGTCCACCAT CGTGGTCAGC | 180 |
| GGCCTGGAGG ATGCGGCCGC AGTGGACTTC CAGTTTTCCA AGGGAGCCGT GTACTGGACA | 240 |
| GACGTGAGCG AGGAGGCCAT CAAGCAGACC TACCTGAACC AGACGGGGGC CGCCGTGCAG | 300 |
| AACGTGGTCA TCTCCGGCCT GGTCTCTCCC GACGGCCTCG CCTGCGACTG GGTGGGCAAG | 360 |
| AAGCTGTACT GGACGGACTC AGAGACCAAC CGCATCGAGG TGGCCAACCT CAATGGCACA | 420 |
| TCCCGGAAGG TGCTCTTCTG GCAGGACCTT GACCAGCCGA GGGCCATCGC CTTGGACCCC | 480 |
| GCTCACGGGT ACATGTACTG GACAGACTGG GGTGAGACGC CCCGGATTGA GCGGGCAGGG | 540 |
| ATGGATGGCA GCACCCGGAA GATCATTGTG GACTCGGACA TTTACTGGCC CAATGGACTG | 600 |
| ACCATCGACC TGGAGGAGCA GAAGCTCTAC TGGGCTGACG CCAAGCTCAG CTTCATCCAC | 660 |
| CGTGCCAACC TGGACGGCTC GTTCCGGCAG AAGGTGGTGG AGGGCAGCCT GACGCACCCC | 720 |
| TTCGCCCTGA CGCTCTCCGG GGACACTCTG TACTGGACAG ACTGGCAGAC CCGCTCCATC | 780 |
| CATGCCTGCA ACAAGCGCAC TGGGGGGAAG AGGAAGGAGA TCCTGAGTGC CCTCTACTCA | 840 |
| CCCATGGACA TCCAGGTGCT GAGCCAGGAG CGGCAGCCTT TCTTCCACAC TCGCTGTGAG | 900 |
| GAGGACAATG GCGGCTGCTC CCACCTGTGC CTGCTGTCCC CAAGCGAGCC TTTCTACACA | 960 |
| TGCGCCTGCC CCACGGGTGT GCAGCTGCAG GACAACGGCA GGACGTGTAA GGCAGGAGCC | 1020 |
| GAGGAGGTGC TGCTGCTGGC CCGGCGGACG GACCTACGGA GGATCTCGCT GGACACGCCG | 1080 |
| GACTTTACCG ACATCGTGCT GCAGGTGGAC GACATCCGGC ACGCCATTGC CATCGACTAC | 1140 |
| GACCCGCTAG AGGGCTATGT CTACTGGACA GATGACGAGG TGCGGGCCAT CCGCAGGGCG | 1200 |
| TACCTGGACG GGTCTGGGGC GCAGACGCTG GTCAACACCG AGATCAACGA CCCCGATGGC | 1260 |
| ATCGCGGTCG ACTGGGTGGC CCGAAACCTC TACTGGACCG ACACGGGCAC GGACCGCATC | 1320 |
| GAGGTGACGC GCCTCAACGG CACCTCCCGC AAGATCCTGG TGTCGGAGGA CCTGGACGAG | 1380 |
| CCCCGAGCCA TCGCACTGCA CCCCGTGATG GGCCTCATGT ACTGGACAGA CTGGGGAGAG | 1440 |

```
AACCCTAAAA TCGAGTGTGC AACTTGGAT GGGCAGGAGC GGCGTGTGCT GGTCAATGCC    1500

TCCCTCGGGT GGCCCAACGG CCTGGCCCTG GACCTGCAGG AGGGGAAGCT CTACTGGGGA    1560

GACGCCAAGA CAGACAAGAT CGAGGTGATC AATGTTGATG GGACGAAGAG GCGGACCCTC    1620

CTGGAGGACA AGCTCCCGCA CATTTTCGGG TTCACGCTGC TGGGGACTT CATCTACTGG    1680

ACTGACTGGC AGCGCCGCAG CATCGAGCGG GTGCACAAGG TCAAGGCCAG CCGGGACGTC    1740

ATCATTGACC AGCTGCCCGA CCTGATGGGG CTCAAAGCTG TGAATGTGGC CAAGGTCGTC    1800

GGAACCAACC CGTGTGCGGA CAGGAACGGG GGGTGCAGCC ACCTGTGCTT CTTCACACCC    1860

CACGCAACCC GGTGTGGCTG CCCCATCGGC CTGGAGCTGC TGAGTGACAT GAAGACCTGC    1920

ATCGTGCCTG AGGCCTTCTT GGTCTTCACC AGCAGAGCCG CCATCCACAG GATCTCCCTC    1980

GAGACCAATA CAACGACGT GGCCATCCCG CTCACGGGCG TCAAGGAGGC CTCAGCCCTG    2040

GACTTTGAGT GTCAACAAC CACATCTACT GGACAGACGT CAGCCTGAAG ACCATCAGCC    2100

GCGCCTTCAT GAACGGGAGC TCGGTGGAGC ACGTGGTGGA GTTTGGCCTT GACTACCCCG    2160

AGGGCATGGC CGTTGACTGG ATGGGCAAGA ACCTCTACTG GCCGACACT GGGACCAACA    2220

GAATCGAAGT GGCGCGGCTG GACGGGCAGT TCCGGCAAGT CCTCGTGTGG AGGGACTTGG    2280

ACAACCCGAG GTCGCTGGCC CTGGATCCCA CCAAGGGCTA CATCTACTGG ACCGAGTGGG    2340

GCGGCAAGCC GAGGATCGTG CGGGCCTTCA TGGACGGGAC CAACTGCATG ACGCTGGTGG    2400

ACAAGGTGGG CCGGGCCAAC GACCTCACCA TTGACTACGC TGACCAGCGC CTCTACTGGA    2460

CCGACCTGGA CACCAACATG ATCGAGTCGT CCAACATGCT GGGTCAGGAG CGGGTCGTGA    2520

TTGCCGACGA TCTCCCGCAC CCGTTCGGTC TGACGCAGTA CAGCGATTAT ATCTACTGGA    2580

CAGACTGGAA TCTGCACAGC ATTGAGCGGG CCGACAAGAC TAGCGGCCGG AACCGCACCC    2640

TCATCCAGGG CCACCTGGAC TTCGTGATGG ACATCCTGGT GTTCCACTCC TCCCGCCAGG    2700

ATGGCCTCAA TGACTGTATG CACAACAACG GGCAGTGTGG GCAGCTGTGC CTTGCCATCC    2760

CCGGCGGCCA CCGCTGCGGC TGCGCCTCAC ACTACACCCT GGACCCCAGC AGCCGCAACT    2820

GCAGCCCGCC CACCACCTTC TTGCTGTTCA GCCAGAAATC TGCCATCAGT CGGATGATCC    2880

CGGACGACCA GCACAGCCCG GATCTCATCC TGCCCCTGCA TGGACTGAGG AACGTCAAAG    2940

CCATCGACTA TGACCCACTG GACAAGTTCA TCTACTGGGT GGATGGGCGC CAGAACATCA    3000

AGCGAGCCAA GGACGACGGG ACCCAGCCCT TTGTTTTGAC CTCTCTGAGC CAAGGCCAAA    3060

ACCCAGACAG GCAGCCCCAC GACCTCAGCA TCGACATCTA CAGCCGGACA CTGTTCTGGA    3120

CGTGCGAGGC CACCAATACC ATCAACGTCC ACAGGCTGAG CGGGGAAGCC ATGGGGGTGG    3180

TGCTGCGTGG GGACCGCGAC AAGCCCAGGG CCATCGTCGT CAACGCGGAG CGAGGGTACC    3240

TGTACTTCAC CAACATGCAG GACCGGGCAG CCAAGATCGA ACGCGCAGCC CTGGACGGCA    3300

CCGAGCGCGA GGTCCTCTTC ACCACCGGCC TCATCCGCCC TGTGGCCCTG GTGGTAGACA    3360

ACACACTGGG CAAGCTGTTC TGGGTGGACG CGGACCTGAA GCGCATTGAG AGCTGTGACC    3420

TGTCAGGGGC CAACCGCCTG ACCCTGGAGG ACGCCAACAT CGTGCAGCCT CTGGGCCTGA    3480

CCATCCTTGG CAAGCATCTC TACTGGATCG ACCGCCAGCA GCAGATGATC GAGCGTGTGG    3540

AGAAGACCAC CGGGGACAAG CGGACTCGCA TCCAGGGCCG TGTCGCCCAC CTCACTGGCA    3600

TCCATGCAGT GGAGGAAGTC AGCCTGGAGG AGTTCTCAGC CCACCCATGT GCCCGTGACA    3660

ATGGTGGCTG CTCCCACATC TGTATTGCCA AGGGTGATGG GACACCACGG TGCTCATGCC    3720

CAGTCCACCT CGTGCTCCTG CAGAACCTGC TGACCTGTGG AGAGCCGCCC ACCTGCTCCC    3780
```

```
-continued

CGGACCAGTT TGCATGTGCC ACAGGGGAGA TCGACTGTAT CCCCGGGGCC TGGCGCTGTG   3840

ACGGCTTTCC CGAGTGCGAT GACCAGAGCG ACGAGGAGGG CTGCCCCGTG TGCTCCGCCG   3900

CCCAGTTCCC CTGCGCGCGG GGTCAGTGTG TGGACCTGCG CCTGCGCTGC GACGGCGAGG   3960

CAGACTGTCA GGACCGCTCA GACGAGGCGG ACTGTGACGC CATCTGCCTG CCCAACCAGT   4020

TCCGGTGTGC GAGCGGCCAG TGTGTCCTCA TCAAACAGCA GTGCGACTCC TTCCCCGACT   4080

GTATCGACGG CTCCGAGAGC TCATGTGTGA AATCACCAAG CCGCCCTCAG ACGACAGCCC   4140

GGCCCACAGC AGTGCCATCG GGCCCGTCAT TGGCATCATC CTCTCTCTCT TCGTCATGGG   4200

TGGTGTCTAT TTTGTGTGCC AGCGCGTGGT GTGCCAGCGC TATGCGGGGG CCAACGGGCC   4260

CTTCCCGCAC GAGTATGTCA GCGGGACCCC GCACGTGCCC CTCAATTTCA TAGCCCCGGG   4320

CGGTTCCCAG CATGGCCCCT TCACAGGCAT CGCATGCGGA AAGTCCATGA TGAGCTCCGT   4380

GAGCCTGATG GGGGGCCGGG GCGGGGTGCC CCTCTACGAC CGGAACCACG TCACAGGGGC   4440

CTCGTCCAGC AGCTCGTCCA GCACGAAGGC CACGCTGTAC CCGCCGATCC TGAACCCGCC   4500

GCCCTCCCCG GCCACGGACC CCTCCCTGTA CAACATGGCA ATGTTCTACT CTTCAAACAT   4560

TCCGGCCACT GTGAGACCGT ACAGGCCCTA CATCATTCGA GGAATGGCGC CCCCGACGAC   4620

GCCCTGCAGC ACCGACGTGT GTGACAGCGA CTACAGCGCC AGCCGCTGGA AGGCCAGCAA   4680

GTACTACCTG GATTTGAACT CGGACTCAGA CCCCTATCCA CCCCCACCCA CGCCCCACAG   4740

CCAGTACCTG TCGGCGGAGG ACAGCTGCCC GCCCTCGCCC GCCACCGAGA GGAGCTACTT   4800

CCATCTCTTC CCGCCCCCTC CGTCCCCCTG CACGGACTCA TCC                    4843

(2) INFORMATION FOR SEQ ID NO:3:

(i) SEQUENCE CHARACTERISTICS:
        (A) LENGTH: 1615 amino acids
        (B) TYPE: amino acid
        (D) TOPOLOGY: linear (xi) SEQUENCE DESCRIPTION: SEQ ID NO:3:

Met Glu Ala Ala Pro Gly Pro Pro Trp Pro Leu Leu Leu Leu
1               5                   10                  15

Leu Leu Leu Ala Leu Cys Gly Cys Pro Ala Pro Ala Ala Ser
            20                  25                  30

Pro Leu Leu Phe Ala Asn Arg Arg Asp Val Arg Leu Val Asp Ala
        35                  40                  45

Gly Gly Val Lys Leu Glu Ser Thr Ile Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
                100                 105                 110

Leu Ala Cys Asp Trp Val Gly Lys Lys Leu Tyr Trp Thr Asp Ser Glu
            115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175
```

-continued

```
Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285

Gln Glu Arg Gln Pro Phe Phe His Thr Arg Cys Glu Glu Asp Asn Gly
    290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
        355                 360                 365

Val Asp Asp Ile Arg His Ala Ile Ala Ile Asp Tyr Asp Pro Leu Glu
    370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
        435                 440                 445

Ser Arg Lys Ile Leu Val Ser Glu Asp Leu Asp Glu Pro Arg Ala Ile
    450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
        515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
```

```
               595                 600                 605
Asn Gly Gly Cys Ser His Leu Cys Phe Phe Thr Pro His Ala Thr Arg
            610                 615                 620
Cys Gly Cys Pro Ile Gly Leu Glu Leu Leu Ser Asp Met Lys Thr Cys
625                 630                 635                 640
Ile Val Pro Glu Ala Phe Leu Val Phe Thr Ser Arg Ala Ala Ile His
                645                 650                 655
Arg Ile Ser Leu Glu Thr Asn Asn Asp Val Ala Ile Pro Leu Thr
            660                 665                 670
Gly Val Lys Glu Ala Ser Ala Leu Asp Phe Asp Val Ser Asn Asn His
                675                 680                 685
Ile Tyr Trp Thr Asp Val Ser Leu Lys Thr Ile Ser Arg Ala Phe Met
            690                 695                 700
Asn Gly Ser Ser Val Glu His Val Val Glu Phe Gly Leu Asp Tyr Pro
705                 710                 715                 720
Glu Gly Met Ala Val Asp Trp Met Gly Lys Asn Leu Tyr Trp Ala Asp
                725                 730                 735
Thr Gly Thr Asn Arg Ile Glu Val Ala Arg Leu Asp Gly Gln Phe Arg
            740                 745                 750
Gln Val Leu Val Trp Arg Asp Leu Asp Asn Pro Arg Ser Leu Ala Leu
                755                 760                 765
Asp Pro Thr Lys Gly Tyr Ile Tyr Trp Thr Glu Trp Gly Gly Lys Pro
770                 775                 780
Arg Ile Val Arg Ala Phe Met Asp Gly Thr Asn Cys Met Thr Leu Val
785                 790                 795                 800
Asp Lys Val Gly Arg Ala Asn Asp Leu Thr Ile Asp Tyr Ala Asp Gln
                805                 810                 815
Arg Leu Tyr Trp Thr Asp Leu Asp Thr Asn Met Ile Glu Ser Ser Asn
            820                 825                 830
Met Leu Gly Gln Glu Arg Val Val Ile Ala Asp Asp Leu Pro His Pro
            835                 840                 845
Phe Gly Leu Thr Gln Tyr Ser Asp Tyr Ile Tyr Trp Thr Asp Trp Asn
            850                 855                 860
Leu His Ser Ile Glu Arg Ala Asp Lys Thr Ser Gly Arg Asn Arg Thr
865                 870                 875                 880
Leu Ile Gln Gly His Leu Asp Phe Val Met Asp Ile Leu Val Phe His
                885                 890                 895
Ser Ser Arg Gln Asp Gly Leu Asn Asp Cys Met His Asn Asn Gly Gln
                900                 905                 910
Cys Gly Gln Leu Cys Leu Ala Ile Pro Gly His Arg Cys Gly Cys
            915                 920                 925
Ala Ser His Tyr Thr Leu Asp Pro Ser Ser Arg Asn Cys Ser Pro Pro
            930                 935                 940
Thr Thr Phe Leu Leu Phe Ser Gln Lys Ser Ala Ile Ser Arg Met Ile
945                 950                 955                 960
Pro Asp Asp Gln His Ser Pro Asp Leu Ile Leu Pro Leu His Gly Leu
                965                 970                 975
Arg Asn Val Lys Ala Ile Asp Tyr Asp Pro Leu Asp Lys Phe Ile Tyr
                980                 985                 990
Trp Val Asp Gly Arg Gln Asn Ile Lys Arg Ala Lys Asp Asp Gly Thr
            995                1000                1005
Gln Pro Phe Val Leu Thr Ser Leu Ser Gln Gly Gln Asn Pro Asp Arg
            1010                1015                1020
```

-continued

Gln Pro His Asp Leu Ser Ile Asp Ile Tyr Ser Arg Thr Leu Phe Trp
1025                1030                1035                1040

Thr Cys Glu Ala Thr Asn Thr Ile Asn Val His Arg Leu Ser Gly Glu
            1045                1050                1055

Ala Met Gly Val Val Leu Arg Gly Asp Arg Asp Lys Pro Arg Ala Ile
            1060                1065                1070

Val Val Asn Ala Glu Arg Gly Tyr Leu Tyr Phe Thr Asn Met Gln Asp
            1075                1080                1085

Arg Ala Ala Lys Ile Glu Arg Ala Ala Leu Asp Gly Thr Glu Arg Glu
            1090                1095                1100

Val Leu Phe Thr Thr Gly Leu Ile Arg Pro Val Ala Leu Val Val Asp
1105                1110                1115                1120

Asn Thr Leu Gly Lys Leu Phe Trp Val Asp Ala Asp Leu Lys Arg Ile
                1125                1130                1135

Glu Ser Cys Asp Leu Ser Gly Ala Asn Arg Leu Thr Leu Glu Asp Ala
            1140                1145                1150

Asn Ile Val Gln Pro Leu Gly Leu Thr Ile Leu Gly Lys His Leu Tyr
                1155                1160                1165

Trp Ile Asp Arg Gln Gln Gln Met Ile Glu Arg Val Glu Lys Thr Thr
    1170                1175                1180

Gly Asp Lys Arg Thr Arg Ile Gln Gly Arg Val Ala His Leu Thr Gly
1185                1190                1195                1200

Ile His Ala Val Glu Glu Val Ser Leu Glu Glu Phe Ser Ala His Pro
                1205                1210                1215

Cys Ala Arg Asp Asn Gly Gly Cys Ser His Ile Cys Ile Ala Lys Gly
                1220                1225                1230

Asp Gly Thr Pro Arg Cys Ser Cys Pro Val His Leu Val Leu Leu Gln
                1235                1240                1245

Asn Leu Leu Thr Cys Gly Glu Pro Pro Thr Cys Ser Pro Asp Gln Phe
                1250                1255                1260

Ala Cys Ala Thr Gly Glu Ile Asp Cys Ile Pro Gly Ala Trp Arg Cys
1265                1270                1275                1280

Asp Gly Phe Pro Glu Cys Asp Asp Gln Ser Asp Glu Glu Gly Cys Pro
                1285                1290                1295

Val Cys Ser Ala Ala Gln Phe Pro Cys Ala Arg Gly Gln Cys Val Asp
                1300                1305                1310

Leu Arg Leu Arg Cys Asp Gly Glu Ala Asp Cys Gln Asp Arg Ser Asp
                1315                1320                1325

Glu Ala Asp Cys Asp Ala Ile Cys Leu Pro Asn Gln Phe Arg Cys Ala
    1330                1335                1340

Ser Gly Gln Cys Val Leu Ile Lys Gln Gln Cys Asp Ser Phe Pro Asp
1345                1350                1355                1360

Cys Ile Asp Gly Ser Asp Glu Leu Met Cys Glu Ile Thr Lys Pro Pro
                1365                1370                1375

Ser Asp Asp Ser Pro Ala His Ser Ser Ala Ile Gly Pro Val Ile Gly
                1380                1385                1390

Ile Ile Leu Ser Leu Phe Val Met Gly Gly Val Tyr Phe Val Cys Gln
                1395                1400                1405

Arg Val Val Cys Gln Arg Tyr Ala Gly Ala Asn Gly Pro Phe Pro His
        1410                1415                1420

Glu Tyr Val Ser Gly Thr Pro His Val Pro Leu Asn Phe Ile Ala Pro
1425                1430                1435                1440

```
Gly Gly Ser Gln His Gly Pro Phe Thr Gly Ile Ala Cys Gly Lys Ser
                1445                1450                1455

Met Met Ser Ser Val Ser Leu Met Gly Gly Arg Gly Gly Val Pro Leu
            1460                1465                1470

Tyr Asp Arg Asn His Val Thr Gly Ala Ser Ser Ser Ser Ser Ser Ser
            1475                1480                1485

Thr Lys Ala Thr Leu Tyr Pro Pro Ile Leu Asn Pro Pro Pro Ser Pro
        1490                1495                1500

Ala Thr Asp Pro Ser Leu Tyr Asn Met Asp Met Phe Tyr Ser Ser Asn
1505                1510                1515                1520

Ile Pro Ala Thr Val Arg Pro Tyr Arg Pro Tyr Ile Ile Arg Gly Met
                1525                1530                1535

Ala Pro Pro Thr Thr Pro Cys Ser Thr Asp Val Cys Asp Ser Asp Tyr
                1540                1545                1550

Ser Ala Ser Arg Trp Lys Ala Ser Lys Tyr Tyr Leu Asp Leu Asn Ser
                1555                1560                1565

Asp Ser Asp Pro Tyr Pro Pro Pro Thr Pro His Ser Gln Tyr Leu
            1570                1575                1580

Ser Ala Glu Asp Ser Cys Pro Pro Ser Pro Ala Thr Glu Arg Ser Tyr
1585                1590                1595                1600

Phe His Leu Phe Pro Pro Pro Ser Pro Cys Thr Asp Ser Ser
                1605                1610                1615

(2) INFORMATION FOR SEQ ID NO:4:

(i) SEQUENCE CHARACTERISTICS:
        (A) LENGTH: 1591 amino acids
        (B) TYPE: amino acid
        (D) TOPOLOGY: linear (xi) SEQUENCE DESCRIPTION: SEQ ID NO:4:

Cys Pro Ala Pro Ala Ala Ala Ser Pro Leu Leu Leu Phe Ala Asn Arg
1               5                   10                  15

Arg Asp Val Arg Leu Val Asp Ala Gly Gly Val Lys Leu Glu Ser Thr
            20                  25                  30

Ile Val Val Ser Gly Leu Glu Asp Ala Ala Ala Val Asp Phe Gln Phe
        35                  40                  45

Ser Lys Gly Ala Val Tyr Trp Thr Asp Val Ser Glu Glu Ala Ile Lys
50              55                  60

Gln Thr Tyr Leu Asn Gln Thr Gly Ala Ala Val Gln Asn Val Val Ile
65                  70                  75                  80

Ser Gly Leu Val Ser Pro Asp Gly Leu Ala Cys Asp Trp Val Gly Lys
                85                  90                  95

Lys Leu Tyr Trp Thr Asp Ser Glu Thr Asn Arg Ile Glu Val Ala Asn
            100                 105                 110

Leu Asn Gly Thr Ser Arg Lys Val Leu Phe Trp Gln Asp Leu Asp Gln
        115                 120                 125

Pro Arg Ala Ile Ala Leu Asp Pro Ala His Gly Tyr Met Tyr Trp Thr
    130                 135                 140

Asp Trp Gly Glu Thr Pro Arg Ile Glu Arg Ala Gly Met Asp Gly Ser
145                 150                 155                 160

Thr Arg Lys Ile Ile Val Asp Ser Asp Ile Tyr Trp Pro Asn Gly Leu
                165                 170                 175

Thr Ile Asp Leu Glu Glu Gln Lys Leu Tyr Trp Ala Asp Ala Lys Leu
            180                 185                 190
```

```
Ser Phe Ile His Arg Ala Asn Leu Asp Gly Ser Phe Arg Gln Lys Val
        195                 200                 205
Val Glu Gly Ser Leu Thr His Pro Phe Ala Leu Thr Leu Ser Gly Asp
    210                 215                 220
Thr Leu Tyr Trp Thr Asp Trp Gln Thr Arg Ser Ile His Ala Cys Asn
225                 230                 235                 240
Lys Arg Thr Gly Gly Lys Arg Lys Glu Ile Leu Ser Ala Leu Tyr Ser
                245                 250                 255
Pro Met Asp Ile Gln Val Leu Ser Gln Glu Arg Gln Pro Phe Phe His
            260                 265                 270
Thr Arg Cys Glu Glu Asp Asn Gly Gly Cys Ser His Leu Cys Leu Leu
        275                 280                 285
Ser Pro Ser Glu Pro Phe Tyr Thr Cys Ala Cys Pro Thr Gly Val Gln
    290                 295                 300
Leu Gln Asp Asn Gly Arg Thr Cys Lys Ala Gly Ala Glu Glu Val Leu
305                 310                 315                 320
Leu Leu Ala Arg Arg Thr Asp Leu Arg Arg Ile Ser Leu Asp Thr Pro
                325                 330                 335
Asp Phe Thr Asp Ile Val Leu Gln Val Asp Asp Ile Arg His Ala Ile
            340                 345                 350
Ala Ile Asp Tyr Asp Pro Leu Glu Gly Tyr Val Tyr Trp Thr Asp Asp
        355                 360                 365
Glu Val Arg Ala Ile Arg Arg Ala Tyr Leu Asp Gly Ser Gly Ala Gln
    370                 375                 380
Thr Leu Val Asn Thr Glu Ile Asn Asp Pro Asp Gly Ile Ala Val Asp
385                 390                 395                 400
Trp Val Ala Arg Asn Leu Tyr Trp Thr Asp Thr Gly Thr Asp Arg Ile
                405                 410                 415
Glu Val Thr Arg Leu Asn Gly Thr Ser Arg Lys Ile Leu Val Ser Glu
            420                 425                 430
Asp Leu Asp Glu Pro Arg Ala Ile Ala Leu His Pro Val Met Gly Leu
        435                 440                 445
Met Tyr Trp Thr Asp Trp Gly Glu Asn Pro Lys Ile Glu Cys Ala Asn
    450                 455                 460
Leu Asp Gly Gln Glu Arg Arg Val Leu Val Asn Ala Ser Leu Gly Trp
465                 470                 475                 480
Pro Asn Gly Leu Ala Leu Asp Leu Gln Glu Gly Lys Leu Tyr Trp Gly
                485                 490                 495
Asp Ala Lys Thr Asp Lys Ile Glu Val Ile Asn Val Asp Gly Thr Lys
            500                 505                 510
Arg Arg Thr Leu Leu Glu Asp Lys Leu Pro His Ile Phe Gly Phe Thr
        515                 520                 525
Leu Leu Gly Asp Phe Ile Tyr Trp Thr Asp Trp Gln Arg Arg Ser Ile
    530                 535                 540
Glu Arg Val His Lys Val Lys Ala Ser Arg Asp Val Ile Ile Asp Gln
545                 550                 555                 560
Leu Pro Asp Leu Met Gly Leu Lys Ala Val Asn Val Ala Lys Val Val
                565                 570                 575
Gly Thr Asn Pro Cys Ala Asp Arg Asn Gly Gly Cys Ser His Leu Cys
            580                 585                 590
Phe Phe Thr Pro His Ala Thr Arg Cys Gly Cys Pro Ile Gly Leu Glu
        595                 600                 605
Leu Leu Ser Asp Met Lys Thr Cys Ile Val Pro Glu Ala Phe Leu Val
```

```
            610                 615                 620
Phe Thr Ser Arg Ala Ala Ile His Arg Ile Ser Leu Glu Thr Asn Asn
625                 630                 635                 640

Asn Asp Val Ala Ile Pro Leu Thr Gly Val Lys Glu Ala Ser Ala Leu
                645                 650                 655

Asp Phe Asp Val Ser Asn Asn His Ile Tyr Trp Thr Asp Val Ser Leu
                660                 665                 670

Lys Thr Ile Ser Arg Ala Phe Met Asn Gly Ser Ser Val Glu His Val
                675                 680                 685

Val Glu Phe Gly Leu Asp Tyr Pro Glu Gly Met Ala Val Asp Trp Met
            690                 695                 700

Gly Lys Asn Leu Tyr Trp Ala Asp Thr Gly Thr Asn Arg Ile Glu Val
705                 710                 715                 720

Ala Arg Leu Asp Gly Gln Phe Arg Gln Val Leu Val Trp Arg Asp Leu
                725                 730                 735

Asp Asn Pro Arg Ser Leu Ala Leu Asp Pro Thr Lys Gly Tyr Ile Tyr
                740                 745                 750

Trp Thr Glu Trp Gly Gly Lys Pro Arg Ile Val Arg Ala Phe Met Asp
            755                 760                 765

Gly Thr Asn Cys Met Thr Leu Val Asp Lys Val Gly Arg Ala Asn Asp
770                 775                 780

Leu Thr Ile Asp Tyr Ala Asp Gln Arg Leu Tyr Trp Thr Asp Leu Asp
785                 790                 795                 800

Thr Asn Met Ile Glu Ser Ser Asn Met Leu Gly Gln Glu Arg Val Val
                805                 810                 815

Ile Ala Asp Asp Leu Pro His Pro Phe Gly Leu Thr Gln Tyr Ser Asp
                820                 825                 830

Tyr Ile Tyr Trp Thr Asp Trp Asn Leu His Ser Ile Glu Arg Ala Asp
                835                 840                 845

Lys Thr Ser Gly Arg Asn Arg Thr Leu Ile Gln Gly His Leu Asp Phe
            850                 855                 860

Val Met Asp Ile Leu Val Phe His Ser Ser Arg Gln Asp Gly Leu Asn
865                 870                 875                 880

Asp Cys Met His Asn Asn Gly Gln Cys Gly Gln Leu Cys Leu Ala Ile
                885                 890                 895

Pro Gly Gly His Arg Cys Gly Cys Ala Ser His Tyr Thr Leu Asp Pro
                900                 905                 910

Ser Ser Arg Asn Cys Ser Pro Pro Thr Thr Phe Leu Leu Phe Ser Gln
            915                 920                 925

Lys Ser Ala Ile Ser Arg Met Ile Pro Asp Asp Gln His Ser Pro Asp
930                 935                 940

Leu Ile Leu Pro Leu His Gly Leu Arg Asn Val Lys Ala Ile Asp Tyr
945                 950                 955                 960

Asp Pro Leu Asp Lys Phe Ile Tyr Trp Val Asp Gly Arg Gln Asn Ile
                965                 970                 975

Lys Arg Ala Lys Asp Asp Gly Thr Gln Pro Phe Val Leu Thr Ser Leu
                980                 985                 990

Ser Gln Gly Gln Asn Pro Asp Arg Gln Pro His Asp Leu Ser Ile Asp
            995                 1000                1005

Ile Tyr Ser Arg Thr Leu Phe Trp Thr Cys Glu Ala Thr Asn Thr Ile
            1010                1015                1020

Asn Val His Arg Leu Ser Gly Glu Ala Met Gly Val Val Leu Arg Gly
1025                1030                1035                1040
```

-continued

```
Asp Arg Asp Lys Pro Arg Ala Ile Val Val Asn Ala Glu Arg Gly Tyr
                1045                1050                1055

Leu Tyr Phe Thr Asn Met Gln Asp Arg Ala Ala Lys Ile Glu Arg Ala
                1060                1065                1070

Ala Leu Asp Gly Thr Glu Arg Glu Val Leu Phe Thr Thr Gly Leu Ile
                1075                1080                1085

Arg Pro Val Ala Leu Val Val Asp Asn Thr Leu Gly Lys Leu Phe Trp
                1090                1095                1100

Val Asp Ala Asp Leu Lys Arg Ile Glu Ser Cys Asp Leu Ser Gly Ala
1105                1110                1115                1120

Asn Arg Leu Thr Leu Glu Asp Ala Asn Ile Val Gln Pro Leu Gly Leu
                1125                1130                1135

Thr Ile Leu Gly Lys His Leu Tyr Trp Ile Asp Arg Gln Gln Gln Met
                1140                1145                1150

Ile Glu Arg Val Glu Lys Thr Thr Gly Asp Lys Arg Thr Arg Ile Gln
                1155                1160                1165

Gly Arg Val Ala His Leu Thr Gly Ile His Ala Val Glu Glu Val Ser
                1170                1175                1180

Leu Glu Glu Phe Ser Ala His Pro Cys Ala Arg Asp Asn Gly Gly Cys
1185                1190                1195                1200

Ser His Ile Cys Ile Ala Lys Gly Asp Gly Thr Pro Arg Cys Ser Cys
                1205                1210                1215

Pro Val His Leu Val Leu Leu Gln Asn Leu Leu Thr Cys Gly Glu Pro
                1220                1225                1230

Pro Thr Cys Ser Pro Asp Gln Phe Ala Cys Ala Thr Gly Glu Ile Asp
                1235                1240                1245

Cys Ile Pro Gly Ala Trp Arg Cys Asp Gly Phe Pro Glu Cys Asp Asp
                1250                1255                1260

Gln Ser Asp Glu Glu Gly Cys Pro Val Cys Ser Ala Ala Gln Phe Pro
1265                1270                1275                1280

Cys Ala Arg Gly Gln Cys Val Asp Leu Arg Leu Arg Cys Asp Gly Glu
                1285                1290                1295

Ala Asp Cys Gln Asp Arg Ser Asp Glu Ala Asp Cys Asp Ala Ile Cys
                1300                1305                1310

Leu Pro Asn Gln Phe Arg Cys Ala Ser Gly Gln Cys Val Leu Ile Lys
                1315                1320                1325

Gln Gln Cys Asp Ser Phe Pro Asp Cys Ile Asp Gly Ser Asp Glu Leu
                1330                1335                1340

Met Cys Glu Ile Thr Lys Pro Pro Ser Asp Ser Pro Ala His Ser
1345                1350                1355                1360

Ser Ala Ile Gly Pro Val Ile Gly Ile Ile Leu Ser Leu Phe Val Met
                1365                1370                1375

Gly Gly Val Tyr Phe Val Cys Gln Arg Val Val Cys Gln Arg Tyr Ala
                1380                1385                1390

Gly Ala Asn Gly Pro Phe Pro His Glu Tyr Val Ser Gly Thr Pro His
                1395                1400                1405

Val Pro Leu Asn Phe Ile Ala Pro Gly Gly Ser Gln His Gly Pro Phe
1410                1415                1420

Thr Gly Ile Ala Cys Gly Lys Ser Met Met Ser Ser Val Ser Leu Met
1425                1430                1435                1440

Gly Gly Arg Gly Gly Val Pro Leu Tyr Asp Arg Asn His Val Thr Gly
                1445                1450                1455
```

```
Ala Ser Ser Ser Ser Ser Ser Thr Lys Ala Thr Leu Tyr Pro Pro
        1460                1465                1470

Ile Leu Asn Pro Pro Pro Ser Pro Ala Thr Asp Pro Ser Leu Tyr Asn
        1475                1480                1485

Met Asp Met Phe Tyr Ser Ser Asn Ile Pro Ala Thr Val Arg Pro Tyr
        1490                1495                1500

Arg Pro Tyr Ile Ile Arg Gly Met Ala Pro Pro Thr Thr Pro Cys Ser
1505                1510                1515                1520

Thr Asp Val Cys Asp Ser Asp Tyr Ser Ala Ser Arg Trp Lys Ala Ser
            1525                1530                1535

Lys Tyr Tyr Leu Asp Leu Asn Ser Asp Ser Asp Pro Tyr Pro Pro Pro
        1540                1545                1550

Pro Thr Pro His Ser Gln Tyr Leu Ser Ala Glu Asp Ser Cys Pro Pro
        1555                1560                1565

Ser Pro Ala Thr Glu Arg Ser Tyr Phe His Leu Phe Pro Pro Pro
        1570                1575                1580

Ser Pro Cys Thr Asp Ser Ser
1585                1590
```

(2) INFORMATION FOR SEQ ID NO:5:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO:5:

```
ATGGAGCCCG AGTGAGCGCG GCGCGGGCCC GTCCGGCCGC CGGACAACAT GGAGGCAGCG     60

CCGCCCGGGC CGCCGTGGCC GCTGCTGCTG CTGCTGCTGC TGCTGCTGGC GCTGTGCGGC    120

TGCCCGGCCC CCGCCGCGGC CTCGCCGCTC CTGCTATTTG CCAACCGCCG GGACGTACGG    180

CTGGTGGACG CCGGCGGAGT CAAGCTGGAG TCCACCATCG TGGTCAGCGG CCTGGAGGAT    240

GCGGCCGCAG TGGACTTCCA GTTTTCCAAG GGAGCCGTGT ACTGGACAGA CGTGAGCGAG    300

GAGGCCATCA AGCAGACCTA CCTGAACCAG ACGGGGGCCG CCGTGCAGAA CGTGGTCATC    360

TCCGGCCTGG TCTCTCCCGA CGGCCTCGCC TGCGACTGGG TGGGCAAGAA GCTGTACTGG    420

ACGGACTCAG AG                                                        432
```

(2) INFORMATION FOR SEQ ID NO:6:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (xi) SEQUENCE DESCRIPTION: SEQ ID NO:6:

```
ACCGCCGCCG CGCGCGCCAT GGAGCCCGAG TGAGCGCGCG GCGCTCCCGG CCGCCGGACG     60

ACATGGAAAC GGCGCCGACC CGGGCCCCTC CGCCGCCGCC GCCGCCGCTG CTGCTGCTGG    120

TGCTGTACTG CAGCTTGGTC CCCGCCGCGG CCTCACCGCT CCTGTTGTTT GCCAACCGCC    180

GGGATGTGCG GCTAGTGGAT GCCGGCGGAG TGAAGCTGGA GTCCACCATT GTGGCCAGTG    240

GCCTGGAGGA TGCAGCTGCT GTAGACTTCC AGTTCTCCAA GGGTGCTGTG TACTGGACAG    300

ATGTGAGCGA GGAGGCCATC AAACAGACCT ACCTGAACCA GACTGAGGT GCTGCACAGA    360

ACATTGTCAT CTCGGGCCTC GTGTCACCTG ATGGCCTGGC CTGTGACTGG GTTGGCAAGA    420
```

-continued

```
AGCTGTACTG GACGGACTCC GAG                                                    443
```

(2) INFORMATION FOR SEQ ID NO:7:

(i) SEQUENCE CHARACTERISTICS:
        (A) LENGTH: 550 amino acids
        (B) TYPE: amino acid
        (D) TOPOLOGY: linear (xi) SEQUENCE DESCRIPTION: SEQ ID NO:7:

```
Met Glu Ala Ala Pro Gly Pro Pro Trp Pro Leu Leu Leu Leu
 1               5                  10                  15

Leu Leu Leu Leu Ala Leu Cys Gly Cys Pro Ala Pro Ala Ala Ala Ser
                20                  25                  30

Pro Leu Leu Leu Phe Ala Asn Arg Arg Asp Val Arg Leu Val Asp Ala
            35                  40                  45

Gly Gly Val Lys Leu Glu Ser Thr Ile Val Ser Gly Leu Glu Asp
        50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
                100                 105                 110

Leu Ala Cys Asp Trp Val Gly Lys Lys Leu Tyr Trp Thr Asp Ser Glu
                115                 120                 125

Thr Asn Arg Ile Glu Val Ala Asn Leu Asn Gly Thr Ser Arg Lys Val
                130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
                180                 185                 190

Asp Ile Tyr Trp Pro Asn Gly Leu Thr Ile Asp Leu Glu Glu Gln Lys
                195                 200                 205

Leu Tyr Trp Ala Asp Ala Lys Leu Ser Phe Ile His Arg Ala Asn Leu
                210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
                260                 265                 270

Glu Ile Leu Ser Ala Leu Tyr Ser Pro Met Asp Ile Gln Val Leu Ser
                275                 280                 285

Gln Glu Arg Gln Pro Phe Phe His Thr Arg Cys Glu Glu Asp Asn Gly
                290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
                340                 345                 350

Arg Arg Ile Ser Leu Asp Thr Pro Asp Phe Thr Asp Ile Val Leu Gln
```

-continued

```
                355                 360                 365
Val Asp Asp Ile Arg His Ala Ile Ala Ile Asp Tyr Asp Pro Leu Glu
            370                 375                 380
Gly Tyr Val Tyr Trp Thr Asp Glu Val Arg Ala Ile Arg Arg Ala
385                 390                 395                 400
Tyr Leu Asp Gly Ser Gly Ala Gln Thr Leu Val Asn Thr Glu Ile Asn
                405                 410                 415
Asp Pro Asp Gly Ile Ala Val Asp Trp Val Ala Arg Asn Leu Tyr Trp
            420                 425                 430
Thr Asp Thr Gly Thr Asp Arg Ile Glu Val Thr Arg Leu Asn Gly Thr
            435                 440                 445
Ser Arg Lys Ile Leu Val Ser Glu Asp Leu Asp Glu Pro Arg Ala Ile
450                 455                 460
Ala Leu His Pro Val Met Gly Leu Met Tyr Trp Thr Asp Trp Gly Glu
465                 470                 475                 480
Asn Pro Lys Ile Glu Cys Ala Asn Leu Asp Gly Gln Glu Arg Arg Val
                485                 490                 495
Leu Val Asn Ala Ser Leu Gly Trp Pro Asn Gly Leu Ala Leu Asp Leu
            500                 505                 510
Gln Glu Gly Lys Leu Tyr Trp Gly Asp Ala Lys Thr Asp Lys Ile Glu
            515                 520                 525
Val Ile Asn Val Asp Gly Thr Lys Arg Arg Thr Leu Leu Glu Asp Lys
530                 535                 540
Leu Pro His Ile Phe Gly
545                 550

(2) INFORMATION FOR SEQ ID NO:8:

(i) SEQUENCE CHARACTERISTICS:
        (A) LENGTH: 533 amino acids
        (B) TYPE: amino acid
        (D) TOPOLOGY: linear (xi) SEQUENCE DESCRIPTION: SEQ ID NO:8:

Met Glu Thr Ala Pro Thr Arg Ala Pro Pro Pro Pro Pro Pro Pro Leu
1               5                   10                  15
Leu Leu Leu Val Leu Tyr Cys Ser Leu Val Pro Ala Ala Ala Ser Pro
                20                  25                  30
Leu Leu Leu Phe Ala Asn Arg Arg Asp Val Arg Leu Val Asp Ala Gly
            35                  40                  45
Gly Val Lys Leu Glu Ser Thr Ile Val Ala Ser Gly Leu Glu Asp Ala
50                  55                  60
Ala Ala Val Asp Phe Gln Phe Ser Lys Gly Ala Val Tyr Trp Thr Asp
65                  70                  75                  80
Val Ser Glu Glu Ala Ile Lys Gln Thr Tyr Leu Asn Gln Thr Gly Gly
                85                  90                  95
Ala Ala Gln Asn Ile Val Ile Ser Gly Leu Val Ser Pro Asp Gly Leu
                100                 105                 110
Ala Cys Asp Trp Val Gly Lys Lys Leu Tyr Trp Thr Asp Ser Glu Thr
            115                 120                 125
Asn Arg Ile Glu Val Ala Asn Leu Asn Gly Thr Ser Arg Lys Val Leu
            130                 135                 140
Phe Trp Gln Asp Leu Asp Gln Pro Arg Ala Ile Ala Leu Asp Pro Ala
145                 150                 155                 160
His Gly Tyr Met Tyr Trp Thr Asp Trp Gly Glu Ala Pro Arg Ile Glu
```

-continued

```
                    165                 170                 175
Arg Ala Gly Met Asp Gly Ser Thr Arg Lys Ile Ile Val Asp Ser Asp
                180                 185                 190
Ile Tyr Trp Pro Asn Gly Leu Thr Ile Asp Leu Glu Glu Gln Lys Leu
            195                 200                 205
Tyr Trp Ala Asp Ala Lys Leu Ser Phe Ile His Arg Ala Asn Leu Asp
        210                 215                 220
Gly Ser Phe Arg Gln Lys Val Glu Gly Ser Leu Thr His Pro Phe
225                 230                 235                 240
Ala Leu Thr Leu Ser Gly Asp Thr Leu Tyr Trp Thr Asp Trp Gln Thr
                245                 250                 255
Arg Ser Ile His Ala Cys Asn Lys Trp Thr Gly Glu Gln Arg Lys Glu
            260                 265                 270
Ile Leu Ser Ala Leu Tyr Ser Pro Met Asp Ile Gln Val Leu Ser Gln
        275                 280                 285
Glu Arg Gln Pro Pro Phe His Thr Pro Cys Glu Glu Asp Asn Gly Gly
290                 295                 300
Cys Ser His Leu Cys Leu Leu Ser Pro Arg Glu Pro Phe Tyr Ser Cys
305                 310                 315                 320
Ala Cys Pro Thr Gly Val Gln Leu Gln Asp Asn Gly Lys Thr Cys Lys
                325                 330                 335
Thr Gly Ala Glu Glu Val Leu Leu Leu Ala Arg Arg Thr Asp Leu Arg
                340                 345                 350
Arg Ile Ser Leu Asp Thr Pro Asp Phe Thr Asp Ile Val Leu Gln Val
            355                 360                 365
Gly Asp Ile Arg His Ala Ile Ala Ile Asp Tyr Asp Pro Leu Glu Gly
        370                 375                 380
Tyr Val Tyr Trp Thr Asp Asp Glu Val Arg Ala Ile Arg Arg Ala Tyr
385                 390                 395                 400
Leu Asp Gly Ser Gly Ala Gln Thr Leu Val Asn Thr Glu Ile Asn Asp
                405                 410                 415
Pro Asp Gly Ile Ala Val Asp Trp Val Ala Arg Asn Leu Tyr Trp Thr
                420                 425                 430
Asp Thr Gly Thr Asp Arg Ile Glu Val Thr Arg Leu Asn Gly Thr Ser
            435                 440                 445
Arg Lys Ile Leu Val Ser Glu Asp Leu Asp Glu Pro Arg Ala Ile Val
        450                 455                 460
Leu His Pro Val Met Gly Leu Met Tyr Trp Thr Asp Trp Gly Glu Asn
465                 470                 475                 480
Pro Lys Ile Glu Cys Ala Asn Leu Asp Gly Arg Asp Arg His Val Leu
                485                 490                 495
Val Asn Thr Ser Leu Gly Trp Pro Asn Gly Leu Ala Leu Asp Leu Gln
                500                 505                 510
Glu Gly Lys Leu Tyr Trp Gly Asp Ala Lys Thr Asp Lys Ile Glu Val
            515                 520                 525
Ile Asn Ile Asp Gly
        530
```

(2) INFORMATION FOR SEQ ID NO:9:

(i) SEQUENCE CHARACTERISTICS:
        (A) LENGTH: 38 amino acids
        (B) TYPE: amino acid
        (D) TOPOLOGY: linear (xi) SEQUENCE DESCRIPTION: SEQ ID NO:9:

Cys Glu Glu Asp Asn Gly Gly Cys Ser His Leu Cys Leu Leu Ser Pro
1               5                   10                  15

Ser Glu Pro Phe Tyr Thr Cys Ala Cys Pro Thr Gly Val Gln Leu Gln
                20                  25                  30

Asp Asn Gly Arg Thr Cys
            35

(2) INFORMATION FOR SEQ ID NO:10:

(i) SEQUENCE CHARACTERISTICS:
        (A) LENGTH: 37 amino acids
        (B) TYPE: amino acid
        (D) TOPOLOGY: linear (xi) SEQUENCE DESCRIPTION: SEQ ID NO:10:

Cys Lys Val Asn Asn Gly Gly Cys Ser Asn Leu Cys Leu Leu Ser Pro
1               5                   10                  15

Gly Gly Gly His Lys Cys Ala Cys Pro Thr Asn Phe Tyr Leu Gly Ser
                20                  25                  30

Asp Gly Arg Thr Cys
            35

(2) INFORMATION FOR SEQ ID NO:11:

(i) SEQUENCE CHARACTERISTICS:
        (A) LENGTH: 41 amino acids
        (B) TYPE: amino acid
        (D) TOPOLOGY: linear (xi) SEQUENCE DESCRIPTION: SEQ ID NO:11:

Gly Thr Asn Pro Cys Ala Asp Arg Asn Gly Gly Cys Ser His Leu Cys
1               5                   10                  15

Phe Phe Thr Pro His Ala Thr Arg Cys Gly Cys Pro Ile Gly Leu Glu
                20                  25                  30

Leu Leu Ser Asp Met Lys Thr Cys Ile
            35                  40

(2) INFORMATION FOR SEQ ID NO:12:

(i) SEQUENCE CHARACTERISTICS:
        (A) LENGTH: 41 amino acids
        (B) TYPE: amino acid
        (D) TOPOLOGY: linear (xi) SEQUENCE DESCRIPTION: SEQ ID NO:12:

Gly Thr Asn Lys Cys Arg Val Asn Asn Gly Gly Cys Ser Ser Leu Cys
1               5                   10                  15

Leu Ala Thr Pro Gly Ser Arg Gln Cys Ala Cys Ala Glu Asp Gln Val
                20                  25                  30

Leu Asp Ala Asp Gly Val Thr Cys Leu
            35                  40

(2) INFORMATION FOR SEQ ID NO:13:

(i) SEQUENCE CHARACTERISTICS:
        (A) LENGTH: 40 amino acids
        (B) TYPE: amino acid
        (D) TOPOLOGY: linear (xi) SEQUENCE DESCRIPTION: SEQ ID NO:13:

Gly Leu Asn Asp Cys Met His Asn Asn Gly Gln Cys Gly Gln Leu Cys

```
            1               5              10              15
Leu Ala Ile Pro Gly Gly His Arg Cys Gly Cys Ala Ser His Tyr Thr
                    20              25              30
Leu Asp Pro Ser Ser Arg Asn Cys
            35              40

(2) INFORMATION FOR SEQ ID NO:14:

(i) SEQUENCE CHARACTERISTICS:
        (A) LENGTH: 40 amino acids
        (B) TYPE: amino acid
        (D) TOPOLOGY: linear (xi) SEQUENCE DESCRIPTION: SEQ ID NO:14:

Gly Thr Asn Lys Cys Arg Val Asn Asn Gly Gly Cys Ser Ser Leu Cys
1               5              10              15
Leu Ala Thr Pro Gly Ser Arg Gln Cys Ala Cys Ala Glu Asp Gln Val
                    20              25              30
Leu Asp Ala Asp Gly Val Thr Cys
            35              40

(2) INFORMATION FOR SEQ ID NO:15:

(i) SEQUENCE CHARACTERISTICS:
        (A) LENGTH: 39 amino acids
        (B) TYPE: amino acid
        (D) TOPOLOGY: linear (xi) SEQUENCE DESCRIPTION: SEQ ID NO:15:

His Pro Cys Ala Arg Asp Asn Gly Gly Cys Ser His Ile Cys Ile Ala
1               5              10              15
Lys Gly Asp Gly Thr Pro Arg Cys Ser Cys Pro Val His Leu Val Leu
                    20              25              30
Leu Gln Asn Leu Leu Thr Cys
            35

(2) INFORMATION FOR SEQ ID NO:16:

(i) SEQUENCE CHARACTERISTICS:
        (A) LENGTH: 39 amino acids
        (B) TYPE: amino acid
        (D) TOPOLOGY: linear (xi) SEQUENCE DESCRIPTION: SEQ ID NO:16:

His Pro Cys Lys Val Asn Asn Gly Gly Cys Ser Asn Leu Cys Leu Leu
1               5              10              15
Ser Pro Gly Gly Gly His Lys Cys Ala Cys Pro Thr Asn Phe Tyr Leu
                    20              25              30
Gly Ser Asp Gly Arg Thr Cys
            35

(2) INFORMATION FOR SEQ ID NO:17:

(i) SEQUENCE CHARACTERISTICS:
        (A) LENGTH: 39 amino acids
        (B) TYPE: amino acid
        (D) TOPOLOGY: linear (xi) SEQUENCE DESCRIPTION: SEQ ID NO:17:

Pro Thr Cys Ser Pro Asp Gln Phe Ala Cys Ala Thr Gly Glu Ile Asp
1               5              10              15
Cys Ile Pro Gly Ala Trp Arg Cys Asp Gly Phe Pro Glu Cys Asp Asp
```

```
              20                  25                  30

Gln Ser Asp Glu Glu Gly Cys
        35

(2) INFORMATION FOR SEQ ID NO:18:

(i) SEQUENCE CHARACTERISTICS:
        (A) LENGTH: 37 amino acids
        (B) TYPE: amino acid
        (D) TOPOLOGY: linear (xi) SEQUENCE DESCRIPTION: SEQ ID NO:18:

Pro Arg Cys Asp Met Asp Gln Phe Gln Cys Lys Ser Gly His Cys Ile
1               5                  10                  15

Pro Leu Arg Trp Arg Cys Asp Ala Asp Ala Asp Cys Met Asp Gly Ser
            20                  25                  30

Asp Glu Glu Ala Cys
        35

(2) INFORMATION FOR SEQ ID NO:19:

(i) SEQUENCE CHARACTERISTICS:
        (A) LENGTH: 36 amino acids
        (B) TYPE: amino acid
        (D) TOPOLOGY: linear (xi) SEQUENCE DESCRIPTION: SEQ ID NO:19:

Cys Ser Ala Ala Gln Phe Pro Cys Ala Arg Gly Gln Cys Val Asp Leu
1               5                  10                  15

Arg Leu Arg Cys Asp Gly Glu Ala Asp Cys Gln Asp Arg Ser Asp Glu
            20                  25                  30

Ala Asp Cys Asp
        35

(2) INFORMATION FOR SEQ ID NO:20:

(i) SEQUENCE CHARACTERISTICS:
        (A) LENGTH: 36 amino acids
        (B) TYPE: amino acid
        (D) TOPOLOGY: linear (xi) SEQUENCE DESCRIPTION: SEQ ID NO:20:

Cys Arg Pro Gly Gln Phe Gln Cys Ser Thr Gly Ile Cys Thr Asn Pro
1               5                  10                  15

Ala Phe Ile Cys Asp Gly Asp Asn Asp Cys Gln Asp Asn Ser Asp Glu
            20                  25                  30

Ala Asn Cys Asp
        35

(2) INFORMATION FOR SEQ ID NO:21:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:21:

Cys Leu Pro Asn Gln Phe Arg Cys Ala Ser Gly Gln Cys Val Leu Ile
1               5                  10                  15

Lys Gln Gln Cys Asp Ser Phe Pro Asp Cys Ile Asp Gly Ser Asp Glu
            20                  25                  30

Leu Met Cys
```

(2) INFORMATION FOR SEQ ID NO:22:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:22:

```
Cys Asp Met Asp Gln Phe Gln Cys Lys Ser Gly His Cys Ile Pro Leu
1               5                   10                  15

Arg Trp Arg Cys Asp Ala Asp Ala Asp Cys Met Asp Gly Ser Asp Glu
            20                  25                  30

Glu Ala Cys
        35
```

(2) INFORMATION FOR SEQ ID NO:23:

(i) SEQUENCE CHARACTERISTICS:
        (A) LENGTH: 5166 base pairs
        (B) TYPE: nucleic acid
        (C) STRANDEDNESS: single
        (D) TOPOLOGY: linear (xi) SEQUENCE DESCRIPTION: SEQ ID NO:23:

```
GAGAGGACAC CGCATTCTTC TTCTCCAGAG GATGCAGCAG CAAGGCGCCA TCTTGAAACC     60

AGAGACCAAA CCAACCAGCA WTTTTGTCTT GAACTTCCCA GCCTCCACAA CTAATATAAA    120

CCCCATGAGG GCAGAGGCGT TCAGCCTGAC TCCAGCCTGG CAAAGCTGTC ACAAATCTGG    180

AGGAACACAC ACGTTCACGG GCACTCAGTT CTGTGAGCCT CGCCGCTCCT GCTATTTGCC    240

AACCGCCGGG ACGTACGGCT GGTGGACGCC GGCGGAGTCA AGCTGGAGTC CACCATCGTG    300

GTCAGCGGCC TGGAGGATGC GGCCGCAGTG GACTTCCAGT TTTCCAAGGG AGCCGTGTAC    360

TGGACAGACG TGAGCGAGGA GGCCATCAAG CAGACCTACC TGAACCAGAC GGGGGCCGCC    420

GTGCAGAACG TGGTCATCTC CGGCCTGGTC TCTCCCGACG GCCTCGCCTG CGACTGGGTG    480

GGCAAGAAGC TGTACTGGAC GGACTCAGAG ACCAACCGCA TCGAGGTGGC CAACCTCAAT    540

GGCACATCCC GGAAGGTGCT CTTCTGGCAG GACCTTGACC AGCCGAGGGC CATCGCCTTG    600

GACCCCGCTC ACGGGTACAT GTACTGGACA GACTGGGGTG AGACGCCCCG GATTGAGCGG    660

GCAGGGATGG ATGGCAGCAC CCGGAAGATC ATTGTGGACT CGGACATTTA CTGGCCCAAT    720

GGACTGACCA TCGACCTGGA GGAGCAGAAG CTCTACTGGG CTGACGCCAA GCTCAGCTTC    780

ATCCACCGTG CCAACCTGGA CGGCTCGTTC CGGCAGAAGG TGGTGGAGGG CAGCCTGACG    840

CACCCCTTCG CCCTGACGCT CTCCGGGGAC ACTCTGTACT GGACAGACTG GCAGACCCGC    900

TCCATCCATG CCTGCAACAA GCGCACTGGG GGGAAGAGGA AGGAGATCCT GAGTGCCCTC    960

TACTCACCCA TGGACATCCA GGTGCTGAGC CAGGAGCGGC AGCCTTTCTT CCACACTCGC   1020

TGTGAGGAGG ACAATGGCGG CTGCTCCCAC CTGTGCCTGC TGTCCCCAAG CGAGCCTTTC   1080

TACACATGCG CCTGCCCCAC GGGTGTGCAG CTGCAGGACA ACGGCAGGAC GTGTAAGGCA   1140

GGAGCCGAGG AGGTGCTGCT GCTGGCCCGG CGGACGGACC TACGGAGGAT CTCGCTGGAC   1200

ACGCCGGACT TTACCGACAT CGTGCTGCAG GTGGACGACA TCCGGCACGC CATTGCCATC   1260

GACTACGACC CGCTAGAGGG CTATGTCTAC TGGACAGATG ACGAGGTGCG GGCCATCCGC   1320

AGGGCGTACC TGGACGGGTC TGGGGCGCAG ACGCTGGTCA ACACCGAGAT CAACGACCCC   1380

GATGGCATCG CGGTCGACTG GGTGGCCCGA AACCTCTACT GGACCGACAC GGGCACGGAC   1440
```

-continued

```
CGCATCGAGG TGACGCGCCT CAACGGCACC TCCCGCAAGA TCCTGGTGTC GGAGGACCTG    1500

GACGAGCCCC GAGCCATCGC ACTGCACCCC GTGATGGGCC TCATGTACTG ACAGACTGG     1560

GGAGAGAACC CTAAAATCGA GTGTGCCAAC TTGGATGGGC AGGAGCGGCG TGTGCTGGTC    1620

AATGCCTCCC TCGGGTGGCC CAACGGCCTG GCCCTGGACC TGCAGGAGGG GAAGCTCTAC    1680

TGGGGAGACG CCAAGACAGA CAAGATCGAG GTGATCAATG TTGATGGGAC GAAGAGGCGG    1740

ACCCTCCTGG AGGACAAGCT CCCGCACATT TTCGGGTTCA CGCTGCTGGG GGACTTCATC    1800

TACTGGACTG ACTGGCAGCG CCGCAGCATC GAGCGGGTGC ACAAGGTCAA GGCCAGCCGG    1860

GACGTCATCA TTGACCAGCT GCCCGACCTG ATGGGGCTCA AGCTGTGAA TGTGGCCAAG     1920

GTCGTCGGAA CCAACCCGTG TGCGGACAGG AACGGGGGGT GCAGCCACCT GTGCTTCTTC    1980

ACACCCCACG CAACCCGGTG TGGCTGCCCC ATCGGCCTGG AGCTGCTGAG TGACATGAAG    2040

ACCTGCATGT GCCTGAGGCC TTCTTGGTCT TCACCAGCAG AGCCGCCATC CACAGGATCT    2100

CCCTCGAGAC CAATAACAAC GACGTGGCCA TCCCGCTCAC GGGCGTCAAG GAGGCCTCAG    2160

CCCTGGACTT TGATGTGTCC AACAACCACA TCTACTGGAC AGACGTCAGC CTGAAGACCA    2220

TCAGCCGCGC CTTCATGAAC GGGAGCTCGG TGGAGCACGT GGTGGAGTTT GGCCTTGACT    2280

ACCCCGAGGG CATGGCCGTT GACTGGATGG CAAGAACCT CTACTGGGCC GACACTGGGA     2340

CCAACAGAAT CGAAGTGGCG CGGCTGGACG GGCAGTTCCG GCAAGTCCTC GTGTGGAGGG    2400

ACTTGGACAA CCCGAGGTCG CTGGCCCTGG ATCCCACCAA GGGCTACATC TACTGGACCG    2460

AGTGGGGCGG CAAGCCGAGG ATCGTGCGGG CCTTCATGGA CGGGACCAAC TGCATGACGC    2520

TGGTGGACAA GGTGGGCCGG GCCAACGACC TCACCATTGA CTACGCTGAC CAGCGCCTCT    2580

ACTGGACCGA CCTGGACACC AACATGATCG AGTCGTCCAA CATGCTGGGT CAGGAGCGGG    2640

TCGTGATTGC CGACGATCTC CCGCACCCGT TCGGTCTGAC GCAGTACAGC GATTATATCT    2700

ACTGGACAGA CTGGAATCTG CACAGCATTG AGCGGGCCGA CAAGACTAGC GGCCGGAACC    2760

GCACCCTCAT CCAGGGCCAC CTGGACTTCG TGATGGACAT CCTGGTGTTC CACTCCTCCC    2820

GCCAGGATGG CCTCAATGAC TGTATGCACA ACAACGGGCA GTGTGGGCAG CTGTGCCTTG    2880

CCATCCCCGG CGGCCACCGC TGCGGCTGCG CCTCACACTA CACCCTGGAC CCCAGCAGCC    2940

GCAACTGCAG CCCGCCCACC ACCTTCTTGC TGTTCAGCCA GAAATCTGCC ATCAGTCGGA    3000

TGATCCCGGA CGACCAGCAC AGCCCGGATC TCATCCTGCC CCTGCATGGA CTGAGGAACG    3060

TCAAAGCCAT CGACTATGAC CCACTGGACA AGTTCATCTA CTGGGTGGAT GGGCGCCAGA    3120

ACATCAAGCG AGCCAAGGAC GACGGGACCC AGCCCTTTGT TTTGACCTCT CTGAGCCAAG    3180

GCCAAAACCC AGACAGGCAG CCCCACGACC TCAGCATCGA CATCTACAGC CGGACACTGT    3240

TCTGGACGTG CGAGGCCACC AATACCATCA ACGTCCACAG GCTGAGCGGG AAGCCATGG    3300

GGGTGGTGCT GCGTGGGGAC CGCGACAAGC CCAGGGCCAT CGTCGTCAAC GCGGAGCGAG    3360

GGTACCTGTA CTTCACCAAC ATGCAGGACC GGGCAGCCAA GATCGAACGC GCAGCCCTGG    3420

ACGGCACCGA GCGCGAGGTC CTCTTCACCA CCGGCCTCAT CCGCCCTGTG GCCCTGGTGG    3480

TAGACAACAC ACTGGGCAAG CTGTTCTGGG TGGACGCGGA CCTGAAGCGC ATTGAGAGCT    3540

GTGACCTGTC AGGGGCCAAC CGCCTGACCC TGGAGGACGC CAACATCGTG CAGCCTCTGG    3600

GCCTGACCAT CCTTGGCAAG CATCTCTACT GGATCGACCG CCAGCAGCAG ATGATCGAGC    3660

GTGTGGAGAA GACCACCGGG GACAAGCGGA CTCGCATCCA GGGCCGTGTC GCCCACCTCA    3720

CTGGCATCCA TGCAGTGGAG GAAGTCAGCC TGGAGGAGTT CTCAGCCCAC CCATGTGCCC    3780
```

-continued

| | |
|---|---|
| GTGACAATGG TGGCTGCTCC CACATCTGTA TTGCCAAGGG TGATGGGACA CCACGGTGCT | 3840 |
| CATGCCCAGT CCACCTCGTG CTCCTGCAGA ACCTGCTGAC CTGTGGAGAG CCGCCCACCT | 3900 |
| GCTCCCCGGA CCAGTTTGCA TGTGCCACAG GGGAGATCGA CTGTATCCCC GGGGCCTGGC | 3960 |
| GCTGTGACGG CTTTCCCGAG TGCGATGACC AGAGCGACGA GGAGGGCTGC CCCGTGTGCT | 4020 |
| CCGCCGCCCA GTTCCCCTGC GCGCGGGGTC AGTGTGTGGA CCTGCGCCTG CGCTGCGACG | 4080 |
| GCGAGGCAGA CTGTCAGGAC CGCTCAGACA GGCGGACTGT GACGCCATCT GCCTGCCCAA | 4140 |
| CCAGTTCCGG TGTGCGAGCG GCCAGTGTGT CCTCATCAAA CAGCAGTGCG ACTCCTTCCC | 4200 |
| CGACTGTATC GACGGCTCCG ACGAGCTCAT GTGTGAAATC ACCAAGCCGC CCTCAGACGA | 4260 |
| CAGCCCGGCC CACAGCAGTG CCATCGGGCC CGTCATTGGC ATCATCCTCT CTCTCTTCGT | 4320 |
| CATGGGTGGT GTCTATTTTG TGTGCCAGCG CGTGGTGTGC CAGCGCTATG CGGGGGCCAA | 4380 |
| CGGGCCCTTC CCGCACGAGT ATGTCAGCGG GACCCCGCAC GTGCCCCTCA ATTTCATAGC | 4440 |
| CCCGGGCGGT TCCCAGCATG GCCCCTTCAC AGGCATCGCA TGCGGAAAGT CCATGATGAG | 4500 |
| CTCCGTGAGC CTGATGGGGG GCCGGGGCGG GGTGCCCCTC TACGACCGGA ACCACGTCAC | 4560 |
| AGGGGCCTCG TCCAGCAGCT CGTCCAGCAC GAAGGCCACG CTGTACCCGC CGATCCTGAA | 4620 |
| CCCGCCGCCC TCCCCGGCCA CGGACCCCTC CCTGTACAAC ATGGACATGT TCTACTCTTC | 4680 |
| AAACATTCCG GCCACTGTGA GACCGTACAG GCCCTACATC ATTCGAGGAA TGGCGCCCCC | 4740 |
| GACGACGCCC TGCAGCACCG ACGTGTGTGA CAGCGACTAC AGCGCCAGCC GCTGGAAGGC | 4800 |
| CAGCAAGTAC TACCTGGATT TGAACTCGGA CTCAGACCCC TATCCACCCC CACCCACGCC | 4860 |
| CCACAGCCAG TACCTGTCGG CGGAGGACAG CTGCCCGCCC TCGCCCGCCA CCGAGAGGAG | 4920 |
| CTACTTCCAT CTCTTCCCGC CCCCTCCGTC CCCCTGCACG GACTCATCCT GACCTCGGCC | 4980 |
| GGGCCACTCT GGCTTCTCTG TGCCCCTGTA AATAGTTTTA AATATGAACA AAGAAAAAAA | 5040 |
| TATATTTTAT GATTTAAAAA ATAAATATAA TTGGGATTTT AAAAACATGA GAAATGTGAA | 5100 |
| CTGTGATGGG GTGGGCAGGG CTGGGAGAAC TTTGTACAGT GGAACAAATA TTTATAAACT | 5160 |
| TAATTT | 5166 |

(2) INFORMATION FOR SEQ ID NO:24:

(i) SEQUENCE CHARACTERISTICS:
        (A) LENGTH: 4351 base pairs
        (B) TYPE: nucleic acid
        (C) STRANDEDNESS: single
        (D) TOPOLOGY: linear (xi) SEQUENCE DESCRIPTION: SEQ ID NO:24:

| | |
|---|---|
| ATGTACTGGA CAGACTGGGG TGAGACGCCC CGGATTGAGC GGGCAGGGAT GGATGGCAGC | 60 |
| ACCCGGAAGA TCATTGTGGA CTCGGACATT TACTGGCCCA ATGGACTGAC CATCGACCTG | 120 |
| GAGGAGCAGA AGCTCTACTG GGCTGACGCC AAGCTCAGCT TCATCCACCG TGCCAACCTG | 180 |
| GACGGCTCGT TCCGGCAGAA GGTGGTGGAG GGCAGCCTGA CGCACCCCTT CGCCCTGACG | 240 |
| CTCTCCGGGG ACACTCTGTA CTGGACAGAC TGGCAGACCC GCTCCATCCA TGCCTGCAAC | 300 |
| AAGCGCACTG GGGGAAGAG GAAGGAGATC CTGAGTGCCC TCTACTCACC CATGGACATC | 360 |
| CAGGTGCTGA GCCAGGAGCG GCAGCCTTTC TTCCACACTC GCTGTGAGGA GGACAATGGC | 420 |
| GGCTGCTCCC ACCTGTGCCT GCTGTCCCCA AGCGAGCCTT CTACACATG CGCCTGCCCC | 480 |
| ACGGGTGTGC AGCTGCAGGA CAACGGCAGG ACGTGTAAGG CAGGAGCCGA GGAGGTGCTG | 540 |
| CTGCTGGCCC GGCGGACGGA CCTACGGAGG ATCTCGCTGG ACACGCCGGA CTTTACCGAC | 600 |

-continued

| | |
|---|---|
| ATCGTGCTGC AGGTGGACGA CATCCGGCAC GCCATTGCCA TCGACTACGA CCCGCTAGAG | 660 |
| GGCTATGTCT ACTGGACAGA TGACGAGGTG CGGGCCATCC GCAGGGCGTA CCTGGACGGG | 720 |
| TCTGGGGCGC AGACGCTGGT CAACACCGAG ATCAACGACC CCGATGGCAT CGCGGTCGAC | 780 |
| TGGGTGGCCC GAAACCTCTA CTGGACCGAC ACGGGCACGG ACCGCATCGA GGTGACGCGC | 840 |
| CTCAACGGCA CCTCCCGCAA GATCCTGGTG TCGGAGGACC TGGACGAGCC CCGAGCCATC | 900 |
| GCACTGCACC CCGTGATGGG CCTCATGTAC TGGACAGACT GGGGAGAGAA CCCTAAAATC | 960 |
| GAGTGTGCCA ACTTGGATGG GCAGGAGCGG CGTGTGCTGG TCAATGCCTC CCTCGGGTGG | 1020 |
| CCCAACGGCC TGGCCCTGGA CCTGCAGGAG GGGAAGCTCT ACTGGGGAGA CGCCAAGACA | 1080 |
| GACAAGATCG AGGTGATCAA TGTTGATGGG ACGAAGAGGC GGACCCTCCT GGAGGACAAG | 1140 |
| CTCCCGCACA TTTTCGGGTT CACGCTGCTG GGGGACTTCA TCTACTGGAC TGACTGGCAG | 1200 |
| CGCCGCAGCA TCGAGCGGGT GCACAAGGTC AAGGCCAGCC GGGACGTCAT CATTGACCAG | 1260 |
| CTGCCCGACC TGATGGGGCT CAAAGCTGTG AATGTGGCCA AGGTCGTCGG AACCAACCCG | 1320 |
| TGTGCGGACA GGAACGGGGG GTGCAGCCAC CTGTGCTTCT TCACACCCCA CGCAACCCGG | 1380 |
| TGTGGCTGCC CCATCGGCCT GGAGCTGCTG AGTGACATGA AGACCTGCAT CGTGCCTGAG | 1440 |
| GCCTTCTTGG TCTTCACCAG CAGAGCCGCC ATCCACAGGA TCTCCCTCGA GACCAATAAC | 1500 |
| AACGACGTGG CCATCCCGCT CACGGGCGTC AAGGAGGCCT CAGCCCTGGA CTTTGATGTG | 1560 |
| TCCAACAACC ACATCTACTG GACAGACGTC AGCCTGAAGA CCATCAGCCG CGCCTTCATG | 1620 |
| AACGGGAGCT CGGTGGAGCA CGTGGTGGAG TTTGGCCTTG ACTACCCCGA GGGCATGGCC | 1680 |
| GTTGACTGGA TGGGCAAGAA CCTCTACTGG GCCGACACTG GACCAACAG AATCGAAGTG | 1740 |
| GCGCGGCTGG ACGGGCAGTT CCGGCAAGTC CTCGTGTGGA GGGACTTGGA CAACCCGAGG | 1800 |
| TCGCTGGCCC TGGATCCCAC CAAGGGCTAC ATCTACTGGA CCGAGTGGGG CGGCAAGCCG | 1860 |
| AGGATCGTGC GGGCCTTCAT GGACGGGACC AACTGCATGA CGCTGGTGGA CAAGGTGGGC | 1920 |
| CGGGCCAACG ACCTCACCAT TGACTACGCT GACCAGCGCC TCTACTGGAC CGACCTGGAC | 1980 |
| ACCAACATGA TCGAGTCGTC CAACATGCTG GGTCAGGAGC GGGTCGTGAT TGCCGACGAT | 2040 |
| CTCCCGCACC GTTCGGTCTG ACGCAGTACA GCGATTATAT CTACTGGACA GACTGGAATC | 2100 |
| TGCACAGCAT TGAGCGGGCC GACAAGACTA GCGGCCGGAA CCGCACCCTC ATCCAGGGCC | 2160 |
| ACCTGGACTT CGTGATGGAC ATCCTGGTGT TCCACTCCTC CCGCCAGGAT GGCCTCAATG | 2220 |
| ACTGTATGCA CAACAACGGG CAGTGTGGGC AGCTGTGCCT TGCCATCCCC GGCGGCCACC | 2280 |
| GCTGCGGCTG CGCCTCACAC TACACCCTGG ACCCCAGCAG CCGCAACTGC AGCCCGCCCA | 2340 |
| CCACCTTCTT GCTGTTCAGC CAGAAATCTG CCATCAGTCG GATGATCCCG GACGACCAGC | 2400 |
| ACAGCCCGGA TCTCATCCTG CCCCTGCATG GACTGAGGAA CGTCAAAGCC ATCGACTATG | 2460 |
| ACCCACTGGA CAAGTTCATC TACTGGGTGG ATGGGCGCCA GAACATCAAG CGAGCCAAGG | 2520 |
| ACGACGGGAC CCAGCCCTTT GTTTTGACCT CTCTGAGCCA AGGCCAAAAC CCAGACAGGC | 2580 |
| AGCCCCACGA CCTCAGCATC GACATCTACA GCCGGACACT GTTCTGGACG TGCGAGGCCA | 2640 |
| CCAATACCAT CAACGTCCAC AGGCTGAGCG GGGAAGCCAT GGGGGTGGTG CTGCGTGGGG | 2700 |
| ACCGCGACAA GCCCAGGGCC ATCGTCGTCA ACGCGGAGCG AGGGTACCTG TACTTCACCA | 2760 |
| ACATGCAGGA CCGGGCAGCC AAGATCGAAC GCGCAGCCCT GGACGGCACC GAGCGCGAGG | 2820 |
| TCCTCTTCAC CACCGGCCTC ATCCGCCCTG TGGCCCTGGT GGTAGACAAC ACACTGGGCA | 2880 |
| AGCTGTTCTG GGTGGACGCG GACCTGAAGC GCATTGAGAG CTGTGACCTG TCAGGGGCCA | 2940 |
| ACCGCCTGAC CCTGGAGGAC GCCAACATCG TGCAGCCTCT GGGCCTGACC ATCCTTGGCA | 3000 |

```
AGCATCTCTA CTGGATCGAC CGCCAGCAGC AGATGATCGA GCGTGTGGAG AAGACCACCG    3060

GGGACAAGCG GACTCGCATC CAGGGCCGTG TCGCCCACCT CACTGGCATC CATGCAGTGG    3120

AGGAAGTCAG CCTGGAGGAG TTCTCAGCCC ACCCATGTGC CCGTGACAAT GGTGGCTGCT    3180

CCCACATCTG TATTGCCAAG GGTGATGGGA CACCACGGTG CTCATGCCCA GTCCACCTCG    3240

TGCTCCTGCA GAACCTGCTG ACCTGTGGAG AGCCGCCCAC CTGCTCCCCG GACCAGTTTG    3300

CATGTGCCAC AGGGGAGATC GACTGTATCC CCGGGGCCTG GCGCTGTGAC GGCTTTCCCG    3360

AGTGCGATGA CCAGAGCGAC GAGGAGGGCT GCCCCGTGTG CTCCGCCGCC CAGTTCCCCT    3420

GCGCGCGGGG TCAGTGTGTG GACCTGCGCC TGCGCTGCGA CGGCGAGGCA GACTGTCAGG    3480

ACCGCTCAGA CGAGGCGGAC TGTGACGCCA TCTGCCTGCC CAACCAGTTC CGGTGTGCGA    3540

GCGGCCAGTG TGTCCTCATC AAACAGCAGT GCGACTCCTT CCCCGACTGT ATCGACGGCT    3600

CCGACGAGCT CATGTGTGAA ATCACCAAGC CGCCCTCAGA CGACAGCCCG GCCCACAGCA    3660

GTGCCATCGG GCCCGTCATT GGCATCATCC TCTCTCTCTT CGTCATGGGT GGTGTCTATT    3720

TTGTGTGCCA GCGCGTGGTG TGCCAGCGCT ATGCGGGGGC CAACGGGCCC TTCCCGCACG    3780

AGTATGTCAG CGGGACCCCG CACGTGCCCC TCAATTTCAT AGCCCCGGGC GGTTCCCAGC    3840

ATGGCCCCTT CACAGGCATC GCATGCGGAA AGTCCATGAT GAGCTCCGTG AGCCTGATGG    3900

GGGGCCGGGG CGGGGTGCCC CTCTACGACC GGAACCACGT CACAGGGGCC TCGTCCAGCA    3960

GCTCGTCCAG CACGAAGGCC ACGCTGTACC CGCCGATCCT GAACCCGCCG CCCTCCCCGG    4020

CCACGGACCC CTCCCTGTAC AACATGGACA TGTTCTACTC TTCAAACATT CCGGCCACTG    4080

TGAGACCGTA CAGGCCCTAC ATCATTCGAG AATGGCGCCC CCGACGACGC CCTGCAGCAC    4140

CGACGTGTGT GACAGCGACT ACAGCGCCAG CCGCTGGAAG GCCAGCAAGT ACTACCTGGA    4200

TTTGAACTCG GACTCAGACC CCTATCCACC CCCACCCACG CCCCACAGCC AGTACCTGTC    4260

GGCGGAGGAC AGCTGCCCGC CCTCGCCCGC CACCGAGAGG AGCTACTTCC ATCTCTTCCC    4320

GCCCCCTCCG TCCCCCTGCA CGGACTCATC C                                  4351

(2) INFORMATION FOR SEQ ID NO:25:

(i) SEQUENCE CHARACTERISTICS:
        (A) LENGTH: 1451 amino acids
        (B) TYPE: amino acid
        (D) TOPOLOGY: linear (xi) SEQUENCE DESCRIPTION: SEQ ID NO:25:

Met Tyr Trp Thr Asp Trp Gly Glu Thr Pro Arg Ile Glu Arg Ala Gly
1               5                   10                  15

Met Asp Gly Ser Thr Arg Lys Ile Ile Val Asp Ser Asp Ile Tyr Trp
            20                  25                  30

Pro Asn Gly Leu Thr Ile Asp Leu Glu Glu Gln Lys Leu Tyr Trp Ala
        35                  40                  45

Asp Ala Lys Leu Ser Phe Ile His Arg Ala Asn Leu Asp Gly Ser Phe
    50                  55                  60

Arg Gln Lys Val Val Glu Gly Ser Leu Thr His Pro Phe Ala Leu Thr
65                  70                  75                  80

Leu Ser Gly Asp Thr Leu Tyr Trp Thr Asp Trp Gln Thr Arg Ser Ile
                85                  90                  95

His Ala Cys Asn Lys Arg Thr Gly Gly Lys Arg Lys Glu Ile Leu Ser
            100                 105                 110

Ala Leu Tyr Ser Pro Met Asp Ile Gln Val Leu Ser Gln Glu Arg Gln
```

-continued

```
            115                 120                 125
    Pro Phe Phe His Thr Arg Cys Glu Glu Asp Asn Gly Gly Cys Ser His
            130                 135                 140
    Leu Cys Leu Leu Ser Pro Ser Glu Pro Phe Tyr Thr Cys Ala Cys Pro
    145                 150                 155                 160
    Thr Gly Val Gln Leu Gln Asp Asn Gly Arg Thr Cys Lys Ala Gly Ala
                        165                 170                 175
    Glu Glu Val Leu Leu Leu Ala Arg Arg Thr Asp Leu Arg Arg Ile Ser
                        180                 185                 190
    Leu Asp Thr Pro Asp Phe Thr Asp Ile Val Leu Gln Val Asp Asp Ile
                        195                 200                 205
    Arg His Ala Ile Ala Ile Asp Tyr Asp Pro Leu Glu Gly Tyr Val Tyr
            210                 215                 220
    Trp Thr Asp Asp Glu Val Arg Ala Ile Arg Arg Ala Tyr Leu Asp Gly
    225                 230                 235                 240
    Ser Gly Ala Gln Thr Leu Val Asn Thr Glu Ile Asn Asp Pro Asp Gly
                        245                 250                 255
    Ile Ala Val Asp Trp Val Ala Arg Asn Leu Tyr Trp Thr Asp Thr Gly
                        260                 265                 270
    Thr Asp Arg Ile Glu Val Thr Arg Leu Asn Gly Thr Ser Arg Lys Ile
                        275                 280                 285
    Leu Val Ser Glu Asp Leu Asp Glu Pro Arg Ala Ile Ala Leu His Pro
            290                 295                 300
    Val Met Gly Leu Met Tyr Trp Thr Asp Trp Gly Glu Asn Pro Lys Ile
    305                 310                 315                 320
    Glu Cys Ala Asn Leu Asp Gly Gln Glu Arg Arg Val Leu Val Asn Ala
                        325                 330                 335
    Ser Leu Gly Trp Pro Asn Gly Leu Ala Leu Asp Leu Gln Glu Gly Lys
                        340                 345                 350
    Leu Tyr Trp Gly Asp Ala Lys Thr Asp Lys Ile Glu Val Ile Asn Val
                        355                 360                 365
    Asp Gly Thr Lys Arg Arg Thr Leu Leu Glu Asp Lys Leu Pro His Ile
            370                 375                 380
    Phe Gly Phe Thr Leu Leu Gly Asp Phe Ile Tyr Trp Thr Asp Trp Gln
    385                 390                 395                 400
    Arg Arg Ser Ile Glu Arg Val His Lys Val Lys Ala Ser Arg Asp Val
                        405                 410                 415
    Ile Ile Asp Gln Leu Pro Asp Leu Met Gly Leu Lys Ala Val Asn Val
                        420                 425                 430
    Ala Lys Val Val Gly Thr Asn Pro Cys Ala Asp Arg Asn Gly Gly Cys
                        435                 440                 445
    Ser His Leu Cys Phe Phe Thr Pro His Ala Thr Arg Cys Gly Cys Pro
            450                 455                 460
    Ile Gly Leu Glu Leu Leu Ser Asp Met Lys Thr Cys Ile Val Pro Glu
    465                 470                 475                 480
    Ala Phe Leu Val Phe Thr Ser Arg Ala Ala Ile His Arg Ile Ser Leu
                        485                 490                 495
    Glu Thr Asn Asn Asn Asp Val Ala Ile Pro Leu Thr Gly Val Lys Glu
                        500                 505                 510
    Ala Ser Ala Leu Asp Phe Asp Val Ser Asn Asn His Ile Tyr Trp Thr
                        515                 520                 525
    Asp Val Ser Leu Lys Thr Ile Ser Arg Ala Phe Met Asn Gly Ser Ser
            530                 535                 540
```

-continued

Val Glu His Val Val Glu Phe Gly Leu Asp Tyr Pro Glu Gly Met Ala
545                 550                 555                 560

Val Asp Trp Met Gly Lys Asn Leu Tyr Trp Ala Asp Thr Gly Thr Asn
            565                 570                 575

Arg Ile Glu Val Ala Arg Leu Asp Gly Gln Phe Arg Gln Val Leu Val
        580                 585                 590

Trp Arg Asp Leu Asp Asn Pro Arg Ser Leu Ala Leu Asp Pro Thr Lys
        595                 600                 605

Gly Tyr Ile Tyr Trp Thr Glu Trp Gly Gly Lys Pro Arg Ile Val Arg
610                 615                 620

Ala Phe Met Asp Gly Thr Asn Cys Met Thr Leu Val Asp Lys Val Gly
625                 630                 635                 640

Arg Ala Asn Asp Leu Thr Ile Asp Tyr Ala Asp Gln Arg Leu Tyr Trp
            645                 650                 655

Thr Asp Leu Asp Thr Asn Met Ile Glu Ser Ser Asn Met Leu Gly Gln
            660                 665                 670

Glu Arg Val Val Ile Ala Asp Asp Leu Pro His Pro Phe Gly Leu Thr
        675                 680                 685

Gln Tyr Ser Asp Tyr Ile Tyr Trp Thr Asp Trp Asn Leu His Ser Ile
690                 695                 700

Glu Arg Ala Asp Lys Thr Ser Gly Arg Asn Arg Thr Leu Ile Gln Gly
705                 710                 715                 720

His Leu Asp Phe Val Met Asp Ile Leu Val Phe His Ser Ser Arg Gln
            725                 730                 735

Asp Gly Leu Asn Asp Cys Met His Asn Asn Gly Gln Cys Gly Gln Leu
            740                 745                 750

Cys Leu Ala Ile Pro Gly Gly His Arg Cys Gly Cys Ala Ser His Tyr
        755                 760                 765

Thr Leu Asp Pro Ser Ser Arg Asn Cys Ser Pro Pro Thr Thr Phe Leu
        770                 775                 780

Leu Phe Ser Gln Lys Ser Ala Ile Ser Arg Met Ile Pro Asp Asp Gln
785                 790                 795                 800

His Ser Pro Asp Leu Ile Leu Pro Leu His Gly Leu Arg Asn Val Lys
            805                 810                 815

Ala Ile Asp Tyr Asp Pro Leu Asp Lys Phe Ile Tyr Trp Val Asp Gly
            820                 825                 830

Arg Gln Asn Ile Lys Arg Ala Lys Asp Asp Gly Thr Gln Pro Phe Val
        835                 840                 845

Leu Thr Ser Leu Ser Gln Gly Gln Asn Pro Asp Arg Gln Pro His Asp
850                 855                 860

Leu Ser Ile Asp Ile Tyr Ser Arg Thr Leu Phe Trp Thr Cys Glu Ala
865                 870                 875                 880

Thr Asn Thr Ile Asn Val His Arg Leu Ser Gly Glu Ala Met Gly Val
            885                 890                 895

Val Leu Arg Gly Asp Arg Asp Lys Pro Arg Ala Ile Val Val Asn Ala
            900                 905                 910

Glu Arg Gly Tyr Leu Tyr Phe Thr Asn Met Gln Asp Arg Ala Ala Lys
        915                 920                 925

Ile Glu Arg Ala Ala Leu Asp Gly Thr Glu Arg Glu Val Leu Phe Thr
        930                 935                 940

Thr Gly Leu Ile Arg Pro Val Ala Leu Val Val Asp Asn Thr Leu Gly
945                 950                 955                 960

-continued

```
Lys Leu Phe Trp Val Asp Ala Asp Leu Lys Arg Ile Glu Ser Cys Asp
                965                 970                 975
Leu Ser Gly Ala Asn Arg Leu Thr Leu Glu Asp Ala Asn Ile Val Gln
            980                 985                 990
Pro Leu Gly Leu Thr Ile Leu Gly Lys His Leu Tyr Trp Ile Asp Arg
        995                1000                1005
Gln Gln Gln Met Ile Glu Arg Val Glu Lys Thr Thr Gly Asp Lys Arg
    1010                1015                1020
Thr Arg Ile Gln Gly Arg Val Ala His Leu Thr Gly Ile His Ala Val
1025                1030                1035                1040
Glu Glu Val Ser Leu Glu Glu Phe Ser Ala His Pro Cys Ala Arg Asp
            1045                1050                1055
Asn Gly Gly Cys Ser His Ile Cys Ile Ala Lys Gly Asp Gly Thr Pro
            1060                1065                1070
Arg Cys Ser Cys Pro Val His Leu Val Leu Leu Gln Asn Leu Leu Thr
        1075                1080                1085
Cys Gly Glu Pro Pro Thr Cys Ser Pro Asp Gln Phe Ala Cys Ala Thr
    1090                1095                1100
Gly Glu Ile Asp Cys Ile Pro Gly Ala Trp Arg Cys Asp Gly Phe Pro
1105                1110                1115                1120
Glu Cys Asp Asp Gln Ser Asp Glu Glu Gly Cys Pro Val Cys Ser Ala
            1125                1130                1135
Ala Gln Phe Pro Cys Ala Arg Gly Gln Cys Val Asp Leu Arg Leu Arg
            1140                1145                1150
Cys Asp Gly Glu Ala Asp Cys Gln Asp Arg Ser Asp Glu Ala Asp Cys
        1155                1160                1165
Asp Ala Ile Cys Leu Pro Asn Gln Phe Arg Cys Ala Ser Gly Gln Cys
    1170                1175                1180
Val Leu Ile Lys Gln Gln Cys Asp Ser Phe Pro Asp Cys Ile Asp Gly
1185                1190                1195                1200
Ser Asp Glu Leu Met Cys Glu Ile Thr Lys Pro Pro Ser Asp Ser
            1205                1210                1215
Pro Ala His Ser Ser Ala Ile Gly Pro Val Ile Gly Ile Ile Leu Ser
            1220                1225                1230
Leu Phe Val Met Gly Gly Val Tyr Phe Val Cys Gln Arg Val Val Cys
        1235                1240                1245
Gln Arg Tyr Ala Gly Ala Asn Gly Pro Phe Pro His Glu Tyr Val Ser
    1250                1255                1260
Gly Thr Pro His Val Pro Leu Asn Phe Ile Ala Pro Gly Gly Ser Gln
1265                1270                1275                1280
His Gly Pro Phe Thr Gly Ile Ala Cys Gly Lys Ser Met Met Ser Ser
            1285                1290                1295
Val Ser Leu Met Gly Gly Arg Gly Gly Val Pro Leu Tyr Asp Arg Asn
            1300                1305                1310
His Val Thr Gly Ala Ser Ser Ser Ser Ser Ser Thr Lys Ala Thr
        1315                1320                1325
Leu Tyr Pro Pro Ile Leu Asn Pro Pro Ser Pro Ala Thr Asp Pro
    1330                1335                1340
Ser Leu Tyr Asn Met Asp Met Phe Tyr Ser Ser Asn Ile Pro Ala Thr
1345                1350                1355                1360
Val Arg Pro Tyr Arg Pro Tyr Ile Ile Arg Gly Met Ala Pro Pro Thr
            1365                1370                1375
Thr Pro Cys Ser Thr Asp Val Cys Asp Ser Asp Tyr Ser Ala Ser Arg
```

-continued

```
                 1380              1385              1390
Trp Lys Ala Ser Lys Tyr Tyr Leu Asp Leu Asn Ser Asp Ser Asp Pro
            1395              1400              1405

Tyr Pro Pro Pro Thr Pro His Ser Gln Tyr Leu Ser Ala Glu Asp
            1410              1415              1420

Ser Cys Pro Pro Ser Pro Ala Thr Glu Arg Ser Tyr Phe His Leu Phe
1425              1430              1435              1440

Pro Pro Pro Pro Ser Pro Cys Thr Asp Ser Ser
                 1445              1450
```

(2) INFORMATION FOR SEQ ID NO:26:

(i) SEQUENCE CHARACTERISTICS:
        (A) LENGTH: 5125 base pairs
        (B) TYPE: nucleic acid
        (C) STRANDEDNESS: single
        (D) TOPOLOGY: linear (xi) SEQUENCE DESCRIPTION: SEQ ID NO:26:

```
TAAATGGCTT GGCAAAGGGA GTTCATTCCT TTTAGCGCTT CCATCTTCTG CAGTGAGAGG      60

ACACCGCATT CTTCTTCTCC AGAGGATGCA GCAGCAAGGC GCCATCTTGA AACCAGAGAC     120

CAAACCAACC AGCAACTTCG TCTTGAACTT CCCAGCCTCC ACAACTCCTC GCCGCTCCTG     180

CTATTTGCCA ACCGCCGGGA CGTACGGCTG GTGGACGCCG GCGGAGTCAA GCTGGAGTCC     240

ACCATCGTGG TCAGCGGCCT GGAGGATGCG GCCGCAGTGG ACTTCCAGTT TTCCAAGGGA     300

GCCGTGTACT GGACAGACGT GAGCGAGGAG GCCATCAAGC AGACCTACCT GAACCAGACG     360

GGGGCCGCCG TGCAGAACGT GGTCATCTCC GGCCTGGTCT CTCCCGACGG CCTCGCCTGC     420

GACTGGGTGG GCAAGAAGCT GTACTGGACG GACTCAGAGA CCAACCGCAT CGAGGTGGCC     480

AACCTCAATG GCACATCCCG GAAGGTGCTC TTCTGGCAGG ACCTTGACCA GCCGAGGGCC     540

ATCGCCTTGG ACCCCGCTCA CGGGTACATG TACTGGACAG ACTGGGGTGA GACGCCCCGG     600

ATTGAGCGGG CAGGGATGGA TGGCAGCACC CGGAAGATCA TTGTGGACTC GGACATTTAC     660

TGGCCCAATG GACTGACCAT CGACCTGGAG GAGCAGAAGC TCTACTGGGC TGACGCCAAG     720

CTCAGCTTCA TCCACCGTGC CAACCTGGAC GGCTCGTTCC GGCAGAAGGT GGTGGAGGGC     780

AGCCTGACGC ACCCCTTCGC CCTGACGCTC TCCGGGGACA CTCTGTACTG GACAGACTGG     840

CAGACCCGCT CCATCCATGC CTGCAACAAG CGCACTGGGG GGAAGAGGAA GGAGATCCTG     900

AGTGCCCTCT ACTCACCCAT GGACATCCAG GTGCTGAGCC AGGAGCGGCA GCCTTTCTTC     960

CACACTCGCT GTGAGGAGGA CAATGGCGGC TGCTCCCACC TGTGCCTGCT GTCCCCAAGC    1020

GAGCCTTTCT ACACATGCGC CTGCCCCACG GGTGTGCAGC TGCAGGACAA CGGCAGGACG    1080

TGTAAGGCAG GAGCCGAGGA GGTGCTGCTG CTGGCCCGGC GGACGGACCT ACGGAGGATC    1140

TCGCTGGACA CGCCGGACTT TACCGACATC GTGCTGCAGG TGGACGACAT CCGGCACGCC    1200

ATTGCCATCG ACTACGACCC GCTAGAGGGC TATGTCTACT GGACAGATGA CGAGGTGCGG    1260

GCCATCCGCA GGGCGTACCT GGACGGGTCT GGGGCGCAGA CGCTGGTCAA CACCGAGATC    1320

AACGACCCCG ATGGCATCGC GGTCGACTGG GTGGCCCGAA ACCTCTACTG GACCGACACG    1380

GGCACGGACC GCATCGAGGT GACGCGCCTC AACGGCACCT CCCGCAAGAT CCTGGTGTCG    1440

GAGGACCTGG ACGAGCCCCG AGCCATCGCA CTGCACCCCG TGATGGGCCT CATGTACTGG    1500

ACAGACTGGG GAGAGAACCC TAAAATCGAG TGTGCCAACT GGATGGGCA GGAGCGGCGT    1560

GTGCTGGTCA ATGCCTCCCT CGGGTGGCCC AACGGCCTGG CCCTGGACCT GCAGGAGGGG    1620
```

-continued

```
AAGCTCTACT GGGGAGACGC CAAGACAGAC AAGATCGAGG TGATCAATGT TGATGGGACG   1680
AAGAGGCGGA CCCTCCTGGA GGACAAGCTC CCGCACATTT TCGGGTTCAC GCTGCTGGGG   1740
GACTTCATCT ACTGGACTGA CTGGCAGCGC CGCAGCATCG AGCGGGTGCA CAAGGTCAAG   1800
GCCAGCCGGG ACGTCATCAT TGACCAGCTG CCCGACCTGA TGGGGCTCAA AGCTGTGAAT   1860
GTGGCCAAGG TCGTCGGAAC CAACCCGTGT GCGGACAGGA ACGGGGGGTG CAGCCACCTG   1920
TGCTTCTTCA CACCCCACGC AACCCGTGT GGCTGCCCCA TCGGCCTGGA GCTGCTGAGT   1980
GACATGAAGA CCTGCATCGT GCCTGAGGCC TTCTTGGTCT TCACCAGCAG AGCCGCCATC   2040
CACAGGATTC CCTCGAGACC AATAACAACG ACGTGGCCAT CCCGCTCACG GGCGTCAAGG   2100
AGGCCTCAGC CCTGGACTTT GATGTGTCCA ACAACCACAT CTACTGGACA GACGTCAGCC   2160
TGAAGACCAT CAGCCGCGCC TTCATGAACG GGAGCTCGGT GGAGCACGTG GTGGAGTTTG   2220
GCCTTGACTA CCCCGAGGGC ATGGCCGTTG ACTGGATGGG CAAGAACCTC TACTGGGCCG   2280
ACACTGGGAC CAACAGAATC GAAGTGGCGC GGCTGGACGG GCAGTTCCGG CAAGTCCTCG   2340
TGTGGAGGGA CTTGGACAAC CCGAGGTCGC TGGCCCTGGA TCCCACCAAG GGCTACATCT   2400
ACTGGACCGA GTGGGGCGGC AAGCCGAGGA TCGTGCGGGC CTTCATGGAC GGGACCAACT   2460
GCATGACGCT GGTGGACAAG GTGGGCCGGG CCAACGACCT CACCATTGAC TACGCTGACC   2520
AGCGCCTCTA CTGGACCGAC CTGGACACCA ACATGATCGA GTCGTCCAAC ATGCTGGGTC   2580
AGGAGCGGGT CGTGATTGCC GACGATCTCC CGCACCCGTT CGGTCTGACG CAGTACAGCG   2640
ATTATATCTA CTGGACAGAC TGGAATCTGC ACAGCATTGA GCGGGCCGAC AAGACTAGCG   2700
GCCGGAACCG CACCCTCATC CAGGGCCACC TGGACTTCGT GATGGACATC CTGGTGTTCC   2760
ACTCCTCCCG CCAGGATGGC CTCAATGACT GTATGCACAA CAACGGGCAG TGTGGGCAGC   2820
TGTGCCTTGC CATCCCCGGC GGCCACCGCT GCGGCTGCGC CTCACACTAC ACCCTGGACC   2880
CCAGCAGCCG CAACTGCAGC CCGCCCACCA CCTTCTTGCT GTTCAGCCAG AAATCTGCCA   2940
TCAGTCGGAT GATCCCGGAC GACCAGCACA GCCCGGATCT CATCCTGCCC CTGCATGGAC   3000
TGAGGAACGT CAAAGCCATC GACTATGACC CACTGGACAA GTTCATCTAC TGGGTGGATG   3060
GGCGCCAGAA CATCAAGCGA GCCAAGGACG ACGGGACCCA GCCCTTTGTT TTGACCTCTC   3120
TGAGCCAAGG CCAAAACCCA GACAGGCAGC CCCACGACCT CAGCATCGAC ATCTACAGCC   3180
GGACACTGTT CTGGACGTGC GAGGCCACCA ATACCATCAA CGTCCACAGG CTGAGCGGGG   3240
AAGCCATGGG GGTGGTGCTG CGTGGGGACC GCGACAAGCC CAGGGCCATC GTCGTCAACG   3300
CGGAGCGAGG GTACCTGTAC TTCACCAACA TGCAGGACCG GGCAGCCAAG ATCGAACGCG   3360
CAGCCCTGGA CGGCACCGAG CGCGAGGTCC TCTTCACCAC CGGCCTCATC CGCCCTGTGG   3420
CCCTGGTGGT AGACAACACA CTGGGCAAGC TGTTCTGGGT GGACGCGGAC CTGAAGCGCA   3480
TTGAGAGCTG TGACCTGTCA GGGGCCAACC GCCTGACCCT GGAGGACGCC AACATCGTGC   3540
AGCCTCTGGG CCTGACCATC CTTGGCAAGC ATCTCTACTG GATCGACCGC CAGCAGCAGA   3600
TGATCGAGCG TGTGGAGAAG ACCACCGGGG ACAAGCGGAC TCGCATCCAG GGCCGTGTCG   3660
CCCACCTCAC TGGCATCCAT GCAGTGGAGG AAGTCAGCCT GGAGGAGTTC TCAGCCCACC   3720
CATGTGCCCG TGACAATGGT GGCTGCTCCC ACATCTGTAT TGCCAAGGGT GATGGGACAC   3780
CACGGTGCTC ATGCCCAGTC CACCTCGTGC TCCTGCAGAA CCTGCTGACC TGTGGAGAGC   3840
CGCCCACCTG CTCCCCGGAC CAGTTTGCAT GTGCCACAGG GGAGATCGAC TGTATCCCCG   3900
GGGCCTGGCG CTGTGACGGC TTTCCCGAGT GCGATGACCA GAGCGACGAG GAGGGCTGCC   3960
CCGTGTGCTC CGCCGCCCAG TTCCCCTGCG CGCGGGGTCA GTGTGTGGAC CTGCGCCTGC   4020
```

```
GCTGCGACGG CGAGGCAGAC TGTCAGGACC GCTCAGACGA GGCGGACTGT GACGCCATCT    4080

GCCTGCCCAA CCAGTTCCGG TGTGCGAGCG GCAGTGTGTC CTCATCAAAC AGCAGTGCGA    4140

CTCCTTCCCC GACTGTATCG ACGGCTCCGA CGAGCTCATG TGTGAAATCA CCAAGCCGCC    4200

CTCAGACGAC AGCCCGGCCC ACAGCAGTGC CATCGGGCCC GTCATTGGCA TCATCCTCTC    4260

TCTCTTCGTC ATGGGTGGTG TCTATTTTGT GTGCCAGCGC GTGGTGTGCC AGCGCTATGC    4320

GGGGGCCAAC GGGCCCTTCC CGCACGAGTA TGTCAGCGGG ACCCCGCACG TGCCCCTCAA    4380

TTTCATAGCC CCGGGCGGTT CCCAGCATGG CCCCTTCACA GGCATCGCAT GCGGAAAGTC    4440

CATGATGAGC TCCGTGAGCC TGATGGGGGG CCGGGGCGGG GTGCCCCTCT ACGACCGGAA    4500

CCACGTCACA GGGGCCTCGT CCAGCAGCTC GTCCAGCACG AAGGCCACGC TGTACCCGCC    4560

GATCCTGAAC CCGCCGCCCT CCCCGGCCAC GGACCCCTCC CTGTACAACA TGGACATGTT    4620

CTACTCTTCA AACATTCCGG CCACTGCGAG ACCGTACAGG CCCTACATCA TTCGAGGAAT    4680

GGCGCCCCCG ACGACGCCCT GCAGCACCGA CGTGTGTGAC AGCGACTACA GCGCCAGCCG    4740

CTGGAAGGCC AGCAAGTACT ACCTGGATTT GAACTCGGAC TCAGACCCCT ATCCACCCCC    4800

ACCCACGCCC CACAGCCAGT ACCTGTCGGC GGAGGACAGC TGCCCGCCCT CGCCCGCCAC    4860

CGAGAGGAGC TACTTCCATC TCTTCCCGCC CCCTCCGTCC CCCTGCACGG ACTCATCCTG    4920

ACCTCGGCCG GGCCACTCTG GCTTCTCTGT GCCCCTGTAA ATAGTTTTAA ATATGAACAA    4980

AGAAAAAAAT ATATTTTATG ATTTAAAAAA TAAATATAAT TGGGATTTTA AAACATGAG    5040

AAATGTGAAC TGTGATGGGG TGGGCAGGGC TGGGAGAACT TTGTACAGTG GAACAAATAT    5100

TTATAAACTT AATTTTGTAA AACAG                                        5125

(2) INFORMATION FOR SEQ ID NO:27:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (xi) SEQUENCE DESCRIPTION: SEQ ID NO:27:

TAAAATGGCT TGGCAAAGGG AGTTCATTCC TTTTAGCGCT TCCATCTTCT GCAGTGAGAG      60

GACACCGCAT TCTTCTTCTC CAGAGGATGC AGCAGCAAGG CGCCATCTTG AAACCAGAGA     120

CCAAACCAAC CAGCAACTTC GTCTTGAACT TCCCAGCCTC CACAACT                   167

(2) INFORMATION FOR SEQ ID NO:28:

(i) SEQUENCE CHARACTERISTICS:
        (A) LENGTH: 4915 base pairs
        (B) TYPE: nucleic acid
        (C) STRANDEDNESS: single
        (D) TOPOLOGY: linear (xi) SEQUENCE DESCRIPTION: SEQ ID NO:28:

ATGGCTTGGC AAAGGGAGTT CATTCCTTTT AGCGCTTCCA TCTTCTGCAG TGAGAGGACA      60

CCGCATTCTT CTTCTCCAGA GGATGCAGCA GCAAGGCGCC ATCTTGAAAC CAGAGACCAA     120

ACCAACCAGC AACTTCGTCT TGAACTTCCC AGCCTCCACA ACTCCTCGCC GCTCCTGCTA     180

TTTGCCAACC GCCGGGACGT ACGGCTGGTG GACGCCGGCG GAGTCAAGCT GGAGTCCACC     240

ATCGTGGTCA GCGGCCTGGA GGATGCGGCC GCAGTGGACT TCCAGTTTTC CAAGGGAGCC     300

GTGTACTGGA CAGACGTGAG CGAGGAGGCC ATCAAGCAGA CCTACCTGAA CCAGACGGGG     360
```

```
GCCGCCGTGC AGAACGTGGT CATCTCCGGC CTGGTCTCTC CCGACGGCCT CGCCTGCGAC    420

TGGGTGGGCA AGAAGCTGTA CTGGACGGAC TCAGAGACCA ACCGCATCGA GGTGGCCAAC    480

CTCAATGGCA CATCCCGGAA GGTGCTCTTC TGGCAGGACC TTGACCAGCC GAGGGCCATC    540

GCCTTGGACC CCGCTCACGG GTACATGTAC TGGACAGACT GGGGTGAGAC GCCCCGGATT    600

GAGCGGGCAG GGATGGATGG CAGCACCCGG AAGATCATTG TGGACTCGGA CATTTACTGG    660

CCCAATGGAC TGACCATCGA CCTGGAGGAG CAGAAGCTCT ACTGGGCTGA CGCCAAGCTC    720

AGCTTCATCC ACCGTGCCAA CCTGGACGGC TCGTTCCGGC AGAAGGTGGT GGAGGGCAGC    780

CTGACGCACC CCTTCGCCCT GACGCTCTCC GGGGACACTC TGTACTGGAC AGACTGGCAG    840

ACCCGCTCCA TCCATGCCTG CAACAAGCGC ACTGGGGGGA AGAGGAAGGA GATCCTGAGT    900

GCCCTCTACT CACCCATGGA CATCCAGGTG CTGAGCCAGG AGCGGCAGCC TTTCTTCCAC    960

ACTCGCTGTG AGGAGGACAA TGGCGGCTGC TCCCACCTGT GCCTGCTGTC CCCAAGCGAG   1020

CCTTTCTACA CATGCGCCTG CCCCACGGGT GTGCAGCTGC AGGACAACGG CAGGACGTGT   1080

AAGGCAGGAG CCGAGGAGGT GCTGCTGCTG GCCCGGCGGA CGGACCTACG GAGGATCTCG   1140

CTGGACACGC CGGACTTTAC CGACATCGTG CTGCAGGTGG ACGACATCCG GCACGCCATT   1200

GCCATCGACT ACGACCCGCT AGAGGGCTAT GTCTACTGGA CAGATGACGA GGTGCGGGCC   1260

ATCCGCAGGG CGTACCTGGA CGGGTCTGGG GCGCAGACGC TGGTCAACAC CGAGATCAAC   1320

GACCCCGATG GCATCGCGGT CGACTGGGTG GCCCGAAACC TCTACTGGAC CGACACGGGC   1380

ACGGACCGCA TCGAGGTGAC GCGCCTCAAC GGCACCTCCC GCAAGATCCT GGTGTCGGAG   1440

GACCTGGACG AGCCCCGAGC CATCGCACTG CACCCCGTGA TGGGCCTCAT GTACTGGACA   1500

GACTGGGGAG AGAACCCTAA AATCGAGTGT GCCAACTTGG ATGGGCAGGA GCGGCGTGTG   1560

CTGGTCAATG CCTCCCTCGG GTGGCCCAAC GGCCTGGCCC TGGACCTGCA GGAGGGGAAG   1620

CTCTACTGGG GAGACGCCAA GACAGACAAG ATCGAGGTGA TCAATGTTGA TGGGACGAAG   1680

AGGCGGACCC TCCTGGAGGA CAAGCTCCCG CACATTTTCG GGTTCACGCT GCTGGGGGAC   1740

TTCATCTACT GGACTGACTG GCAGCGCCGC AGCATCGAGC GGGTGCACAA GGTCAAGGCC   1800

AGCCGGGACG TCATCATTGA CCAGCTGCCC GACCTGATGG GGCTCAAAGC TGTGAATGTG   1860

GCCAAGGTCG TCGGAACCAA CCCGTGTGCG GACAGGAACG GGGGGTGCAG CCACCTGTGC   1920

TTCTTCACAC CCCACGCAAC CCGGTGTGGC TGCCCCATCG GCCTGGAGCT GCTGAGTGAC   1980

ATGAAGACCT GCATCGTGCC TGAGGCCTTC TTGGTCTTCA CCAGCAGAGC CGCCATCCAC   2040

AGGATCTCCT CGAGACCAAT AACAACGACG TGGCCATCCC GCTCACGGGC GTCAAGGAGG   2100

CCTCAGCCCT GGACTTTGAT GTGTCCAACA ACCACATCTA CTGGACAGAC GTCAGCCTGA   2160

AGACCATCAG CCGCGCCTTC ATGAACGGGA GCTCGGTGGA GCACGTGGTG GAGTTTGGCC   2220

TTGACTACCC CGAGGGCATG GCCGTTGACT GGATGGGCAA GAACCTCTAC TGGGCCGACA   2280

CTGGGACCAA CAGAATCGAA GTGGCGCGGC TGGACGGGCA GTTCCGGCAA GTCCTCGTGT   2340

GGAGGGACTT GGACAACCCG AGGTCGCTGG CCCTGGATCC CACCAAGGGC TACATCTACT   2400

GGACCGAGTG GGGCGGCAAG CCGAGGATCG TGCGGGCCTT CATGGACGGG ACCAACTGCA   2460

TGACGCTGGT GGACAAGGTG GGCCGGGCCA ACGACCTCAC CATTGACTAC GCTGACCAGC   2520

GCCTCTACTG GACCGACCTG GACACCAACA TGATCGAGTC GTCCAACATG CTGGGTCAGG   2580

AGCGGGTCGT GATTGCCGAC GATCTCCCGC ACCCGTTCGG TCTGACGCAG TACAGCGATT   2640

ATATCTACTG GACAGACTGG AATCTGCACA GCATTGAGCG GGCCGACAAG ACTAGCGGCC   2700

GGAACCGCAC CCTCATCCAG GGCCACCTGG ACTTCGTGAT GGACATCCTG GTGTTCCACT   2760
```

```
CCTCCCGCCA GGATGGCCTC AATGACTGTA TGCACAACAA CGGGCAGTGT GGGCAGCTGT    2820

GCCTTGCCAT CCCCGGCGGC CACCGCTGCG GCTGCGCCTC ACACTACACC CTGGACCCCA    2880

GCAGCCGCAA CTGCAGCCCG CCCACCACCT TCTTGCTGTT CAGCCAGAAA TCTGCCATCA    2940

GTCGGATGAT CCCGGACGAC CAGCACAGCC CGGATCTCAT CCTGCCCCTG CATGGACTGA    3000

GGAACGTCAA AGCCATCGAC TATGACCCAC TGGACAAGTT CATCTACTGG GTGGATGGGC    3060

GCCAGAACAT CAAGCGAGCC AAGGACGACG GGACCCAGCC CTTTGTTTTG ACCTCTCTGA    3120

GCCAAGGCCA AAACCCAGAC AGGCAGCCCC ACGACCTCAG CATCGACATC TACAGCCGGA    3180

CACTGTTCTG GACGTGCGAG GCCACCAATA CCATCAACGT CCACAGGCTG AGCGGGGAAG    3240

CCATGGGGGT GGTGCTGCGT GGGGACCGCG ACAAGCCCGG GGCCATCGTC GTCAACGCGG    3300

AGCGAGGGTA CCTGTACTTC ACCAACATGC AGGACCGGGC AGCCAAGATC GAACGCGCAG    3360

CCCTGGACGG CACCGAGCGC GAGGTCCTCT TCACCACCGG CCTCATCCGC CCTGTGGCCC    3420

TGGTGGTAGA CAACACACTG GGCAAGCTGT TCTGGGTGGA CGCGGACCTG AAGCGCATTG    3480

AGAGCTGTGA CCTGTCAGGG GCCAACCGCC TGACCCTGGA GGACGCCAAC ATCGTGCAGC    3540

CTCTGGGCCT GACCATCCTT GGCAAGCATC TCTACTGGAT CGACCGCCAG CAGCAGATGA    3600

TCGAGCGTGT GGAGAAGACC ACCGGGGACA AGCGGACTCG CATCCAGGGC CGTGTCGCCC    3660

ACCTCACTGG CATCCATGCA GTGGAGGAAG TCAGCCTGGA GGAGTTCTCA GCCCACCCAT    3720

GTGCCCGTGA CAATGGTGGC TGCTCCCACA TCTGTATTGC CAAGGGTGAT GGGACACCAC    3780

GGTGCTCATG CCCAGTCCAC CTCGTGCTCC TGCAGAACCT GCTGACCTGT GGAGAGCCGC    3840

CCACCTGCTC CCCGGACCAG TTTGCATGTG CCACAGGGGA GATCGACTGT ATCCCCGGGG    3900

CCTGGCGCTG TGACGGCTTT CCCGAGTGCG ATGACCAGAG CGACGAGGAG GGCTGCCCCG    3960

TGTGCTCCGC CGCCCAGTTC CCCTGCGCGC GGGGTCAGTG TGTGGACCTG CGCCTGCGCT    4020

GCGACGGCGA GGCAGACTGT CAGGACCGCT CAGACGAGGC GGACTGTGAC GCCATCTGCC    4080

TGCCCAACCA GTTCCGGTGT GCGAGCGGCA GTGTGTCCTC ATCAAACAGC AGTGCGACTC    4140

CTTCCCCGAC TGTATCGACG GCTCCGACGA GCTCATGTGT GAAATCACCA AGCCGCCCTC    4200

AGACGACAGC CCGGCCCACA GCAGTGCCAT CGGGCCCGTC ATTGGCATCA TCCTCTCTCT    4260

CTTCGTCATG GGTGGTGTCT ATTTTGTGTG CCAGCGCGTG GTGTGCCAGC GCTATGCGGG    4320

GGCCAACGGG CCCTTCCCGC ACGAGTATGT CAGCGGGACC CCGCACGTGC CCCTCAATTT    4380

CATAGCCCCG GGCGGTTCCC AGCATGGCCC CTTCACAGGC ATCGCATGCG GAAAGTCCAT    4440

GATGAGCTCC GTGAGCCTGA TGGGGGGCCG GGGCGGGGTG CCCCTCTACG ACCGGAACCA    4500

CGTCACAGGG GCCTCGTCCA GCAGCTCGTC CAGCACGAAG GCCACGCTGT ACCCGCCGAT    4560

CCTGAACCCG CCGCCCTCCC CGGCCACGGA CCCCTCCCTG TACAACATGG ACATGTTCTA    4620

CTCTTCAAAC ATTCCGGCCA CTGCGAGACC GTACAGGCCC TACATCATTC GAGGAATGGC    4680

GCCCCCGACG ACGCCCTGCA GCACCGACGT GTGTGACAGC GACTACAGCG CCAGCCGCTG    4740

GAAGGCCAGC AAGTACTACC TGGATTTGAA CTCGGACTCA GACCCCTATC CACCCCCACC    4800

CACGCCCCAC AGCCAGTACC TGTCGGCGGA GGACAGCTGC CCGCCCTCGC CGCCACCGA    4860

GAGGAGCTAC TTCCATCTCT TCCCGCCCCC TCCGTCCCCC TGCACGGACT CATCC         4915
```

(2) INFORMATION FOR SEQ ID NO:29:

(i) SEQUENCE CHARACTERISTICS:
        (A) LENGTH: 1639 amino acids
        (B) TYPE: amino acid (D) TOPOLOGY: linear (xi) SEQUENCE DESCRIPTION: SEQ ID NO:29:

| Met | Ala | Trp | Gln | Arg | Glu | Phe | Ile | Pro | Phe | Ser | Ala | Ser | Ile | Phe | Cys |
|---|---|---|---|---|---|---|---|---|---|---|---|---|---|---|---|
| 1 | | | | 5 | | | | | 10 | | | | | 15 | |

| Ser | Glu | Arg | Thr | Pro | His | Ser | Ser | Pro | Glu | Asp | Ala | Ala | Arg |
|---|---|---|---|---|---|---|---|---|---|---|---|---|---|
| | | | 20 | | | | | 25 | | | | 30 | |

Arg His Leu Glu Thr Arg Asp Gln Thr Asn Gln Gln Leu Arg Leu Glu
         35                  40                  45

Leu Pro Ser Leu His Asn Ser Ser Pro Leu Leu Phe Ala Asn Arg
 50                      55                  60

Arg Asp Val Arg Leu Val Asp Ala Gly Val Lys Leu Glu Ser Thr
65              70              75                      80

Ile Val Val Ser Gly Leu Glu Asp Ala Ala Val Asp Phe Gln Phe
                 85              90              95

Ser Lys Gly Ala Val Tyr Trp Thr Asp Val Ser Glu Glu Ala Ile Lys
             100             105             110

Gln Thr Tyr Leu Asn Gln Thr Gly Ala Ala Val Gln Asn Val Val Ile
         115             120             125

Ser Gly Leu Val Ser Pro Asp Gly Leu Ala Cys Asp Trp Val Gly Lys
 130             135             140

Lys Leu Tyr Trp Thr Asp Ser Glu Thr Asn Arg Ile Glu Val Ala Asn
145             150             155             160

Leu Asn Gly Thr Ser Arg Lys Val Leu Phe Trp Gln Asp Leu Asp Gln
                 165             170             175

Pro Arg Ala Ile Ala Leu Asp Pro Ala His Gly Tyr Met Tyr Trp Thr
             180             185             190

Asp Trp Gly Glu Thr Pro Arg Ile Glu Arg Ala Gly Met Asp Gly Ser
         195             200             205

Thr Arg Lys Ile Ile Val Asp Ser Asp Ile Tyr Trp Pro Asn Gly Leu
 210             215             220

Thr Ile Asp Leu Glu Glu Gln Lys Leu Tyr Trp Ala Asp Ala Lys Leu
225             230             235             240

Ser Phe Ile His Arg Ala Asn Leu Asp Gly Ser Phe Arg Gln Lys Val
                 245             250             255

Val Glu Gly Ser Leu Thr His Pro Phe Ala Leu Thr Leu Ser Gly Asp
             260             265             270

Thr Leu Tyr Trp Thr Asp Trp Gln Thr Arg Ser Ile His Ala Cys Asn
         275             280             285

Lys Arg Thr Gly Gly Lys Arg Lys Glu Ile Leu Ser Ala Leu Tyr Ser
 290             295             300

Pro Met Asp Ile Gln Val Leu Ser Gln Glu Arg Gln Pro Phe Phe His
305             310             315             320

Thr Arg Cys Glu Glu Asp Asn Gly Gly Cys Ser His Leu Cys Leu Leu
                 325             330             335

Ser Pro Ser Glu Pro Phe Tyr Thr Cys Ala Cys Pro Thr Gly Val Gln
             340             345             350

Leu Gln Asp Asn Gly Arg Thr Cys Lys Ala Gly Ala Glu Glu Val Leu
         355             360             365

Leu Leu Ala Arg Arg Thr Asp Leu Arg Arg Ile Ser Leu Asp Thr Pro
 370             375             380

Asp Phe Thr Asp Ile Val Leu Gln Val Asp Asp Ile Arg His Ala Ile
385             390             395             400

```
Ala Ile Asp Tyr Asp Pro Leu Glu Gly Tyr Val Tyr Trp Thr Asp Asp
            405                 410                 415
Glu Val Arg Ala Ile Arg Arg Ala Tyr Leu Asp Gly Ser Gly Ala Gln
        420                 425                 430
Thr Leu Val Asn Thr Glu Ile Asn Asp Pro Asp Gly Ile Ala Val Asp
            435                 440                 445
Trp Val Ala Arg Asn Leu Tyr Trp Thr Asp Thr Gly Thr Asp Arg Ile
    450                 455                 460
Glu Val Thr Arg Leu Asn Gly Thr Ser Arg Lys Ile Leu Val Ser Glu
465                 470                 475                 480
Asp Leu Asp Glu Pro Arg Ala Ile Ala Leu His Pro Val Met Gly Leu
            485                 490                 495
Met Tyr Trp Thr Asp Trp Gly Glu Asn Pro Lys Ile Glu Cys Ala Asn
            500                 505                 510
Leu Asp Gly Gln Glu Arg Arg Val Leu Val Asn Ala Ser Leu Gly Trp
            515                 520                 525
Pro Asn Gly Leu Ala Leu Asp Leu Gln Glu Gly Lys Leu Tyr Trp Gly
            530                 535                 540
Asp Ala Lys Thr Asp Lys Ile Glu Val Ile Asn Val Asp Gly Thr Lys
545                 550                 555                 560
Arg Arg Thr Leu Leu Glu Asp Lys Leu Pro His Ile Phe Gly Phe Thr
            565                 570                 575
Leu Leu Gly Asp Phe Ile Tyr Trp Thr Asp Trp Gln Arg Arg Ser Ile
            580                 585                 590
Glu Arg Val His Lys Val Lys Ala Ser Arg Asp Val Ile Ile Asp Gln
            595                 600                 605
Leu Pro Asp Leu Met Gly Leu Lys Ala Val Asn Val Ala Lys Val Val
    610                 615                 620
Gly Thr Asn Pro Cys Ala Asp Arg Asn Gly Gly Cys Ser His Leu Cys
625                 630                 635                 640
Phe Phe Thr Pro His Ala Thr Arg Cys Gly Cys Pro Ile Gly Leu Glu
            645                 650                 655
Leu Leu Ser Asp Met Lys Thr Cys Ile Val Pro Glu Ala Phe Leu Val
            660                 665                 670
Phe Thr Ser Arg Ala Ala Ile His Arg Ile Ser Leu Glu Thr Asn Asn
            675                 680                 685
Asn Asp Val Ala Ile Pro Leu Thr Gly Val Lys Glu Ala Ser Ala Leu
    690                 695                 700
Asp Phe Asp Val Ser Asn Asn His Ile Tyr Trp Thr Asp Val Ser Leu
705                 710                 715                 720
Lys Thr Ile Ser Arg Ala Phe Met Asn Gly Ser Ser Val Glu His Val
            725                 730                 735
Val Glu Phe Gly Leu Asp Tyr Pro Glu Gly Met Ala Val Asp Trp Met
            740                 745                 750
Gly Lys Asn Leu Tyr Trp Ala Asp Thr Gly Thr Asn Arg Ile Glu Val
            755                 760                 765
Ala Arg Leu Asp Gly Gln Phe Arg Gln Val Leu Val Trp Arg Asp Leu
    770                 775                 780
Asp Asn Pro Arg Ser Leu Ala Leu Asp Pro Thr Lys Gly Tyr Ile Tyr
785                 790                 795                 800
Trp Thr Glu Trp Gly Gly Lys Pro Arg Ile Val Arg Ala Phe Met Asp
            805                 810                 815
Gly Thr Asn Cys Met Thr Leu Val Asp Lys Val Gly Arg Ala Asn Asp
```

-continued

```
                820                 825                 830
Leu Thr Ile Asp Tyr Ala Asp Gln Arg Leu Tyr Trp Thr Asp Leu Asp
            835                 840                 845
Thr Asn Met Ile Glu Ser Ser Asn Met Leu Gly Gln Glu Arg Val Val
850                 855                 860
Ile Ala Asp Asp Leu Pro His Pro Phe Gly Leu Thr Gln Tyr Ser Asp
865                 870                 875                 880
Tyr Ile Tyr Trp Thr Asp Trp Asn Leu His Ser Ile Glu Arg Ala Asp
                885                 890                 895
Lys Thr Ser Gly Arg Asn Arg Thr Leu Ile Gln Gly His Leu Asp Phe
            900                 905                 910
Val Met Asp Ile Leu Val Phe His Ser Ser Arg Gln Asp Gly Leu Asn
        915                 920                 925
Asp Cys Met His Asn Asn Gly Gln Cys Gly Gln Leu Cys Leu Ala Ile
    930                 935                 940
Pro Gly Gly His Arg Cys Gly Cys Ala Ser His Tyr Thr Leu Asp Pro
945                 950                 955                 960
Ser Ser Arg Asn Cys Ser Pro Thr Thr Phe Leu Leu Phe Ser Gln
                965                 970                 975
Lys Ser Ala Ile Ser Arg Met Ile Pro Asp Asp Gln His Ser Pro Asp
            980                 985                 990
Leu Ile Leu Pro Leu His Gly Leu Arg Asn Val Lys Ala Ile Asp Tyr
        995                 1000                1005
Asp Pro Leu Asp Lys Phe Ile Tyr Trp Val Asp Gly Arg Gln Asn Ile
    1010                1015                1020
Lys Arg Ala Lys Asp Asp Gly Thr Gln Pro Phe Val Leu Thr Ser Leu
1025                1030                1035                1040
Ser Gln Gly Gln Asn Pro Asp Arg Gln Pro His Asp Leu Ser Ile Asp
                1045                1050                1055
Ile Tyr Ser Arg Thr Leu Phe Trp Thr Cys Glu Ala Thr Asn Thr Ile
            1060                1065                1070
Asn Val His Arg Leu Ser Gly Glu Ala Met Gly Val Val Leu Arg Gly
        1075                1080                1085
Asp Arg Asp Lys Pro Arg Ala Ile Val Val Asn Ala Glu Arg Gly Tyr
    1090                1095                1100
Leu Tyr Phe Thr Asn Met Gln Asp Arg Ala Ala Lys Ile Glu Arg Ala
1105                1110                1115                1120
Ala Leu Asp Gly Thr Glu Arg Glu Val Leu Phe Thr Thr Gly Leu Ile
                1125                1130                1135
Arg Pro Val Ala Leu Val Val Asp Asn Thr Leu Gly Lys Leu Phe Trp
            1140                1145                1150
Val Asp Ala Asp Leu Lys Arg Ile Glu Ser Cys Asp Leu Ser Gly Ala
        1155                1160                1165
Asn Arg Leu Thr Leu Glu Asp Ala Asn Ile Val Gln Pro Leu Gly Leu
    1170                1175                1180
Thr Ile Leu Gly Lys His Leu Tyr Trp Ile Asp Arg Gln Gln Gln Met
1185                1190                1195                1200
Ile Glu Arg Val Glu Lys Thr Thr Gly Asp Lys Arg Thr Arg Ile Gln
                1205                1210                1215
Gly Arg Val Ala His Leu Thr Gly Ile His Ala Val Glu Glu Val Ser
            1220                1225                1230
Leu Glu Glu Phe Ser Ala His Pro Cys Ala Arg Asp Asn Gly Gly Cys
        1235                1240                1245
```

```
Ser His Ile Cys Ile Ala Lys Gly Asp Gly Thr Pro Arg Cys Ser Cys
    1250                1255                1260

Pro Val His Leu Val Leu Leu Gln Asn Leu Leu Thr Cys Gly Glu Pro
1265                1270                1275                1280

Pro Thr Cys Ser Pro Asp Gln Phe Ala Cys Ala Thr Gly Glu Ile Asp
                1285                1290                1295

Cys Ile Pro Gly Ala Trp Arg Cys Asp Gly Phe Pro Glu Cys Asp Asp
            1300                1305                1310

Gln Ser Asp Glu Glu Gly Cys Pro Val Cys Ser Ala Ala Gln Phe Pro
        1315                1320                1325

Cys Ala Arg Gly Gln Cys Val Asp Leu Arg Leu Arg Cys Asp Gly Glu
    1330                1335                1340

Ala Asp Cys Gln Asp Arg Ser Asp Glu Ala Asp Cys Asp Ala Ile Cys
1345                1350                1355                1360

Leu Pro Asn Gln Phe Arg Cys Ala Ser Gly Gln Cys Val Leu Ile Lys
                1365                1370                1375

Gln Gln Cys Asp Ser Phe Pro Asp Cys Ile Asp Gly Ser Asp Glu Leu
            1380                1385                1390

Met Cys Glu Ile Thr Lys Pro Pro Ser Asp Asp Ser Pro Ala His Ser
        1395                1400                1405

Ser Ala Ile Gly Pro Val Ile Gly Ile Ile Leu Ser Leu Phe Val Met
    1410                1415                1420

Gly Gly Val Tyr Phe Val Cys Gln Arg Val Val Cys Gln Arg Tyr Ala
1425                1430                1435                1440

Gly Ala Asn Gly Pro Phe Pro His Glu Tyr Val Ser Gly Thr Pro His
                1445                1450                1455

Val Pro Leu Asn Phe Ile Ala Pro Gly Gly Ser Gln His Gly Pro Phe
            1460                1465                1470

Thr Gly Ile Ala Cys Gly Lys Ser Met Met Ser Ser Val Ser Leu Met
        1475                1480                1485

Gly Gly Arg Gly Gly Val Pro Leu Tyr Asp Arg Asn His Val Thr Gly
    1490                1495                1500

Ala Ser Ser Ser Ser Ser Ser Thr Lys Ala Thr Leu Tyr Pro Pro
1505                1510                1515                1520

Ile Leu Asn Pro Pro Ser Pro Ala Thr Asp Pro Ser Leu Tyr Asn
                1525                1530                1535

Met Asp Met Phe Tyr Ser Ser Asn Ile Pro Ala Thr Ala Arg Pro Tyr
            1540                1545                1550

Arg Pro Tyr Ile Ile Arg Gly Met Ala Pro Thr Thr Pro Cys Ser
        1555                1560                1565

Thr Asp Val Cys Asp Ser Asp Tyr Ser Ala Ser Arg Trp Lys Ala Ser
    1570                1575                1580

Lys Tyr Tyr Leu Asp Leu Asn Ser Asp Ser Asp Pro Tyr Pro Pro Pro
1585                1590                1595                1600

Pro Thr Pro His Ser Gln Tyr Leu Ser Ala Glu Asp Ser Cys Pro Pro
                1605                1610                1615

Ser Pro Ala Thr Glu Arg Ser Tyr Phe His Leu Phe Pro Pro Pro
        1620                1625                1630

Ser Pro Cys Thr Asp Ser Ser
        1635

(2) INFORMATION FOR SEQ ID NO:30:
```

(i) SEQUENCE CHARACTERISTICS:
    (A) LENGTH: 91 base pairs
    (B) TYPE: nucleic acid
    (C) STRANDEDNESS: single
    (D) TOPOLOGY: linear (xi) SEQUENCE DESCRIPTION: SEQ ID NO:30:

| | | | | | |
|---|---|---|---|---|---|
| TATAAAATGG | CTTGGCAAAG | GGAGTTCATT | CCTTTTAGCG | CTTCCATCTT | CTGCAGTGAG | 60 |
| AGGACACCGC | ATTCTTCTTC | TCCAGAGGAT | G | | | 91 |

(2) INFORMATION FOR SEQ ID NO:31:

(i) SEQUENCE CHARACTERISTICS:
        (A) LENGTH: 5263 base pairs
        (B) TYPE: nucleic acid
        (C) STRANDEDNESS: single
        (D) TOPOLOGY: linear (xi) SEQUENCE DESCRIPTION: SEQ ID NO:31:

| | | | | | |
|---|---|---|---|---|---|
| TAAGAGTATA | AAGGGCTCCT | GAGACCAAAA | AGGTTGAGAA | CCAGTGCTTT | AAAGCTTGAT | 60 |
| GTTTCTCAGG | GTTTCATCCT | TTGTGGATTA | ATGCCCATTA | TAAAATGGCT | TGGCAAAGGG | 120 |
| AGTTCATTCC | TTTTAGCGCT | TCCATCTTCT | GCAGTGAGAG | GACACCGCAT | TCTTCTTCTC | 180 |
| CAGAGGATGC | AGCAGCAAGG | CGCCATCTTG | AAACCAGAGA | CCAAACCAAC | CAGCAACTTC | 240 |
| GTCTTGAACT | TCCCAGCCTC | CACAACTCAG | CAGTCTGTGC | AGGACCCTGT | GAGCAGAGCC | 300 |
| GCAGCCTCGC | CGCTCCTGCT | ATTTGCCAAC | CGCCGGACG | TACGGCTGGT | GGACGCCGGC | 360 |
| GGAGTCAAGC | TGGAGTCCAC | CATCGTGGTC | AGCGGCCTGG | AGGATGCGGC | CGCAGTGGAC | 420 |
| TTCCAGTTTT | CCAAGGGAGC | CGTGTACTGG | ACAGACGTGA | GCGAGGAGGC | CATCAAGCAG | 480 |
| ACCTACCTGA | ACCAGACGGG | GGCCGCCGTG | CAGAACGTGG | TCATCTCCGG | CCTGGTCTCT | 540 |
| CCCGACGGCC | TCGCCTGCGA | CTGGGTGGGC | AAGAAGCTGT | ACTGGACGGA | CTCAGAGACC | 600 |
| AACCGCATCG | AGGTGGCCAA | CCTCAATGGC | ACATCCCGGA | AGGTGCTCTT | CTGGCAGGAC | 660 |
| CTTGACCAGC | CGAGGGCCAT | CGCCTTGGAC | CCCGCTCACG | GTACATGTA | CTGGACAGAC | 720 |
| TGGGGTGAGA | CGCCCCGGAT | TGAGCGGGCA | GGGATGGATG | GCAGCACCCG | GAAGATCATT | 780 |
| GTGGACTCGG | ACATTTACTG | GCCCAATGGA | CTGACCATCG | ACCTGGAGGA | GCAGAAGCTC | 840 |
| TACTGGGCTG | ACGCCAAGCT | CAGCTTCATC | CACCGTGCCA | ACCTGGACGG | CTCGTTCCGG | 900 |
| CAGAAGGTGG | TGGAGGGCAG | CCTGACGCAC | CCCTTCGCCC | TGACGCTCTC | CGGGGACACT | 960 |
| CTGTACTGGA | CAGACTGGCA | GACCCGCTCC | ATCCATGCCT | GCAACAAGCG | CACTGGGGGG | 1020 |
| AAGAGGAAGG | AGATCCTGAG | TGCCCTCTAC | TCACCCATGG | ACATCCAGGT | GCTGAGCCAG | 1080 |
| GAGCGGCAGC | CTTTCTTCCA | CACTCGCTGT | GAGGAGGACA | ATGGCGGCTG | CTCCCACCTG | 1140 |
| TGCCTGCTGT | CCCCAAGCGA | GCCTTTCTAC | ACATGCGCCT | GCCCCACGGG | TGTGCAGCTG | 1200 |
| CAGGACAACG | GCAGGACGTG | TAAGGCAGGA | GCCGAGGAGG | TGCTGCTGCT | GGCCCGGCGG | 1260 |
| ACGGACCTAC | GGAGGATCTC | GCTGGACACG | CCGGACTTTA | CCGACATCGT | GCTGCAGGTG | 1320 |
| GACGACATCC | GGCACGCCAT | TGCCATCGAC | TACGACCCGC | TAGAGGGCTA | TGTCTACTGG | 1380 |
| ACAGATGACG | AGGTGCGGGC | CATCCGCAGG | GCGTACCTGG | ACGGGTCTGG | GGCGCAGACG | 1440 |
| CTGGTCAACA | CCGAGATCAA | CGACCCCGAT | GGCATCGCGG | TCGACTGGGT | GGCCCGAAAC | 1500 |
| CTCTACTGGA | CCGACACGGG | CACGGACCGC | ATCGAGGTGA | CGCGCCTCAA | CGGCACCTCC | 1560 |
| CGCAAGATCC | TGGTGTCGGA | GGACCTGGAC | GAGCCCCGAG | CCATCGCACT | GCACCCCGTG | 1620 |
| ATGGGCCTCA | TGTACTGGAC | AGACTGGGGA | GAGAACCCTA | AAATCGAGTG | TGCCAACTTG | 1680 |

-continued

```
GATGGGCAGG AGCGGCGTGT GCTGGTCAAT GCCTCCCTCG GGTGGCCCAA CGGCCTGGCC    1740

CTGGACCTGC AGGAGGGGAA GCTCTACTGG GGAGACGCCA AGACAGACAA GATCGAGGTG    1800

ATCAATGTTG ATGGGACGAA GAGGCGGACC CTCCTGGAGG ACAAGCTCCC GCACATTTTC    1860

GGGTTCACGC TGCTGGGGGA CTTCATCTAC TGGACTGACT GGCAGCGCCG CAGCATCGAG    1920

CGGGTGCACA AGGTCAAGGC CAGCCGGGAC GTCATCATTG ACCAGCTGCC CGACCTGATG    1980

GGGCTCAAAG CTGTGAATGT GGCCAAGGTC GTCGGAACCA ACCCGTGTGC GGACAGGAAC    2040

GGGGGGTGAG CCACCTGTGC TTCTTCACAC CCCACGCAAC CCGGTGTGGC TGCCCCATCG    2100

GCCTGGAGCT GCTGAGTGAC ATGAAGACCT GCATCGTGCC TGAGGCCTTC TTGGTCTTCA    2160

CCAGCAGAGC CGCCATCCAC AGGATCTCCC TCGAGACCAA TAACAACGAC GTGGCCATCC    2220

CGCTCACGGG CGTCAAGGAG GCCTCAGCCC TGGACTTTGA TGTGTCCAAC AACCACATCT    2280

ACTGGACAGA CGTCAGCCTG AAGACCATCA GCCGCGCCTT CATGAACGGG AGCTCGGTGG    2340

AGCACGTGGT GGAGTTTGGC CTTGACTACC CCGAGGGCAT GGCCGTTGAC TGGATGGGCA    2400

AGAACCTCTA CTGGGCCGAC ACTGGGACCA ACAGAATCGA AGTGGCGCGG CTGGACGGGC    2460

AGTTCCGGCA AGTCCTCGTG TGGAGGGACT TGGACAACCC GAGGTCGCTG GCCCTGGATC    2520

CCACCAAGGG CTACATCTAC TGGACCGAGT GGGGCGGCAA GCCGAGGATC GTGCGGGCCT    2580

TCATGGACGG GACCAACTGC ATGACGCTGG TGGACAAGGT GGGCCGGGCC AACGACCTCA    2640

CCATTGACTA CGCTGACCAG CGCCTCTACT GGACCGACCT GGACACCAAC ATGATCGAGT    2700

CGTCCAACAT GCTGGGTCAG GAGCGGGTCG TGATTGCCGA CGATCTCCCG CACCCGTTCG    2760

GTCTGACGCA GTACAGCGAT TATATCTACT GGACAGACTG GAATCTGCAC AGCATTGAGC    2820

GGGCCGACAA GACTAGCGGC CGGAACCGCA CCCTCATCCA GGGCCACCTG GACTTCGTGA    2880

TGGACATCCT GGTGTTCCAC TCCTCCCGCC AGGATGGCCT CAATGACTGT ATGCACAACA    2940

ACGGGCAGTG TGGGCAGCTG TGCCTTGCCA TCCCCGGCGG CCACCGCTGC GGCTGCGCCT    3000

CACACTACAC CCTGGACCCC AGCAGCCGCA ACTGCAGCCC GCCCACCACC TTCTTGCTGT    3060

TCAGCCAGAA ATCTGCCATC AGTCGGATGA TCCCGGACGA CCAGCACAGC CCGGATCTCA    3120

TCCTGCCCCT GCATGGACTG AGGAACGTCA AAGCCATCGA CTATGACCCA CTGGACAAGT    3180

TCATCTACTG GGTGGATGGG CGCCAGAACA TCAAGCGAGC CAAGGACGAC GGGACCCAGC    3240

CCTTTGTTTT GACCTCTCTG AGCCAAGGCC AAAACCCAGA CAGGCAGCCC CACGACCTCA    3300

GCATCGACAT CTACAGCCGG ACACTGTTCT GGACGTGCGA GGCACCAATA CCATCAACG    3360

TCCACAGGCT GAGCGGGGAA GCCATGGGGG TGGTGCTGCG TGGGGACCGC GACAAGCCCA    3420

GGGCCATCGT CGTCAACGCG GAGCGAGGGT ACCTGTACTT CACCAACATG CAGGACCGGG    3480

CAGCCAAGAT CGAACGCGCA GCCCTGGACG GCACCGAGCG CGAGGTCCTC TTCACCACCG    3540

GCCTCATCCG CCCTGTGGCC CTGGTGGTAG ACAACACACT GGGCAAGCTG TTCTGGGTGG    3600

ACGCGGACCT GAAGCGCATT GAGAGCTGTG ACCTGTCAGG GGCCAACCGC CTGACCCTGG    3660

AGGACGCCAA CATCGTGCAG CCTCTGGGCC TGACCATCCT TGGCAAGCAT CTCTACTGGA    3720

TCGACCGCCA GCAGCAGATG ATCGAGCGTG TGGAGAAGAC CACCGGGGAC AAGCGGACTC    3780

GCATCCAGGG CCGTGTCGCC CACCTCACTG GCATCCATGC AGTGGAGGAA GTCAGCCTGG    3840

AGGAGTTCTC AGCCCACCCA TGTGCCCGTG ACAATGGTGG CTGCTCCCAC ATCTGTATTG    3900

CCAAGGGTGA TGGGACACCA CGGTGCTCAT GCCCAGTCCA CCTCGTGCTC CTGCAGAACC    3960

TGCTGACCTG TGGAGAGCCG CCCACCTGCT CCCCGGACCA GTTTGCATGT GCCACAGGGG    4020

AGATCGACTG TATCCCCGGG GCCTGGCGCT GTGACGGCTT TCCCGAGTGC GATGACCAGA    4080
```

```
GCGACGAGGA GGGCTGCCCC GTGGCTCCGC CGCCCAGTTC CCCTGCGCGC GGGGTCAGTG      4140

TGTGGACCTG CGCCTGCGCT GCGACGGCGA GGCAGACTGT CAGGACCGCT CAGACGAGGC      4200

GGACTGTGAC GCCATCTGCC TGCCCAACCA GTTCCGGTGT GCGAGCGGCC AGTGTGTCCT      4260

CATCAAACAG CAGTGCGACT CCTTCCCCGA CTGTATCGAC GGCTCCGACG AGCTCATGTG      4320

TGAAATCACC AAGCCGCCCT CAGACGACAG CCCGGCCCAC AGCAGTGCCA TCGGGCCCGT      4380

CATTGGCATC ATCCTCTCTC TCTTCGTCAT GGGTGGTGTC TATTTTGTGT GCCAGCGCGT      4440

GGTGTGCCAG CGCTATGCGG GGGCCAACGG GCCCTTCCCG CACGAGTATG TCAGCGGGAC      4500

CCCGCACGTG CCCCTCAATT TCATAGCCCC GGGCGGTTCC CAGCATGGCC CCTTCACAGG      4560

CATCGCATGC GGAAAGTCCA TGATGAGCTC CGTGAGCCTG ATGGGGGCC GGGGCGGGGT      4620

GCCCCTCTAC GACCGGAACC ACGTCACAGG GGCCTCGTCC AGCAGCTCGT CCAGCACGAA      4680

GGCCACGCTG TACCCGCGGA TCCTGAACCC GCCGCCCTCC CCGGCCACGG ACCCCTCCCT      4740

GTACAACATG GACATGTTCT ACTCTTCAAA CATTCCGGCC ACTGCGAGAC CGTACAGGCC      4800

CTACATCATT CGAGGAATGG CGCCCCCGAC GACGCCCTGC AGCACCGACG TGTGTGACAG      4860

CGACTACAGC GCCAGCCGCT GGAAGGCCAG CAAGTACTAC CTGGATTTGA ACTCGGACTC      4920

AGACCCCTAT CCACCCCCAC CCACGCCCCA CAGCCAGTAC CTGTCGGCGG AGGACAGCTG      4980

CCCGCCCTCG CCCGCCACCG AGAGGAGCTA CTTCCATCTC TTCCCGCCCC CTCCGTCCCC      5040

CTGCACGGAC TCATCCTGAC CTCGGCCGGG CCACTCTGGC TTCTCTGTGC CCCTGTAAAT      5100

AGTTTTAAAT ATGAACAAAG AAAAAAATAT ATTTTATGAT TTAAAAAATA AATATAATTG      5160

GGATTTTAAA AACATGAGAA ATGTGAACTG TGATGGGGTG GGCAGGGCTG GGAGAACTTT      5220

GTACAGTGGA ACAAATATTT ATAAACTTAA TTTTGTAAAA CAG                        5263

(2) INFORMATION FOR SEQ ID NO:32:

(i) SEQUENCE CHARACTERISTICS:
        (A) LENGTH: 5022 base pairs
        (B) TYPE: nucleic acid
        (C) STRANDEDNESS: single
        (D) TOPOLOGY: linear (xi) SEQUENCE DESCRIPTION: SEQ ID NO:32:

GGCTGGTCTT GAACTCCTGG CCTGAGATGA TCCTCTCTCC TCGGAAAGTG CTGGGATTAT        60

AGCCTCGCCG CTCCTGCTAT TTGCCAACCG CCGGGACGTA CGGCTGGTGG ACGCCGGCGG       120

AGTCAAGCTG GAGTCCACCA TCGTGGTCAG CGGCCTGGAG GATGCGGCCG CAGTGGACTT       180

CCAGTTTTCC AAGGGAGCCG TGTACTGGAC AGACGGAGCG AGGAGGCCAT CAAGCAGACC       240

TACCTGAACC AGACGGGGGC CGCCGTGCAG AACGTGGTCA TCTCCGGCCT GGTCTCTCCC       300

GACGGCCTCG CCTGCGACTG GGTGGGCAAG AAGCTGTACT GGACGGACTC AGAGACCAAC       360

CGCATCGAGG TGGCCAACCT CAATGGCACA TCCCGGAAGG TGCTCTTCTG GCAGGACCTT       420

GACCAGCCGA GGGCCATCGC CTTGGACCCC GCTCACGGGT ACATGTACTG GACAGACTGG       480

GGTGAGACGC CCCGGATTGA GCGGGCAGGG ATGGATGGCA GCACCCGGAA GATCATTGTG       540

GACTCGGACA TTTACTGGCC CAATGGACTG ACCATCGACC TGGAGGAGCA GAAGCTCTAC       600

TGGGCTGACG CCAAGCTCAG CTTCATCCAC CGTGCCAACC TGGACGGCTC GTTCCGGCAG       660

AAGGTGGTGG AGGGCAGCCT GACGCACCCC TTCGCCCTGA CGCTCTCCGG GGACACTCTG       720

TACTGGACAG ACTGGCAGAC CCGCTCCATC CATGCCTGCA ACAAGCGCAC TGGGGGGAAG       780

AGGAAGGAGA TCCTGAGTGC CCTCTACTCA CCCATGGACA TCCAGGTGCT GAGCCAGGAG       840
```

```
CGGCAGCCTT TCTTCCACAC TCGCTGTGAG GAGGACAATG GCGGCTGCTC CCACCTGTGC    900

CTGCTGTCCC CAAGCGAGCC TTTCTACACA TGCGCCTGCC CCACGGGTGT GCAGCTGCAG    960

GACAACGGCA GGACGTGTAA GGCAGGAGCC GAGGAGGTGC TGCTGCTGGC CCGGCGGACG   1020

GACCTACGGA GGATCTCGCT GGACACGCCG GACTTTACCG ACATCGTGCT GCAGGTGGAC   1080

GACATCCGGC ACGCCATTGC CATCGACTAC GACCCGCTAG AGGGCTATGT CTACTGGACA   1140

GATGACGAGG TGCGGGCCAT CCGCAGGGCG TACCTGGACG GGTCTGGGGC GCAGACGCTG   1200

GTCAACACCG AGATCAACGA CCCCGATGGC ATCGCGGTCG ACTGGGTGGC CCGAAACCTC   1260

TACTGGACCG ACACGGGCAC GGACCGCATC GAGGTGACGC GCCTCAACGG CACCTCCCGC   1320

AAGATCCTGG TGTCGGAGGA CCTGGACGAG CCCCGAGCCA TCGCACTGCA CCCCGTGATG   1380

GGCCTCATGT ACTGGACAGA CTGGGGAGAG AACCCTAAAA TCGAGTGTGC CAACTTGGAT   1440

GGGCAGGAGC GGCGTGTGCT GGTCAATGCC TCCCTCGGGT GGCCCAACGG CCTGGCCCTG   1500

GACCTGCAGG AGGGGAAGCT CTACTGGGGA GACGCCAAGA CAGACAAGAT CGAGGTGATC   1560

AATGTTGATG GACGAAGAG GCGGACCCTC CTGGAGGACA AGCTCCCGCA CATTTTCGGG   1620

TTCACGCTGC TGGGGACTT CATCTACTGG ACTGACTGGC AGCGCCGCAG CATCGAGCGG   1680

GTGCACAAGG TCAAGGCCAG CCGGGACGTC ATCATTGACC AGCTGCCCGA CCTGATGGGG   1740

CTCAAAGCTG TGAATGTGGC CAAGGTCGTC GGAACCAACC CGTGTGCGGA CAGGAACGGG   1800

GGGTGCAGCC ACCTGTGCTT CTTCACACCC CACGCAACCC GGTGTGGCTG CCCCATCGGC   1860

CTGGAGCTGC TGAGTGACAT GAAGACCTGC ATCGTGCCTG AGGCCTTCTT GGTCTTCACC   1920

AGCAGAGCCG CCATCCACAG GATCTCCCTC GAGACCAATA CAACGACGT GGCCATCCCG   1980

CTCACGGGCG TCAAGGAGGC CTCAGCCCTG GACTTTGATG TGTCCAACAA CCACATCTAC   2040

TGGACAGACG TCAGCCTGAA GACCATCAGC CGCGCCTTCA TGAACGGGAG CTCGGTGGAG   2100

CACGTGGTGG AGTTTGGCCT TGACTACCCC GAGGGCATGG CCGTTGACTG GATGGGCAAG   2160

AACCTCTACT GGGCCGACAC TGGGACCAAC AGAATCGAAG TGGCGCGGCT GGACGGGCAG   2220

TTCCGGCAAG TCCTCGTGTG GAGGGACTTG GACAACCCGA GGTCGCTGGC CCTGGATCCC   2280

ACCAAGGGCT ACATCTACTG GACCGAGTGG GGCGGCAAGC CGAGGATCGT GCGGGCCTTC   2340

ATGGACGGGA CCAACTGCAT GACGCTGGTG GACAAGGTGG GCCGGGCCAA CGACCTCACC   2400

ATTGACTACG CTGACCAGCG CCTCTACTGG ACCGACCTGG ACACCAACAT GATCGAGTCG   2460

TCCAACATGC TGGGTCAGGA GCGGGTCGTG ATTGCCGACG ATCTCCCGCA CCCGTTCGGT   2520

CTGACGCAGT ACAGCGATTA TATCTACTGG ACAGACTGGA ATCTGCACAG CATTGAGCGG   2580

GCCGACAAGA CTAGCGGCCG GAACCGCACC CTCATCCAGG GCCACCTGGA CTTCGTGATG   2640

GACATCCTGG TGTTCCACTC CTCCCGCCAG GATGGCCTCA ATGACTGTAT GCACAACAAC   2700

GGGCAGTGTG GCAGCTGTG CCTTGCCATC CCCGGCGGCC ACCGCTGCGG CTGCGCCTCA   2760

CACTACACCC TGGACCCCAG CAGCCGCAAC TGCAGCCCGC CCACCACCTT CTTGCTGTTC   2820

AGCCAGAAAT CTGCCATCAG TCGGATGATC CCGGACGACC AGCACAGCCC GGATCTCATC   2880

CTGCCCCTGC ATGGACTGAG GAACGTCAAA GCCATCGACT ATGACCCACT GGACAAGTTC   2940

ATCTACTGGG TGGATGGGCG CCAGAACATC AAGCGAGCCA AGGACGACGG GACCCAGCCC   3000

TTTGTTTTGA CCTCTCTGAG CCAAGGCCAA AACCCAGACA GGCAGCCCCA CGACCTCAGC   3060

ATCGACATCT ACAGCCGGAC ACTGTTCTGG ACGTGCGAGG CCACCAATAC CATCAACGTC   3120

CACAGGCTGA GCGGGGAAGC CATGGGGGTG GTGCTGCGTG GGGACCGCGA CAAGCCCAGG   3180
```

-continued

```
GCCATCGTCG TCAACGCGGA GCGAGGGTAC CTGTACTTCA CCAACATGCA GGACCGGGCA      3240

GCCAAGATCG AACGCGCAGC CCTGGACGGC ACCGAGCGCG AGGTCCTCTT CACCACCGGC      3300

CTCATCCGCC CTGTGGCCCT GGTGGTAGAC AACACACTGG GCAAGCTGTT CTGGGTGGAC      3360

GCGGACCTGA AGCGCATTGA GAGCTGTGAC CTGTCAGGGG CCAACCGCCT GACCCTGGAG      3420

GACGCCAACA TCGTGCAGCC TCTGGGCCTG ACCATCCTTG GCAAGCATCT CTACTGGATC      3480

GACCGCCAGC AGCAGATGAT CGAGCGTGTG GAGAAGACCA CCGGGGACAA GCGGACTCGC      3540

ATCCAGGGCC GTGTCGCCCA CCTCACTGGC ATCCATGCAG TGGAGGAAGT CAGCCTGGAG      3600

GAGTTCTCAG CCCACCCATG TGCCCGTGAC AATGGTGGCT GCTCCCACAT CTGTATTGCC      3660

AAGGGTGATG GGACACCACG GTGCTCATGC CCAGTCCACC TCGTGCTCCT GCAGAACCTG      3720

CTGACCTGTG GAGAGCCGCC CACCTGCTCC CCGGACCAGT TTGCATGTGC CACAGGGGAG      3780

ATCGACTGTA TCCCCGGGGC CTGGCGCTGT GACGGCTTTC CCGAGTGCGA TGACCAGAGC      3840

GACGAGGAGG GCTGCCCCGT GTGCTCCGCC GCCCAGTTCC CCTGCGCGCG GGGTCAGTGT      3900

GTGGACCTGC GCCTGCGCTG CGACGGCGAG GCAGACTGTC AGGACCGCTC AGACGAGGCG      3960

GACTGTGACG CCATCTGCCT GCCCAACCAG TTCCGTGTGT CGAGCGGCCA GTGTGTCCTC      4020

ATCAAACAGC AGTGCGACTC CTTCCCCGAC TGTATCGACG GCTCCGACGA GCTCATGTGT      4080

GAAATCACCA AGCCGCCCTC AGACGACAGC CCGGCCCACA GCAGTGCCAT CGGGCCCGTC      4140

ATTGGCATCA TCCTCTCTCT CTTCGTCATG GGTGGTGTCT ATTTTGTGTG CCAGCGCGTG      4200

GTGTGCCAGC GCTATGCGGG GGCCAACGGG CCCTTCCCGC ACGAGTATGT CAGCGGGACC      4260

CCGCACGTGC CCCTCAATTT CATAGCCCCG GGCGGTTCCC AGCATGGCCC CTTCACAGGC      4320

ATCGCATGCG GAAAGTCCAT GATGAGCTCC GTGAGCCTGA TGGGGGGCCG GGGCGGGGTG      4380

CCCCTCTACG ACCGGAACCA CGTCACAGGG GCCTCGTCCA GCAGCTCGTC CAGCACGAAG      4440

GCCACGCTGT ACCCGCCGAT CCTGAACCCG CCGCCCTCCC CGGCCACGGA CCCCTCCCTG      4500

TACAACATGG ACATGTTCTA CTCTTCAAAC ATTCCGGCCA CTGTGAGACC GTACAGGCCC      4560

TACATCATTC GAGGAATGGC GCCCCGACG ACGCCCTGCA GCACCGACGT GTGTGACAGC      4620

GACTACAGCG CCAGCCGCTG GAAGGCCAGC AAGTACTACC TGGATTTGAA CTCGGACTCA      4680

GACCCCTATC CACCCCCACC CACGCCCCAC AGCCAGTACC TGTCGGCGGA GGACAGCTGC      4740

CCGCCCTCGC CGCCACCGA GAGGAGCTAC TTCCATCTCT TCCCGCCCCC TCCGTCCCCC      4800

TGCACGGACT CATCCTGACC TCGGCCGGGC CACTCTGGCT TCTCTGTGCC CCTGTAAATA      4860

GTTTTAAATA TGAACAAAGA AAAAAATATA TTTTATGATT TAAAAAATAA ATATAATTGG      4920

GATTTTAAAA ACATGAGAAA TGTGAACTGT GATGGGGTGG GCAGGGCTGG GAGAACTTTG      4980

TACAGTGGAA CAAATATTTA TAAACTTAAT TTTGTAAAAC AG                        5022
```

(2) INFORMATION FOR SEQ ID NO:33:

(i) SEQUENCE CHARACTERISTICS:
        (A) LENGTH: 5162 base pairs
        (B) TYPE: nucleic acid
        (C) STRANDEDNESS: single
        (D) TOPOLOGY: linear (xi) SEQUENCE DESCRIPTION: SEQ ID NO:33:

```
AGGCTGGTCT CAAACTCCTG GCCTTAAGTG ATCTGCCCGC CTCGGCCTCC CAAAGTGCTG        60

AGATGACAGG TGTGAGCCAC CGTGCCCGGC CCAGAACTCT TTAATTCCCA CCTGAAACTT       120

GCCGCCTTAA GCAGGTCCCC AGTCTCCCTC CCCTAGTCCC TGGTCCCACC ATTCTGCTTT       180
```

-continued

| | | | | |
|---|---|---|---|---|
| CTGTCTCAAT | GAATTTGCCT | ACCCCTCGCC | GCTCCTGCTA | TTTGCCAACC | GCCGGGACGT | 240 |
| ACGGCTGGTG | GACGCCGGCG | GAGTCAAGCT | GGAGTCCACC | ATCGTGGTCA | GCGGCCTGGA | 300 |
| GGATGCGGCC | GCAGTGGACT | TCCAGTTTTC | CAAGGGAGCC | GTGTACTGGA | CAGACGTGAG | 360 |
| CGAGGAGGCC | ATCAAGCAGA | CCTACCTGAA | CCAGACGGGG | GCCGCCGTGC | AGAACGTGGT | 420 |
| CATCTCCGGC | CTGGTCTCTC | CCGACGGCCT | CGCCTGCGAC | TGGGTGGGCA | AGAAGCTGTA | 480 |
| CTGGACGGAC | TCAGAGACCA | ACCGCATCGA | GGTGGCCAAC | CTCAATGGCA | CATCCCGGAA | 540 |
| GGTGCTCTTC | TGGCAGGACC | TTGACCAGCC | GAGGGCCATC | GCCTTGGACC | CCGCTCACGG | 600 |
| GTACATGTAC | TGGACAGACT | GGGGTGAGAC | GCCCCGGATT | GAGCGGGCAG | GGATGGATGG | 660 |
| CAGCACCCGG | AAGATCATTG | TGGACTCGGA | CATTTACTGG | CCCAATGGAC | TGACCATCGA | 720 |
| CCTGGAGGAG | CAGAAGCTCT | ACTGGGCTGA | CGCCAAGCTC | AGCTTCATCC | ACCGTGCCAA | 780 |
| CCTGGACGGC | TCGTTCCGGC | AGAAGGTGGT | GGAGGGCAGC | CTGACGCACC | CCTTCGCCCT | 840 |
| GACGCTCTCC | GGGGACACTC | TGTACTGGAC | AGACTGGCAG | ACCCGCTCCA | TCCATGCCTG | 900 |
| CAACAAGCGC | ACTGGGGGGA | AGAGGAAGGA | GATCCTGAGT | GCCCTCTACT | CACCCATGGA | 960 |
| CATCCAGGTG | CTGAGCCAGG | AGCGGCAGCC | TTTCTTCCAC | ACTCGCTGTG | AGGAGGACAA | 1020 |
| TGGCGGCTGC | TCCCACCTGT | GCCTGCTGTC | CCCAAGCGAG | CCTTTCTACA | CATGCGCCTG | 1080 |
| CCCCACGGGT | GTGCAGCTGC | AGGACAACGG | CAGGACGTGT | AAGGCAGGAG | CCGAGGAGGT | 1140 |
| GCTGCTGCTG | GCCGGCGGA | CGGACCTACG | AGGATCTCG | CTGGACACGC | CGGACTTTAC | 1200 |
| CGACATCGTG | CTGCAGGTGG | ACGACATCCG | GCACGCCATT | GCCATCGACT | ACGACCCGCT | 1260 |
| AGAGGGCTAT | GTCTACTGGA | CAGATGACGA | GGTGCGGGCC | ATCCGCAGGG | CGTACCTGGA | 1320 |
| CGGGTCTGGG | GCGCAGACGC | TGGTCAACAC | CGAGATCAAC | GACCCCGATG | GCATCGCGGT | 1380 |
| CGACTGGGTG | GCCCGAAACC | TCTACTGGAC | CGACACGGGC | ACGGACCGCA | TCGAGGTGAC | 1440 |
| GCGCCTCAAC | GGCACCTCCC | GCAAGATCCT | GGTGTCGGAG | GACCTGGACG | AGCCCCGAGC | 1500 |
| CATCGCACTG | CACCCCGTGA | TGGGCCTCAT | GTACTGGACA | GACTGGGGAG | AGAACCCTAA | 1560 |
| AATCGAGTGT | GCCAACTTGG | ATGGGCAGGA | GCGGCGTGTG | CTGGTCAATG | CCTCCCTCGG | 1620 |
| GTGGCCCAAC | GGCCTGGCCC | TGGACCTGCA | GGAGGGGAAG | CTCTACTGGG | AGACGCCAA | 1680 |
| GACAGACAAG | ATCGAGGTGA | TCAATGTTGA | TGGGACGAAG | AGGCGGACCC | TCCTGGAGGA | 1740 |
| CAAGCTCCCG | CACATTTTCG | GGTTCACGCT | GCTGGGGGAC | TTCATCTACT | GGACTGACTG | 1800 |
| GCAGCGCCGC | AGCATCGAGC | GGGTGCACAA | GGTCAAGGCC | AGCCGGGACG | TCATCATTGA | 1860 |
| CCAGCTGCCC | GACCTGATGG | GGCTCAAAGC | TGTGAATGTG | GCCAAGGTCG | TCGGAACCAA | 1920 |
| CCCGTGTGCG | GACAGGAACG | GGGGGTGCAG | CCACCTGTGC | TTCTTCACAC | CCCACGCAAC | 1980 |
| CCGGTGTGGC | TGCCCCATCG | GCCTGGAGCT | GCTGAGTGAC | ATGAAGACCT | GCATCGTGCC | 2040 |
| TGAGGCCTCT | TGGTCTTCAC | CAGCAGAGCC | GCCATCCACA | GGATCTCCCT | CGAGACCAAT | 2100 |
| AACAACGACG | TGGCCATCCC | GCTCACGGGC | GTCAAGGAGG | CCTCAGCCCT | GGACTTTGAT | 2160 |
| GTGTCCAACA | ACCACATCTA | CTGGACAGAC | GTCAGCCTGA | AGACCATCAG | CCGCGCCTTC | 2220 |
| ATGAACGGGA | GCTCGGTGGA | GCACGTGGTG | GAGTTTGGCC | TTGACTACCC | CGAGGGCATG | 2280 |
| GCCGTTGACT | GGATGGGCAA | GAACCTCTAC | TGGGCCGACA | CTGGGACCAA | CAGAATCGAA | 2340 |
| GTGGCGCGGC | TGGACGGGCA | GTTCCGGCAA | GTCCTCGTGT | GGAGGGACTT | GGACAACCCG | 2400 |
| AGGTCGCTGG | CCCTGGATCC | CACCAAGGGC | TACATCTACT | GGACCGAGTG | GGGCGGCAAG | 2460 |
| CCGAGGATCG | TGCGGGCCTT | CATGGACGGG | ACCAACTGCA | TGACGCTGGT | GGACAAGGTG | 2520 |
| GGCCGGGCCA | ACGACCTCAC | CATTGACTAC | GCTGACCAGC | GCCTCTACTG | GACCGACCTG | 2580 |

```
GACACCAACA TGATCGAGTC GTCCAACATG CTGGGTCAGG AGCGGGTCGT GATTGCCGAC    2640

GATCTCCCGC ACCCGTTCGG TCTGACGCAG TACAGCGATT ATATCTACTG GACAGACTGG    2700

AATCTGCACA GCATTGAGCG GGCCGACAAG ACTAGCGGCC GGAACCGCAC CCTCATCCAG    2760

GGCCACCTGG ACTTCGTGAT GGACATCCTG GTGTTCCACT CCTCCCGCCA GGATGGCCTC    2820

AATGACTGTA TGCACAACAA CGGGCAGTGT GGGCAGCTGT GCCTTGCCAT CCCCGGCGGC    2880

CACCGCTGCG GCTGCGCCTC ACACTACACC CTGGACCCCA GCAGCCGCAA CTGCAGCCCG    2940

CCCACCACCT TCTTGCTGTT CAGCCAGAAA TCTGCCATCA GTCGGATGAT CCCGGACGAC    3000

CAGCACAGCC CGGATCTCAT CCTGCCCCTG CATGGACTGA GGAACGTCAA AGCCATCGAC    3060

TATGACCCAC TGGACAAGTT CATCTACTGG GTGGATGGGC GCCAGAACAT CAAGCGAGCC    3120

AAGGACGACG GGACCCAGCC CTTTGTTTTG ACCTCTCTGA GCCAAGGCCA AACCCAGAC     3180

AGGCAGCCCC ACGACCTCAG CATCGACATC TACAGCCGGA CACTGTTCTG GACGTGCGAG    3240

GCCACCAATA CCATCAACGT CCACAGGCTG AGCGGGAAG CCATGGGGGT GGTGCTGCGT     3300

GGGGACCGCG ACAAGCCCAG GGCCATCGTC GTCAACGCGG AGCGAGGGTA CCTGTACTTC    3360

ACCAACATGC AGGACCGGGC AGCCAAGATC GAACGCGCAG CCCTGGACGG CACCGAGCGC    3420

GAGGTCCTCT TCACCACCGG CCTCATCCGC CCTGTGGCCC TGGTGGTAGA CAACACACTG    3480

GGCAAGCTGT TCTGGGTGGA CGCGGACCTG AAGCGCATTG AGAGCTGTGA CCTGTCAGGG    3540

GCCAACCGCC TGACCCTGGA GGACGCCAAC ATCGTGCAGC CTCTGGGCCT GACCATCCTT    3600

GGCAAGCATC TCTACTGGAT CGACCGCCAG CAGCAGATGA TCGAGCGTGT GGAGAAGACC    3660

ACCGGGGACA AGCGGACTCG CATCCAGGGC CGTGTCGCCC ACCTCACTGG CATCCATGCA    3720

GTGGAGGAAG TCAGCCTGGA GGAGTTCTCA GCCCACCCAT GTGCCCGTGA CAATGGTGGC    3780

TGCTCCCACA TCTGTATTGC CAAGGGTGAT GGGACACCAC GGTGCTCATG CCCAGTCCAC    3840

CTCGTGCTCC TGCAGAACCT GCTGACCTGT GGAGAGCCGC CCACCTGCTC CCCGGACCAG    3900

TTTGCATGTG CCACAGGGGA GATCGACTGT ATCCCCGGGG CCTGGCGCTG TGACGGCTTT    3960

CCCGAGTGCG ATGACCAGAG CGACGAGGAG GGCTGCCCCG TGTGCTCCGC CGCCCAGTTC    4020

CCCTGCGCGC GGGGTCAGTG TGTGGACCTG CGCCTGCGCT GCGACGGCGA GGCAGACTGT    4080

CAGGACCGCT CAGACGAGGC GGACTGTGAC GCCATCGCCT GCCCAACCAG TTCCGGTGTG    4140

CGAGCGGCCA GTGTGTCCTC ATCAAACAGC AGTGCGACTC CTTCCCCGAC TGTATCGACG    4200

GCTCCGACGA GCTCATGTGT GAAATCACCA AGCCGCCCTC AGACGACAGC CCGGCCCACA    4260

GCAGTGCCAT CGGGCCCGTC ATTGGCATCA TCCTCTCTCT CTTCGTCATG GGTGGTGTCT    4320

ATTTTGTGTG CCAGCGCGTG GTGTGCCAGC GCTATGCGGG GGCCAACGGG CCCTTCCCGC    4380

ACGAGTATGT CAGCGGGACC CCGCACGTGC CCCTCAATTT CATAGCCCCG GGCGGTTCCC    4440

AGCATGGCCC CTTCACAGGC ATCGCATGCG GAAAGTCCAT GATGAGCTCC GTGAGCCTGA    4500

TGGGGGGCCG GGGCGGGGTG CCCCTCTACG ACCGGAACCA CGTCACAGGG GCCTCGTCCA    4560

GCAGCTCGTC CAGCACGAAG GCCACGCTGT ACCCGCGGAT CCTGAACCCG CCGCCCTCCC    4620

CGGCCACGGA CCCCTCCCTG TACAACATGG ACATGTTCTA CTCTTCAAAC ATTCCGGCCA    4680

CTGCGAGACC GTACAGGCCC TACATCATTC GAGGAATGGC GCCCCGACG ACGCCCTGCA      4740

GCACCGACGT GTGTGACAGC GACTACAGCG CCAGCCGCTG GAAGGCCAGC AAGTACTACC    4800

TGGATTTGAA CTCGGACTCA GACCCCTATC CACCCCCACC CACGCCCCAC AGCCAGTACC    4860

TGTCGGCGGA GGACAGCTGC CCGCCCTCGC CCGCCACCGA GAGGAGCTAC TTCCATCTCT    4920
```

-continued

| | | | | | |
|---|---|---|---|---|---|
| TCCCGCCCCC | TCCGTCCCCC | TGCACGGACT | CATCCTGACC | TCGGCCGGGC | CACTCTGGCT | 4980 |
| TCTCTGTGCC | CCTGTAAATA | GTTTTAAATA | TGAACAAAGA | AAAAAATATA | TTTTATGATT | 5040 |
| TAAAAAATAA | ATATAATTGG | GATTTTAAAA | ACATGAGAAA | TGTGAACTGT | GATGGGGTGG | 5100 |
| GCAGGGCTGG | GAGAACTTTG | TACAGTGGAA | CAAATATTTA | TAAACTTAAT | TTTGTAAAAC | 5160 |
| AG | | | | | | 5162 |

(2) INFORMATION FOR SEQ ID NO:34:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO:34:

| | | | | | |
|---|---|---|---|---|---|
| CAATGTCCAG | TTCCGCTGCA | GTTATAACAT | CCCATTTTTT | GATTTCTTTT | TATTTTTTCC | 60 |
| TTTTTCTTTT | TGAGATGGAG | TCTCGCTCTG | TCACCCAGGC | TGGAGTGCAA | TGGG | 114 |

(2) INFORMATION FOR SEQ ID NO:35:

(i) SEQUENCE CHARACTERISTICS:
        (A) LENGTH: 1711 base pairs
        (B) TYPE: nucleic acid
        (C) STRANDEDNESS: single
        (D) TOPOLOGY: linear (xi) SEQUENCE DESCRIPTION: SEQ ID NO:35:

| | | | | | |
|---|---|---|---|---|---|
| GCCGCGGCGC | CCGAGGCGGG | AGCAAGAGGC | GCCGGGAGCC | GCGAGGATCC | ACCGCCGCCG | 60 |
| CGCGCGCCAT | GGAGCCCGAG | TGAGCGCGCG | GCGCTCCCGG | CCGCCGGACG | ACATGGAAAC | 120 |
| GGCGCCGACC | CGGGCCCCTC | CGCCGCCGCC | GCCGCCGCTG | CTGCTGCTGG | TGCTGTACTG | 180 |
| CAGCTTGGTC | CCCGCCGCGG | CCTCACCGCT | CCTGTTGTTT | GCCAACCGCC | GGGATGTGCG | 240 |
| GCTAGTGGAT | GCCGGCGGAG | TGAAGCTGGA | GTCCACCATT | GTGGCCAGTG | GCCTGGAGGA | 300 |
| TGCAGCTGCT | GTAGACTTCC | AGTTCTCCAA | GGGTGCTGTG | TACTGGACAG | ATGTGAGCGA | 360 |
| GGAGGCCATC | AAACAGACCT | ACCTGAACCA | GACTGGAGGT | GCTGCACAGA | ACATTGTCAT | 420 |
| CTCGGGCCTC | GTGTCACCTG | ATGGCCTGGC | CTGTGACTGG | GTTGGCAAGA | AGCTGTACTG | 480 |
| GACGGACTCC | GAGACCAACC | GCATTGAGGT | TGCCAACCTC | AATGGGACGT | CCCGTAAGGT | 540 |
| TCTCTTCTGG | CAGGACCTGG | ACCAGCCAAG | GGCCATTGCC | CTGGATCCTG | CACATGGGTA | 600 |
| CATGTACTGG | ACTGACTGGG | GGGAAGCACC | CCGGATCGAG | CGGGCAGGGA | TGGATGGCAG | 660 |
| TACCCGGAAG | ATCATTGTAG | ACTCCGACAT | TTACTGGCCC | AATGGGCTGA | CCATCGACCT | 720 |
| GGAGGAACAG | AAGCTGTACT | GGGCCGATGC | CAAGCTCAGC | TTCATCCACC | GTGCCAACCT | 780 |
| GGACGGCTCC | TTCCGGCAGA | AGGTGGTGGA | GGGCAGCCTC | ACTCACCCTT | TTGCCCTGAC | 840 |
| ACTCTCTGGG | GACACACTCT | ACTGGACAGA | CTGGCAGACC | CGCTCCATCC | ACGCCTGCAA | 900 |
| CAAGTGGACA | GGGGAGCAGA | GGAAGGAGAT | CCTTAGTGCT | CTGTACTCAC | CCATGGACAT | 960 |
| CCAAGTGCTG | AGCCAGGAGC | GGCAGCCTCC | CTTCCACACA | CCATGCGAGG | AGGACAACGG | 1020 |
| TGGCTGTTCC | CACCTGTGCC | TGCTGTCCCC | GAGGGAGCCT | TTCTACTCCT | GTGCCTGCCC | 1080 |
| CACTGGTGTG | CAGTTGCAGG | ACAATGGCAA | GACGTGCAAG | ACAGGGGCTG | AGGAAGTGCT | 1140 |
| GCTGCTGGCT | CGGAGGACAG | ACCTGAGGAG | GATCTCTCTG | GACACCCCTG | ACTTCACAGA | 1200 |
| CATAGTGCTG | CAGGTGGGCG | ACATCCGGCA | TGCCATTGCC | ATTGACTACG | ATCCCCTGGA | 1260 |
| GGGCTACGTG | TACTGGACCG | ATGATGAGGT | GCGGGCTATC | CGCAGGGCGT | ACCTAGATGG | 1320 |

-continued

| | |
|---|---|
| CTCAGGTGCG CAGACACTTG TGAACACTGA GATCAATGAC CCCGATGGCA TTGCTGTGGA | 1380 |
| CTGGGTCGCC CGGAACCTCT ACTGGACAGA TACAGGCACT GACAGAATTG AGGTGACTCG | 1440 |
| CCTCAACGGC ACCTCCCGAA AGATCCTGGT ATCTGAGGAC CTGGACGAAC CGCGAGCCAT | 1500 |
| TGTGTTGCAC CCTGTGATGG GCCTCATGTA CTGGACAGAC TGGGGGGAGA ACCCCAAAAT | 1560 |
| CGAATGCGCC AACCTAGATG GGAGAGATCG GCATGTCCTG GTGAACACCT CCCTTGGGTG | 1620 |
| GCCCAATGGA CTGGCCCTGG ACCTGCAGGA GGGCAAGCTG TACTGGGGGG ATGCCAAAAC | 1680 |
| TGATAAAATC GAGGTGATCA ACATAGACGG G | 1711 |

(2) INFORMATION FOR SEQ ID NO:36:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (xi) SEQUENCE DESCRIPTION: SEQ ID NO:36:

| | |
|---|---|
| GCCGCGGCGC CCGAGGCGGG AGCAAGAGGC GCCGGGAGCC GCGAGGATCC ACCGCCGCCG | 60 |
| CGCGCGCCAT GGAGCCCGAG TGAGCGCGCG GCGCTCCCGG CCGCCGGACG ACATGGAAAC | 120 |
| GGCGCCGACC CGGGCCCCTC CGCCGCCGCC GCCGCCGCTG CTGCTGCTGG TGCTGTACTG | 180 |
| CAGCTTGGTC CCCGCCGCGG | 200 |

(2) INFORMATION FOR SEQ ID NO:37:

(i) SEQUENCE CHARACTERISTICS:
        (A) LENGTH: 1599 base pairs
        (B) TYPE: nucleic acid
        (C) STRANDEDNESS: single
        (D) TOPOLOGY: linear (xi) SEQUENCE DESCRIPTION: SEQ ID NO:37:

| | |
|---|---|
| ATGGAAACGG CGCCGACCCG GGCCCCTCCG CCGCCGCCGC CGCCGCTGCT GCTGCTGGTG | 60 |
| CTGTACTGCA GCTTGGTCCC CGCCGCGGCC TCACCGCTCC TGTTGTTTGC CAACCGCCGG | 120 |
| GATGTGCGGC TAGTGGATGC CGGCGGAGTG AAGCTGGAGT CCACCATTGT GGCCAGTGGC | 180 |
| CTGGAGGATG CAGCTGCTGT AGACTTCCAG TTCTCCAAGG GTGCTGTGTA CTGGACAGAT | 240 |
| GTGAGCGAGG AGGCCATCAA ACAGACCTAC CTGAACCAGA CTGGAGGTGC TGCACAGAAC | 300 |
| ATTGTCATCT CGGGCCTCGT GTCACCTGAT GGCCTGGCCT GTGACTGGGT TGGCAAGAAG | 360 |
| CTGTACTGGA CGGACTCCGA GACCAACCGC ATTGAGGTTG CCAACCTCAA TGGGACGTCC | 420 |
| CGTAAGGTTC TCTTCTGGCA GGACCTGGAC CAGCCAAGGG CCATTGCCCT GGATCCTGCA | 480 |
| CATGGGTACA TGTACTGGAC TGACTGGGGG GAAGCACCCC GGATCGAGCG GCAGGGATG | 540 |
| GATGGCAGTA CCCGGAAGAT CATTGTAGAC TCCGACATTT ACTGGCCCAA TGGGCTGACC | 600 |
| ATCGACCTGG AGGAACAGAA GCTGTACTGG GCCGATGCCA AGCTCAGCTT CATCCACCGT | 660 |
| GCCAACCTGG ACGGCTCCTT CCGGCAGAAG GTGGTGGAGG CAGCCTCAC TCACCCTTTT | 720 |
| GCCCTGACAC TCTCTGGGGA CACACTCTAC TGGACAGACT GGCAGACCCG CTCCATCCAC | 780 |
| GCCTGCAACA AGTGGACAGG GGAGCAGAGG AAGGAGATCC TTAGTGCTCT GTACTCACCC | 840 |
| ATGGACATCC AAGTGCTGAG CCAGGAGCGG CAGCCTCCCT TCCACACACC ATGCGAGGAG | 900 |
| GACAACGGTG GCTGTTCCCA CCTGTGCCTG CTGTCCCCGA GGGAGCCTTT CTACTCCTGT | 960 |
| GCCTGCCCCA CTGGTGTGCA GTTGCAGGAC AATGGCAAGA CGTGCAAGAC AGGGGCTGAG | 1020 |

```
GAAGTGCTGC TGCTGGCTCG GAGGACAGAC CTGAGGAGGA TCTCTCTGGA CACCCCTGAC    1080

TTCACAGACA TAGTGCTGCA GGTGGGCGAC ATCCGGCATG CCATTGCCAT TGACTACGAT    1140

CCCCTGGAGG GCTACGTGTA CTGGACCGAT GATGAGGTGC GGGCTATCCG CAGGGCGTAC    1200

CTAGATGGCT CAGGTGCGCA GACACTTGTG AACACTGAGA TCAATGACCC CGATGGCATT    1260

GCTGTGGACT GGGTCGCCCG GAACCTCTAC TGGACAGATA CAGGCACTGA CAGAATTGAG    1320

GTGACTCGCC TCAACGGCAC CTCCCGAAAG ATCCTGGTAT CTGAGGACCT GGACGAACCG    1380

CGAGCCATTG TGTTGCACCC TGTGATGGGC CTCATGTACT GGACAGACTG GGGGGAGAAC    1440

CCCAAAATCG AATGCGCCAA CCTAGATGGG AGAGATCGGC ATGTCCTGGT GAACACCTCC    1500

CTTGGGTGGC CCAATGGACT GGCCCTGGAC CTGCAGGAGG GCAAGCTGTA CTGGGGGGAT    1560

GCCAAAACTG ATAAAATCGA GGTGATCAAC ATAGACGGG                           1599
```

(2) INFORMATION FOR SEQ ID NO:38:

(i) SEQUENCE CHARACTERISTICS:
        (A) LENGTH: 4959 base pairs
        (B) TYPE: nucleic acid
        (C) STRANDEDNESS: double
        (D) TOPOLOGY: linear (xi) SEQUENCE DESCRIPTION: SEQ ID NO:38:

```
CCTCGCCGCT CCTGCTATTT GCCAACCGCC GGGACGTACG GCTGGTGGAC GCCGGCGGAG     60

TCAAGCTGGA GTCCACCATC GTGGTCAGCG GCCTGGAGGA TGCGGCCGCA GTGGACTTCC    120

AGTTTTCCAA GGGAGCCGTG TACTGGACAG ACGTGAGCGA GGAGGCCATC AAGCAGACCT    180

ACCTGAACCA GACGGGGGCC GCCGTGCAGA ACGTGGTCAT CTCCGGCCTG GTCTCTCCCG    240

ACGGCCTCGC CTGCGACTGG GTGGGCAAGA AGCTGTACTG GACGGACTCA GAGACCAACC    300

GCATCGAGGT GGCCAACCTC AATGGCACAT CCCGGAAGGT GCTCTTCTGG CAGGACCTTG    360

ACCAGCCGAG GGCCATCGCC TTGGACCCCG CTCACGGGTA CATGTACTGG ACAGACTGGG    420

GTGAGACGCC CCGGATTGAG CGGGCAGGGA TGGATGGCAG CACCCGGAAG ATCATTGTGG    480

ACTCGGACAT TTACTGGCCC AATGGACTGA CCATCGACCT GGAGGAGCAG AAGCTCTACT    540

GGGCTGACGC CAAGCTCAGC TTCATCCACC GTGCCAACCT GGACGGCTCG TTCCGGCAGA    600

AGGTGGTGGA GGGCAGCCTG ACGCACCCCT TCGCCCTGAC GCTCTCCGGG GACACTCTGT    660

ACTGGACAGA CTGGCAGACC CGCTCCATCC ATGCCTGCAA CAAGCGCACT GGGGGGAAGA    720

GGAAGGAGAT CCTGAGTGCC CTCTACTCAC CCATGGACAT CCAGGTGCTG AGCCAGGAGC    780

GGCAGCCTTT CTTCCACACT CGCTGTGAGG AGGACAATGG CGGCTGCTCC CACCTGTGCC    840

TGCTGTCCCC AAGCGAGCCT TTCTACACAT GCGCCTGCCC CACGGGTGTG CAGCTGCAGG    900

ACAACGGCAG GACGTGTAAG GCAGGAGCCG AGGAGGTGCT GCTGCTGGCC CGGCGGACGG    960

ACCTACGGAG GATCTCGCTG GACACGCCGG ACTTTACCGA CATCGTGCTG CAGGTGGACG   1020

ACATCCGGCA CGCCATTGCC ATCGACTACG ACCCGCTAGA GGGCTATGTC TACTGGACAG   1080

ATGACGAGGT GCGGGCCATC CGCAGGGCGT ACCTGGACGG GTCTGGGGCG CAGACGCTGG   1140

TCAACACCGA GATCAACGAC CCCGATGGCA TCGCGGTCGA CTGGGTGGCC CGAAACCTCT   1200

ACTGGACCGA CACGGGCACG GACCGCATCG AGGTGACGCG CCTCAACGGC ACCTCCCGCA   1260

AGATCCTGGT GTCGGAGGAC CTGGACGAGC CCCGAGCCAT CGCACTGCAC CCCGTGATGG   1320

GCCTCATGTA CTGGACAGAC TGGGGAGAGA ACCCTAAAAT CGAGTGTGCC AACTTGGATG   1380

GGCAGGAGCG GCGTGTGCTG GTCAATGCCT CCCTCGGGTG GCCCAACGGC CTGGCCCTGG   1440
```

-continued

```
ACCTGCAGGA GGGGAAGCTC TACTGGGGAG ACGCCAAGAC AGACAAGATC GAGGTGATCA   1500

ATGTTGATGG GACGAAGAGG CGGACCCTCC TGGAGGACAA GCTCCCGCAC ATTTTCGGGT   1560

TCACGCTGCT GGGGGACTTC ATCTACTGGA CTGACTGGCA GCGCCGCAGC ATCGAGCGGG   1620

TGCACAAGGT CAAGGCCAGC CGGGACGTCA TCATTGACCA GCTGCCCGAC CTGATGGGGC   1680

TCAAAGCTGT GAATGTGGCC AAGGTCGTCG GAACCAACCC GTGTGCGGAC AGGAACGGGG   1740

GGTGCAGCCA CCTGTGCTTC TTCACACCCC ACGCAACCCG GTGTGGCTGC CCCATCGGCC   1800

TGGAGCTGCT GAGTGACATG AAGACCTGCA TCGTGCCTGA GGCCTTCTTG GTCTTCACCA   1860

GCAGAGCCGC CATCCACAGG ATCTCCCTCG AGACCAATAA CAACGACGTG CCATCCCGC   1920

TCACGGGCGT CAAGGAGGCC TCAGCCCTGG ACTTTGATGT GTCCAACAAC ACATCTACT   1980

GGACAGACGT CAGCCTGAAG ACCATCAGCC GCGCCTTCAT GAACGGGAGC TCGGTGGAGC   2040

ACGTGGTGAG TTTGGCCTTG ACTACCCCGA GGGCATGGCC GTTGACTGGA TGGGCAAGAA   2100

CCTCTACTGG GCCGACACTG GGACCAACAG AATCGAAGTG GCGCGGCTGG ACGGGCAGTT   2160

CCGGCAAGTC CTCGTGTGGA GGGACTTGGA CAACCCGAGG TCGCTGGCCC TGGATCCCAC   2220

CAAGGGCTAC ATCTACTGGA CCGAGTGGGG CGGCAAGCCG AGGATCGTGC GGGCCTTCAT   2280

GGACGGGACC AACTGCATGA CGCTGGTGGA CAAGGTGGGC CGGGCCAACG ACCTCACCAT   2340

TGACTACGCT GACCAGCGCC TCTACTGGAC CGACCTGGAC ACCAACATGA TCGAGTCGTC   2400

CAACATGCTG GGTCAGGAGC GGGTCGTGAT TGCCGACGAT CTCCCGCACC CGTTCGGTCT   2460

GACGCAGTAC AGCGATTATA TCTACTGGAC AGACTGGAAT CTGCACAGCA TTGAGCGGGC   2520

CGACAAGACT AGCGGCCGGA ACCGCACCCT CATCCAGGGC CACCTGGACT TCGTGATGGA   2580

CATCCTGGTG TTCCACTCCT CCCGCCAGGA TGGCCTCAAT GACTGTATGC ACAACAACGG   2640

GCAGTGTGGG CAGCTGTGCC TTGCCATCCC CGGCGGCCAC CGCTGCGGCT GCGCCTCACA   2700

CTACACCCTG GACCCCAGCA GCCGCAACTG CAGCCCGCCC ACCACCTTCT TGCTGTTCAG   2760

CCAGAAATCT GCCATCAGTC GGATGATCCC GGACGACCAG CACAGCCCGG ATCTCATCCT   2820

GCCCCTGCAT GGACTGAGGA ACGTCAAAGC CATCGACTAT GACCCACTGG ACAAGTTCAT   2880

CTACTGGGTG GATGGGCGCC AGAACATCAA GCGAGCCAAG GACGACGGGA CCCAGCCCTT   2940

TGTTTTGACC TCTCTGAGCC AAGGCCAAAA CCCAGACAGG CAGCCCCACG ACCTCAGCAT   3000

CGACATCTAC AGCCGGACAC TGTTCTGGAC GTGCGAGGCC ACCAATACCA TCAACGTCCA   3060

CAGGCTGAGC GGGGAAGCCA TGGGGGTGGT GCTGCGTGGG GACCGCGACA GCCCAGGGC   3120

CATCGTCGTC AACGCGGAGC GAGGGTACCT GTACTTCACC AACATGCAGG ACCGGGCAGC   3180

CAAGATCGAA CGCGCAGCCC TGGACGGCAC CGAGCGCGAG GTCCTCTTCA CCACCGGCCT   3240

CATCCGCCCT GTGGCCCTGG TGGTAGACAA CACACTGGGC AAGCTGTTCT GGGTGGACGC   3300

GGACCTGAAG CGCATTGAGA GCTGTGACCT GTCAGGGGCC AACCGCCTGA CCCTGGAGGA   3360

CGCCAACATC GTGCAGCCTC TGGGCCTGAC CATCCTTGGC AAGCATCTCT ACTGGATCGA   3420

CCGCCAGCAG CAGATGATCG AGCGTGTGGA GAAGACCACC GGGGACAAGC GGACTCGCAT   3480

CCAGGGCCGT GTCGCCCACC TCACTGGCAT CCATGCAGTG GAGGAAGTCA GCCTGGAGGA   3540

GTTCTCAGCC CACCCATGTG CCCGTGACAA TGGTGGCTGC TCCCACATCT GTATTGCCAA   3600

GGGTGATGGG ACACCACGGT GCTCATGCCC AGTCCACCTC GTGCTCCTGC AGAACCTGCT   3660

GACCTGTGGA GAGCCGCCCA CCTGCTCCCC GGACCAGTTT GCATGTGCCA CAGGGGAGAT   3720

CGACTGTATC CCCGGGGCCT GGCGCTGTGA CGGCTTTCCC GAGTGCGATG ACCAGAGCGA   3780

CGAGGAGGGC TGCCCCGTGT GCTCCGCCGC CCAGTTCCCC TGCGCGCGGG GTCAGTGTGT   3840
```

```
GGACCTGCGC CTGCGCTGCG ACGGCGAGGC AGACTGTCAG GACCGCTCAG ACGAGGCGGA    3900

CTGTGACGCC ATCTGCCTGC CCAACCAGTT CCGGTGTGCG AGCGGCCAGT GTGTCCTCAT    3960

CAAACAGCAG TGCGACTCCT TCCCCGACTG TATCGACGGC TCCGACGAGC TCATGTGTGA    4020

AATCACCAAG CCGCCCTCAG ACGACAGCCC GGCCCACAGC AGTGCCATCG GCCCCGTCAT    4080

TGGCATCATC CTCTCTCTCT TCGTCATGGG TGGTGTCTAT TTTGTGTGCC AGCGCGTGGT    4140

GTGCCAGCGC TATGCGGGGG CCAACGGCCC TTCCCGCACG AGTATGTCAG CGGGACCCCG    4200

CACGTGCCCC TCAATTTCAT AGCCCCGGGC GGTTCCCAGC ATGGCCCCTT CACAGGCATC    4260

GCATGCGGAA AGTCCATGAT GAGCTCCGTG AGCCTGATGG GGGGCCGGGG CGGGGTGCCC    4320

CTCTACGACC GGAACCACGT CACAGGGGCC TCGTCCAGCA GCTCGTCCAG CACGAAGGCC    4380

ACGCTGTACC CGCCGATCCT GAACCCGCCG CCCTCCCCGG CCACGGACCC CTCCCTGTAC    4440

AACATGGACA TGTTCTACTC TTCAAACATT CCGGCCACTG TGAGACCGTA CAGGCCCTAC    4500

ATCATTCGAG GAATGGCGCC CCCGACGACG CCCTGCAGCA CCGACGTGTG TGACAGCGAC    4560

TACAGCGCCA GCCGCTGGAA GGCCAGCAAG TACTACCTGG ATTTGAACTC GGACTCAGAC    4620

CCCTATCCAC CCCCACCCAC GCCCCACAGC CAGTACCTGT CGGCGGAGGA CAGCTGCCCG    4680

CCCTCGCCCG CCACCGAGAG GAGCTACTTC CATCTCTTCC CGCCCCCTCC GTCCCCCTGC    4740

ACGGACTCAT CCTGACCTCG GCCGGGCCAC TCTGGCTTCT CTGTGCCCCT GTAAATAGTT    4800

TTAAATATGA ACAAAGAAAA AAATATATTT TATGATTTAA AAAATAAATA TAATTGGGAT    4860

TTTAAAAACA TGAGAAATGT GAACTGTGAT GGGGTGGGCA GGGCTGGGAG AACTTTGTAC    4920

AGTGGAACAA ATATTTATAA ACTTAATTTT GTAAAACAG                           4959
```

(2) INFORMATION FOR SEQ ID NO:39:

(i) SEQUENCE CHARACTERISTICS:
        (A) LENGTH: 1584 amino acids
        (B) TYPE: amino acid
        (D) TOPOLOGY: linear (xi) SEQUENCE DESCRIPTION: SEQ ID NO:39:

```
Ser Pro Leu Leu Leu Phe Ala Asn Arg Arg Asp Val Arg Leu Val Asp
1               5                   10                  15

Ala Gly Gly Val Lys Leu Glu Ser Thr Ile Val Val Ser Gly Leu Glu
            20                  25                  30

Asp Ala Ala Ala Val Asp Phe Gln Phe Ser Lys Gly Ala Val Tyr Trp
        35                  40                  45

Thr Asp Val Ser Glu Glu Ala Ile Lys Gln Thr Tyr Leu Asn Gln Thr
    50                  55                  60

Gly Ala Ala Val Gln Asn Val Val Ile Ser Gly Leu Val Ser Pro Asp
65                  70                  75                  80

Gly Leu Ala Cys Asp Trp Val Gly Lys Lys Leu Tyr Trp Thr Asp Ser
                85                  90                  95

Glu Thr Asn Arg Ile Glu Val Ala Asn Leu Asn Gly Thr Ser Arg Lys
            100                 105                 110

Val Leu Phe Trp Gln Asp Leu Asp Gln Pro Arg Ala Ile Ala Leu Asp
        115                 120                 125

Pro Ala His Gly Tyr Met Tyr Trp Thr Asp Trp Gly Glu Thr Pro Arg
    130                 135                 140

Ile Glu Arg Ala Gly Met Asp Gly Ser Thr Arg Lys Ile Ile Val Asp
145                 150                 155                 160
```

-continued

```
Ser Asp Ile Tyr Trp Pro Asn Gly Leu Thr Ile Asp Leu Glu Glu Gln
            165                 170                 175

Lys Leu Tyr Trp Ala Asp Ala Lys Leu Ser Phe Ile His Arg Ala Asn
            180                 185                 190

Leu Asp Gly Ser Phe Arg Gln Lys Val Val Glu Gly Ser Leu Thr His
            195                 200                 205

Pro Phe Ala Leu Thr Leu Ser Gly Asp Thr Leu Tyr Trp Thr Asp Trp
    210                 215                 220

Gln Thr Arg Ser Ile His Ala Cys Asn Lys Arg Thr Gly Lys Arg
225                 230                 235                 240

Lys Glu Ile Leu Ser Ala Leu Tyr Ser Pro Met Asp Ile Gln Val Leu
                245                 250                 255

Ser Gln Glu Arg Gln Pro Phe Phe His Thr Arg Cys Glu Glu Asp Asn
            260                 265                 270

Gly Gly Cys Ser His Leu Cys Leu Leu Ser Pro Ser Glu Pro Phe Tyr
            275                 280                 285

Thr Cys Ala Cys Pro Thr Gly Val Gln Leu Gln Asp Asn Gly Arg Thr
    290                 295                 300

Cys Lys Ala Gly Ala Glu Val Leu Leu Leu Ala Arg Arg Thr Asp
305                 310                 315                 320

Leu Arg Arg Ile Ser Leu Asp Thr Pro Asp Phe Thr Asp Ile Val Leu
                325                 330                 335

Gln Val Asp Asp Ile Arg His Ala Ile Ala Ile Asp Tyr Asp Pro Leu
            340                 345                 350

Glu Gly Tyr Val Tyr Trp Thr Asp Asp Glu Val Arg Ala Ile Arg Arg
            355                 360                 365

Ala Tyr Leu Asp Gly Ser Gly Ala Gln Thr Leu Val Asn Thr Glu Ile
    370                 375                 380

Asn Asp Pro Asp Gly Ile Ala Val Asp Trp Val Ala Arg Asn Leu Tyr
385                 390                 395                 400

Trp Thr Asp Thr Gly Thr Asp Arg Ile Glu Val Thr Arg Leu Asn Gly
                405                 410                 415

Thr Ser Arg Lys Ile Leu Val Ser Glu Asp Leu Asp Glu Pro Arg Ala
            420                 425                 430

Ile Ala Leu His Pro Val Met Gly Leu Met Tyr Trp Thr Asp Trp Gly
            435                 440                 445

Glu Asn Pro Lys Ile Glu Cys Ala Asn Leu Asp Gly Gln Glu Arg Arg
    450                 455                 460

Val Leu Val Asn Ala Ser Leu Gly Trp Pro Asn Gly Leu Ala Leu Asp
465                 470                 475                 480

Leu Gln Glu Gly Lys Leu Tyr Trp Gly Asp Ala Lys Thr Asp Lys Ile
                485                 490                 495

Glu Val Ile Asn Val Asp Gly Thr Lys Arg Arg Thr Leu Leu Glu Asp
            500                 505                 510

Lys Leu Pro His Ile Phe Gly Phe Thr Leu Leu Gly Asp Phe Ile Tyr
            515                 520                 525

Trp Thr Asp Trp Gln Arg Arg Ser Ile Glu Arg Val His Lys Val Lys
    530                 535                 540

Ala Ser Arg Asp Val Ile Ile Asp Gln Leu Pro Asp Leu Met Gly Leu
545                 550                 555                 560

Lys Ala Val Asn Val Ala Lys Val Val Gly Thr Asn Pro Cys Ala Asp
                565                 570                 575

Arg Asn Gly Gly Cys Ser His Leu Cys Phe Phe Thr Pro His Ala Thr
```

-continued

```
              580                 585                 590
Arg Cys Gly Cys Pro Ile Gly Leu Glu Leu Leu Ser Asp Met Lys Thr
            595                 600                 605
Cys Ile Val Pro Glu Ala Phe Leu Val Phe Thr Ser Arg Ala Ala Ile
610                 615                 620
His Arg Ile Ser Leu Glu Thr Asn Asn Asn Asp Val Ala Ile Pro Leu
625                 630                 635                 640
Thr Gly Val Lys Glu Ala Ser Ala Leu Asp Phe Asp Val Ser Asn Asn
                645                 650                 655
His Ile Tyr Trp Thr Asp Val Ser Leu Lys Thr Ile Ser Arg Ala Phe
                660                 665                 670
Met Asn Gly Ser Ser Val Glu His Val Val Glu Phe Gly Leu Asp Tyr
                675                 680                 685
Pro Glu Gly Met Ala Val Asp Trp Met Gly Lys Asn Leu Tyr Trp Ala
            690                 695                 700
Asp Thr Gly Thr Asn Arg Ile Glu Val Ala Arg Leu Asp Gly Gln Phe
705                 710                 715                 720
Arg Gln Val Leu Val Trp Arg Asp Leu Asp Asn Pro Arg Ser Leu Ala
                725                 730                 735
Leu Asp Pro Thr Lys Gly Tyr Ile Tyr Trp Thr Glu Trp Gly Gly Lys
            740                 745                 750
Pro Arg Ile Val Arg Ala Phe Met Asp Gly Thr Asn Cys Met Thr Leu
            755                 760                 765
Val Asp Lys Val Gly Arg Ala Asn Asp Leu Thr Ile Asp Tyr Ala Asp
770                 775                 780
Gln Arg Leu Tyr Trp Thr Asp Leu Asp Thr Asn Met Ile Glu Ser Ser
785                 790                 795                 800
Asn Met Leu Gly Gln Glu Arg Val Val Ile Ala Asp Asp Leu Pro His
                805                 810                 815
Pro Phe Gly Leu Thr Gln Tyr Ser Asp Tyr Ile Tyr Trp Thr Asp Trp
                820                 825                 830
Asn Leu His Ser Ile Glu Arg Ala Asp Lys Thr Ser Gly Arg Asn Arg
                835                 840                 845
Thr Leu Ile Gln Gly His Leu Asp Phe Val Met Asp Ile Leu Val Phe
            850                 855                 860
His Ser Ser Arg Gln Asp Gly Leu Asn Asp Cys Met His Asn Asn Gly
865                 870                 875                 880
Gln Cys Gly Gln Leu Cys Leu Ala Ile Pro Gly Gly His Arg Cys Gly
                885                 890                 895
Cys Ala Ser His Tyr Thr Leu Asp Pro Ser Ser Arg Asn Cys Ser Pro
                900                 905                 910
Pro Thr Thr Phe Leu Leu Phe Ser Gln Lys Ser Ala Ile Ser Arg Met
                915                 920                 925
Ile Pro Asp Asp Gln His Ser Pro Asp Leu Ile Leu Pro Leu His Gly
            930                 935                 940
Leu Arg Asn Val Lys Ala Ile Asp Tyr Asp Pro Leu Asp Lys Phe Ile
945                 950                 955                 960
Tyr Trp Val Asp Gly Arg Gln Asn Ile Lys Arg Ala Lys Asp Asp Gly
                965                 970                 975
Thr Gln Pro Phe Val Leu Thr Ser Leu Ser Gln Gly Gln Asn Pro Asp
                980                 985                 990
Arg Gln Pro His Asp Leu Ser Ile Asp Ile Tyr Ser Arg Thr Leu Phe
            995                 1000                1005
```

-continued

Trp Thr Cys Glu Ala Thr Asn Thr Ile Asn Val His Arg Leu Ser Gly
    1010                1015                1020
Glu Ala Met Gly Val Val Leu Arg Gly Asp Arg Asp Lys Pro Arg Ala
1025                1030                1035                1040
Ile Val Val Asn Ala Glu Arg Gly Tyr Leu Tyr Phe Thr Asn Met Gln
                1045                1050                1055
Asp Arg Ala Ala Lys Ile Glu Arg Ala Ala Leu Asp Gly Thr Glu Arg
                1060                1065                1070
Glu Val Leu Phe Thr Thr Gly Leu Ile Arg Pro Val Ala Leu Val Val
            1075                1080                1085
Asp Asn Thr Leu Gly Lys Leu Phe Trp Val Asp Ala Asp Leu Lys Arg
        1090                1095                1100
Ile Glu Ser Cys Asp Leu Ser Gly Ala Asn Arg Leu Thr Leu Glu Asp
1105                1110                1115                1120
Ala Asn Ile Val Gln Pro Leu Gly Leu Thr Ile Leu Gly Lys His Leu
                1125                1130                1135
Tyr Trp Ile Asp Arg Gln Gln Met Ile Glu Arg Val Glu Lys Thr
                1140                1145                1150
Thr Gly Asp Lys Arg Thr Arg Ile Gln Gly Arg Val Ala His Leu Thr
            1155                1160                1165
Gly Ile His Ala Val Glu Glu Val Ser Leu Glu Glu Phe Ser Ala His
        1170                1175                1180
Pro Cys Ala Arg Asp Asn Gly Gly Cys Ser His Ile Cys Ile Ala Lys
1185                1190                1195                1200
Gly Asp Gly Thr Pro Arg Cys Ser Cys Pro Val His Leu Val Leu Leu
                1205                1210                1215
Gln Asn Leu Leu Thr Cys Gly Glu Pro Pro Thr Cys Ser Pro Asp Gln
                1220                1225                1230
Phe Ala Cys Ala Thr Gly Glu Ile Asp Cys Ile Pro Gly Ala Trp Arg
            1235                1240                1245
Cys Asp Gly Phe Pro Glu Cys Asp Asp Gln Ser Asp Glu Glu Gly Cys
        1250                1255                1260
Pro Val Cys Ser Ala Ala Gln Phe Pro Cys Ala Arg Gly Gln Cys Val
1265                1270                1275                1280
Asp Leu Arg Leu Arg Cys Asp Gly Glu Ala Asp Cys Gln Asp Arg Ser
                1285                1290                1295
Asp Glu Ala Asp Cys Asp Ala Ile Cys Leu Pro Asn Gln Phe Arg Cys
                1300                1305                1310
Ala Ser Gly Gln Cys Val Leu Ile Lys Gln Gln Cys Asp Ser Phe Pro
            1315                1320                1325
Asp Cys Ile Asp Gly Ser Asp Glu Leu Met Cys Glu Ile Thr Lys Pro
        1330                1335                1340
Pro Ser Asp Asp Ser Pro Ala His Ser Ser Ala Ile Gly Pro Val Ile
1345                1350                1355                1360
Gly Ile Ile Leu Ser Leu Phe Val Met Gly Gly Val Tyr Phe Val Cys
                1365                1370                1375
Gln Arg Val Val Cys Gln Arg Tyr Ala Gly Ala Asn Gly Pro Phe Pro
                1380                1385                1390
His Glu Tyr Val Ser Gly Thr Pro His Val Pro Leu Asn Phe Ile Ala
            1395                1400                1405
Pro Gly Gly Ser Gln His Gly Pro Phe Thr Gly Ile Ala Cys Gly Lys
        1410                1415                1420

```
Ser Met Met Ser Ser Val Ser Leu Met Gly Gly Arg Gly Gly Val Pro
1425                1430                1435                1440

Leu Tyr Asp Arg Asn His Val Thr Gly Ala Ser Ser Ser Ser Ser
            1445                1450                1455

Ser Thr Lys Ala Thr Leu Tyr Pro Pro Ile Leu Asn Pro Pro Ser
            1460                1465                1470

Pro Ala Thr Asp Pro Ser Leu Tyr Asn Met Asp Met Phe Tyr Ser Ser
        1475                1480                1485

Asn Ile Pro Ala Thr Val Arg Pro Tyr Arg Pro Tyr Ile Ile Arg Gly
        1490                1495                1500

Met Ala Pro Pro Thr Thr Pro Cys Ser Thr Asp Val Cys Asp Ser Asp
1505                1510                1515                1520

Tyr Ser Ala Ser Arg Trp Lys Ala Ser Lys Tyr Tyr Leu Asp Leu Asn
            1525                1530                1535

Ser Asp Ser Asp Pro Tyr Pro Pro Pro Thr Pro His Ser Gln Tyr
            1540                1545                1550

Leu Ser Ala Glu Asp Ser Cys Pro Pro Ser Pro Ala Thr Glu Arg Ser
            1555                1560                1565

Tyr Phe His Leu Phe Pro Pro Pro Ser Pro Cys Thr Asp Ser Ser
            1570                1575                1580
```

(2) INFORMATION FOR SEQ ID NO:40:

(i) SEQUENCE CHARACTERISTICS:
        (A) LENGTH: 5117 base pairs
        (B) TYPE: nucleic acid
        (C) STRANDEDNESS: single
        (D) TOPOLOGY: linear (xi) SEQUENCE DESCRIPTION: SEQ ID NO:40:

```
GCCGCGGCGC CGAGGCGGG AGCAAGAGGC GCCGGGAGCC GCGAGGATCC ACCGCCGCCG        60

CGCGCGCCAT GGAGCCCGAG TGAGCGCGCG GCGCTCCCGG CCGCCGGACG ACATGGAAAC      120

GGCGCCGACC CGGGCCCCTC CGCCGCCGCC GCCGCCGCTG CTGCTGCTGG TGCTGTACTG      180

CAGCTTGGTC CCCGCCGCGG CCTCACCGCT CCTGTTGTTT GCCAACCGCC GGGATGTGCG      240

GCTAGTGGAT GCCGGCGGAG TGAAGCTGGA GTCCACCATT GTGGCCAGTG GCCTGGAGGA      300

TGCAGCTGCT GTAGACTTCC AGTTCTCCAA GGGTGCTGTG TACTGGACAG ATGTGAGCGA      360

GGAGGCCATC AAAACAGACCT ACCTGAACCA GACTGGAGCT GCTGCACAGA ACATTGTCAT     420

CTCGGGCCTC GTGTCACCTG ATGGCCTGGC CTGTGACTGG GTTGGCAAGA AGCTGTACTG      480

GACGGACTCC GAGACCAACC GCATTGAGGT TGCCAACCTC AATGGGACGT CCCGTAAGGT      540

TCTCTTCTGG CAGGACCTGG ACCAGCCAAG GGCCATTGCC CTGGATCCTG CACATGGGTA      600

CATGTACTGG ACTGACTGGG GGGAAGCACC CCGGATCGAG CGGGCAGGGA TGGATGGCAG      660

TACCCGGAAG ATCATTGTAG ACTCCGACAT TTACTGGCCC AATGGGCTGA CCATCGACCT      720

GGAGGAACAG AAGCTGTACT GGGCCGATGC CAAGCTCAGC TTCATCCACC GTGCCAACCT      780

GGACGGCTCC TTCCGGCAGA AGGTGGTGGA GGGCAGCCTC ACTCACCCTT TTGCCCTGAC      840

ACTCTCTGGG GACACACTCT ACTGGACAGA CTGGCAGACC CGCTCCATCC ACGCCTGCAA      900

CAAGTGGACA GGGGAGCAGA GGAAGGAGAT CCTTAGTGCT CTGTACTCAC CCATGGACAT      960

CCAAGTGCTG AGCCAGGAGC GGCAGCCTCC CTTCCACACA CCATGCGAGG AGGACAACGG     1020

TGGCTGTTCC CACCTGTGCC TGCTGTCCCC GAGGGAGCCT TCTACTCCT GTGCCTGCCC      1080

CACTGGTGTG CAGTTGCAGG ACAATGGCAA GACGTGCAAG ACAGGGGCTG AGGAAGTGCT     1140
```

-continued

```
GCTGCTGGCT CGGAGGACAG ACCTGAGGAG GATCTCTCTG GACACCCCTG ACTTCACAGA    1200

CATAGTGCTG CAGGTGGGCG ACATCCGGCA TGCCATTGCC ATTGACTACG ATCCCCTGGA    1260

GGGCTACGTG TACTGGACCG ATGATGAGGT GCGGGCTATC CGCAGGGCGT ACCTAGATGG    1320

CTCAGGTGCG CAGACACTTG TGAACACTGA GATCAATGAC CCCGATGGCA TTGCTGTGGA    1380

CTGGGTCGCC CGGAACCTCT ACTGGACAGA TACAGGCACT GACAGAATTG AGGTGACTCG    1440

CCTCAACGGC ACCTCCCGAA AGATCCTGGT ATCTGAGGAC CTGGACGAAC CGCGAGCCAT    1500

TGTGTTGCAC CCTGTGATGG GCCTCATGTA CTGGACAGAC TGGGGGGAGA ACCCCAAAAT    1560

CGAATGCGCC AACCTAGATG GGAGAGATCG GCATGTCCTG GTGAACACCT CCCTTGGGTG    1620

GCCCAATGGA CTGGCCCTGG ACCTGCAGGA GGGCAAGCTG TACTGGGGGG ATGCCAAAAC    1680

TGATAAAATC GAGGTGATCA ACATAGACGG GACAAAGCGG AAGACCCTGC TTGAGGACAA    1740

GCTCCCACAC ATTTTTGGGT TCACACTGCT GGGGGACTTC ATCTACTGGA CCGACTGGCA    1800

GAGACGCAGT ATTGAAAGGG TCCACAAGGT CAAGGCCAGC CGGGATGTCA TCATTGATCA    1860

ACTCCCCGAC CTGATGGGAC TCAAAGCCGT GAATGTGGCC AAGGTTGTCG GAACCAACCC    1920

ATGTGCGGAT GGAAATGGAG GGTGCAGCCA TCTGTGCTTC TTCACCCCAC GTGCCACCAA    1980

GTGTGGCTGC CCCATTGGCC TGGAGCTGTT GAGTGACATG AAGACCTGCA TAATCCCCGA    2040

GGCCTTCCGG TATTCACCAG CAGAGCCACC ATCCACAGGA TCTCCCTGGA GACTAACAAC    2100

AACGATGTGG CTATCCCACT CACGGGTGTC AAAGAGGCCT CTGCACTGGA CTTTGATGTG    2160

TCCAACAATC ACATCTACTG GACTGATGTT AGCCTCAAGA CGATCAGCCG AGCCTTCATG    2220

AATGGGAGCT CAGTGGAGCA CGTGATTGAG TTTGGCCTCG ACTACCCTGA AGGAATGGCT    2280

GTGGACTGGA TGGGCAAGAA CCTCTATTGG GCGGACACAG GGACCAACAG GATTGAGGTG    2340

GCCCGGCTGG ATGGGCAGTT CCGGCAGGTG CTTGTGTGGA GAGACCTTGA CAACCCCAGG    2400

TCTCTGGCTC TGGATCCTAC TAAAGGCTAC ATCTACTGGA CTGAGTGGGG TGGCAAGCCA    2460

AGGATTGTGC GGGCCTTCAT GGATGGGACC AATTGTATGA CACTGGTAGA CAAGGTGGGC    2520

CGGGCCAACG ACCTCACCAT TGATTATGCC GACCAGCGAC TGTACTGGAC TGACCTGGAC    2580

ACCAACATGA TTGAGTCTTC CAACATGCTG GGTCAGGAGC GCATGGTGAT AGCTGACGAT    2640

CTGCCCTACC CGTTTGGCCT GACTCAATAT AGCGATTACA TCTACTGGAC TGACTGGAAC    2700

CTGCATAGCA TTGAACGGGC GGACAAGACC AGTGGGCGGA ACCGCACCCT CATCCAGGGT    2760

CACCTGGACT TCGTCATGGA CATCCTGGTG TTCCACTCCT CCCGTCAGGA TGGCCTCAAC    2820

GACTGCGTGC ACAGCAATGG CCAGTGTGGG CAGCTGTGCC TCGCCATCCC CGGAGGCCAC    2880

CGCTGTGGCT GTGCTTCACA CTACACGCTG GACCCCAGCA GCCGCAACTG CAGCCCGCCC    2940

TCCACCTTCT TGCTGTTCAG CCAGAAATTT GCCATCAGCC GGATGATCCC CGATGACCAG    3000

CTCAGCCCGG ACCTTGTCCT ACCCCTTCAT GGGCTGAGGA ACGTCAAAGC CATCAACTAT    3060

GACCCGCTGG ACAAGTTCAT CTACTGGGTG GACGGGCGCC AGAACATCAA GAGGGCCAAG    3120

GACGACGGTA CCCAGCCCTC CATGCTGACC TCTCCCAGCC AAAGCCTGAG CCCAGACAGA    3180

CAGCCACACG ACCTCAGCAT TGACATCTAC AGCCGGACAC TGTTCTGGAC CTGTGAGGCC    3240

ACCAACACTA TCAATGTCCA CCGGCTGGAT GGGGATGCCA TGGAGTGGTG CTTCGAGGG     3300

GACCGTGACA AGCCAAGGGC CATTGCTGTC AATGCTGAGC GAGGGTACAT GTACTTTACC    3360

AACATGCAGG ACCATGCTGC CAAGATCGAG CGAGCCTCCC TGGATGGCAC AGAGCGGGAG    3420

GTCCTCTTCA CCACAGGCCT CATCCGTCCC GTGGCCCTTG TGGTGGACAA TGCTCTGGGC    3480

AAGCTCTTCT GGGTGGATGC CGACCTAAAG CGAATCGAAA GCTGTGACCT CTCTGGGGCC    3540
```

```
AACCGCCTGA CCCTGGAAGA TGCCAACATC GTACAGCCAG TAGGTCTGAC AGTGCTGGGC    3600

AGGCACCTCT ACTGGATCGA CCGCCAGCAG CAGATGATCG AGCGCGTGGA GAAGACCACT    3660

GGGGACAAGC GGACTAGGGT TCAGGGCCGT GTCACCCACC TGACAGGCAT CCATGCCGTG    3720

GAGGAAGTCA GCCTGGAGGA GTTCTCAGCC CATCCTTGTG CCCGAGACAA TGGCGGCTGC    3780

TCCCACATCT GTATCGCCAA GGGTGATGGA ACACCGCGCT GCTCGTGCCC TGTCCACCTG    3840

GTGCTCCTGC AGAACCTGCT GACTTGTGGT GAGCCTCCTA CCTGCTCCCC TGATCAGTTT    3900

GCATGTACCA CTGGTGAGAT CGACTGCATC CCCGGAGCCT GGCGCTGTGA CGGCTTCCCT    3960

GAGTGTGCTG ACCAGAGTGA TGAAGAAGGC TGCCCAGTGT GCTCCGCCTC TCAGTTCCCC    4020

TGCGCTCGAG GCCAGTGTGT GGACCTGCGG TTACGCTGCG ACGGTGAGGC CGACTGCCAG    4080

GATCGCTCTG ATGAAGTAAC TGCGATGCTG TCTGTCTGCC CAATCAGTTC CGGTGCACCA    4140

GCGGCCAGTG TGTCCTCATC AAGCAACAGT GTGACTCCTT CCCCGACTGT GCTGATGGGT    4200

CTGATGAGCT CATGTGTGAA ATCAACAAGC CACCCTCTGA TGACATCCCA GCCCACAGCA    4260

GTGCCATTGG GCCCGTCATT GGTATCATCC TCTCCCTCTT CGTCATGGGC GGGGTCTACT    4320

TTGTCTGCCA GCGTGTGATG TGCCAGCGCT ACACAGGGGC CAGTGGGCCC TTTCCCCACG    4380

AGTATGTTGG TGGAGCCCCT CATGTGCCTC TCAACTTCAT AGCCCCAGGT GGCTCACAGC    4440

ACGGTCCCTT CCCAGGCATC CGTGCAGCA AGTCCGTGAT GAGCTCCATG AGCCTGGTGG    4500

GGGGGCGCGG CAGCGTGCCC CTCTATGACC GGAATCACGT CACTGGGCC TCATCCAGCA    4560

GCTCGTCCAG CACAAAGGCC ACACTATATC CGCCGATCCT GAACCCACCC CGTCCCCGG    4620

CCACAGACCC CTCTCTCTAC AACGTGGACG TGTTTTATTC TTCAGGCATC CCGGCCACCG    4680

CTAGACCATA CAGGCCCTAC GTCATTCGAG GTATGGCACC CCCAACAACA CCGTGCAGCA    4740

CAGATGTGTG TGACAGTGAC TACAGCATCA GTCGCTGGAA GAGCAGCAAA TACTACCTGG    4800

ACTTGAATTC GGACTCAGAC CCCTACCCCC CCCCGCCCAC CCCCACAGC CAGTACCTAT    4860

CTGCAGAGGA CAGCTGCCCA CCCTCACCAG GCACTGAGAG GAGTTACTGC CACCTCTTCC    4920

CGCCCCCACC GTCCCCCTGC ACGGACTCGT CCTGACCTCG GCCGTCCACC CGGCCCTGCT    4980

GCCTCCCTGT AAATATTTTT AAATATGAAC AAAGGAAAAA TATATTTTAT GATTTAAAAA    5040

ATAAATATAA TTGGGGTTTT TAACAAGTGA GAAATGTGAG CGGTGAAGGG GTGGGCAGGG    5100

CTGGGAAACT TTTCTAG                                                  5117

(2) INFORMATION FOR SEQ ID NO:41:

(i) SEQUENCE CHARACTERISTICS:
        (A) LENGTH: 4843 base pairs
        (B) TYPE: nucleic acid
        (C) STRANDEDNESS: single
        (D) TOPOLOGY: linear (xi) SEQUENCE DESCRIPTION: SEQ ID NO:41:

ATGGAAACGG CGCCGACCCG GGCCCCTCCG CCGCCGCCGC CGCCGCTGCT GCTGCTGGTG      60

CTGTACTGCA GCTTGGTCCC CGCCGCGGCC TCACCGCTCC TGTTGTTTGC CAACCGCCGG     120

GATGTGCGGC TAGTGGATGC CGGCGGAGTG AAGCTGGAGT CCACCATTGT GGCCAGTGGC     180

CTGGAGGATG CAGCTGCTGT AGACTTCCAG TTCTCCAAGG GTGCTGTGTA CTGGACAGAT     240

GTGAGCGAGG AGGCCATCAA ACAGACCTAC CTGAACCAGA CTGGAGCTGC TGCACAGAAC     300

ATTGTCATCT CGGGCCTCGT GTCACCTGAT GGCCTGGCCT GTGACTGGGT TGGCAAGAAG     360

CTGTACTGGA CGGACTCCGA GACCAACCGC ATTGAGGTTG CCAACCTCAA TGGGACGTCC     420
```

```
CGTAAGGTTC TCTTCTGGCA GGACCTGGAC CAGCCAAGGG CCATTGCCCT GGATCCTGCA    480
CATGGGTACA TGTACTGGAC TGACTGGGGG AAGCACCCC GGATCGAGCG GGCAGGGATG     540
GATGGCAGTA CCCGGAAGAT CATTGTAGAC TCCGACATTT ACTGGCCCAA TGGGCTGACC    600
ATCGACCTGG AGGAACAGAA GCTGTACTGG GCCGATGCCA AGCTCAGCTT CATCCACCGT    660
GCCAACCTGG ACGGCTCCTT CCGGCAGAAG GTGGTGGAGG GCAGCCTCAC TCACCCTTTT    720
GCCCTGACAC TCTCTGGGGA CACACTCTAC TGGACAGACT GGCAGACCCG CTCCATCCAC    780
GCCTGCAACA AGTGGACAGG GGAGCAGAGG AAGGAGATCC TTAGTGCTCT GTACTCACCC    840
ATGGACATCC AAGTGCTGAG CCAGGAGCGG CAGCCTCCCT TCCACACACC ATGCGAGGAG    900
GACAACGGTG GCTGTTCCCA CCTGTGCCTG CTGTCCCCGA GGGAGCCTTT CTACTCCTGT    960
GCCTGCCCCA CTGGTGTGCA GTTGCAGGAC AATGGCAAGA CGTGCAAGAC AGGGGCTGAG   1020
GAAGTGCTGC TGCTGGCTCG GAGGACAGAC CTGAGGAGGA TCTCTCTGGA CACCCCTGAC   1080
TTCACAGACA TAGTGCTGCA GGTGGGCGAC ATCCGGCATG CCATTGCCAT TGACTACGAT   1140
CCCCTGGAGG GCTACGTGTA CTGGACCGAT GATGAGGTGC GGGCTATCCG CAGGGCGTAC   1200
CTAGATGGCT CAGGTGCGCA GACACTTGTG AACACTGAGA TCAATGACCC CGATGGCATT   1260
GCTGTGGACT GGGTCGCCCG GAACCTCTAC TGGACAGATA CAGGCACTGA CAGAATTGAG   1320
GTGACTCGCC TCAACGGCAC CTCCCGAAAG ATCCTGGTAT CTGAGGACCT GGACGAACCG   1380
CGAGCCATTG TGTTGCACCC TGTGATGGGC CTCATGTACT GGACAGACTG GGGGGAGAAC   1440
CCCAAAATCG AATGCGCCAA CCTAGATGGG AGAGATCGGC ATGTCCTGGT GAACACCTCC   1500
CTTGGGTGGC CAATGGACT GGCCCTGGAC CTGCAGGAGG GCAAGCTGTA CTGGGGGAT    1560
GCCAAAACTG ATAAAATCGA GGTGATCAAC ATAGACGGGA CAAAGCGGAA GACCCTGCTT   1620
GAGGACAAGC TCCCACACAT TTTTGGGTTC ACACTGCTGG GGGACTTCAT CTACTGGACC   1680
GACTGGCAGA GACGCAGTAT TGAAAGGGTC CACAAGGTCA AGGCCAGCCG GGATGTCATC   1740
ATTGATCAAC TCCCCGACCT GATGGGACTC AAAGCCGTGA ATGTGGCCAA GGTTGTCGGA   1800
ACCAACCCAT GTGCGGATGG AAATGGAGGG TGCAGCCATC TGTGCTTCTT CACCCCACGT   1860
GCCACCAAGT GTGGCTGCCC CATTGGCCTG GAGCTGTTGA GTGACATGAA GACCTGCATA   1920
ATCCCCGAGG CCTTCCTGGT ATTCACCAGC AGAGCCACCA TCCACAGGAT CTCCCTGGAG   1980
ACTAACAACA ACGATGTGGC TATCCCACTC ACGGGTGTCA AGGAGGCCTC TGCACTGGAC   2040
TTTGATGTTC CAACAATCAC ATCTACTGGA CTGATGTTAG CCTCAAGACG ATCAGCCGAG   2100
CCTTCATGAA TGGGAGCTCA GTGGAGCACG TGATTGAGTT TGGCCTCGAC TACCCTGAAG   2160
GAATGGCTGT GGACTGGATG GGCAAGAACC TCTATTGGGC GGACACAGGG ACCAACAGGA   2220
TTGAGGTGGC CCGGCTGGAT GGGCAGTTCC GGCAGGTGCT TGTGTGGAGA GACCTTGACA   2280
ACCCCAGGTC TCTGGCTCTG GATCCTACTA AAGGCTACAT CTACTGGACT GAGTGGGGTG   2340
GCAAGCCAAG GATTGTGCGG GCCTTCATGG ATGGGACCAA TTGTATGACA CTGGTAGACA   2400
AGGTGGGCCG GGCCAACGAC CTCACCATTG ATTATGCCGA CCAGCGACTG TACTGGACTG   2460
ACCTGGACAC CAACATGATT GAGTCTTCCA ACATGCTGGG TCAGGAGCGC ATGGTGATAG   2520
CTGACGATCT GCCCTACCCG TTTGGCCTGA CTCAATATAG CGATTACATC TACTGGACTG   2580
ACTGGAACCT GCATAGCATT GAACGGGCGG ACAAGACCAG TGGGCGGAAC CGCACCCTCA   2640
TCCAGGGTCA CCTGGACTTC GTCATGGACA TCCTGGTGTT CCACTCCTCC CGTCAGGATG   2700
GCCTCAACGA CTGCGTGCAC AGCAATGGCC AGTGTGGGCA GCTGTGCCTC GCCATCCCCG   2760
```

| | | | | |
|---|---|---|---|---|
| GAGGCCACCG | CTGTGGCTGT | GCTTCACACT | ACACGCTGGA | CCCCAGCAGC CGCAACTGCA | 2820 |
| GCCCGCCCTC | CACCTTCTTG | CTGTTCAGCC | AGAAATTTGC | CATCAGCCGG ATGATCCCCG | 2880 |
| ATGACCAGCT | CAGCCCGGAC | CTTGTCCTAC | CCCTTCATGG | GCTGAGGAAC GTCAAAGCCA | 2940 |
| TCAACTATGA | CCCGCTGGAC | AAGTTCATCT | ACTGGGTGGA | CGGGCGCCAG AACATCAAGA | 3000 |
| GGGCCAAGGA | CGACGGTACC | CAGCCCTCCA | TGCTGACCTC | TCCCAGCCAA AGCCTGAGCC | 3060 |
| CAGACAGACA | GCCACACGAC | CTCAGCATTG | ACATCTACAG | CCGGACACTG TTCTGGACCT | 3120 |
| GTGAGGCCAC | CAACACTATC | AATGTCCACC | GGCTGGATGG | GGATGCCATG GGAGTGGTGC | 3180 |
| TTCGAGGGGA | CCGTGACAAG | CCAAGGGCCA | TTGCTGTCAA | TGCTGAGCGA GGGTACATGT | 3240 |
| ACTTTACCAA | CATGCAGGAC | CATGCTGCCA | AGATCGAGCG | AGCCTCCCTG GATGGCACAG | 3300 |
| AGCGGGAGGT | CCTCTTCACC | ACAGGCCTCA | TCCGTCCCGT | GGCCCTTGTG GTGGACAATG | 3360 |
| CTCTGGGCAA | GCTCTTCTGG | GTGGATGCCG | ACCTAAAGCG | AATCGAAAGC TGTGACCTCT | 3420 |
| CTGGGGCCAA | CCGCCTGACC | CTGGAAGATG | CCAACATCGT | ACAGCCAGTA GGTCTGACAG | 3480 |
| TGCTGGGCAG | GCACCTCTAC | TGGATCGACC | GCCAGCAGCA | GATGATCGAG CGCGTGGAGA | 3540 |
| AGACCACTGG | GGACAAGCGG | ACTAGGGTTC | AGGGCCGTGT | CACCCACCTG ACAGGCATCC | 3600 |
| ATGCCGTGGA | GGAAGTCAGC | CTGGAGGAGT | TCTCAGCCCA | TCCTTGTGCC CGAGACAATG | 3660 |
| GCGGCTGCTC | CCACATCTGT | ATCGCCAAGG | GTGATGGAAC | ACCGCGCTGC TCGTGCCCTG | 3720 |
| TCCACCTGGT | GCTCCTGCAG | AACCTGCTGA | CTTGTGGTGA | GCCTCCTACC TGCTCCCCTG | 3780 |
| ATCAGTTTGC | ATGTACCACT | GGTGAGATCG | ACTGCATCCC | CGGAGCCTGG CGCTGTGACG | 3840 |
| GCTTCCCTGA | GTGTGCTGAC | CAGAGTGATG | AAGAAGGCTG | CCCAGTGTGC TCCGCCTCTC | 3900 |
| AGTTCCCCTG | CGCTCGAGGC | CAGTGTGTGG | ACCTGCGGTT | ACGCTGCGAC GGTGAGGCCG | 3960 |
| ACTGCCAGGA | TCGCTCTGAT | GAAGCTAACT | GCGATGCTGT | CTGTCTGCCC AATCAGTTCC | 4020 |
| GGTGCACCAG | CGGCCAGTGT | GTCCTCATCA | AGCAACAGTG | TGACTCCTTC CCCGACTGTG | 4080 |
| CTGATGGGTC | TGATGACTCA | TGTGTGAAAT | CAACAAGCCA | CCCTCTGATG ACATCCCAGC | 4140 |
| CCACAGCAGT | GCCATTGGGC | CCGTCATTGG | TATCATCCTC | TCCCTCTTCG TCATGGGCGG | 4200 |
| GGTCTACTTT | GTCTGCCAGC | GTGTGATGTG | CCAGCGCTAC | ACAGGGGCCA GTGGGCCCTT | 4260 |
| TCCCCACGAG | TATGTTGGTG | GAGCCCCTCA | TGTGCCTCTC | AACTTCATAG CCCCAGGTGG | 4320 |
| CTCACAGCAC | GGTCCCTTCC | CAGGCATCCC | GTGCAGCAAG | TCCGTGATGA GCTCCATGAG | 4380 |
| CCTGGTGGGG | GGGCGCGGCA | GCGTGCCCCT | CTATGACCGG | AATCACGTCA CTGGGGCCTC | 4440 |
| ATCCAGCAGC | TCGTCCAGCA | CAAAGGCCAC | ACTATATCCG | CCGATCCTGA ACCCACCCCC | 4500 |
| GTCCCCGGCC | ACAGACCCCT | CTCTCTACAA | CGTGGACGTG | TTTTATTCTT CAGGCATCCC | 4560 |
| GGCCACCGCT | AGACCATACA | GGCCCTACGT | CATTCGAGGT | ATGGCACCCC CAACAACACC | 4620 |
| GTGCAGCACA | GATGTGTGTG | ACAGTGACTA | CAGCATCAGT | CGCTGGAAGA GCAGCAAATA | 4680 |
| CTACCTGGAC | TTGAATTCGG | ACTCAGACCC | CTACCCCCCC | CCGCCCACCC CCCACAGCCA | 4740 |
| GTACCTATCT | GCAGAGGACA | GCTGCCCACC | CTCACCAGGC | ACTGAGAGGA GTTACTGCCA | 4800 |
| CCTCTTCCCG | CCCCCACCGT | CCCCCTGCAC | GGACTCGTCC | TGA | 4843 |

(2) INFORMATION FOR SEQ ID NO:42:

(i) SEQUENCE CHARACTERISTICS:
        (A) LENGTH: 1614 amino acids
        (B) TYPE: amino acid
        (D) TOPOLOGY: linear (xi) SEQUENCE DESCRIPTION: SEQ ID NO:42:

```
Met Glu Thr Ala Pro Thr Arg Ala Pro Pro Pro Pro Pro Pro Leu
1               5                   10                  15

Leu Leu Leu Val Leu Tyr Cys Ser Leu Val Pro Ala Ala Ser Pro
            20                  25                  30

Leu Leu Leu Phe Ala Asn Arg Arg Asp Val Arg Leu Val Asp Ala Gly
            35                  40                  45

Gly Val Lys Leu Glu Ser Thr Ile Val Ala Ser Gly Leu Glu Asp Ala
        50                  55                  60

Ala Ala Val Asp Phe Gln Phe Ser Lys Gly Ala Val Tyr Trp Thr Asp
65                  70                  75                  80

Val Ser Glu Glu Ala Ile Lys Gln Thr Tyr Leu Asn Gln Thr Gly Ala
                85                  90                  95

Ala Ala Gln Asn Ile Val Ile Ser Gly Leu Val Ser Pro Asp Gly Leu
            100                 105                 110

Ala Cys Asp Trp Val Gly Lys Lys Leu Tyr Trp Thr Asp Ser Glu Thr
            115                 120                 125

Asn Arg Ile Glu Val Ala Asn Leu Asn Gly Thr Ser Arg Lys Val Leu
            130                 135                 140

Phe Trp Gln Asp Leu Asp Gln Pro Arg Ala Ile Ala Leu Asp Pro Ala
145                 150                 155                 160

His Gly Tyr Met Tyr Trp Thr Asp Trp Gly Glu Ala Pro Arg Ile Glu
                165                 170                 175

Arg Ala Gly Met Asp Gly Ser Thr Arg Lys Ile Ile Val Asp Ser Asp
            180                 185                 190

Ile Tyr Trp Pro Asn Gly Leu Thr Ile Asp Leu Glu Glu Gln Lys Leu
            195                 200                 205

Tyr Trp Ala Asp Ala Lys Leu Ser Phe Ile His Arg Ala Asn Leu Asp
210                 215                 220

Gly Ser Phe Arg Gln Lys Val Val Glu Gly Ser Leu Thr His Pro Phe
225                 230                 235                 240

Ala Leu Thr Leu Ser Gly Asp Thr Leu Tyr Trp Thr Asp Trp Gln Thr
            245                 250                 255

Arg Ser Ile His Ala Cys Asn Lys Trp Thr Gly Glu Gln Arg Lys Glu
            260                 265                 270

Ile Leu Ser Ala Leu Tyr Ser Pro Met Asp Ile Gln Val Leu Ser Gln
            275                 280                 285

Glu Arg Gln Pro Phe His Thr Pro Cys Glu Asp Asn Gly Gly
            290                 295                 300

Cys Ser His Leu Cys Leu Leu Ser Pro Arg Glu Pro Phe Tyr Ser Cys
305                 310                 315                 320

Ala Cys Pro Thr Gly Val Gln Leu Gln Asp Asn Gly Lys Thr Cys Lys
                325                 330                 335

Thr Gly Ala Glu Glu Val Leu Leu Ala Arg Arg Thr Asp Leu Arg
            340                 345                 350

Arg Ile Ser Leu Asp Thr Pro Asp Phe Thr Asp Ile Val Leu Gln Val
            355                 360                 365

Gly Asp Ile Arg His Ala Ile Ala Ile Asp Tyr Asp Pro Leu Glu Gly
    370                 375                 380

Tyr Val Tyr Trp Thr Asp Asp Glu Val Arg Ala Ile Arg Arg Ala Tyr
385                 390                 395                 400

Leu Asp Gly Ser Gly Ala Gln Thr Leu Val Asn Thr Glu Ile Asn Asp
            405                 410                 415
```

-continued

```
Pro Asp Gly Ile Ala Val Asp Trp Val Ala Arg Asn Leu Tyr Trp Thr
            420                 425                 430

Asp Thr Gly Thr Asp Arg Ile Glu Val Thr Arg Leu Asn Gly Thr Ser
        435                 440                 445

Arg Lys Ile Leu Val Ser Glu Asp Leu Asp Glu Pro Arg Ala Ile Val
    450                 455                 460

Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
                485                 490                 495

Val Asn Thr Ser Leu Gly Trp Pro Asn Gly Leu Ala Leu Asp Leu Gln
            500                 505                 510

Glu Gly Lys Leu Tyr Trp Gly Asp Ala Lys Thr Asp Lys Ile Glu Val
        515                 520                 525

Ile Asn Ile Asp Gly Thr Lys Arg Lys Thr Leu Leu Glu Asp Lys Leu
    530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                565                 570                 575

Arg Asp Val Ile Ile Asp Gln Leu Pro Asp Leu Met Gly Leu Lys Ala
            580                 585                 590

Val Asn Val Ala Lys Val Val Gly Thr Asn Pro Cys Ala Asp Gly Asn
        595                 600                 605

Gly Gly Cys Ser His Leu Cys Phe Phe Thr Pro Arg Ala Thr Lys Cys
    610                 615                 620

Gly Cys Pro Ile Gly Leu Glu Leu Leu Ser Asp Met Lys Thr Cys Ile
625                 630                 635                 640

Ile Pro Glu Ala Phe Leu Val Phe Thr Ser Arg Ala Thr Ile His Arg
                645                 650                 655

Ile Ser Leu Glu Thr Asn Asn Asn Asp Val Ala Ile Pro Leu Thr Gly
            660                 665                 670

Val Lys Glu Ala Ser Ala Leu Asp Phe Asp Val Ser Asn Asn His Ile
        675                 680                 685

Tyr Trp Thr Asp Val Ser Leu Lys Thr Ile Ser Arg Ala Phe Met Asn
    690                 695                 700

Gly Ser Ser Val Glu His Val Ile Glu Phe Gly Leu Asp Tyr Pro Glu
705                 710                 715                 720

Gly Met Ala Val Asp Trp Met Gly Lys Asn Leu Tyr Trp Ala Asp Thr
                725                 730                 735

Gly Thr Asn Arg Ile Glu Val Ala Arg Leu Asp Gly Gln Phe Arg Gln
            740                 745                 750

Val Leu Val Trp Arg Asp Leu Asp Asn Pro Arg Ser Leu Ala Leu Asp
        755                 760                 765

Pro Thr Lys Gly Tyr Ile Tyr Trp Thr Glu Trp Gly Gly Lys Pro Arg
    770                 775                 780

Ile Val Arg Ala Phe Met Asp Gly Thr Asn Cys Met Thr Leu Val Asp
785                 790                 795                 800

Lys Val Gly Arg Ala Asn Asp Leu Thr Ile Asp Tyr Ala Asp Gln Arg
                805                 810                 815

Leu Tyr Trp Thr Asp Leu Asp Thr Asn Met Ile Glu Ser Ser Asn Met
            820                 825                 830

Leu Gly Gln Glu Arg Met Val Ile Ala Asp Asp Leu Pro Tyr Pro Phe
```

-continued

```
                835                 840                 845
Gly Leu Thr Gln Tyr Ser Asp Tyr Ile Tyr Trp Thr Asp Trp Asn Leu
    850                 855                 860
His Ser Ile Glu Arg Ala Asp Lys Thr Ser Gly Arg Asn Arg Thr Leu
865                 870                 875                 880
Ile Gln Gly His Leu Asp Phe Val Met Asp Ile Leu Val Phe His Ser
                885                 890                 895
Ser Arg Gln Asp Gly Leu Asn Asp Cys Val His Ser Asn Gly Gln Cys
            900                 905                 910
Gly Gln Leu Cys Leu Ala Ile Pro Gly Gly His Arg Cys Gly Cys Ala
            915                 920                 925
Ser His Tyr Thr Leu Asp Pro Ser Ser Arg Asn Cys Ser Pro Pro Ser
    930                 935                 940
Thr Phe Leu Leu Phe Ser Gln Lys Phe Ala Ile Ser Arg Met Ile Pro
945                 950                 955                 960
Asp Asp Gln Leu Ser Pro Asp Leu Val Leu Pro Leu His Gly Leu Arg
                965                 970                 975
Asn Val Lys Ala Ile Asn Tyr Asp Pro Leu Asp Lys Phe Ile Tyr Trp
            980                 985                 990
Val Asp Gly Arg Gln Asn Ile Lys Arg Ala Lys Asp Asp Gly Thr Gln
            995                 1000                1005
Pro Ser Met Leu Thr Ser Pro Ser Gln Ser Leu Ser Pro Asp Arg Gln
    1010                1015                1020
Pro His Asp Leu Ser Ile Asp Ile Tyr Ser Arg Thr Leu Phe Trp Thr
1025                1030                1035                1040
Cys Glu Ala Thr Asn Thr Ile Asn Val His Arg Leu Asp Gly Asp Ala
                1045                1050                1055
Met Gly Val Val Leu Arg Gly Asp Arg Asp Lys Pro Arg Ala Ile Ala
            1060                1065                1070
Val Asn Ala Glu Arg Gly Tyr Met Tyr Phe Thr Asn Met Gln Asp His
            1075                1080                1085
Ala Ala Lys Ile Glu Arg Ala Ser Leu Asp Gly Thr Glu Arg Glu Val
    1090                1095                1100
Leu Phe Thr Thr Gly Leu Ile Arg Pro Val Ala Leu Val Val Asp Asn
1105                1110                1115                1120
Ala Leu Gly Lys Leu Phe Trp Val Asp Ala Asp Leu Lys Arg Ile Glu
                1125                1130                1135
Ser Cys Asp Leu Ser Gly Ala Asn Arg Leu Thr Leu Glu Asp Ala Asn
            1140                1145                1150
Ile Val Gln Pro Val Gly Leu Thr Val Leu Gly Arg His Leu Tyr Trp
            1155                1160                1165
Ile Asp Arg Gln Gln Gln Met Ile Glu Arg Val Glu Lys Thr Thr Gly
    1170                1175                1180
Asp Lys Arg Thr Arg Val Gln Gly Arg Val Thr His Leu Thr Gly Ile
1185                1190                1195                1200
His Ala Val Glu Glu Val Ser Leu Glu Glu Phe Ser Ala His Pro Cys
                1205                1210                1215
Ala Arg Asp Asn Gly Gly Cys Ser His Ile Cys Ile Ala Lys Gly Asp
            1220                1225                1230
Gly Thr Pro Arg Cys Ser Cys Pro Val His Leu Val Leu Leu Gln Asn
            1235                1240                1245
Leu Leu Thr Cys Gly Glu Pro Pro Thr Cys Ser Pro Asp Gln Phe Ala
    1250                1255                1260
```

```
Cys Thr Thr Gly Glu Ile Asp Cys Ile Pro Gly Ala Trp Arg Cys Asp
1265                1270                1275                1280

Gly Phe Pro Glu Cys Ala Asp Gln Ser Asp Glu Glu Gly Cys Pro Val
                1285                1290                1295

Cys Ser Ala Ser Gln Phe Pro Cys Ala Arg Gly Gln Cys Val Asp Leu
                1300                1305                1310

Arg Leu Arg Cys Asp Gly Glu Ala Asp Cys Gln Asp Arg Ser Asp Glu
            1315                1320                1325

Ala Asn Cys Asp Ala Val Cys Leu Pro Asn Gln Phe Arg Cys Thr Ser
            1330                1335                1340

Gly Gln Cys Val Leu Ile Lys Gln Gln Cys Asp Ser Phe Pro Asp Cys
1345                1350                1355                1360

Ala Asp Gly Ser Asp Glu Leu Met Cys Glu Ile Asn Lys Pro Pro Ser
                1365                1370                1375

Asp Asp Ile Pro Ala His Ser Ser Ala Ile Gly Pro Val Ile Gly Ile
                1380                1385                1390

Ile Leu Ser Leu Phe Val Met Gly Gly Val Tyr Phe Val Cys Gln Arg
            1395                1400                1405

Val Met Cys Gln Arg Tyr Thr Gly Ala Ser Gly Pro Phe Pro His Glu
    1410                1415                1420

Tyr Val Gly Gly Ala Pro His Val Pro Leu Asn Phe Ile Ala Pro Gly
1425                1430                1435                1440

Gly Ser Gln His Gly Pro Phe Pro Gly Ile Pro Cys Ser Lys Ser Val
                1445                1450                1455

Met Ser Ser Met Ser Leu Val Gly Gly Arg Gly Ser Val Pro Leu Tyr
                1460                1465                1470

Asp Arg Asn His Val Thr Gly Ala Ser Ser Ser Ser Ser Ser Ser Thr
                1475                1480                1485

Lys Ala Thr Leu Tyr Pro Pro Ile Leu Asn Pro Pro Ser Pro Ala
            1490                1495                1500

Thr Asp Pro Ser Leu Tyr Asn Val Asp Val Phe Tyr Ser Ser Gly Ile
1505                1510                1515                1520

Pro Ala Thr Ala Arg Pro Tyr Arg Pro Tyr Val Ile Arg Gly Met Ala
                1525                1530                1535

Pro Pro Thr Thr Pro Cys Ser Thr Asp Val Cys Asp Ser Asp Tyr Ser
                1540                1545                1550

Ile Ser Arg Trp Lys Ser Ser Lys Tyr Tyr Leu Asp Leu Asn Ser Asp
                1555                1560                1565

Ser Asp Pro Tyr Pro Pro Pro Thr Pro His Ser Gln Tyr Leu Ser
    1570                1575                1580

Ala Glu Asp Ser Cys Pro Pro Ser Pro Gly Thr Glu Arg Ser Tyr Cys
1585                1590                1595                1600

His Leu Phe Pro Pro Pro Ser Pro Cys Thr Asp Ser Ser
                1605                1610

(2) INFORMATION FOR SEQ ID NO:43:

(i) SEQUENCE CHARACTERISTICS:
        (A) LENGTH: 1591 amino acids
        (B) TYPE: amino acid
        (D) TOPOLOGY: linear (xi) SEQUENCE DESCRIPTION: SEQ ID NO:43:

Cys Pro Ala Pro Ala Ala Ala Ser Pro Leu Leu Leu Phe Ala Asn Arg
1               5                   10                  15
```

-continued

```
Arg Asp Val Arg Leu Val Asp Ala Gly Gly Val Lys Leu Glu Ser Thr
             20                  25                  30

Ile Val Val Ser Gly Leu Glu Asp Ala Ala Val Asp Phe Gln Phe
             35                  40                  45

Ser Lys Gly Ala Val Tyr Trp Thr Asp Val Ser Glu Ala Ile Lys
             50                  55                  60

Gln Thr Tyr Leu Asn Gln Thr Gly Ala Ala Val Gln Asn Val Val Ile
 65                  70                  75                  80

Ser Gly Leu Val Ser Pro Asp Gly Leu Ala Cys Asp Trp Val Gly Lys
                     85                  90                  95

Lys Leu Tyr Trp Thr Asp Ser Glu Thr Asn Arg Ile Glu Val Ala Asn
                    100                 105                 110

Leu Asn Gly Thr Ser Arg Lys Val Leu Phe Trp Gln Asp Leu Asp Gln
             115                 120                 125

Pro Arg Ala Ile Ala Leu Asp Pro Ala His Gly Tyr Met Tyr Trp Thr
             130                 135                 140

Asp Trp Gly Glu Thr Pro Arg Ile Glu Arg Ala Gly Met Asp Gly Ser
145                 150                 155                 160

Thr Arg Lys Ile Ile Val Asp Ser Asp Ile Tyr Trp Pro Asn Gly Leu
                    165                 170                 175

Thr Ile Asp Leu Glu Glu Gln Lys Leu Tyr Trp Ala Asp Ala Lys Leu
             180                 185                 190

Ser Phe Ile His Arg Ala Asn Leu Asp Gly Ser Phe Arg Gln Lys Val
             195                 200                 205

Val Glu Gly Ser Leu Thr His Pro Phe Ala Leu Thr Leu Ser Gly Asp
             210                 215                 220

Thr Leu Tyr Trp Thr Asp Trp Gln Thr Arg Ser Ile His Ala Cys Asn
225                 230                 235                 240

Lys Arg Thr Gly Gly Lys Arg Lys Glu Ile Leu Ser Ala Leu Tyr Ser
                    245                 250                 255

Pro Met Asp Ile Gln Val Leu Ser Gln Glu Arg Gln Pro Phe Phe His
             260                 265                 270

Thr Arg Cys Glu Glu Asp Asn Gly Gly Cys Ser His Leu Cys Leu Leu
             275                 280                 285

Ser Pro Ser Glu Pro Phe Tyr Thr Cys Ala Cys Pro Thr Gly Val Gln
             290                 295                 300

Leu Gln Asp Asn Gly Arg Thr Cys Lys Ala Gly Ala Glu Glu Val Leu
305                 310                 315                 320

Leu Leu Ala Arg Arg Thr Asp Leu Arg Arg Ile Ser Leu Asp Thr Pro
             325                 330                 335

Asp Phe Thr Asp Ile Val Leu Gln Val Asp Asp Ile Arg His Ala Ile
             340                 345                 350

Ala Ile Asp Tyr Asp Pro Leu Glu Gly Tyr Val Tyr Trp Thr Asp Asp
             355                 360                 365

Glu Val Arg Ala Ile Arg Arg Ala Tyr Leu Asp Gly Ser Gly Ala Gln
             370                 375                 380

Thr Leu Val Asn Thr Glu Ile Asn Asp Pro Asp Gly Ile Ala Val Asp
385                 390                 395                 400

Trp Val Ala Arg Asn Leu Tyr Trp Thr Asp Thr Gly Thr Asp Arg Ile
                    405                 410                 415

Glu Val Thr Arg Leu Asn Gly Ser Arg Lys Ile Leu Val Ser Glu
             420                 425                 430
```

-continued

```
Asp Leu Asp Glu Pro Arg Ala Ile Ala Leu His Pro Val Met Gly Leu
        435                 440                 445

Met Tyr Trp Thr Asp Trp Gly Glu Asn Pro Lys Ile Glu Cys Ala Asn
    450                 455                 460

Leu Asp Gly Gln Glu Arg Arg Val Leu Val Asn Ala Ser Leu Gly Trp
465                 470                 475                 480

Pro Asn Gly Leu Ala Leu Asp Leu Gln Glu Gly Lys Leu Tyr Trp Gly
                485                 490                 495

Asp Ala Lys Thr Asp Lys Ile Glu Val Ile Asn Val Asp Gly Thr Lys
            500                 505                 510

Arg Arg Thr Leu Leu Glu Asp Lys Leu Pro His Ile Phe Gly Phe Thr
        515                 520                 525

Leu Leu Gly Asp Phe Ile Tyr Trp Thr Asp Trp Gln Arg Arg Ser Ile
    530                 535                 540

Glu Arg Val His Lys Val Lys Ala Ser Arg Asp Val Ile Ile Asp Gln
545                 550                 555                 560

Leu Pro Asp Leu Met Gly Leu Lys Ala Val Asn Val Ala Lys Val Val
                565                 570                 575

Gly Thr Asn Pro Cys Ala Asp Arg Asn Gly Gly Cys Ser His Leu Cys
            580                 585                 590

Phe Phe Thr Pro His Ala Thr Arg Cys Gly Cys Pro Ile Gly Leu Glu
        595                 600                 605

Leu Leu Ser Asp Met Lys Thr Cys Ile Val Pro Glu Ala Phe Leu Val
    610                 615                 620

Phe Thr Ser Arg Ala Ala Ile His Arg Ile Ser Leu Glu Thr Asn Asn
625                 630                 635                 640

Asn Asp Val Ala Ile Pro Leu Thr Gly Val Lys Glu Ala Ser Ala Leu
                645                 650                 655

Asp Phe Asp Val Ser Asn Asn His Ile Tyr Trp Thr Asp Val Ser Leu
            660                 665                 670

Lys Thr Ile Ser Arg Ala Phe Met Asn Gly Ser Ser Val Glu His Val
        675                 680                 685

Val Glu Phe Gly Leu Asp Tyr Pro Glu Gly Met Ala Val Asp Trp Met
    690                 695                 700

Gly Lys Asn Leu Tyr Trp Ala Asp Thr Gly Thr Asn Arg Ile Glu Val
705                 710                 715                 720

Ala Arg Leu Asp Gly Gln Phe Arg Gln Val Leu Val Trp Arg Asp Leu
                725                 730                 735

Asp Asn Pro Arg Ser Leu Ala Leu Asp Pro Thr Lys Gly Tyr Ile Tyr
            740                 745                 750

Trp Thr Glu Trp Gly Gly Lys Pro Arg Ile Val Arg Ala Phe Met Asp
        755                 760                 765

Gly Thr Asn Cys Met Thr Leu Val Asp Lys Val Gly Arg Ala Asn Asp
    770                 775                 780

Leu Thr Ile Asp Tyr Ala Asp Gln Arg Leu Tyr Trp Thr Asp Leu Asp
785                 790                 795                 800

Thr Asn Met Ile Glu Ser Ser Asn Met Leu Gly Gln Glu Arg Val Val
                805                 810                 815

Ile Ala Asp Asp Leu Pro His Pro Phe Gly Leu Thr Gln Tyr Ser Asp
            820                 825                 830

Tyr Ile Tyr Trp Thr Asp Trp Asn Leu His Ser Ile Glu Arg Ala Asp
        835                 840                 845

Lys Thr Ser Gly Arg Asn Arg Thr Leu Ile Gln Gly His Leu Asp Phe
```

-continued

```
            850                 855                 860
Val Met Asp Ile Leu Val Phe His Ser Ser Arg Gln Asp Gly Leu Asn
865                 870                 875                 880

Asp Cys Met His Asn Asn Gly Gln Cys Gly Gln Leu Cys Leu Ala Ile
                885                 890                 895

Pro Gly Gly His Arg Cys Gly Cys Ala Ser His Tyr Thr Leu Asp Pro
            900                 905                 910

Ser Ser Arg Asn Cys Ser Pro Thr Thr Phe Leu Leu Phe Ser Gln
            915                 920                 925

Lys Ser Ala Ile Ser Arg Met Ile Pro Asp Asp Gln His Ser Pro Asp
            930                 935                 940

Leu Ile Leu Pro Leu His Gly Leu Arg Asn Val Lys Ala Ile Asp Tyr
945                 950                 955                 960

Asp Pro Leu Asp Lys Phe Ile Tyr Trp Val Asp Gly Arg Gln Asn Ile
                965                 970                 975

Lys Arg Ala Lys Asp Asp Gly Thr Gln Pro Phe Val Leu Thr Ser Leu
            980                 985                 990

Ser Gln Gly Gln Asn Pro Asp Arg Gln Pro His Asp Leu Ser Ile Asp
            995                 1000                1005

Ile Tyr Ser Arg Thr Leu Phe Trp Thr Cys Glu Ala Thr Asn Thr Ile
1010                1015                1020

Asn Val His Arg Leu Ser Gly Glu Ala Met Gly Val Val Leu Arg Gly
1025                1030                1035                1040

Asp Arg Asp Lys Pro Arg Ala Ile Val Val Asn Ala Glu Arg Gly Tyr
                1045                1050                1055

Leu Tyr Phe Thr Asn Met Gln Asp Arg Ala Ala Lys Ile Glu Arg Ala
            1060                1065                1070

Ala Leu Asp Gly Thr Glu Arg Glu Val Leu Phe Thr Thr Gly Leu Ile
            1075                1080                1085

Arg Pro Val Ala Leu Val Val Asp Asn Thr Leu Gly Lys Leu Phe Trp
            1090                1095                1100

Val Asp Ala Asp Leu Lys Arg Ile Glu Ser Cys Asp Leu Ser Gly Ala
1105                1110                1115                1120

Asn Arg Leu Thr Leu Glu Asp Ala Asn Ile Val Gln Pro Leu Gly Leu
            1125                1130                1135

Thr Ile Leu Gly Lys His Leu Tyr Trp Ile Asp Arg Gln Gln Gln Met
            1140                1145                1150

Ile Glu Arg Val Glu Lys Thr Thr Gly Asp Lys Arg Thr Arg Ile Gln
            1155                1160                1165

Gly Arg Val Ala His Leu Thr Gly Ile His Ala Val Glu Glu Val Ser
            1170                1175                1180

Leu Glu Glu Phe Ser Ala His Pro Cys Ala Arg Asp Asn Gly Gly Cys
1185                1190                1195                1200

Ser His Ile Cys Ile Ala Lys Gly Asp Gly Thr Pro Arg Cys Ser Cys
            1205                1210                1215

Pro Val His Leu Val Leu Leu Gln Asn Leu Leu Thr Cys Gly Glu Pro
            1220                1225                1230

Pro Thr Cys Ser Pro Asp Gln Phe Ala Cys Ala Thr Gly Glu Ile Asp
            1235                1240                1245

Cys Ile Pro Gly Ala Trp Arg Cys Asp Gly Phe Pro Glu Cys Asp Asp
            1250                1255                1260

Gln Ser Asp Glu Glu Gly Cys Pro Val Cys Ser Ala Ala Gln Phe Pro
1265                1270                1275                1280
```

-continued

```
Cys Ala Arg Gly Gln Cys Val Asp Leu Arg Leu Arg Cys Asp Gly Glu
                1285                1290                1295

Ala Asp Cys Gln Asp Arg Ser Asp Glu Ala Asp Cys Asp Ala Ile Cys
            1300                1305                1310

Leu Pro Asn Gln Phe Arg Cys Ala Ser Gly Gln Cys Val Leu Ile Lys
            1315                1320                1325

Gln Gln Cys Asp Ser Phe Pro Asp Cys Ile Asp Gly Ser Asp Glu Leu
        1330                1335                1340

Met Cys Glu Ile Thr Lys Pro Pro Ser Asp Ser Pro Ala His Ser
1345                1350                1355                1360

Ser Ala Ile Gly Pro Val Ile Gly Ile Ile Leu Ser Leu Phe Val Met
                1365                1370                1375

Gly Gly Val Tyr Phe Val Cys Gln Arg Val Val Cys Gln Arg Tyr Ala
                1380                1385                1390

Gly Ala Asn Gly Pro Phe Pro His Glu Tyr Val Ser Gly Thr Pro His
                1395                1400                1405

Val Pro Leu Asn Phe Ile Ala Pro Gly Gly Ser Gln His Gly Pro Phe
            1410                1415                1420

Thr Gly Ile Ala Cys Gly Lys Ser Met Met Ser Ser Val Ser Leu Met
1425                1430                1435                1440

Gly Gly Arg Gly Gly Val Pro Leu Tyr Asp Arg Asn His Val Thr Gly
                1445                1450                1455

Ala Ser Ser Ser Ser Ser Ser Thr Lys Ala Thr Leu Tyr Pro Pro
                1460                1465                1470

Ile Leu Asn Pro Pro Pro Ser Pro Ala Thr Asp Pro Ser Leu Tyr Asn
            1475                1480                1485

Met Asp Met Phe Tyr Ser Ser Asn Ile Pro Ala Thr Val Arg Pro Tyr
            1490                1495                1500

Arg Pro Tyr Ile Ile Arg Gly Met Ala Pro Pro Thr Thr Pro Cys Ser
1505                1510                1515                1520

Thr Asp Val Cys Asp Ser Asp Tyr Ser Ala Ser Arg Trp Lys Ala Ser
                1525                1530                1535

Lys Tyr Tyr Leu Asp Leu Asn Ser Asp Ser Asp Pro Tyr Pro Pro Pro
            1540                1545                1550

Pro Thr Pro His Ser Gln Tyr Leu Ser Ala Glu Asp Ser Cys Pro Pro
        1555                1560                1565

Ser Pro Ala Thr Glu Arg Ser Tyr Phe His Leu Phe Pro Pro Pro Pro
    1570                1575                1580

Ser Pro Cys Thr Asp Ser Ser
1585                1590
```

(2) INFORMATION FOR SEQ ID NO:44:

(i) SEQUENCE CHARACTERISTICS:
        (A) LENGTH: 1586 amino acids
        (B) TYPE: amino acid
        (D) TOPOLOGY: linear (xi) SEQUENCE DESCRIPTION: SEQ ID NO:44:

```
Ala Ala Ser Pro Leu Leu Leu Phe Ala Asn Arg Arg Asp Val Arg Leu
1               5                   10                  15

Val Asp Ala Gly Gly Val Lys Leu Glu Ser Thr Ile Val Ala Ser Gly
                20                  25                  30

Leu Glu Asp Ala Ala Ala Val Asp Phe Gln Phe Ser Lys Gly Ala Val
            35                  40                  45
```

-continued

```
Tyr Trp Thr Asp Val Ser Glu Glu Ala Ile Lys Gln Thr Tyr Leu Asn
 50                  55                  60

Gln Thr Gly Ala Ala Gln Asn Ile Val Ile Ser Gly Leu Val Ser
 65              70                  75                  80

Pro Asp Gly Leu Ala Cys Asp Trp Val Gly Lys Lys Leu Tyr Trp Thr
                 85                  90                  95

Asp Ser Glu Thr Asn Arg Ile Glu Val Ala Asn Leu Asn Gly Thr Ser
                100                 105                 110

Arg Lys Val Leu Phe Trp Gln Asp Leu Asp Gln Pro Arg Ala Ile Ala
             115                 120                 125

Leu Asp Pro Ala His Gly Tyr Met Tyr Trp Thr Asp Trp Gly Glu Ala
     130                 135                 140

Pro Arg Ile Glu Arg Ala Gly Met Asp Gly Ser Thr Arg Lys Ile Ile
145                 150                 155                 160

Val Asp Ser Asp Ile Tyr Trp Pro Asn Gly Leu Thr Ile Asp Leu Glu
                165                 170                 175

Glu Gln Lys Leu Tyr Trp Ala Asp Ala Lys Leu Ser Phe Ile His Arg
             180                 185                 190

Ala Asn Leu Asp Gly Ser Phe Arg Gln Lys Val Val Glu Gly Ser Leu
         195                 200                 205

Thr His Pro Phe Ala Leu Thr Leu Ser Gly Asp Thr Leu Tyr Trp Thr
     210                 215                 220

Asp Trp Gln Thr Arg Ser Ile His Ala Cys Asn Lys Trp Thr Gly Glu
225                 230                 235                 240

Gln Arg Lys Glu Ile Leu Ser Ala Leu Tyr Ser Pro Met Asp Ile Gln
                245                 250                 255

Val Leu Ser Gln Glu Arg Gln Pro Pro Phe His Thr Pro Cys Glu Glu
             260                 265                 270

Asp Asn Gly Gly Cys Ser His Leu Cys Leu Leu Ser Pro Arg Glu Pro
         275                 280                 285

Phe Tyr Ser Cys Ala Cys Pro Thr Gly Val Gln Leu Gln Asp Asn Gly
     290                 295                 300

Lys Thr Cys Lys Thr Gly Ala Glu Glu Val Leu Leu Leu Ala Arg Arg
305                 310                 315                 320

Thr Asp Leu Arg Arg Ile Ser Leu Asp Thr Pro Asp Phe Thr Asp Ile
                325                 330                 335

Val Leu Gln Val Gly Asp Ile Arg His Ala Ile Ala Ile Asp Tyr Asp
             340                 345                 350

Pro Leu Glu Gly Tyr Val Tyr Trp Thr Asp Asp Glu Val Arg Ala Ile
         355                 360                 365

Arg Arg Ala Tyr Leu Asp Gly Ser Gly Ala Gln Thr Leu Val Asn Thr
     370                 375                 380

Glu Ile Asn Asp Pro Asp Gly Ile Ala Val Asp Trp Val Ala Arg Asn
385                 390                 395                 400

Leu Tyr Trp Thr Asp Thr Gly Thr Asp Arg Ile Glu Val Thr Arg Leu
                405                 410                 415

Asn Gly Thr Ser Arg Lys Ile Leu Val Ser Glu Asp Leu Asp Glu Pro
             420                 425                 430

Arg Ala Ile Val Leu His Pro Val Met Gly Leu Met Tyr Trp Thr Asp
         435                 440                 445

Trp Gly Glu Asn Pro Lys Ile Glu Cys Ala Asn Leu Asp Gly Arg Asp
     450                 455                 460
```

-continued

```
Arg His Val Leu Val Asn Thr Ser Leu Gly Trp Pro Asn Gly Leu Ala
465                 470                 475                 480

Leu Asp Leu Gln Glu Gly Lys Leu Tyr Trp Gly Asp Ala Lys Thr Asp
            485                 490                 495

Lys Ile Glu Val Ile Asn Ile Asp Gly Thr Lys Arg Lys Thr Leu Leu
            500                 505                 510

Glu Asp Lys Leu Pro His Ile Phe Gly Phe Thr Leu Leu Gly Asp Phe
            515                 520                 525

Ile Tyr Trp Thr Asp Trp Gln Arg Arg Ser Ile Glu Arg Val His Lys
530                 535                 540

Val Lys Ala Ser Arg Asp Val Ile Asp Gln Leu Pro Asp Leu Met
545                 550                 555                 560

Gly Leu Lys Ala Val Asn Val Ala Lys Val Gly Thr Asn Pro Cys
            565                 570                 575

Ala Asp Gly Asn Gly Gly Cys Ser His Leu Cys Phe Phe Thr Pro Arg
            580                 585                 590

Ala Thr Lys Cys Gly Cys Pro Ile Gly Leu Glu Leu Ser Asp Met
            595                 600                 605

Lys Thr Cys Ile Ile Pro Glu Ala Phe Leu Val Phe Thr Ser Arg Ala
            610                 615                 620

Thr Ile His Arg Ile Ser Leu Glu Thr Asn Asn Asn Asp Val Ala Ile
625                 630                 635                 640

Pro Leu Thr Gly Val Lys Glu Ala Ser Ala Leu Asp Phe Asp Val Ser
            645                 650                 655

Asn Asn His Ile Tyr Trp Thr Asp Val Ser Leu Lys Thr Ile Ser Arg
            660                 665                 670

Ala Phe Met Asn Gly Ser Ser Val Glu His Val Ile Glu Phe Gly Leu
            675                 680                 685

Asp Tyr Pro Glu Gly Met Ala Val Asp Trp Met Gly Lys Asn Leu Tyr
            690                 695                 700

Trp Ala Asp Thr Gly Thr Asn Arg Ile Glu Val Ala Arg Leu Asp Gly
705                 710                 715                 720

Gln Phe Arg Gln Val Leu Val Trp Arg Asp Leu Asp Asn Pro Arg Ser
            725                 730                 735

Leu Ala Leu Asp Pro Thr Lys Gly Tyr Ile Tyr Trp Thr Glu Trp Gly
            740                 745                 750

Gly Lys Pro Arg Ile Val Arg Ala Phe Met Asp Gly Thr Asn Cys Met
            755                 760                 765

Thr Leu Val Asp Lys Val Gly Arg Ala Asn Asp Leu Thr Ile Asp Tyr
770                 775                 780

Ala Asp Gln Arg Leu Tyr Trp Thr Asp Leu Asp Thr Asn Met Ile Glu
785                 790                 795                 800

Ser Ser Asn Met Leu Gly Gln Glu Arg Met Val Ile Ala Asp Asp Leu
            805                 810                 815

Pro Tyr Pro Phe Gly Leu Thr Gln Tyr Ser Asp Tyr Ile Tyr Trp Thr
            820                 825                 830

Asp Trp Asn Leu His Ser Ile Glu Arg Ala Asp Lys Thr Ser Gly Arg
            835                 840                 845

Asn Arg Thr Leu Ile Gln Gly His Leu Asp Phe Val Met Asp Ile Leu
            850                 855                 860

Val Phe His Ser Ser Arg Gln Asp Gly Leu Asn Asp Cys Val His Ser
865                 870                 875                 880

Asn Gly Gln Cys Gly Gln Leu Cys Leu Ala Ile Pro Gly Gly His Arg
```

-continued

```
                885                 890                 895
Cys Gly Cys Ala Ser His Tyr Thr Leu Asp Pro Ser Ser Arg Asn Cys
                900                 905                 910
Ser Pro Pro Ser Thr Phe Leu Leu Phe Ser Gln Lys Phe Ala Ile Ser
                915                 920                 925
Arg Met Ile Pro Asp Asp Gln Leu Ser Pro Asp Leu Val Leu Pro Leu
                930                 935                 940
His Gly Leu Arg Asn Val Lys Ala Ile Asn Tyr Asp Pro Leu Asp Lys
945                 950                 955                 960
Phe Ile Tyr Trp Val Asp Gly Arg Gln Asn Ile Lys Arg Ala Lys Asp
                965                 970                 975
Asp Gly Thr Gln Pro Ser Met Leu Thr Ser Pro Ser Gln Ser Leu Ser
                980                 985                 990
Pro Asp Arg Gln Pro His Asp Leu Ser Ile Asp Ile Tyr Ser Arg Thr
                995                 1000                1005
Leu Phe Trp Thr Cys Glu Ala Thr Asn Thr Ile Asn Val His Arg Leu
                1010                1015                1020
Asp Gly Asp Ala Met Gly Val Val Leu Arg Gly Asp Arg Asp Lys Pro
1025                1030                1035                1040
Arg Ala Ile Ala Val Asn Ala Glu Arg Gly Tyr Met Tyr Phe Thr Asn
                1045                1050                1055
Met Gln Asp His Ala Ala Lys Ile Glu Arg Ala Ser Leu Asp Gly Thr
                1060                1065                1070
Glu Arg Glu Val Leu Phe Thr Thr Gly Leu Ile Arg Pro Val Ala Leu
                1075                1080                1085
Val Val Asp Asn Ala Leu Gly Lys Leu Phe Trp Val Asp Ala Asp Leu
                1090                1095                1100
Lys Arg Ile Glu Ser Cys Asp Leu Ser Gly Ala Asn Arg Leu Thr Leu
1105                1110                1115                1120
Glu Asp Ala Asn Ile Val Gln Pro Val Gly Leu Thr Val Leu Gly Arg
                1125                1130                1135
His Leu Tyr Trp Ile Asp Arg Gln Gln Gln Met Ile Glu Arg Val Glu
                1140                1145                1150
Lys Thr Thr Gly Asp Lys Arg Thr Arg Val Gln Gly Arg Val Thr His
                1155                1160                1165
Leu Thr Gly Ile His Ala Val Glu Glu Val Ser Leu Glu Glu Phe Ser
                1170                1175                1180
Ala His Pro Cys Ala Arg Asp Asn Gly Gly Cys Ser His Ile Cys Ile
1185                1190                1195                1200
Ala Lys Gly Asp Gly Thr Pro Arg Cys Ser Cys Pro Val His Leu Val
                1205                1210                1215
Leu Leu Gln Asn Leu Leu Thr Cys Gly Glu Pro Pro Thr Cys Ser Pro
                1220                1225                1230
Asp Gln Phe Ala Cys Thr Thr Gly Glu Ile Asp Cys Ile Pro Gly Ala
                1235                1240                1245
Trp Arg Cys Asp Gly Phe Pro Glu Cys Ala Asp Gln Ser Asp Glu Glu
                1250                1255                1260
Gly Cys Pro Val Cys Ser Ala Ser Gln Phe Pro Cys Ala Arg Gly Gln
1265                1270                1275                1280
Cys Val Asp Leu Arg Leu Arg Cys Asp Gly Glu Ala Asp Cys Gln Asp
                1285                1290                1295
Arg Ser Asp Glu Ala Asn Cys Asp Ala Val Cys Leu Pro Asn Gln Phe
                1300                1305                1310
```

```
Arg Cys Thr Ser Gly Gln Cys Val Leu Ile Lys Gln Gln Cys Asp Ser
        1315                1320                1325
Phe Pro Asp Cys Ala Asp Gly Ser Asp Glu Leu Met Cys Glu Ile Asn
1330                1335                1340
Lys Pro Pro Ser Asp Asp Ile Pro Ala His Ser Ser Ala Ile Gly Pro
1345                1350                1355                1360
Val Ile Gly Ile Ile Leu Ser Leu Phe Val Met Gly Val Tyr Phe
                1365                1370                1375
Val Cys Gln Arg Val Met Cys Gln Arg Tyr Thr Gly Ala Ser Gly Pro
                1380                1385                1390
Phe Pro His Glu Tyr Val Gly Gly Ala Pro His Val Pro Leu Asn Phe
        1395                1400                1405
Ile Ala Pro Gly Gly Ser Gln His Gly Pro Phe Pro Gly Ile Pro Cys
        1410                1415                1420
Ser Lys Ser Val Met Ser Ser Met Ser Leu Val Gly Gly Arg Gly Ser
1425                1430                1435                1440
Val Pro Leu Tyr Asp Arg Asn His Val Thr Gly Ala Ser Ser Ser Ser
                1445                1450                1455
Ser Ser Ser Thr Lys Ala Thr Leu Tyr Pro Pro Ile Leu Asn Pro Pro
        1460                1465                1470
Pro Ser Pro Ala Thr Asp Pro Ser Leu Tyr Asn Val Asp Val Phe Tyr
        1475                1480                1485
Ser Ser Gly Ile Pro Ala Thr Ala Arg Pro Tyr Arg Pro Tyr Val Ile
        1490                1495                1500
Arg Gly Met Ala Pro Pro Thr Thr Pro Cys Ser Thr Asp Val Cys Asp
1505                1510                1515                1520
Ser Asp Tyr Ser Ile Ser Arg Trp Lys Ser Ser Lys Tyr Tyr Leu Asp
                1525                1530                1535
Leu Asn Ser Asp Ser Asp Pro Tyr Pro Pro Pro Thr Pro His Ser
                1540                1545                1550
Gln Tyr Leu Ser Ala Glu Asp Ser Cys Pro Pro Ser Pro Gly Thr Glu
        1555                1560                1565
Arg Ser Tyr Cys His Leu Phe Pro Pro Pro Ser Pro Cys Thr Asp
        1570                1575                1580
Ser Ser
1585

(2) INFORMATION FOR SEQ ID NO:45:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:45:

Asn Pro Xaa Tyr
1

(2) INFORMATION FOR SEQ ID NO:46:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:46:

Tyr Trp Thr Asp
```

(2) INFORMATION FOR SEQ ID NO:47:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:47:

Asn Gly Gly Cys
1

(2) INFORMATION FOR SEQ ID NO:48:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:48:

Val Pro Leu Tyr
1

(2) INFORMATION FOR SEQ ID NO:49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:49:

ATGGAGCCCG AGTGAGC                                                  17

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:50:

ATGGTGGACT CCAGCTTGAC                                               20

(2) INFORMATION FOR SEQ ID NO:51:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:51:

TTCCAGTTTT CCAAGGGAG                                                19

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:52:

AAAACTGGAA GTCCACTGCG                                               20

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:53:

GGTCTGCTTG ATGGCCTC                                      18

(2) INFORMATION FOR SEQ ID NO:54:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:54:

GTGCAGAACG TGGTCATCT                                   19

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:55:

AGTCCACAAT GATCTTCCGG                                20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:56:

CCAATGGACT GACCATCGAC                                20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:57:

GTCGATGGTC AGTCCATTGG                                20

(2) INFORMATION FOR SEQ ID NO:58:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:58:

TTGTCCTCCT CACAGCGAG                                   19

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:59:

GGACTTCATC TACTGGACTG          20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:60:

CAGTCTGTCC AGTACATGAG          20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:61:

GCCTTCTTGG TCTTCACCAG          20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:62:

GGACCAACAG AATCGAAGTG          20

(2) INFORMATION FOR SEQ ID NO:63:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:63:

GTCAATGGTG AGGTCGT          17

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:64:

ACACCAACAT GATCGAGTCG          20

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:65:

ACAAGTTCAT CTACTGGGTG                                               20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:66:

CGGACACTGT TCTGGACGTG                                               20

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:67:

CACGTCCAGA ACAGTGTCCG                                               20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:68:

TCCAGTAGAG ATGCTTGCCA                                               20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:69:

ATCGAGCGTG TGGAGAAGAC                                               20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:70:

TCCTCATCAA ACAGCAGTGC                                               20

(2) INFORMATION FOR SEQ ID NO:71:

-continued (i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:71:

CGGCTTGGTG ATTTCACAC                                            19

(2) INFORMATION FOR SEQ ID NO:72:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:72:

GTGTGTGACA GCGACTACAG C                                         21

(2) INFORMATION FOR SEQ ID NO:73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:73:

GCTGTAGTCG CTGTCACACA C                                         21

(2) INFORMATION FOR SEQ ID NO:74:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:74:

GTACAAAGTT CTCCCAGCCC                                           20

(2) INFORMATION FOR SEQ ID NO:75:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:75:

TCTTCTCAG AGGATGCAGC                                            20

(2) INFORMATION FOR SEQ ID NO:76:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:76:

TTCGTCTTGA ACTTCCCAGC                                           20

(2) INFORMATION FOR SEQ ID NO:77:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:77:

TCTTCTTCTC CAGAGGATGC A                                       21

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:78:

AGGCTGGTCT CAAACTCCTG                                         20

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:79:

GGGGATGTGC TGCAAGGCGA                                         20

(2) INFORMATION FOR SEQ ID NO:80:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:80:

CCAGGGTTTT CCCAGTCACG AC                                      22

(2) INFORMATION FOR SEQ ID NO:81:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:81:

TTGTGTGGAA TTGTGAGCGG ATAAC                                   25

(2) INFORMATION FOR SEQ ID NO:82:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:82:

CCCAGGCTTT ACACTTTATG CTTCC                                   25

(2) INFORMATION FOR SEQ ID NO:83:

(i) SEQUENCE CHARACTERISTICS:
        (A) LENGTH: 20 base pairs (B) TYPE: nucleic acid
            (C) STRANDEDNESS: single
            (D) TOPOLOGY: linear (xi) SEQUENCE DESCRIPTION: SEQ ID NO:83:

CAGGGTTTCA TCCTTTGTGG                                                            20

(2) INFORMATION FOR SEQ ID NO:84:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:84:

TGTAAAACGA CGGCCAGTCA GGGTTTCATC CTTTGTGG                                        38

(2) INFORMATION FOR SEQ ID NO:85:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:85:

GCTATGACCA TGATTACGCC CAGGGTTTCA TCCTTTGTGG                                      40

(2) INFORMATION FOR SEQ ID NO:86:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:86:

TGACGGGAAG AGTTCCTCAG                                                            20

(2) INFORMATION FOR SEQ ID NO:87:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:87:

GCTATGACCA TGATTACGCC TGACGGGAAG AGTTCCTCAG                                      40

(2) INFORMATION FOR SEQ ID NO:88:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:88:

TCTGCTCTTC CTGAACTGCC                                                            20

(2) INFORMATION FOR SEQ ID NO:89:

(i) SEQUENCE CHARACTERISTICS:
            (A) LENGTH: 38 base pairs
            (B) TYPE: nucleic acid

```
        (C) STRANDEDNESS: single
        (D) TOPOLOGY: linear (xi) SEQUENCE DESCRIPTION: SEQ ID NO:89:

TGTAAAACGA CGGCCAGTTC TGCTCTTCCT GAACTGCC                              38

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:90:

TTGAGTCCTT CAACAAGCCC                                                  20

(2) INFORMATION FOR SEQ ID NO:91:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:91:

GCTATGACCA TGATTACGCC TTGAGTCCTT CAACAAGCCC                            40

(2) INFORMATION FOR SEQ ID NO:92:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:92:

TGTAAAACGA CGGCCAGTTT CCCCACTCAT AGAGGCTC                              38

(2) INFORMATION FOR SEQ ID NO:93:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:93:

GCTATGACCA TGATTACGCC GCTCCCAACT CGCCAAGT                              38

(2) INFORMATION FOR SEQ ID NO:94:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:94:

TGTAAAACGA CGGCCAGTGG TCAACATGGA GGCAGC                                36

(2) INFORMATION FOR SEQ ID NO:95:

(i) SEQUENCE CHARACTERISTICS:
        (A) LENGTH: 38 base pairs
        (B) TYPE: nucleic acid
        (C) STRANDEDNESS: single
```

(D) TOPOLOGY: linear (xi) SEQUENCE DESCRIPTION: SEQ ID NO:95:

GCTATGACCA TGATTACGCC CAGGTGTCAG TCCGCTTG                           38

(2) INFORMATION FOR SEQ ID NO:96:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:96:

TGTAAAACGA CGGCCAGTGC AGAGAAGTTC TGAGC                              35

(2) INFORMATION FOR SEQ ID NO:97:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:97:

GCTATGACCA TGATTACGCC CACTTGGCCA GCCATACTC                          39

(2) INFORMATION FOR SEQ ID NO:98:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:98:

TGTAAAACGA CGGCCAGTCA AGCAAGCCTC TTGCTACC                           38

(2) INFORMATION FOR SEQ ID NO:99:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:99:

GCTATGACCA TGATTACGCC ACTGCAATGA GGTGAAAGGC                         40

(2) INFORMATION FOR SEQ ID NO:100:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:100:

TGTAAAACGA CGGCCAGTCA GGTGAGAACA AGTGTCCG                           38

(2) INFORMATION FOR SEQ ID NO:101:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:101:

GCTATGACCA TGATTACGCC GCTGCCTCCA TGTTGACC                                38

(2) INFORMATION FOR SEQ ID NO:102:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:102:

TGTAAAACGA CGGCCAGTTG TGCCTGGGTG AGATTCT                                 37

(2) INFORMATION FOR SEQ ID NO:103:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:103:

GCTATGACCA TGATTACGCC TGTGGAGCCT CTATGAGTGG                              40

(2) INFORMATION FOR SEQ ID NO:104:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:104:

TGTAAAACGA CGGCCAGTGG GTGACAGGTG GCAGTAG                                 37

(2) INFORMATION FOR SEQ ID NO:105:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:105:

GCTATGACCA TGATTACGCC GGAAGGAAGG ACACTTGAGC                              40

(2) INFORMATION FOR SEQ ID NO:106:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:106:

TGTAAAACGA CGGCCAGTCC TGGTGTGTTT GAGAACCC                                38

(2) INFORMATION FOR SEQ ID NO:107:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:107:

GCTATGACCA TGATTACGCC CAATGGGAAG CCAGGCTAG                    39

(2) INFORMATION FOR SEQ ID NO:108:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:108:

ATCTTGCTGG CTTAGCCAGT                                         20

(2) INFORMATION FOR SEQ ID NO:109:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:109:

TGTAAAACGA CGGCCAGTAT CTTGCTGGCT TAGCCAGT                     38

(2) INFORMATION FOR SEQ ID NO:110:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:110:

GCTATGACCA TGATTACGCC ATCTTGCTGG CTTAGCCAGT                   40

(2) INFORMATION FOR SEQ ID NO:111:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:111:

GCTCATGCAA ATTCGAGAGA G                                       21

(2) INFORMATION FOR SEQ ID NO:112:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:112:

GCTATGACCA TGATTACGCC GCTCATGCAA ATTCGAGAGA G                 41

(2) INFORMATION FOR SEQ ID NO:113:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:113:

```
CCTGTTGGTT ATTTCCGATG G                                              21

(2) INFORMATION FOR SEQ ID NO:114:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:114:

TGTAAAACGA CGGCCAGTCC TGTTGGTTAT TTCCGATGG                            39

(2) INFORMATION FOR SEQ ID NO:115:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:115:

GCTATGACCA TGATTACGCC CCTGTTGGTT ATTTCCGATG G                         41

(2) INFORMATION FOR SEQ ID NO:116:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:116:

CCTGAGTTAA GAAGGAACGC C                                              21

(2) INFORMATION FOR SEQ ID NO:117:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:117:

GCTATGACCA TGATTACGCC CCTGAGTTAA GAAGGAACGC C                         41

(2) INFORMATION FOR SEQ ID NO:118:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:118:

AATTGGGTCA GCAGCAATG                                                 19

(2) INFORMATION FOR SEQ ID NO:119:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:119:
```

```
GCTATGACCA TGATTACGCC AATTGGGTCA GCAGCAATG                                    39

(2) INFORMATION FOR SEQ ID NO:120:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:120:

AATTGGGTCA GCAGCAATG                                                         19

(2) INFORMATION FOR SEQ ID NO:121:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:121:

TGTAAAACGA CGGCCAGTAA TTGGGTCAGC AGCAATG                                     37

(2) INFORMATION FOR SEQ ID NO:122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:122:

TTGGATCGCT AGAGATTGGG                                                        20

(2) INFORMATION FOR SEQ ID NO:123:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:123:

GCTATGACCA TGATTACGCC TTGGATCGCT AGAGATTGGG                                  40

(2) INFORMATION FOR SEQ ID NO:124:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:124:

GCACCCTAAT TGGCACTCA                                                         19

(2) INFORMATION FOR SEQ ID NO:125:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:125:

GCTATGACCA TGATTACGCC GCACCCTAAT TGGCACTCA                                   39
```

(2) INFORMATION FOR SEQ ID NO:126:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:126:

TGACGGTCCT CTTCTGGAAC          20

(2) INFORMATION FOR SEQ ID NO:127:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:127:

GCTATGACCA TGATTACGCC TGACGGTCCT CTTCTGGAAC          40

(2) INFORMATION FOR SEQ ID NO:128:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:128:

CGAGGCAGGA TGTGACTCAT          20

(2) INFORMATION FOR SEQ ID NO:129:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:129:

TGTAAAACGA CGGCCAGTCG AGGCAGGATG TGACTCAT          38

(2) INFORMATION FOR SEQ ID NO:130:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:130:

GCTATGACCA TGATTACGCC CGAGGCAGGA TGTGACTCAT          40

(2) INFORMATION FOR SEQ ID NO:131:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:131:

AGTGGATCAT TTCGAACGG          19

(2) INFORMATION FOR SEQ ID NO:132:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:132:

GCTATGACCA TGATTACGCC AGTGGATCAT TTCGAACGG        39

(2) INFORMATION FOR SEQ ID NO:133:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:133:

CCAACTCAGC TTCCCGAGTA        20

(2) INFORMATION FOR SEQ ID NO:134:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:134:

GCTATGACCA TGATTACGCC CCAACTCAGC TTCCCGAGTA        40

(2) INFORMATION FOR SEQ ID NO:135:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:135:

TGGCTGAGTA TTTCCCTTGC        20

(2) INFORMATION FOR SEQ ID NO:136:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:136:

TGTAAAACGA CGGCCAGTTG GCTGAGTATT TCCCTTGC        38

(2) INFORMATION FOR SEQ ID NO:137:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:137:

GCTATGACCA TGATTACGCC TGGCTGAGTA TTTCCCTTGC        40

(2) INFORMATION FOR SEQ ID NO:138:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (xi) SEQUENCE DESCRIPTION: SEQ ID NO:138:

TTTAACAAGC CCTCCTCCG                                              19

(2) INFORMATION FOR SEQ ID NO:139:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (xi) SEQUENCE DESCRIPTION: SEQ ID NO:139:

GCTATGACCA TGATTACGCC TTTAACAAGC CCTCCTCCG                         39

(2) INFORMATION FOR SEQ ID NO:140:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (xi) SEQUENCE DESCRIPTION: SEQ ID NO:140:

CAACGCCAGC ATCTACTGA                                              19

(2) INFORMATION FOR SEQ ID NO:141:

(i) SEQUENCE CHARACTERISTICS:
           (A) LENGTH: 37 base pairs
           (B) TYPE: nucleic acid
           (C) STRANDEDNESS: single
           (D) TOPOLOGY: linear (xi) SEQUENCE DESCRIPTION: SEQ ID NO:141:

TGTAAAACGA CGGCCAGTCA ACGCCAGCAT CTACTGA                           37

(2) INFORMATION FOR SEQ ID NO:142:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (xi) SEQUENCE DESCRIPTION: SEQ ID NO:142:

GCTATGACCA TGATTACGCC CAACGCCAGC ATCTACTGA                         39

(2) INFORMATION FOR SEQ ID NO:143:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:143:

CAAATAGCAG AGCACAGGCA                                             20

(2) INFORMATION FOR SEQ ID NO:144:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:144:

GCTATGACCA TGATTACGCC CAAATAGCAG AGCACAGGCA                     40

(2) INFORMATION FOR SEQ ID NO:145:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:145:

TGAAGTTGCT GCTCTTGGG                                            19

(2) INFORMATION FOR SEQ ID NO:146:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:146:

TGTAAAACGA CGGCCAGTTG AAGTTGCTGC TCTTGGG                        37

(2) INFORMATION FOR SEQ ID NO:147:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:147:

GCTATGACCA TGATTACGCC TGAAGTTGCT GCTCTTGGG                      39

(2) INFORMATION FOR SEQ ID NO:148:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:148:

CACTTCCTCC TCATGCAAGT C                                         21

(2) INFORMATION FOR SEQ ID NO:149:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:149:

GCTATGACCA TGATTACGCC CACTTCCTCC TCATGCAAGT C                   41

(2) INFORMATION FOR SEQ ID NO:150:

(i) SEQUENCE CHARACTERISTICS:

(A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:150:

AGACTGGAGC CTCTGTGTTC G                                          21

(2) INFORMATION FOR SEQ ID NO:151:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:151:

TGTAAAACGA CGGCCAGTAG ACTGGAGCCT CTGTGTTCG                        39

(2) INFORMATION FOR SEQ ID NO:152:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:152:

GCTATGACCA TGATTACGCC AGACTGGAGC CTCTGTGTTC G                     41

(2) INFORMATION FOR SEQ ID NO:153:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:153:

TGTGTGTCTA CCGGACTTGC                                             20

(2) INFORMATION FOR SEQ ID NO:154:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:154:

GCTATGACCA TGATTACGCC TGTGTGTCTA CCGGACTTGC                       40

(2) INFORMATION FOR SEQ ID NO:155:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:155:

GAACAGAGGC AAGGTTTTCC C                                           21

(2) INFORMATION FOR SEQ ID NO:156:

(i) SEQUENCE CHARACTERISTICS:
        (A) LENGTH: 41 base pairs (B) TYPE: nucleic acid
        (C) STRANDEDNESS: single
        (D) TOPOLOGY: linear (xi) SEQUENCE DESCRIPTION: SEQ ID NO:156:

GCTATGACCA TGATTACGCC GAACAGAGGC AAGGTTTTCC C           41

(2) INFORMATION FOR SEQ ID NO:157:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:157:

AGAATCGCTT GAACCCAGG                                    19

(2) INFORMATION FOR SEQ ID NO:158:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:158:

GCTATGACCA TGATTACGCC AGAATCGCTT GAACCCAGG              39

(2) INFORMATION FOR SEQ ID NO:159:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:159:

GCTGGTTCCT AAAATGTGGC                                   20

(2) INFORMATION FOR SEQ ID NO:160:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:160:

TGTAAAACGA CGGCCAGTGC TGGTTCCTAA AATGTGGC               38

(2) INFORMATION FOR SEQ ID NO:161:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:161:

GCTATGACCA TGATTACGCC GCTGGTTCCT AAAATGTGGC             40

(2) INFORMATION FOR SEQ ID NO:162:

(i) SEQUENCE CHARACTERISTICS:
        (A) LENGTH: 22 base pairs
        (B) TYPE: nucleic acid (C) STRANDEDNESS: single
            (D) TOPOLOGY: linear (xi) SEQUENCE DESCRIPTION: SEQ ID NO:162:

CATACGAGGT GAACACAAGG AC                                                22

(2) INFORMATION FOR SEQ ID NO:163:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:163:

GCTATGACCA TGATTACGCC CATACGAGGT GAACACAAGG AC                          42

(2) INFORMATION FOR SEQ ID NO:164:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:164:

TGAAGAGGTG GGGACAGTTG                                                   20

(2) INFORMATION FOR SEQ ID NO:165:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:165:

GCTATGACCA TGATTACGCC TGAAGAGGTG GGGACAGTTG                             40

(2) INFORMATION FOR SEQ ID NO:166:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:166:

CTTGTGCCTT CCAGCTACAT C                                                 21

(2) INFORMATION FOR SEQ ID NO:167:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:167:

TGTAAAACGA CGGCCAGTCT TGTGCCTTCC AGCTACATC                              39

(2) INFORMATION FOR SEQ ID NO:168:

(i) SEQUENCE CHARACTERISTICS:
            (A) LENGTH: 41 base pairs
            (B) TYPE: nucleic acid
            (C) STRANDEDNESS: single (D) TOPOLOGY: linear (xi) SEQUENCE DESCRIPTION: SEQ ID NO:168:

GCTATGACCA TGATTACGCC CTTGTGCCTT CCAGCTACAT C                                41

(2) INFORMATION FOR SEQ ID NO:169:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:169:

AGTCCTGGCA CAGGGATTAG                                                        20

(2) INFORMATION FOR SEQ ID NO:170:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:170:

GCTATGACCA TGATTACGCC AGTCCTGGCA CAGGGATTAG                                  40

(2) INFORMATION FOR SEQ ID NO:171:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:171:

ATAACTGCAG CAAAGGCACC                                                        20

(2) INFORMATION FOR SEQ ID NO:172:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:172:

GCTATGACCA TGATTACGCC ATAACTGCAG CAAAGGCACC                                  40

(2) INFORMATION FOR SEQ ID NO:173:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:173:

GCTTCAGTGG ATCTTGCTGG                                                        20

(2) INFORMATION FOR SEQ ID NO:174:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:174:

TGTAAAACGA CGGCCAGTGC TTCAGTGGAT CTTGCTGG                    38

(2) INFORMATION FOR SEQ ID NO:175:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:175:

GCTATGACCA TGATTACGCC GCTTCAGTGG ATCTTGCTGG                  40

(2) INFORMATION FOR SEQ ID NO:176:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:176:

TGTGCAGTGC ACAACCTACC                                        20

(2) INFORMATION FOR SEQ ID NO:177:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:177:

GCTATGACCA TGATTACGCC TGTGCAGTGC ACAACCTACC                  40

(2) INFORMATION FOR SEQ ID NO:178:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:178:

GTTGTCGAGT GGCGTGCTAT                                        20

(2) INFORMATION FOR SEQ ID NO:179:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:179:

TGTAAAACGA CGGCCAGTGT TGTCGAGTGG CGTGCTAT                    38

(2) INFORMATION FOR SEQ ID NO:180:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:180:

GCTATGACCA TGATTACGCC GTTGTCGAGT GGCGTGCTAT                40

(2) INFORMATION FOR SEQ ID NO:181:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:181:

AAAAGTCCTG TGGGGTCTGA                                     20

(2) INFORMATION FOR SEQ ID NO:182:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:182:

GCTATGACCA TGATTACGCC AAAAGTCCTG TGGGGTCTGA                40

(2) INFORMATION FOR SEQ ID NO:183:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:183:

AGAAGTGTGG CCTCTGCTGT                                     20

(2) INFORMATION FOR SEQ ID NO:184:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:184:

TGTAAAACGA CGGCCAGTAG AAGTGTGGCC TCTGCTGT                  38

(2) INFORMATION FOR SEQ ID NO:185:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:185:

GCTATGACCA TGATTACGCC AGAAGTGTGG CCTCTGCTGT                40

(2) INFORMATION FOR SEQ ID NO:186:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:186:

```
GTGAAAGAGC CTGTGTTTGC T                                                       21
```

(2) INFORMATION FOR SEQ ID NO:187:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:187:

```
GCTATGACCA TGATTACGCC GTGAAAGAGC CTGTGTTTGC T                                  41
```

(2) INFORMATION FOR SEQ ID NO:188:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:188:

```
AGACCCTGCT TCCAAATAAG C                                                       21
```

(2) INFORMATION FOR SEQ ID NO:189:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:189:

```
TGTAAAACGA CGGCCAGTAG ACCCTGCTTC CAAATAAGC                                     39
```

(2) INFORMATION FOR SEQ ID NO:190:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:190:

```
GCTATGACCA TGATTACGCC AGACCCTGCT TCCAAATAAG C                                  41
```

(2) INFORMATION FOR SEQ ID NO:191:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:191:

```
ACTCATTTTC TGCCTCTGCC                                                         20
```

(2) INFORMATION FOR SEQ ID NO:192:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:192:

```
GCTATGACCA TGATTACGCC ACTCATTTTC TGCCTCTGCC                                40

(2) INFORMATION FOR SEQ ID NO:193:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:193:

TGGCAGTCCT GTCAACCTCT                                                     20

(2) INFORMATION FOR SEQ ID NO:194:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:194:

TGTAAAACGA CGGCCAGTTG GCAGTCCTGT CAACCTCT                                 38

(2) INFORMATION FOR SEQ ID NO:195:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:195:

GCTATGACCA TGATTACGCC TGGCAGTCCT GTCAACCTCT                                40

(2) INFORMATION FOR SEQ ID NO:196:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:196:

CACACAGGAT CTTGCACTGG                                                     20

(2) INFORMATION FOR SEQ ID NO:197:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:197:

GCTATGACCA TGATTACGCC CACACAGGAT CTTGCACTGG                                40

(2) INFORMATION FOR SEQ ID NO:198:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:198:

AGGGCCAGTT CTCATGAGTT                                                     20
```

```
(2) INFORMATION FOR SEQ ID NO:199:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:199:

TGTAAAACGA CGGCCAGTAG GGCCAGTTCT CATGAGTT                                38

(2) INFORMATION FOR SEQ ID NO:200:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:200:

GCTATGACCA TGATTACGCC AGGGCCAGTT CTCATGAGTT                              40

(2) INFORMATION FOR SEQ ID NO:201:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:201:

GGGCAAAGGA AGACACAATC                                                   20

(2) INFORMATION FOR SEQ ID NO:202:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:202:

GCTATGACCA TGATTACGCC GGGCAAAGGA AGACACAATC                              40

(2) INFORMATION FOR SEQ ID NO:203:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:203:

CAACTTCTGC TTTGAAGCCC                                                   20

(2) INFORMATION FOR SEQ ID NO:204:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:204:

TGTAAAACGA CGGCCAGTCA ACTTCTGCTT TGAAGCCC                                38
```

(2) INFORMATION FOR SEQ ID NO:205:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:205:

GCTATGACCA TGATTACGCC CAACTTCTGC TTTGAAGCCC                40

(2) INFORMATION FOR SEQ ID NO:206:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:206:

GACAGACTTG GCAATCTCCC                                     20

(2) INFORMATION FOR SEQ ID NO:207:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:207:

GCTATGACCA TGATTACGCC GACAGACTTG GCAATCTCCC                40

(2) INFORMATION FOR SEQ ID NO:208:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:208:

TCTGCTCTCT GTTTGGAGTC C                                   21

(2) INFORMATION FOR SEQ ID NO:209:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:209:

TGTAAAACGA CGGCCAGTTC TGCTCTCTGT TTGGAGTCC                 39

(2) INFORMATION FOR SEQ ID NO:210:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:210:

GCTATGACCA TGATTACGCC TCTGCTCTCT GTTTGGAGTC C              41

```
(2) INFORMATION FOR SEQ ID NO:211:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:211:

CCCTAAACTC CACGTTCCTG                                                   20

(2) INFORMATION FOR SEQ ID NO:212:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:212:

GCTATGACCA TGATTACGCC CCCTAAACTC CACGTTCCTG                              40

(2) INFORMATION FOR SEQ ID NO:213:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:213:

GGGTTAATGT TGGCCACATC                                                   20

(2) INFORMATION FOR SEQ ID NO:214:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:214:

GCTATGACCA TGATTACGCC GGGTTAATGT TGGCCACATC                              40

(2) INFORMATION FOR SEQ ID NO:215:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:215:

TTGGCAGGGA TGTGTTGAG                                                    19

(2) INFORMATION FOR SEQ ID NO:216:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:216:

TGTAAAACGA CGGCCAGTTT GGCAGGGATG TGTTGAG                                 37

(2) INFORMATION FOR SEQ ID NO:217:
```

(i) SEQUENCE CHARACTERISTICS:
    (A) LENGTH: 39 base pairs
    (B) TYPE: nucleic acid
    (C) STRANDEDNESS: single
    (D) TOPOLOGY: linear (xi) SEQUENCE DESCRIPTION: SEQ ID NO:217:

GCTATGACCA TGATTACGCC TTGGCAGGGA TGTGTTGAG                                    39

(2) INFORMATION FOR SEQ ID NO:218:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:218:

GTCTGCCACA TGTGCAAGAG                                                         20

(2) INFORMATION FOR SEQ ID NO:219:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:219:

GCTATGACCA TGATTACGCC GTCTGCCACA TGTGCAAGAG                                   40

(2) INFORMATION FOR SEQ ID NO:220:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:220:

TGGTCTGAGT CTCGTGGGTA                                                         20

(2) INFORMATION FOR SEQ ID NO:221:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:221:

TGTAAAACGA CGGCCAGTTG GTCTGAGTCT CGTGGGTA                                     38

(2) INFORMATION FOR SEQ ID NO:222:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:222:

GCTATGACCA TGATTACGCC TGGTCTGAGT CTCGTGGGTA                                   40

(2) INFORMATION FOR SEQ ID NO:223:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:223:

GAGGTGGATT TGGGTGAGAT T                                              21

(2) INFORMATION FOR SEQ ID NO:224:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:224:

GCTATGACCA TGATTACGCC GAGGTGGATT TGGGTGAGAT T                        41

(2) INFORMATION FOR SEQ ID NO:225:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:225:

AGCCCTCTCT GCAAGGAAAG                                                20

(2) INFORMATION FOR SEQ ID NO:226:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:226:

TGTAAAACGA CGGCCAGTAG CCCTCTCTGC AAGGAAAG                            38

(2) INFORMATION FOR SEQ ID NO:227:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:227:

GCTATGACCA TGATTACGCC AGCCCTCTCT GCAAGGAAAG                          40

(2) INFORMATION FOR SEQ ID NO:228:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:228:

CAGAACGTGG AGTTCTGCTG                                                20

(2) INFORMATION FOR SEQ ID NO:229:

(i) SEQUENCE CHARACTERISTICS:
```

(A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:229:

GCTATGACCA TGATTACGCC CAGAACGTGG AGTTCTGCTG                                40

(2) INFORMATION FOR SEQ ID NO:230:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:230:

TACCGAATCC CACTCCTCTG                                                     20

(2) INFORMATION FOR SEQ ID NO:231:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:231:

TGTAAAACGA CGGCCAGTTA CCGAATCCCA CTCCTCTG                                  38

(2) INFORMATION FOR SEQ ID NO:232:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:232:

GCTATGACCA TGATTACGCC TACCGAATCC CACTCCTCTG                                40

(2) INFORMATION FOR SEQ ID NO:233:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:233:

CATGGTAGAG GTGGGACCAT                                                     20

(2) INFORMATION FOR SEQ ID NO:234:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:234:

TGTAAAACGA CGGCCAGTCA TGGTAGAGGT GGGACCAT                                  38

(2) INFORMATION FOR SEQ ID NO:235:

(i) SEQUENCE CHARACTERISTICS:
        (A) LENGTH: 40 base pairs (B) TYPE: nucleic acid
        (C) STRANDEDNESS: single
        (D) TOPOLOGY: linear (xi) SEQUENCE DESCRIPTION: SEQ ID NO:235:

GCTATGACCA TGATTACGCC CATGGTAGAG GTGGGACCAT                      40

(2) INFORMATION FOR SEQ ID NO:236:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:236:

GATATCCACC TCTGCCCAAG                                            20

(2) INFORMATION FOR SEQ ID NO:237:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:237:

GCTATGACCA TGATTACGCC GATATCCACC TCTGCCCAAG                      40

(2) INFORMATION FOR SEQ ID NO:238:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:238:

TTACAGGGGC ACAGAGAAGC                                            20

(2) INFORMATION FOR SEQ ID NO:239:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:239:

GCTATGACCA TGATTACGCC TTACAGGGGC ACAGAGAAGC                      40

(2) INFORMATION FOR SEQ ID NO:240:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:240:

GCAACAGAGC AAGACCCTGT                                            20

(2) INFORMATION FOR SEQ ID NO:241:

(i) SEQUENCE CHARACTERISTICS:
        (A) LENGTH: 40 base pairs
        (B) TYPE: nucleic acid

```
        (C) STRANDEDNESS: single
        (D) TOPOLOGY: linear (xi) SEQUENCE DESCRIPTION: SEQ ID NO:241:

GCTATGACCA TGATTACGCC GCAACAGAGC AAGACCCTGT                    40

(2) INFORMATION FOR SEQ ID NO:242:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:242:

AAATTAGCCA GGCATGGTG                                           19

(2) INFORMATION FOR SEQ ID NO:243:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:243:

GCTATGACCA TGATTACGCC AAATTAGCCA GGCATGGTG                     39

(2) INFORMATION FOR SEQ ID NO:244:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:244:

TGTAAAACGA CGGCCAGTGC AACAGAGCAA GACCCTGT                      38

(2) INFORMATION FOR SEQ ID NO:245:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:245:

CCTGCAGAAG GAAACCTGAC                                          20

(2) INFORMATION FOR SEQ ID NO:246:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:246:

GCTATGACCA TGATTACGCC CCTGCAGAAG GAAACCTGAC                    40

(2) INFORMATION FOR SEQ ID NO:247:

(i) SEQUENCE CHARACTERISTICS:
        (A) LENGTH: 19 base pairs
        (B) TYPE: nucleic acid
        (C) STRANDEDNESS: single
```

(D) TOPOLOGY: linear (xi) SEQUENCE DESCRIPTION: SEQ ID NO:247:

CTGCATCTTT GCCACCATG                                                            19

(2) INFORMATION FOR SEQ ID NO:248:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:248:

GCTATGACCA TGATTACGCC CTGCATCTTT GCCACCATG                                      39

(2) INFORMATION FOR SEQ ID NO:249:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:249:

TGTAAAACGA CGGCCAGTCC TGCAGAAGGA AACCTGAC                                       38

(2) INFORMATION FOR SEQ ID NO:250:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:250:

TTCCCAGGAG GCAAGTTATG                                                           20

(2) INFORMATION FOR SEQ ID NO:251:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:251:

GCTATGACCA TGATTACGCC TTCCCAGGAG GCAAGTTATG                                     40

(2) INFORMATION FOR SEQ ID NO:252:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:252:

TGGGCTTAGG TGATCCTCAC                                                           20

(2) INFORMATION FOR SEQ ID NO:253:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:253:

GCTATGACCA TGATTACGCC TGGGCTTAGG TGATCCTCAC                              40

(2) INFORMATION FOR SEQ ID NO:254:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:254:

TGTAAAACGA CGGCCAGTTT CCCAGGAGGC AAGTTATG                                38

(2) INFORMATION FOR SEQ ID NO:255:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:255:

ACCAAGCCCA ACTAATCAGC                                                    20

(2) INFORMATION FOR SEQ ID NO:256:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:256:

GCTATGACCA TGATTACGCC ACCAAGCCCA ACTAATCAGC                              40

(2) INFORMATION FOR SEQ ID NO:257:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:257:

ATGCCTGTAA TCCCAGCACT                                                    20

(2) INFORMATION FOR SEQ ID NO:258:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:258:

GCTATGACCA TGATTACGCC ATGCCTGTAA TCCCAGCACT                              40

(2) INFORMATION FOR SEQ ID NO:259:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:259:

TGTAAAACGA CGGCCAGTAC CAAGCCCAAC TAATCAGC                      38

(2) INFORMATION FOR SEQ ID NO:260:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:260:

ACTGCAAGCC CTCTCTGAAC                                          20

(2) INFORMATION FOR SEQ ID NO:261:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:261:

CGAAGACTGC GAAACAGACA                                          20

(2) INFORMATION FOR SEQ ID NO:262:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:262:

CTAGTGCCGT GCAGAATGAG                                          20

(2) INFORMATION FOR SEQ ID NO:263:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:263:

GGCCACTGCA ATGAGATACA                                          20

(2) INFORMATION FOR SEQ ID NO:264:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:264:

GAGAAACAGT TCCAGGGTGG                                          20

(2) INFORMATION FOR SEQ ID NO:265:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:265:

```
GCTATGACCA TGATTACGCC GAGAAACAGT TCCAGGGTGG                    40

(2) INFORMATION FOR SEQ ID NO:266:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:266:

AAACTGAGGC TGGGAGAGGT                                         20

(2) INFORMATION FOR SEQ ID NO:267:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:267:

GCTATGACCA TGATTACGCC AAACTGAGGC TGGGAGAGGT                    40

(2) INFORMATION FOR SEQ ID NO:268:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:268:

TGTTCTTCCT CACAGGGAGG                                         20

(2) INFORMATION FOR SEQ ID NO:269:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:269:

GCTATGACCA TGATTACGCC TGTTCTTCCT CACAGGGAGG                    40

(2) INFORMATION FOR SEQ ID NO:270:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:270:

TCCCCAAATC TGTCCAGTTC                                         20

(2) INFORMATION FOR SEQ ID NO:271:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:271:
```

```
GCTATGACCA TGATTACGCC TCCCCAAATC TGTCCAGTTC                              40

(2) INFORMATION FOR SEQ ID NO:272:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:272:

CATACCTGGA GGGATGCTTG                                                   20

(2) INFORMATION FOR SEQ ID NO:273:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:273:

GCTATGACCA TGATTACGCC CATACCTGGA GGGATGCTTG                              40

(2) INFORMATION FOR SEQ ID NO:274:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:274:

TAGGTTGCTG TGTGGCTTCA                                                   20

(2) INFORMATION FOR SEQ ID NO:275:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:275:

GCTATGACCA TGATTACGCC TAGGTTGCTG TGTGGCTTCA                              40

(2) INFORMATION FOR SEQ ID NO:276:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:276:

CTTCTGACAA AGCAGAGGCC                                                   20

(2) INFORMATION FOR SEQ ID NO:277:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:277:

GCTATGACCA TGATTACGCC CTTCTGACAA AGCAGAGGCC                              40
```

(2) INFORMATION FOR SEQ ID NO:278:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:278:

GCTGTTAGGG TTACCATCGC                                        20

(2) INFORMATION FOR SEQ ID NO:279:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:279:

GCTATGACCA TGATTACGCC GCTGTTAGGG TTACCATCGC                  40

(2) INFORMATION FOR SEQ ID NO:280:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:280:

CCACAGGGTG ATATGCTGTC                                        20

(2) INFORMATION FOR SEQ ID NO:281:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:281:

GCTATGACCA TGATTACGCC CCACAGGGTG ATATGCTGTC                  40

(2) INFORMATION FOR SEQ ID NO:282:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:282:

CGCCTGGCTA CTTTGGTACT                                        20

(2) INFORMATION FOR SEQ ID NO:283:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:283:

GCTATGACCA TGATTACGCC CGCCTGGCTA CTTTGGTACT                  40

(2) INFORMATION FOR SEQ ID NO:284:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:284:

CCAAATGAAC CTGGGCAAC                                                                                                                               19

(2) INFORMATION FOR SEQ ID NO:285:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:285:

GCTATGACCA TGATTACGCC CCAAATGAAC CTGGGCAAC                                     39

(2) INFORMATION FOR SEQ ID NO:286:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:286:

GTCTTGGCTC ACTGCAACCT                                                                                                              20

(2) INFORMATION FOR SEQ ID NO:287:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:287:

GCTATGACCA TGATTACGCC GTCTTGGCTC ACTGCAACCT                                   40

(2) INFORMATION FOR SEQ ID NO:288:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:288:

GCCAAGACTG TGCTACTGCA                                                                                                              20

(2) INFORMATION FOR SEQ ID NO:289:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:289:

CAGGGAGCAG ATCTTACCCA                                                                                                              20

(2) INFORMATION FOR SEQ ID NO:290:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:290:

TGGGATTAAC TAGGGAGGGG                                                   20

(2) INFORMATION FOR SEQ ID NO:291:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (xi) SEQUENCE DESCRIPTION: SEQ ID NO:291:

GCTATGACCA TGATTACGCC TGGGATTAAC TAGGGAGGGG                              40

(2) INFORMATION FOR SEQ ID NO:292:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:292:

TGCTGCTGTC TCCATCTCTG                                                   20

(2) INFORMATION FOR SEQ ID NO:293:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (xi) SEQUENCE DESCRIPTION: SEQ ID NO:293:

GCTATGACCA TGATTACGCC TGCTGCTGTC TCCATCTCTG                              40

(2) INFORMATION FOR SEQ ID NO:294:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:294:

ACAGACCAGC AGTGAAACCT G                                                 21

(2) INFORMATION FOR SEQ ID NO:295:

(i) SEQUENCE CHARACTERISTICS:
       (A) LENGTH: 41 base pairs
       (B) TYPE: nucleic acid
       (C) STRANDEDNESS: single
       (D) TOPOLOGY: linear (xi) SEQUENCE DESCRIPTION: SEQ ID NO:295:

GCTATGACCA TGATTACGCC ACAGACCAGC AGTGAAACCT G                            41

(2) INFORMATION FOR SEQ ID NO:296:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:296:

GTTCACTGCA ACCTCTGCCT                                                   20

(2) INFORMATION FOR SEQ ID NO:297:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:297:

GCTATGACCA TGATTACGCC GTTCACTGCA ACCTCTGCCT                              40

(2) INFORMATION FOR SEQ ID NO:298:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:298:

GTTCTCGTAG ATGCTTGCAG G                                                 21

(2) INFORMATION FOR SEQ ID NO:299:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:299:

GCTATGACCA TGATTACGCC GTTCTCGTAG ATGCTTGCAG G                            41

(2) INFORMATION FOR SEQ ID NO:300:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:300:

GAGGCAGGAG GATCACTTGA                                                   20

(2) INFORMATION FOR SEQ ID NO:301:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:301:

GCTATGACCA TGATTACGCC GAGGCAGGAG GATCACTTGA                              40

(2) INFORMATION FOR SEQ ID NO:302:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:302:

TGAGCTGAGA TCACACCGCT                                                     20

(2) INFORMATION FOR SEQ ID NO:303:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:303:

GCTATGACCA TGATTACGCC TGAGCTGAGA TCACACCGCT                                40

(2) INFORMATION FOR SEQ ID NO:304:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:304:

AGTTGACACT TTGCTGGCCT                                                     20

(2) INFORMATION FOR SEQ ID NO:305:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:305:

GCTATGACCA TGATTACGCC AGTTGACACT TTGCTGGCCT                                40

(2) INFORMATION FOR SEQ ID NO:306:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:306:

CTCTGCATGG CTTAGGGACA                                                     20

(2) INFORMATION FOR SEQ ID NO:307:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:307:

GCTATGACCA TGATTACGCC CTCTGCATGG CTTAGGGACA                                40

(2) INFORMATION FOR SEQ ID NO:308:

(i) SEQUENCE CHARACTERISTICS:

(A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:308:

GGCTGCTCTC TGCATTCTCT                                          20

(2) INFORMATION FOR SEQ ID NO:309:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (xi) SEQUENCE DESCRIPTION: SEQ ID NO:309:

GCTATGACCA TGATTACGCC GGCTGCTCTC TGCATTCTCT                     40

(2) INFORMATION FOR SEQ ID NO:310:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO:310:

CTGGCTTTAG CTTGCATTTC C                                        21

(2) INFORMATION FOR SEQ ID NO:311:

(i) SEQUENCE CHARACTERISTICS:
          (A) LENGTH: 41 base pairs
          (B) TYPE: nucleic acid
          (C) STRANDEDNESS: single
          (D) TOPOLOGY: linear (xi) SEQUENCE DESCRIPTION: SEQ ID NO:311:

GCTATGACCA TGATTACGCC CTGGCTTTAG CTTGCATTTC C                   41

(2) INFORMATION FOR SEQ ID NO:312:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO:312:

TGCCTCAGTT TTCTCACCTG T                                        21

(2) INFORMATION FOR SEQ ID NO:313:

(i) SEQUENCE CHARACTERISTICS:
          (A) LENGTH: 41 base pairs
          (B) TYPE: nucleic acid
          (C) STRANDEDNESS: single
          (D) TOPOLOGY: linear (xi) SEQUENCE DESCRIPTION: SEQ ID NO:313:

GCTATGACCA TGATTACGCC TGCCTCAGTT TTCTCACCTG T                   41

(2) INFORMATION FOR SEQ ID NO:314:

(i) SEQUENCE CHARACTERISTICS:
          (A) LENGTH: 20 base pairs (B) TYPE: nucleic acid
        (C) STRANDEDNESS: single
        (D) TOPOLOGY: linear (xi) SEQUENCE DESCRIPTION: SEQ ID NO:314:

CAAACAGCCA CTGAGCATGT                                                    20

(2) INFORMATION FOR SEQ ID NO:315:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:315:

GCTATGACCA TGATTACGCC CAAACAGCCA CTGAGCATGT                               40

(2) INFORMATION FOR SEQ ID NO:316:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:316:

TCCTCCTGTA GATGCCCAAG                                                    20

(2) INFORMATION FOR SEQ ID NO:317:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:317:

GCTATGACCA TGATTACGCC TCCTCCTGTA GATGCCCAAG                               40

(2) INFORMATION FOR SEQ ID NO:318:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:318:

GCCGAGAATT GTCATCTTAA CT                                                 22

(2) INFORMATION FOR SEQ ID NO:319:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:319:

GGATTGAAAG CTGCAAACTA CA                                                 22

(2) INFORMATION FOR SEQ ID NO:320:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (xi) SEQUENCE DESCRIPTION: SEQ ID NO:320:

GGAGCCACCA CATCCAGTTA                                                    20

(2) INFORMATION FOR SEQ ID NO:321:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:321:

TGGAGGGATT GCTTGAGG                                                      18

(2) INFORMATION FOR SEQ ID NO:322:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:322:

AGGTGTACAC CACCATGCCT                                                    20

(2) INFORMATION FOR SEQ ID NO:323:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:323:

TGGTGCCAAT TATTGCTGC                                                     19

(2) INFORMATION FOR SEQ ID NO:324:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:324:

AGATCTTATA CACATGTGCG CG                                                 22

(2) INFORMATION FOR SEQ ID NO:325:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:325:

AGGTGACATC ACTTACAGCG G                                                  21

(2) INFORMATION FOR SEQ ID NO:326:

(i) SEQUENCE CHARACTERISTICS:
        (A) LENGTH: 18 base pairs
        (B) TYPE: nucleic acid
        (C) STRANDEDNESS: single
```

(D) TOPOLOGY: linear (xi) SEQUENCE DESCRIPTION: SEQ ID NO:326:

ATTACCCAGG CATGGTGC                                                    18

(2) INFORMATION FOR SEQ ID NO:327:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:327:

CAGGCACTTC TTCCAGGTCT                                                  20

(2) INFORMATION FOR SEQ ID NO:328:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:328:

AGGGTTACAC TGGAGTTTGC                                                  20

(2) INFORMATION FOR SEQ ID NO:329:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:329:

AAACCTTCAA TGTGTTCATT AAAAC                                            25

(2) INFORMATION FOR SEQ ID NO:330:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:330:

TCAACTTTAT TGGGGGTTTA                                                  20

(2) INFORMATION FOR SEQ ID NO:331:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:331:

AAGGTAAAAG TCCAAAATGG                                                  20

(2) INFORMATION FOR SEQ ID NO:332:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:332:

GGACAGTCAG TTATTGAAAT G                                              21

(2) INFORMATION FOR SEQ ID NO:333:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (xi) SEQUENCE DESCRIPTION: SEQ ID NO:333:

TTTCCTCTCT GGGAGTCTCT                                                20

(2) INFORMATION FOR SEQ ID NO:334:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (xi) SEQUENCE DESCRIPTION: SEQ ID NO:334:

TCAAGCTGGA GTCCACCATC                                                20

(2) INFORMATION FOR SEQ ID NO:335:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (xi) SEQUENCE DESCRIPTION: SEQ ID NO:335:

CACTCGCTGT GAGGAGGAC                                                 19

(2) INFORMATION FOR SEQ ID NO:336:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (xi) SEQUENCE DESCRIPTION: SEQ ID NO:336:

ACAACGGCAG GACGTGTAAG                                                20

(2) INFORMATION FOR SEQ ID NO:337:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (xi) SEQUENCE DESCRIPTION: SEQ ID NO:337:

ATTGCCATCG ACTACGACC                                                 19

(2) INFORMATION FOR SEQ ID NO:338:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (xi) SEQUENCE DESCRIPTION: SEQ ID NO:338:

TGGTCAACAC CGAGATCAAC                                           20

(2) INFORMATION FOR SEQ ID NO:339:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:339:

AACCTCTACT GGACCGACAC                                           20

(2) INFORMATION FOR SEQ ID NO:340:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:340:

CTCATGTACT GGACAGACT                                            19

(2) INFORMATION FOR SEQ ID NO:341:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:341:

GAGACGCCAA GACAGACAAG                                           20

(2) INFORMATION FOR SEQ ID NO:342:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:342:

CAGTCCAGTA GATGAAGTCC                                           20

(2) INFORMATION FOR SEQ ID NO:343:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:343:

GTGAAGAAGC ACAGGTGGCT                                           20

(2) INFORMATION FOR SEQ ID NO:344:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:344:

TCATGTCACT CAGCAGCTCC                                                    20

(2) INFORMATION FOR SEQ ID NO:345:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:345:

CCGTTGTTGT GCATACAGTC                                                    20

(2) INFORMATION FOR SEQ ID NO:346:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:346:

GTGGCACATG CAAACTGGTC                                                    20

(2) INFORMATION FOR SEQ ID NO:347:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:347:

GCTCTAGAGT ACAAAGTTCT CCCAGCCC                                           28

(2) INFORMATION FOR SEQ ID NO:348:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:348:

ATCCTCGGGG TCTTCCGGGG CGAGTTCTGG CTGGCTACTG CTGTGGGCCG GGCT              54

(2) INFORMATION FOR SEQ ID NO:349:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:349:

TGGATATCTC AGTGGTGGTG GTGGTGGTGC TCGACATCCT CGGGGTCTTC CGGG              54

(2) INFORMATION FOR SEQ ID NO:350:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:350:

```
TAGAATTCGC CGCCACCATG GAGGCAGCGC CGCCC                                    35

(2) INFORMATION FOR SEQ ID NO:351:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (xi) SEQUENCE DESCRIPTION: SEQ ID NO:351:

GAGGCGGGAG CAAGAGG                                                        17

(2) INFORMATION FOR SEQ ID NO:352:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (xi) SEQUENCE DESCRIPTION: SEQ ID NO:352:

GCAAGCTTCA TGGAGCCCGA GTGAGC                                              26

(2) INFORMATION FOR SEQ ID NO:353:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (xi) SEQUENCE DESCRIPTION: SEQ ID NO:353:

ATGGAGCCCG AGTGAGC                                                        17

(2) INFORMATION FOR SEQ ID NO:354:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (xi) SEQUENCE DESCRIPTION: SEQ ID NO:354:

TCACTCGGGC TCCATGG                                                        17

(2) INFORMATION FOR SEQ ID NO:355:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:355:

TGCTGTACTG CAGCTTGGTC                                                     20

(2) INFORMATION FOR SEQ ID NO:356:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO:356:

ATGCAGCTGC TGTAGACTTC C                                                   21
```

-continued (2) INFORMATION FOR SEQ ID NO:357:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:357:

GTCTGTTTGA TGGCCTCCTC                                              20

(2) INFORMATION FOR SEQ ID NO:358:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:358:

ATGTTCTGTG CAGCACCTCC                                              20

(2) INFORMATION FOR SEQ ID NO:359:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:359:

GCCATCAGGT GACACGAG                                                  18

(2) INFORMATION FOR SEQ ID NO:360:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:360:

AAGGTTCTCT TCTGGCAGGA C                                           21

(2) INFORMATION FOR SEQ ID NO:361:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:361:

CCAGTCAGTC CAGTACATG                                               19

(2) INFORMATION FOR SEQ ID NO:362:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:362:

TCGACCTGGA GGAACAGAAG                                              20

(2) INFORMATION FOR SEQ ID NO:363:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:363:

AAGCTCAGCT TCATCCACCG                                          20

(2) INFORMATION FOR SEQ ID NO:364:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:364:

ATGAAGCTGA GCTTGGCATC                                          20

(2) INFORMATION FOR SEQ ID NO:365:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:365:

AGCAGAGGAA GGAGATCCTT AG                                       22

(2) INFORMATION FOR SEQ ID NO:366:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:366:

TCCATGGGTG AGTACAGAGC                                          20

(2) INFORMATION FOR SEQ ID NO:367:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:367:

ATTGTCCTGC AACTGCACAC                                          20

(2) INFORMATION FOR SEQ ID NO:368:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:368:

GCCATTGCCA TTGACTACG                                           19

(2) INFORMATION FOR SEQ ID NO:369:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:369:

GGATCGTAGT CAATGGCAAT G        21

(2) INFORMATION FOR SEQ ID NO:370:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:370:

GAATTGAGGT GACTCGCCTC        20

(2) INFORMATION FOR SEQ ID NO:371:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:371:

CCTCAATTCT GTAGTGCCTG        20

(2) INFORMATION FOR SEQ ID NO:372:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:372:

TGTGTTGCAC CCTGTGATG        19

(2) INFORMATION FOR SEQ ID NO:373:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:373:

ATCTAGGTTG GCGCATTCG        19

(2) INFORMATION FOR SEQ ID NO:374:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:374:

AGGTGTTCAC CAGGACATG        19

(2) INFORMATION FOR SEQ ID NO:375:

```
    (i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:375:

GCGAGCTCCC GTCTATGTTG ATCACCTCG                                    29

(2) INFORMATION FOR SEQ ID NO:376:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:376:

GACCTGATGG GACTCAAAGC                                              20

(2) INFORMATION FOR SEQ ID NO:377:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:377:

GCTGGTGAAT ACCAGGAAGG                                              20

(2) INFORMATION FOR SEQ ID NO:378:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:378:

ACGATGTGGC TATCCCACTC                                              20

(2) INFORMATION FOR SEQ ID NO:379:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:379:

AGTAGGATCC AGAGCCAGAG                                              20

(2) INFORMATION FOR SEQ ID NO:380:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:380:

AGCGCATGGT GATAGCTGAC                                              20

(2) INFORMATION FOR SEQ ID NO:381:
```

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:381:

CGTTCAATGC TATGCAGGTT C                                              21

(2) INFORMATION FOR SEQ ID NO:382:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:382:

GTGCTTCACA CTACACGCTG                                                20

(2) INFORMATION FOR SEQ ID NO:383:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:383:

CAGCCAGAAA TTTGCCATC                                                 19

(2) INFORMATION FOR SEQ ID NO:384:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:384:

TCCGGCTGTA GATGTCAATG                                                20

(2) INFORMATION FOR SEQ ID NO:385:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:385:

AGGCCACCAA CACTATCAAT G                                              21

(2) INFORMATION FOR SEQ ID NO:386:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:386:

TACCCTCGCT CAGCATTGAC                                                20

(2) INFORMATION FOR SEQ ID NO:387:

(i) SEQUENCE CHARACTERISTICS:
```

(A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:387:

CTGGAAGATG CCAACATCG                                                    19

(2) INFORMATION FOR SEQ ID NO:388:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:388:

TGAACCCTAG TCCGCTTGTC                                                   20

(2) INFORMATION FOR SEQ ID NO:389:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:389:

CTGCAGAACC TGCTGACTTG                                                   20

(2) INFORMATION FOR SEQ ID NO:390:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:390:

CCAGAGTGAT GAAGAAGGCT G                                                 21

(2) INFORMATION FOR SEQ ID NO:391:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:391:

TCACTCTGGT CAGCACACTC                                                   20

(2) INFORMATION FOR SEQ ID NO:392:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:392:

CAGGATCGCT CTGATGAAGC                                                   20

(2) INFORMATION FOR SEQ ID NO:393:

(i) SEQUENCE CHARACTERISTICS:
        (A) LENGTH: 21 base pairs (B) TYPE: nucleic acid
            (C) STRANDEDNESS: single
            (D) TOPOLOGY: linear (xi) SEQUENCE DESCRIPTION: SEQ ID NO:393:

GCAGTTAGCT TCATCAGAGC G                                              21

(2) INFORMATION FOR SEQ ID NO:394:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:394:

ACCCTCTGAT GACATCCCAG                                                20

(2) INFORMATION FOR SEQ ID NO:395:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:395:

AATGGCACTG CTGTGGGC                                                  18

(2) INFORMATION FOR SEQ ID NO:396:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:396:

AGGCTCATGG AGCTCATCAC                                                20

(2) INFORMATION FOR SEQ ID NO:397:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:397:

ATAGTGTGGC CTTTGTGCTG                                                20

(2) INFORMATION FOR SEQ ID NO:398:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:398:

GTCATTCGAG GTATGGCACC                                                20

(2) INFORMATION FOR SEQ ID NO:399:

(i) SEQUENCE CHARACTERISTICS:
            (A) LENGTH: 21 base pairs
            (B) TYPE: nucleic acid (C) STRANDEDNESS: single
        (D) TOPOLOGY: linear (xi) SEQUENCE DESCRIPTION: SEQ ID NO:399:

GGTAGTATTT GCTGCTCTTC C                                          21

(2) INFORMATION FOR SEQ ID NO:400:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:400:

GCTCTAGAAA AGTTTCCCAG CCCTGCC                                    27

(2) INFORMATION FOR SEQ ID NO:401:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:401:

CTGGAAGATG CCAACATCG                                             19

(2) INFORMATION FOR SEQ ID NO:402:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:402:

GCTCTAGACT AGTGATGGTG ATGGTGATGA CTGCTGTGGG CTGGGATGTC ATCAGAGGGT     60

GG                                                               62

(2) INFORMATION FOR SEQ ID NO:403:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:403:

Ser Tyr Phe His Leu Phe Pro Pro Pro Ser Pro Cys Thr Asp Ser
1               5                   10                  15

Ser (2) INFORMATION FOR SEQ ID NO:404:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:404:

Val Asp Gly Arg Gln Asn Ile Lys Arg Ala Lys Asp Asp Gly Thr
1               5                   10                  15

(2) INFORMATION FOR SEQ ID NO:405:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:405:

Glu Val Leu Phe Thr Thr Gly Leu Ile Arg Pro Val Ala Leu Val Val
1               5                   10                  15

Asp Asn (2) INFORMATION FOR SEQ ID NO:406:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:406:

Ile Gln Gly His Leu Asp Phe Val Met Asp Ile Leu Val Phe His Ser
1               5                   10                  15

(2) INFORMATION FOR SEQ ID NO:407:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:407:

CCATCCTAAT ACGACTCACT ATAGGGC                                               27

(2) INFORMATION FOR SEQ ID NO:408:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:408:

ACTCACTATA GGGCTCGAGC GGC                                                   23

(2) INFORMATION FOR SEQ ID NO:409:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:409:

TGTAAAACGA CGGCCAGT                                                         18

(2) INFORMATION FOR SEQ ID NO:410:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:410:

GCTATGACCA TGATTACGCC                                                       20

(2) INFORMATION FOR SEQ ID NO:411:

-continued (i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:411:

CCGGGTCAAC ATGGAG                                                     16

(2) INFORMATION FOR SEQ ID NO:412:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:412:

CCGCGGGTAG GTGGGC                                                     16

(2) INFORMATION FOR SEQ ID NO:413:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:413:

TGCCCCACAG CCTCGC                                                     16

(2) INFORMATION FOR SEQ ID NO:414:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:414:

TCACGGGTAA ACCCTG                                                     16

(2) INFORMATION FOR SEQ ID NO:415:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:415:

CCCGTCACAG GTACAT                                                     16

(2) INFORMATION FOR SEQ ID NO:416:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:416:

GTTCCGGTAG GTACCC                                                     16

(2) INFORMATION FOR SEQ ID NO:417:

(i) SEQUENCE CHARACTERISTICS:
    (A) LENGTH: 16 base pairs
    (B) TYPE: nucleic acid
    (C) STRANDEDNESS: double
    (D) TOPOLOGY: linear (xi) SEQUENCE DESCRIPTION: SEQ ID NO:417:

CTGACTGCAG GCAGAA                                                16

(2) INFORMATION FOR SEQ ID NO:418:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:418:

CTTTCTGTGA GTGCCG                                                16

(2) INFORMATION FOR SEQ ID NO:419:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:419:

GTTTTCCCAG TCCACA                                                16

(2) INFORMATION FOR SEQ ID NO:420:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:420:

AGGCAGGTGA GGCGGT                                                16

(2) INFORMATION FOR SEQ ID NO:421:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:421:

GTCTCCACAG GAGCCG                                                16

(2) INFORMATION FOR SEQ ID NO:422:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:422:

GATGGGGTAA GACGGG                                                16

(2) INFORMATION FOR SEQ ID NO:423:

(i) SEQUENCE CHARACTERISTICS:

(A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:423:

TCTTCTCCAG CCTCAT                                                     16

(2) INFORMATION FOR SEQ ID NO:424:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:424:

ATCGAGGTGA GGCTCC                                                     16

(2) INFORMATION FOR SEQ ID NO:425:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:425:

CGTCCTGCAG GTGATC                                                     16

(2) INFORMATION FOR SEQ ID NO:426:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:426:

TCGTCGGTGA GTCCGG                                                     16

(2) INFORMATION FOR SEQ ID NO:427:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:427:

TCGCTTCCAG GAACCA                                                     16

(2) INFORMATION FOR SEQ ID NO:428:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:428:

CTGAAGGTAG CGTGGG                                                     16

(2) INFORMATION FOR SEQ ID NO:429:

(i) SEQUENCE CHARACTERISTICS:
        (A) LENGTH: 16 base pairs (B) TYPE: nucleic acid
            (C) STRANDEDNESS: double
            (D) TOPOLOGY: linear (xi) SEQUENCE DESCRIPTION: SEQ ID NO:429:

CTGCTGCCAG ACCATC                                                       16

(2) INFORMATION FOR SEQ ID NO:430:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:430:

CAAGGGGTAA GTGTTT                                                       16

(2) INFORMATION FOR SEQ ID NO:431:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:431:

TGCCTTCCAG CTACAT                                                       16

(2) INFORMATION FOR SEQ ID NO:432:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:432:

TGCTGGGTGA GGGCCG                                                       16

(2) INFORMATION FOR SEQ ID NO:433:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:433:

GTTCATGCAG GTCAGG                                                       16

(2) INFORMATION FOR SEQ ID NO:434:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:434:

GCAGCCGTAA GTGCCT                                                       16

(2) INFORMATION FOR SEQ ID NO:435:

(i) SEQUENCE CHARACTERISTICS:
            (A) LENGTH: 16 base pairs
            (B) TYPE: nucleic acid

```
        (C) STRANDEDNESS: double
        (D) TOPOLOGY: linear (xi) SEQUENCE DESCRIPTION: SEQ ID NO:435:

CCTCCTCTAG CGCCCA                                                   16

(2) INFORMATION FOR SEQ ID NO:436:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:436:

ACCCAGGCAG GTGCCC                                                   16

(2) INFORMATION FOR SEQ ID NO:437:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:437:

TGTCTTACAG CCCTTT                                                   16

(2) INFORMATION FOR SEQ ID NO:438:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:438:

GCGAGGGTAG GAGGCC                                                   16

(2) INFORMATION FOR SEQ ID NO:439:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:439:

CCTCCCGCAG GTACCT                                                   16

(2) INFORMATION FOR SEQ ID NO:440:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:440:

TGTCAGGTAA GGGGCC                                                   16

(2) INFORMATION FOR SEQ ID NO:441:

(i) SEQUENCE CHARACTERISTICS:
        (A) LENGTH: 16 base pairs
        (B) TYPE: nucleic acid
        (C) STRANDEDNESS: double
```

(D) TOPOLOGY: linear (xi) SEQUENCE DESCRIPTION: SEQ ID NO:441:

CTGCTTGCAG GGGCCA                                                    16

(2) INFORMATION FOR SEQ ID NO:442:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:442:

AGTTCTGTAC GTGGGG                                                    16

(2) INFORMATION FOR SEQ ID NO:443:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:443:

GTCTTTGCAG CAGCCC                                                    16

(2) INFORMATION FOR SEQ ID NO:444:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:444:

GTGGAGGTAG GTGTGA                                                    16

(2) INFORMATION FOR SEQ ID NO:445:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:445:

CCTCCCCCAG AGCCGC                                                    16

(2) INFORMATION FOR SEQ ID NO:446:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:446:

GTGACGGTGA GGCCCT                                                    16

(2) INFORMATION FOR SEQ ID NO:447:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (xi) SEQUENCE DESCRIPTION: SEQ ID NO:447:

TCCCTTGCAG CCATCT                                                   16

(2) INFORMATION FOR SEQ ID NO:448:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:448:

TGTGTGGTGA GCCAGC                                                   16

(2) INFORMATION FOR SEQ ID NO:449:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:449:

TCTCTGGCAG AAATCA                                                   16

(2) INFORMATION FOR SEQ ID NO:450:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:450:

TCACAGGTAA GGAGCC                                                   16

(2) INFORMATION FOR SEQ ID NO:451:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:451:

TCCCTGCCAG GCATCG                                                   16

(2) INFORMATION FOR SEQ ID NO:452:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:452:

CCGCCGGTGA GGGGCG                                                   16

(2) INFORMATION FOR SEQ ID NO:453:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:453:

CTCTCCTCAG ATCCTG                                                            16

(2) INFORMATION FOR SEQ ID NO:454:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:454:

GTACAGGTAG GACATC                                                            16

(2) INFORMATION FOR SEQ ID NO:455:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:455:

TCCCTTTCAG GCCCTA                                                            16